United States Patent [19]

Yanni et al.

[11] Patent Number: 4,950,674
[45] Date of Patent: * Aug. 21, 1990

[54] ARYLALKYLHETEROCYCLIC AMINES,N-SUBSTITUTED BY ARYLOXYALKYL GROUP IN A METHOD FOR ALLERGY TREATMENT

[75] Inventors: John M. Yanni, Midlothian; David A. Walsh, Richmond, both of Va.

[73] Assignee: A. H. Robins Company, Incorporated, Richmond, Va.

[ * ] Notice: The portion of the term of this patent subsequent to Mar. 7, 2006 has been disclaimed.

[21] Appl. No.: 159,940

[22] Filed: Feb. 24, 1988

Related U.S. Application Data

[63] Continuation-in-part of Ser. No. 811,799, Dec. 20, 1985, Pat. No. 4,810,713.

[51] Int. Cl.$^5$ .......................................... A61K 31/445
[52] U.S. Cl. ................................ 514/317; 514/318; 514/319; 514/326; 514/428; 514/826
[58] Field of Search ............... 514/317, 318, 319, 326, 514/428, 826

[56] References Cited

U.S. PATENT DOCUMENTS

| | | | |
|---|---|---|---|
| 3,806,526 | 4/1974 | Carr et al. | 546/213 X |
| 3,862,173 | 1/1975 | Carr et al. | 546/213 |
| 3,922,276 | 11/1975 | Duncan et al. | 546/226 |
| 3,941,795 | 3/1976 | Carr et al. | 546/213 X |
| 3,956,296 | 5/1976 | Duncan et al. | 546/226 X |
| 4,032,642 | 6/1977 | Duncan et al. | 514/316 X |
| 4,810,713 | 3/1989 | Yanni et al. | |

Primary Examiner—Leonard Schenkman

[57] ABSTRACT

A method of inhibiting Type 1 allergic responses in a living animal body with substituted heterocyclic amines is disclosed wherein the active agents are expressed generally by the formula which includes certain known and certain known compounds:

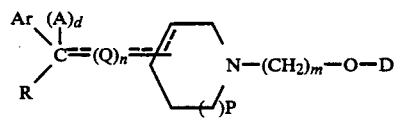

wherein P is zero, one or two; m is one to six inclusive; A is selected from hydrogen, hydroxy or cyano; d is zero or one; Q is —CH—, $CH_2$— or

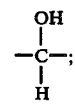

n is zero or one and when Q is —CH— and n is one, a double bond is formed with one of the adjacent carbons but not both at the same time, and when n and d are zero at the same time, a double bond is formed between the α carbon and a carbon of the central heterocyclic amine ring; Ar, D and R are selected from phenyl, substituted phenyl, pyridinyl, thienyl, furanyl or naphthyl and in addition, R may have the values benzyl, substituted benzyl, cycloalkyl or loweralkyl and D may additionally have the values: 2H-1-benzopyran-2-one,4-oxo-4H-1-benzopyran-2-carboxylic acid loweralkyl ester, 2,3-dihydro-4H-1-benzopyran-4-one, 1,4-benzodioxanloweralkyl-2-yl or 1,1'-biphenyl-4-yl and the pharmaceutically acceptable salts thereof.

57 Claims, No Drawings

ARYLALKYLHETEROCYCLIC AMINES,N-SUBSTITUTED BY ARYLOXYALKYL GROUP IN A METHOD FOR ALLERGY TREATMENT

This application is a continuation-in-part application of copending U.S. patent application Ser. No. 811,799 filed Dec. 20, 1985 now U.S. Pat. No. 4,810,713, issued Mar. 7, 1989.

BACKGROUND OF THE INVENTION

1. Field of Invention

This invention relates to a method of inhibiting Type I allergic responses (Gell and Coombs classification of Immune Responses) in a living animal body with piperidinyl, pyrrolidinyl, and homopiperidinyl derivatives substituted on nitrogen by aryloxyalkyl radicals and otherwise substituted by aryl (or diaryl)-alkanol, aryl (or diaryl)-alkyl, aryl or (diaryl)cyano methyl and aryl (or diaryl)alkylidine radicals. The compounds prevent release of histamine and synthesis of 5-lypoxygenase metabolites as well as antagonize end organ effects of mediators involved in the immediate hypertensivity response and, as such, are useful in treating allergic phenomena which includes asthma, rhinitis, atopic dermatitis, chronic hives, allergic conjunctivitis, and the like.

2. Information Disclosure Statement

Various systemic anti-allergy agents have long been known prior to this invention including, among others, aminophylline, theophylline, corticosteroids, the disodium salt of 1,3-bis(2-carboxychromon-5-yloxy)-2-hydroxypropane, α-[(tertbutylamino)methyl]-3,5-dihydroxybenzylalcohol sulfate and oxatomide. The efficacy of some has suffered from undesirable side effects while others which are effective prophylactically are ineffective in acute manifestations of the allergic attack. By way of comparison, for example, the preferred compounds of the present invention are many times more potent than aminophylline and several times more potent than oxatomide.

Olefinic-4-substituted piperidino derivatives useful as antihistaminic, antiallergy agents and bronchodilators are represented by the formula:

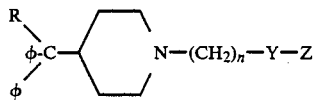

are disclosed in U.S. Pat. No. 3,862,173 wherein R represents hydrogen or forms a double bond, Y represents —CH=CH— and Z represents thienyl, phenyl or phenyl substituted by halogen, alkyl, loweralkoxy, diloweralkylamino, pyrrolidino, piperidino, morpholino or N-loweralkylpiperazino. Compounds useful in the present invention differ in that an ether linkage is present and there is no unsaturation in the alkyl chain.

Diphenylmethylenepiperidineacetic acid derivatives useful as antiallergic, antihistaminic, and broncholytic agents are disclosed in European Pat. No. 48705B and have the formula:

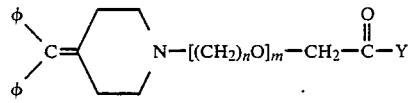

wherein Y is OH or $NR_1R_2$; compounds useful in the present invention have an aryl group next to the ether oxygen.

U.S. Pat. No. 3,806,526 discloses 1-aroylalkyl-4-diphenylmethylpiperidines having antihistaminic, antiallergenic and bronchodilator activity. In contrast, the compounds useful in the present invention have an aryloxyalkyl radical on piperidine and pyrrolidine nitrogen rather than an aroylalkyl radical.

A number of the compounds useful in the present method of treating allergy have been disclosed specifically and under generic formulas in U.S. Pat. Nos. 3,922,276 and 3,956,296 as being useful as antiinflammatory agents, tranquilizers and sedatives. These activities are not suggestive of use in treating allergy.

The compound 4-diphenylmethylene-1-benzylpiperidine maleate is disclosed in Japanese Kokai No. 62,145,018 to be an antiallergy agent not liberating histamine. The compound is not encompassed by Formula I.

SUMMARY OF THE INVENTION

The heterocyclic amines useful in the antiallergy method of this invention are disubstituted and have the general formula:

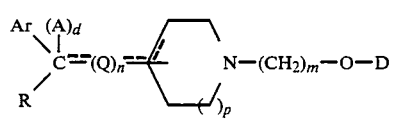

Formula I wherein:

P is zero, one or two;
m is one to six inclusive;
A is hydrogen, hydroxy, or cyano;
d is zero or one;
Q is —CH—, —CH$_2$— or

n is zero or one;
and when Q is —CH— and n is 1, a double bond is formed with one of the adjacent carbons, but not both, and when n and d are zero at the same time, a double bond is formed between the α-carbon and a carbon of the central heterocyclic amine ring;

Ar, D and R are selected from the group consisting of:

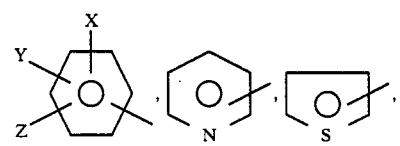

-continued

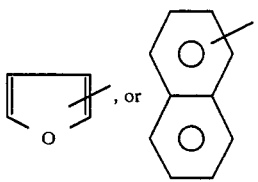

and in addition, R may have the values:

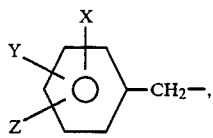

cycloalkyl or lower alkyl; and D may have additionally the values:

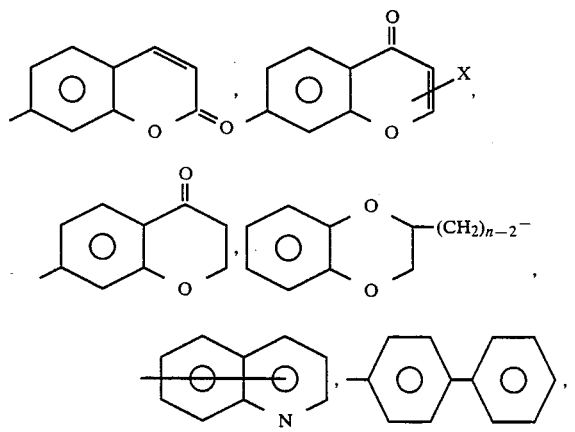

or $AR(CH_2)_{1-4}$—; X, Y, and Z are selected from the group consisting of hydrogen, loweralkyl, halogen,

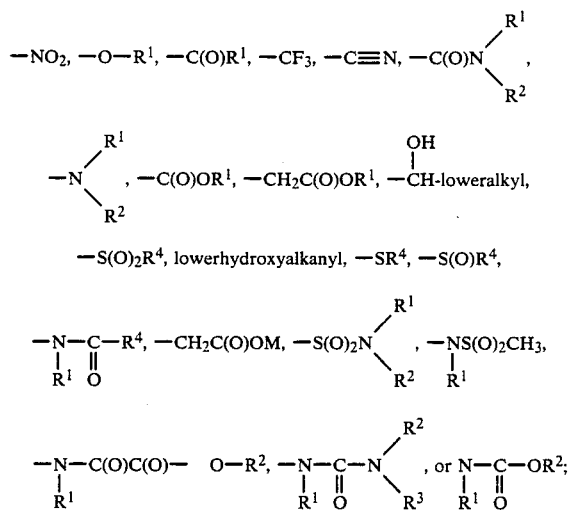

$R^1$, $R^2$ and $R^3$, same or different, are selected from hydrogen, loweralkyl, phenyl and phenylloweralkyl; $R_4$ is selected from loweralkyl, phenyl and phenylloweralkyl; M is a pharmaceutically acceptable metal ion, and the pharmaceutically acceptable salts thereof, including acid addition salts, quaternary salts and hydrates and alcoholates thereof.

In the further definition of symbols in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl, and octyl radicals and the like. The term "loweralkoxy" has the formula —O—loweralkyl. The term "lowerhydroxyalkanyl" refers to loweralkyl radicals carrying a hydroxy radical.

The term "cycloalkyl" as used herein includes primarily cyclic alkyl radicals containing 3–7 carbon atoms inclusive and includes such groups as cyclopropyl, cyclobutyl, cyclopentyl, cyclohexyl, cycloheptyl and methylcyclohexyl and the like.

The term "halo" or "halogen" when referred to herein includes fluorine, chlorine, bromide and iodine unless otherwise stated.

The term "central heterocyclic amine ring" refers to that portion of Formula I represented by

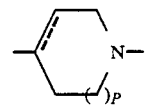

The term "phenylloweralkyl" includes phenyl connected by hydrocarbon chains exemplified by loweralkyl above and wherein phenyl may be substituted by nonreactive or noninterfering radicals such as halo, loweralkyl, loweralkoxy, and the like.

"Pharmaceutically acceptable salts" include acid addition salts, hydrates, alcoholates and quaternary salts of the compounds of Formula I which are physiologically compatible in warm-blooded animals. The acid addition salts may be formed by either strong or walk acids. Representative of strong acids are hydrochloric, hydrobromic, sulfuric, and phosphoric acids. Representative of weak acids are fumaric, maleic, mandelic, tartaric, citric, oxalic, succinic, hexamic, and the like. Suitable quaternary salts include and the loweralkyl halides and loweralkyl sulfates.

The primary screening method used to detect antiallergy properties of the compounds of Formula I is a modification of the procedure of R. R. Martel and J. Klicius, Intern. Arch. Allergy Appl. Immunology, vol. 54, pp. 205–209 (1977) which measures the effect of oral administration of the compound on the volume of a rat paw which was previously injected with anti-egg albumin serum and is described in detail under Pharmacology Methods hereinbelow.

A method of studying potency in preventing guinea pig anaphylaxis relative to known antiallergy drugs is also described hereinbelow under Pharmacology Methods. Generally, about 200 times more theophylline and 5–15 times more oxatomide are required than the more active compounds used in the present method.

The Gell and Coombs Classification of Immune Responses referred to hereinabove is well known in the art and is described in ESSENTIAL IMMUNOLOGY 3rd Ed (1977), (Blackwell Scientific Publications) printed by William Clowers & Sons, Limited, London, Beccles & Colchester.

DETAILED DESCRIPTION OF THE INVENTION

Antiallergy agents of Formula I above useful in the method of treating allergy of this invention may be prepared by methods described in U.S. Pat. Nos. 3,922,276 and 4,032,642. One of the general methods used in the detailed examples hereinbelow is outlined by equation in Chart I (Method A). This reaction can be carried out in alcoholic solvents, preferably refluxing butanol or in dimethylformamide, dimethoxyethane in the presence of an acid receptor as, for example, an alkali-metal carbonate, and preferably using potassium iodide catalyst. The reaction time may vary from a few hours to 24 hr, depending on reactivity of the aryloxyalkyl halide and temperature. Temperature can vary from about 80° C. to 145° C. Products are isolated, usually by partitioning in a solvent such as methylene chloride, chloroform or benzene and the like and a weak basic aqueous solution and washing, drying and concentrating the organic layer to give the free base which may then be converted, if desired, to an acid addition salt in a conventional manner.

Alternate Method B is shown by equation in Chart II. This reaction may be carried out in a suitable solvent such as tetrahydrofuran at room temperature for several hours. Preparation and isolation of the free base and a salt is typically described in Example 4.

Alternate Method C is shown by equation in Chart III. This reaction is suitable only when there is no other hydroxy radical present.

Mesylation or tosylation with such as mesyl or tosyl chloride is conducted in the presence of an acid receptor such as a tertiary amine; e.g., triethylamine, while cooling. The final reaction of the mesylate or tosylate with the D—OM+ is conducted in a suitable organic solvent and the product free base is isolated by conventional means such as washing, extracting with an acid solution and an organic solvent and evaporating the solvent.

Alternate Method D is shown by equation in Chart IV. The method is limited to preparation of certain derivatives such as wherein D is 2-pyridinyl or 2-quinolinyl. Dimethyl sulfoxide is a suitable solvent and 60° C. is a suitable temperature for the reaction.

CHART I
Preparation of Compounds of Formula I:

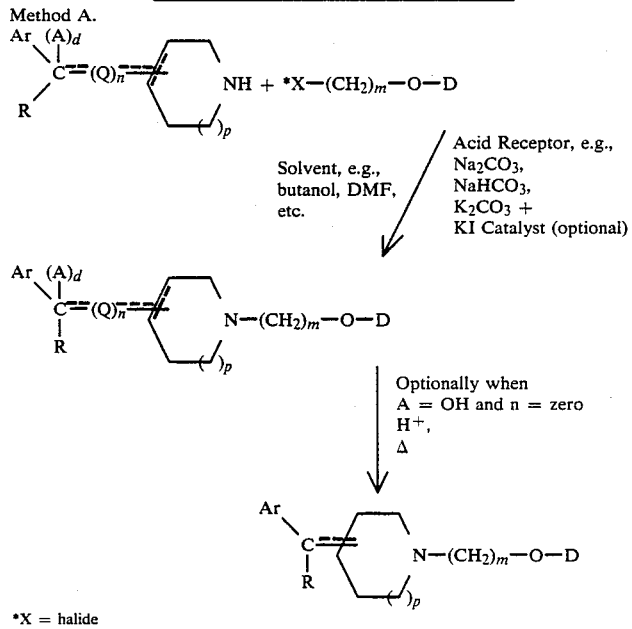

*X = halide

CHART II
Alternate Preparation of Compounds of Formula I:
Method B.

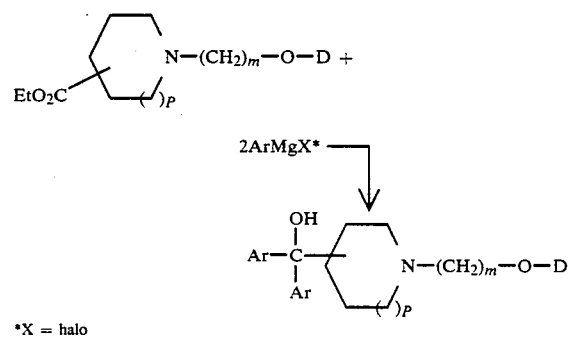

*X = halo

CHART III
Alternate Preparation of Compounds of Formula I:
Method C. When No Other Hydroxy is Present.

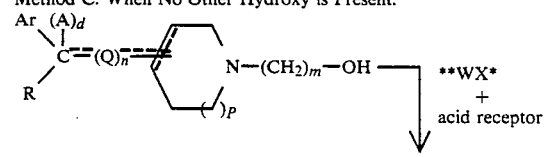

-continued
CHART III
Alternate Preparation of Compounds of Formula I:

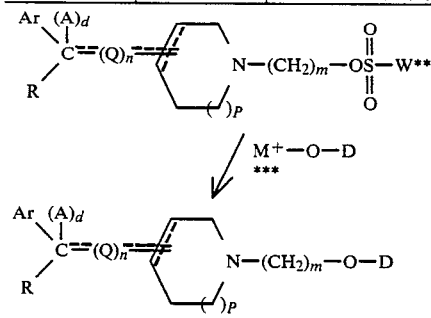

Footnotes:
*X = halo.
**W = mesyl, tosyl, etc.
***M = alkali-metal ion.

CHART IV
Alternate Preparation of Compounds of Formula I:
Method D.

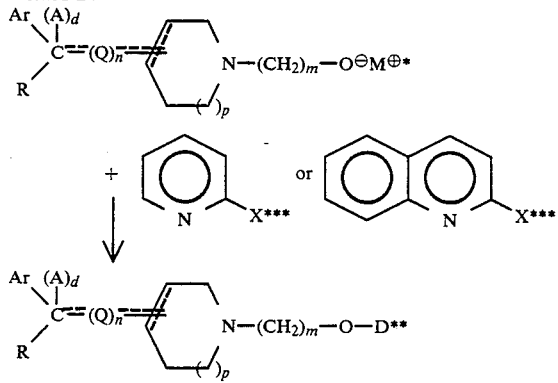 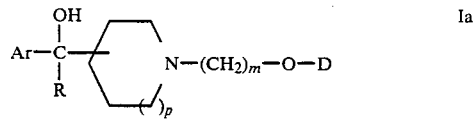

Footnotes:
*M⊕ = alkali-metal cation.
**D = pyridin-2-yl or quinolin-2-yl.
***X = halo (Br, Cl).

To prepare acid addition salts, the free base is reacted with the calculated amount or organic or inorganic acid in aqueous miscible solvent such as ethanol or 2-propanol, with isolation by concentrating and/or cooling, or the base is reacted with an excess of the acid in aqueous immiscible solvent such as diethyl ether or 2-propyl ether, with the desired salt separating directly. Exemplary of such organic salts are those formed with oxalic, maleic, fumaric, benzoic, ascorbic, pamoic, succinic, methanesulfonic, acetic, propionic, tartaric, citric, lactic, malic, citraconic, itaconic, hexamic, p-aminobenzoic, glutamic and stearic acid and the like. Exemplary of such inorganic salts are those formed with hydrochloric, hydrobromic, sulfuric, sulfamic, phosphoric and nitric acids.

If desired, the free base may be regenerated by proportioning the acid addition salt between an organic solvent such as methylene chloride and a wealkly basic aqueous solution of, for example, sodium bicarbonate and separating the methylene chloride layer and evaporating it.

While, as stated above, the compounds of Formula I have generally exhibited positive antiallergy utility, certain compounds encompassed by Formula I are more potent and therefore preferred and have the formula:

$$\text{Ar}-\underset{\underset{R}{|}}{\overset{\overset{OH}{|}}{C}}-\underset{\diagdown}{\diagup}N-(CH_2)_m-O-D \qquad \text{Ia}$$

wherein p is zero or one; Ar, R, m and D have the values assigned under Formula I, and the pharmaceutically acceptable acid salts thereof.

Precursors (Chemical Intermediates) used in the synthesis of compounds of Formula I are prepared in a number of ways as illustrated by the following (1) to (9) sets of equations which are also applicable to pyrrolidinyl and homopiperidinyl derivatives. (See also U.S. Pat. Nos. 3,922,276 and 3,956,296):

(1)

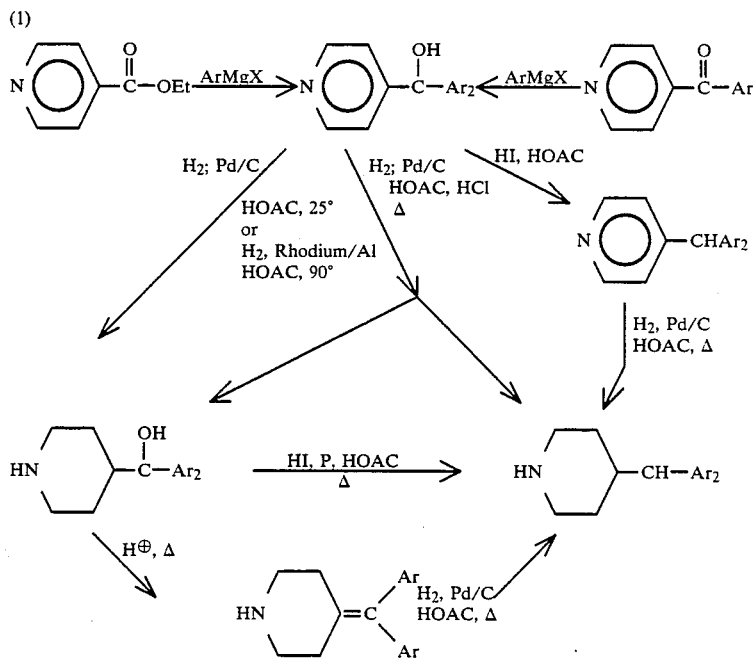

-continued
(2)
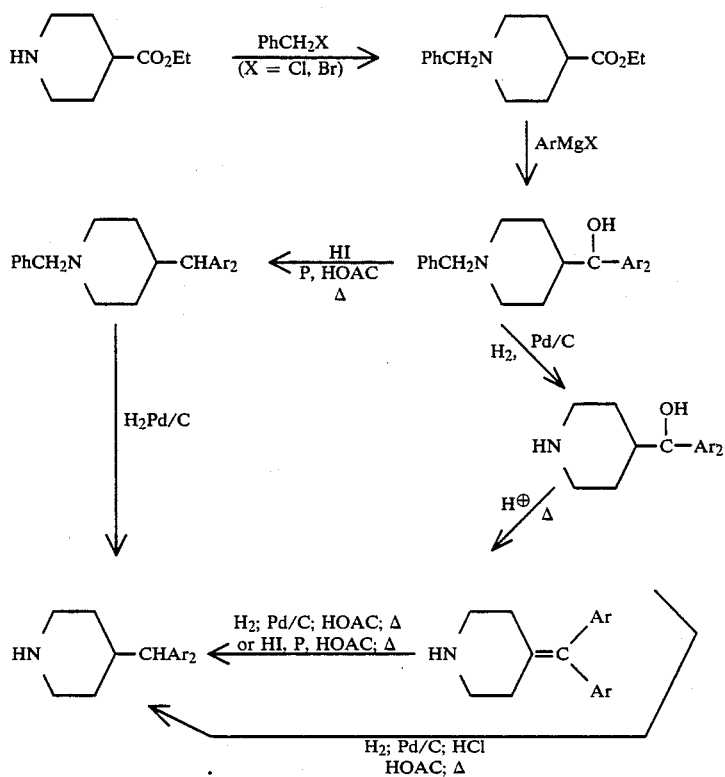
Ph = phenyl.
(3)
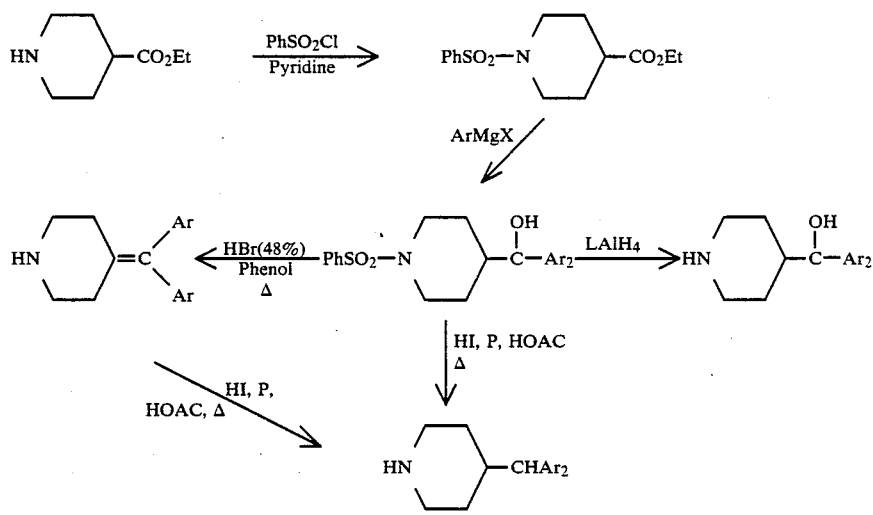
(4)
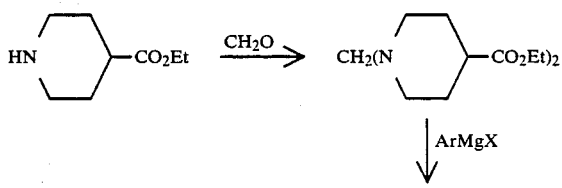

-continued
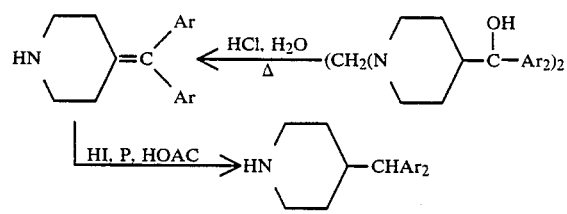
(5)
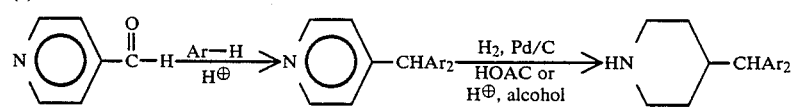
(6)
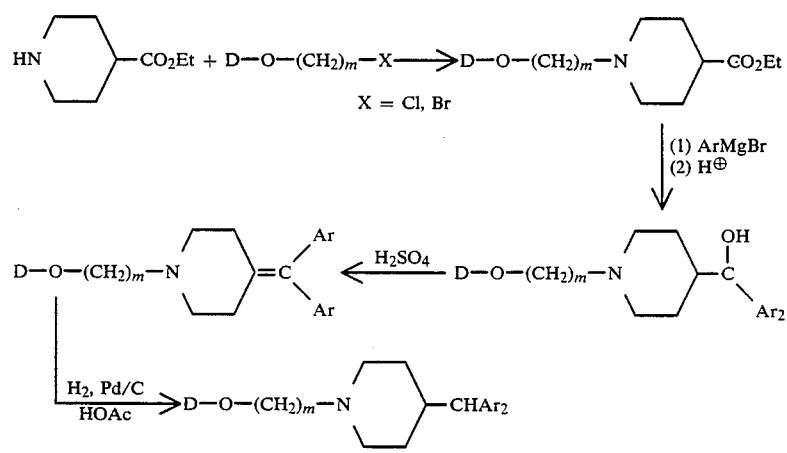
Ph = phenyl.
(7)
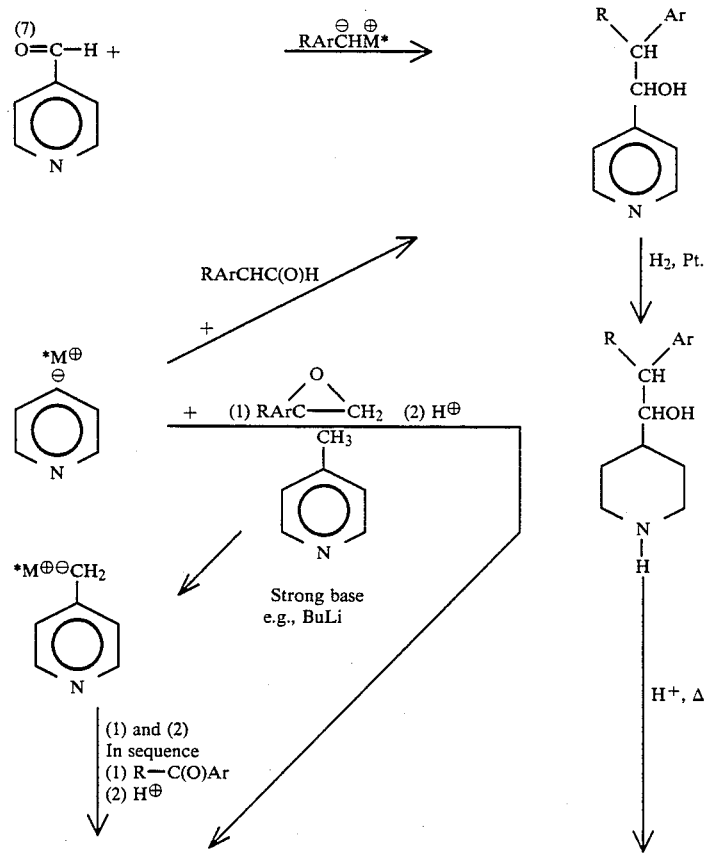

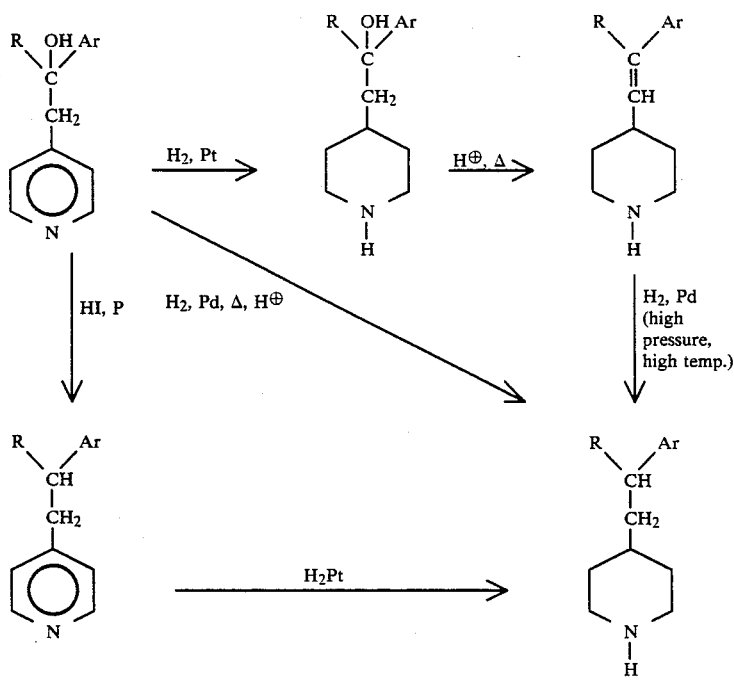
*M⊕ = Li⊕ or MgBr⊕
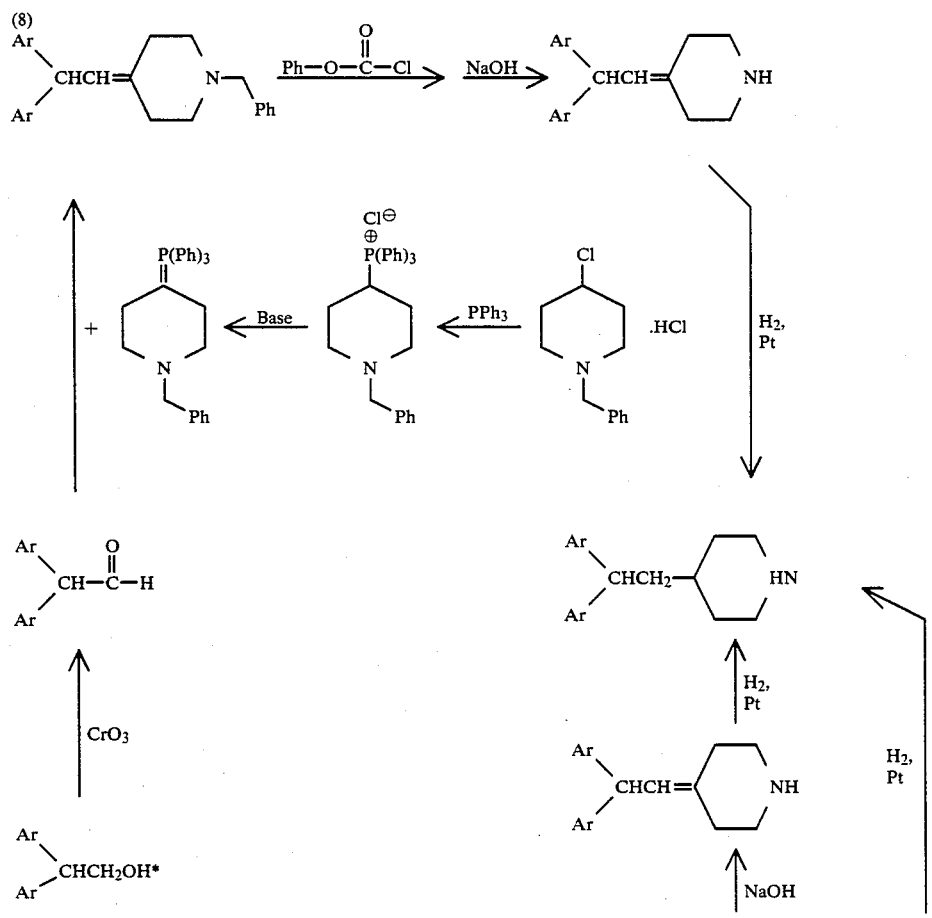

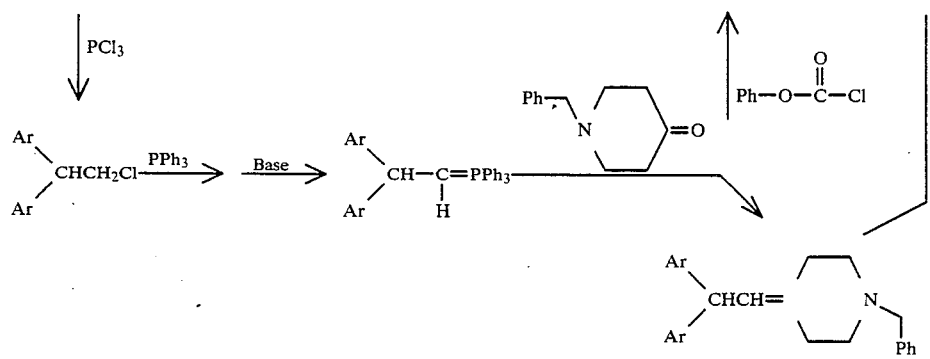
*Commercially available
Ph = phenyl
(9)
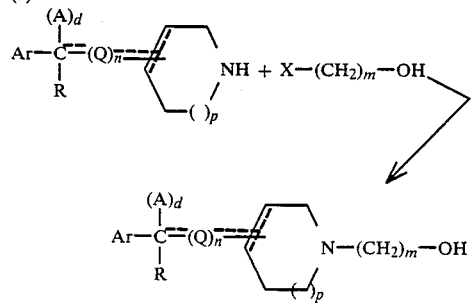
X = halo.
(10)
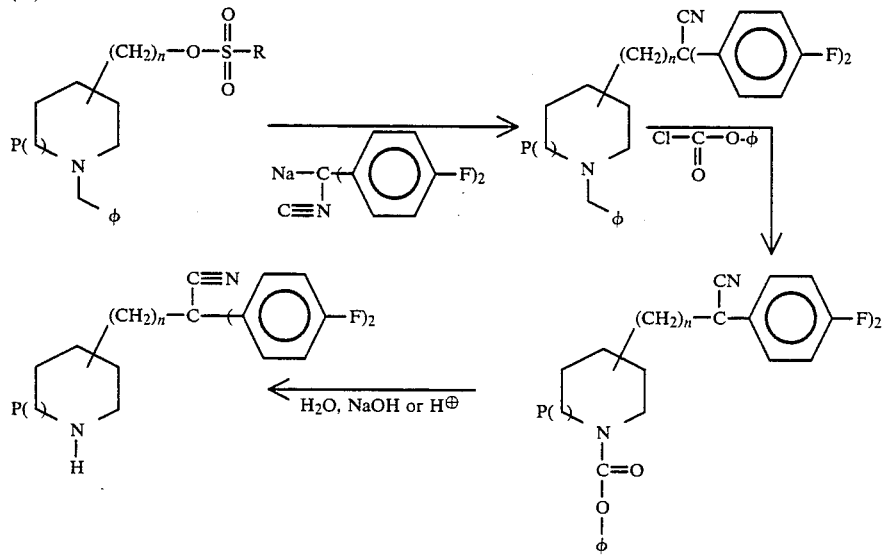
φ = phenyl
R = φ, —⟨phenyl⟩—CH₃
n = 0,1
The method of preparation of certain starting materials wherein D is phenyl substituted by hydroxy is illustrated by the following equations:
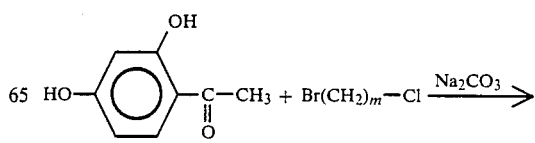

The preparation of certain substituted phenol starting materials is illustrated by the following equations:

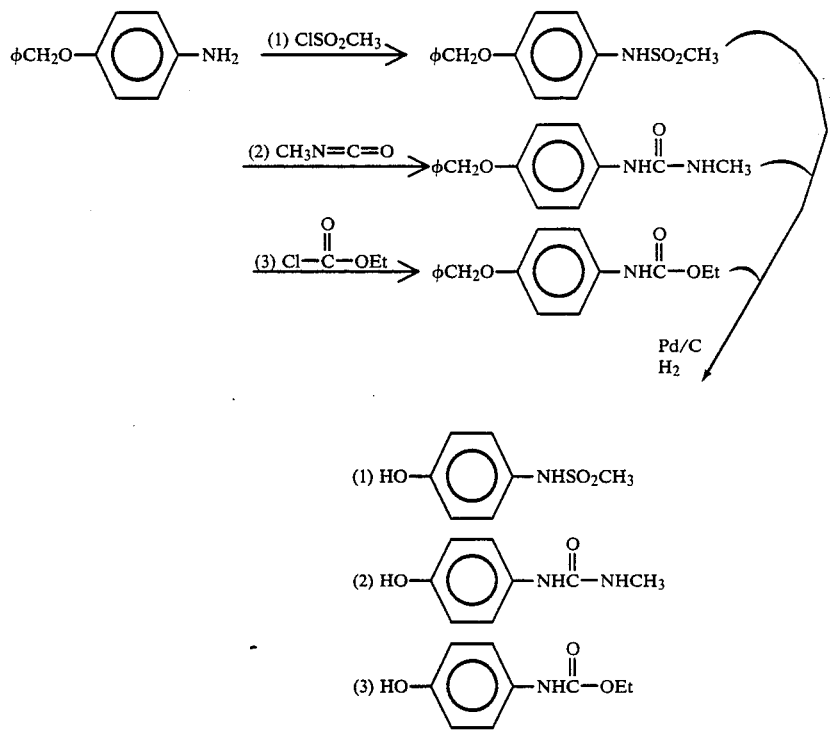

φ = phenyl.

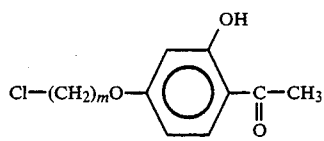

The preparation of other hydroxyphenyl intermediates and compounds is illustrated by the following equation:

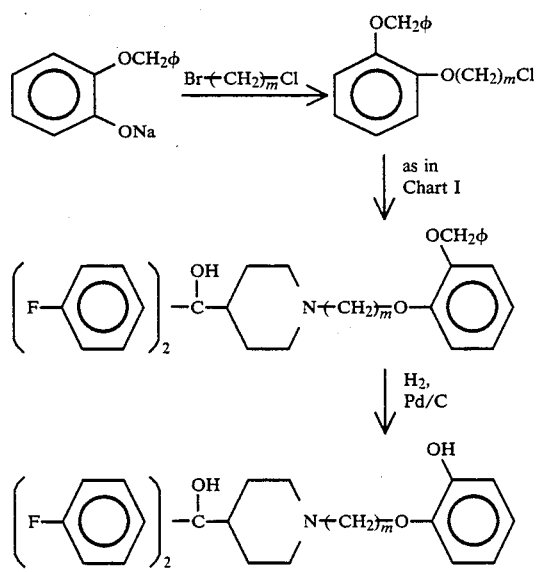

φ = phenyl.

The preparation of chemical intermediates is further illustrated in the following Preparations 1 to 158. Examples 1 to 188 illustrate the synthesis methods for preparing compounds of Formula I. The scope of the invention is not limited by the descriptive methods and procedures of the preparations and examples, however.

PREPARATION 1

4-Diphenylmethylenepiperidine

A solution of 7.0 g of 1-acetyl-4-diphenylhydroxymethylpiperidine in 30 ml of absolute alcohol and 76 ml of concentrated hydrochloric acid was heated at reflux for seven hours, cooled and made basic with 50% sodium hydroxide. The oil which separated was extracted with benzene and the combined extracts washed with water. After drying over magnesium sulfate the solvent was evaporated at reduced pressure. The residual oil which crystallized on cooling was recrystallized twice from petroleum ether to give 4.0 g (73.0%) of white crystals, m.p. 85°–86° C.

Analysis: Calculated for $C_{18}H_{19}N$: C,86.70; H, 7.68; N, 5.62. Found: C,86.70;H, 7.83;N, 5.73.

PREPARATION 2

[α,α-Bis(p-fluorophenyl)]-4-piperidinemethanol hydrochloride hydrate [1:1:0.5]

This compound was prepared by the method described in Preparation 1 of U.S. Pat. No. 4,032,642, m.p. 243°–243.5° C. from the Grignard reagent formed with p-flurobromobenzene and 1-acetyl-4-(p-flurobenzoyl)-piperidine followed by hydrolysis and conversion to the salt.

PREPARATION 3

1-(Phenylmethyl)-4-piperidinecarboxylic acid ethyl ester hydrochloride [1:1]

1-(Phenylmethyl)-4-piperidinecarboxylic acid ethyl ester hydrochloride [1:1]

A mixture of 100 g (0.637 mole) of ethyl isonipecotate, 80.64 g (0.64 mole) of benzyl chloride and 67.84 g (0.64 mole) of sodium carbonate in 1 liter of absolute ethanol was heated at reflux for 8 hours and then was stirred at room temperature for 10 hours. The solvent was removed in vacuo, and the residue was partitioned between methylene chloride and dilute sodium hydroxide. The methylene chloride phase was dried over magnesium sulfate and the solvent was removed in vacuo to give the free base of the title compound as a liquid. The free base was converted to the hydrochloric acid salt, and the salt was recrystallized from ethanol-ether to give 89.33 g (49.7%) of white, crystalline solid, m.p. 154°–155° C.

Analysis: Calculated for $C_{15}H_{22}ClNO_2$: C,63.48;H,7.81;N,4.94. Found: C,63.07;H,7.82;N,4.91.

PREPARATION 4

α,α-Bis-(4-fluorophenyl)-1-(phenylmethyl)-4-piperidinemethanol

To a 6.08 g (0.25 mole) of magnesium turnings and an iodine crystal in 600 ml of dry tetrahydrofuran and under an atmosphere of nitrogen was added, dropwise, a solution of p-bromofluorobenzene in 125 ml of tetrahydrofuran. The temperature of the reaction was kept below 10° C. by cooling in an ice-methanol bath. The mixture was stirred at room temperature for 1.5 hours. A solution of 24.7 g (0.10 mole) of 1-(phenylmethyl)-4-piperidinecarboxylic acid ethyl ester in tetrahydrofuran was added, and the mixture was stirred at room temperature for 17 hours. The reaction was poured into an icy, aqueous solution of ammonium chloride, and the resulting solution was extracted with methylene chloride. The methylene chloride solution was extracted with dilute sodium hydroxide and was dried over magnesium sulfate. The solvent was removed in vacuo to give an oil. This was crystallized from ether-hexane to give 19.87 g (51%) of the title compound, m.p. 113°–15° C.

Analysis: Calculated for $C_{25}H_{25}F_2NO$: C, 76.31;H, 6.40;N,3.56. Found: C,76.24;H,6.38;N,3.50.

PREPARATION 5

[α,α-Bis(p-fluorophenyl)]-4-piperidinemethanol

A solution of 31.2 g (0.079 mole) of α,α-bis-(4-fluorophenyl)-1-(phenylmethyl)4-piperidinemethanol in 400 ml of absolute ethanol was hydrogenated at 50 psi and 70° C. over 5% palladium on carbon over the weekend. The mixture was filtered and the filtrate was concentrated under reduced pressure to give a gum as residue. Methylene chloride was added to the residue and the gum crystallized. The mixture was diluted with petroleum ether and the solid was collected by filtration, washed with petroleum ether, and dried to yield 22 g (92%) of white solid which was recrystallized from 2-propyl ether/2-propanol, m.p. 159.5°–160.5° C.

Analysis: Calculated for $C_{18}H_{19}F_2NO$: C,71.27;H, 6.31;N,4.62. Found: C,70.93;H,6.71N,4.38.

PREPARATION 6

1-(phenylsulfonyl)-4-piperidinecarboxylic acid, ethyl ester.

To a solution of 10.1 g (0.0642 mole) of ethyl isonipecotate in 300 ml of pyridine and cooled in an ice bath was added 13.2 g (0.075 mole) of benzene sulfonyl chloride. The mixture was stirred for 2 hours at room temperature, and the solvent was removed in vacuo. The residue was partitioned between methylene chloride and dilute sodium hydroxide. The methylene chloride solution was dried over magnesium sulfate, and the solvent was removed in vacuo to give a solid. This was recrystllized from ethanol-ether to give 4.59 g (24.1%) of crystalline solid; m.p. 85°–86° C.

Analysis: Calculated for $C_{14}H_{19}NO_4S$: C,56.55;H,6.44N,4.71. Found: C,56.53;H,6.55;N,4.67.

In another preparation, 100 g (0.634 mole) of ethyl nipecotate and 130.4 g (0.74 mole) of benzene sulfonyl chloride were reacted by the above procedure for 4.5 hr to give the title product in 78.1% yield.

PREPARATION 7

α,α-Bis(4-fluorophenyl)-1-(phenylsulfonyl)-4-piperidinemethanol

To a suspension of 33.78 g (1.39 mole) of magnesium trimmings in 1 liter of tetrahydrofuran (dried over molecular sieves 5A) under an atmosphere of nitrogen and cooled in an ice bath was added dropwise a solution of 243.25 g (1.39 mole) of p-bromoflurobenzene in 150 of tetrahydrofuran. The mixture was stirred for 2 hr after the addition was completed. To this mixture was added 103 g (0.346 mole) of 1-(phenylsulfonyl)-4-piperidinecarboxylic acid ethyl ester as a solid, and the solution was stirred at ambient temperature for 5 hr. The reaction mixture was poured into an icy aqueous solution of ammonium chloride. The phases was separated, and the solvent was removed in vacuo from the organic phase. The residue was partitioned between methylene chloride and dilute sodium hydroxide. The methylene chloride solution was dried over magnesium sulfate and was reduced in vacuo to ≃1 liter volume. The title compound was obtained by adding hexane and cooling, recrystallizing and the precipitate from ethyl acetate and hexane and drying the solid under high vacuum at 130° C. for 45 min at which time the product had partially melted, m.p. 142.5°–144° C.

Analysis: Calculated for $C_{24}H_{23}F_2NO_3S$: C,65.00;H,5.23:N,3.16. Found: C,65.21;H,5.30;N,3.10.

PREPARATION 8

4-[Bis(4-fluorophenyl)methylene]-1-(phenylsulfonyl)-piperidine

A solution of 5.23 g (0.0118 mole) of α,α-bis(4-fluorophenyl)-1-(phenylsulfonyl)-4-piperidinemethanol in 100 ml of acetic acid and 20 ml of 2M sulfuric acid was heated at reflux for 2.5 hours and then poured over ice. The mixture was made basic with 50% sodium hydroxide and the basic mixture was extracted with methylene chloride. The methylene chloride solution was dried (anhydrous sodium sulfate), and the solvent was removed in vacuo. The residue was recrystallized from ether-hexane to give 3.23 g (64.4%) of white, crystalline, solid, m.p. 90°–92.5° C.

Analysis: Calculated for $C_{24}H_{21}F_2NO_2S$: C,67.75;H,4.98;N,3.29. Found: C,67.73;H,500;N,3.21.

PREPARATION 9

4-[Bis(4-fluorophenyl)methylene]piperidine hydrobromide [1:1]

A mixture of 164 g (0.342 mole) of α,α-bis(4-fluorophenyl)-1-(phenylsulfonyl)-4-piperidinemethanol and 80 g (80 g) of phenol in 700 ml of 48% hydrobromic acid was heated at reflux for 7 hr and then was stirred at room temperature for 9 hr. The hydrobromic acid solution was decanted from a gum in the bottom of the reaction flask. The gum was triturated with ~1 liter of ether, and a tan solid formed. The solid was washed with several portions of ether and was dried under high vacuum to give 9.13 g (73%) of slightly impure title product, m.p. 211°–215° C. A small sample of this solid was recrystallized from methanol to give an analytically pure sample as a crystalline solid; m.p. 216°–218° C.

Analysis: Calculated for $C_{18}H_{18}BrF_2N$: C,59.03;H,4.95;N,3.82. Found: C,58.96;H,4.98;N,3.76.

PREPARATION 10

4-[Bis(4-fluorophenyl)methyl]piperdine fumarate hydrate [1:0.5:0.5]

A mixture of 30.6 g (0.99 mole) of phosphorus and 15.1 g (0.059 mole) of iodine in 90 ml of glacial acetic acid was stirred for 20 min at room temperature. A mixture of 6 ml of water, 70 ml of methanesulfonic acid, 56.19 g (0.197 mole) of 4-[bis(4-fluorophenyl)methylene]piperidine and 110 ml of glacial acetic acid was added, and the mixture was heated at reflux for 7 hr. The solvent was removed in vacuo, and the resulting viscous liquid was poured over ice. The icy mixture was made basic with 50% sodium hydroxide, and the basic suspension was extracted with methylene chloride. The methylene chloride solution was extracted with an aqueous solution of sodium thiosulfate and was dried over anhydrous sodium sulfate, and the solution was filtered through Celite ®. The solvent was removed in vacuo to give a gum. The gum was dissolved in 400 ml of hot methanol, and 4.25 g of an unknown tan solid was collected from the warm solution. Fumaric acid (22 g, 0.190 mole) was added to the methanolic solution followed by the addition of ether. A white precipitate was collected to give 22.55 g (32.3%) of crystalline solid; m.p. 208°–209° C.

Analysis: Calculated for $C_{20}H_{21}F_2NO_2.0.5H_2O$: C,67.78;H,6.26;N,3.95. Found: C,67.78;H,6.26;N,3.95.

PREPARATION 11

4-[α-(p-Fluorophenyl)-α-phenylmethyl]piperidine hydrochloride [1:1]

This compound was prepared as described in U.S. Pat. No. 4,032,642 by hydrogenation of α-(p-flurophenyl)benzylidinepiperidine over palladium charcoal catalyst, m.p. 81°–82° C.

Analysis: Calculated for $C_{18}H_{21}ClFN$: C,70.69;H,6.92;N,4.58. Found: C,70.69;H,6.93;N,4.52.

PREPARATION 12

1-[4-(3-Chloropropoxy)-3-methoxyphenyl]ethanone

To a mixture of 15.15 kg (96.26 mole) of 1-bromo-3-chloropropane and 25 liter of water heated to 86° C. was added a solution of 8 kg (48.13 mole) of acetovanillone in 3.93 kg (48.6 mole) of 50% aqueous sodium hydroxide and 89 liter of water over a 2.5 hr period. The mixture was heated at 80°–85° C. for 2.5 hr after addition was complete. The mixture was cooled and extracted twice with 49 kg portions of toluene. The combined extracts were washed once with 1.9 kg of 50% sodium hydroxide diluted to 5 gal and once with 5 gal of water. The toluene layer was dried over 3 lb of anhydrous sodium sulfate and concentrated under reduced pressure. The residue was heated to reflux in 15 gal of isopropylether, filtered, and the filtrate cooled. The crystallized title compound obtained by filtration together with additional compound obtained by concentrating the filtrate to 25% of its original volume amounted to 4.2 kg (36%). Acetovanillone recovered was 3.4 kg. The product was recrystallized twice from cyclohexane and twice from ligroin, m.p. 57.8°–58.5° C.

analysis: Calculated for $C_{12}H_{15}ClO_3$: C,59.39;H,6.23. Found: C,59.07;H,6.22.

PREPARATION 13

1-(3-Phenoxypropyl)-4-piperidinecarboxylic acid ethyl ester oxalate [1:1]

A mixture of ethyl isonipecotate (35.5 g 0.226 mole) 3-phenoxy-1-bromopropane (51.6 g, 0.24 mole) and sodium carbonate (25.4 g, 0.24 mole) in 500 ml of absolute ethanol was heated at reflux for 16 hr. The solvent was removed in vacuo, and the residue was partitioned between methylene chloride and dilute sodium hydroxide. The solution was dried over anhydrous sodium sulfate and the solvent was removed in vacuo to give a liquid. The liquid was dissolved in absolute ethanol, and a solution of oxalic acid (~0.23 mole) in absolute ethanol was added. The product 73.43 g (87.7%) precipitated as a white, crystalline solid, m.p. 180°–181° C.

Analysis: Calculated for $C_{19}H_{27}NO_7$; c,59.83;H,7.14N,3.67. Found: C,59.76;H,7.17;N,3.64.

PREPARATION 14

4-[Bis(4-fluorophenyl)methylene]-1-(phenylmethyl)-piperidine maleate [1:1]

A mixture of α-α-bis(4-fluorophenyl)-1-(phenylmethyl)-4-piperidinemethanol (5.09 g, 0.013 mole) in 200 ml of 2M sulfuric acid was heated at reflux for 2 hr. The solvent was removed in vacuo, and the residue was partitioned between methylene chloride and dilute sodium hydroxide. The methylene chloride solution was dried over magnesium sulfate and the solvent was removed in vacuo to give the free base of the title compound as a solid. The free base was dissolved in methanol-ethylether and maleic acid (excess) was added. The product 5.24 g (82.1%) precipitated as a white, crystalline solid, m.p. 180°–181.5° C.

Analysis: Calculated for $C_{29}H_{27}F_2NO_4$: C,70.86;H,5.54;N,2.85. Found: C,70.80;H,5.45;N,2.79.

PREPARATION 15

α-αBis(4-fluorophenyl)-4-pyridinemethanol

The Grignard reagent was prepared from 4-bromofluorobenzene (66.6 g, 0.381 mole) and magnesium (9.13 g, 0.381 mole) in tetrahydrofuran (ice bath). The Grignard reagent was stirred at room temperature for 1.5 hr and transferred (under nitrogen) to an addition funnel. This solution was added dropwise to a tetrahydrofuran solution of ethyl isonicotinate (25.0 g, 0.165 mole) (ice bath cooling). The reaction mixture was stirred 3 hr at room temperature and poured onto ice containing ammonium chloride (28 g, 0.5 mole). The mixture was allowed to stand overnight. The reaction mixture was diluted to 3 liter with water and extracted with chloroform. The chloroform layer was back extracted with dilute sodium hydroxide. Removal of chloroform gave a gummy brown solid. The brown solid was triturated with methanol-ethyl ether (10–120 v/v) and placed in the refrigerator freezer. Solid was collected by filtration and dried overnight in vacuo at 80° C. to give 11.86 g (24%) of white, crystalline produce, m.p. 185°–189° C.

Analysis: Calculated for $C_{18}H_{13}F_2NO$: C,72.72;H,4.41;N,4.71 Found: C,72.76;H,4.39;N4.67.

PREPARATION 16

4-[Bis(4-Fluorophenyl)methyl]--1-(phenylmethyl)piperidine, fumarate [1:1]

A mixture of 4.3 g (0.139 mole) of phosphorus, 44 g (0.196 mole) of a 75% aqueous solution of hydrogen iodide and 4.15 g (0.0106 mole) 4-[bis(4-fluorophenyl)-methylene]-1-(phenylmethyl)piperidine in 60 ml of glacial acetic acid was heated at reflux for 1 hr. The mixture was poured over ice and was made with 50% sodium hydroxide. The aqueous mixture was extracted with methylene chloride. The methylene chloride solution was extracted with an aqueous solution of sodium sulfite and was dried over magnesium sulfate. The solvent was removed in vacuo to give 8.89 g (89%) of the free base of the title compound. The free base was converted to the fumarate salt, and the salt was recrystallized from methanol-ether to give 3.62 g (69.3%) white solid; m.p. 201°–202° C.

Analysis: Calculated for $C_{29}H_{29}F_2NO_4$: C,70.57;H,5.92;N,2.84. Found: C,70.69;H,5.95;N,2.81.

PREPARATION 17

4-(2-Chloroethoxy)benzoic acid ethyl ester

A mixture of 71.7 g (0.5 mole) of 1-bromo-2-chloroethane, 83.1 g (0.5 mole) of ethyl p-hydroxybenzoate and 69.1 g (0.5 mole) of potassium carbonate in 200 ml of acetone was heated at reflux for 40 hr. The solids were removed by filtration and the filtrate was evaporated under reduced pressure to leave a semi-solid residue. The residue was triturated with 200 ml of 5% sodium hydroxide solution and filtered.[1] The filter cake was washed with water (100 ml) and dried to give 42.4 g (80%)[2] of a solid. A sample was recrystallized from benzene-petroleum ether (30°–60° C.) to give white solid, m.p. 74°–76° C.

[1] The filtrate pH was adjusted to 2 with concentrated hydrochloric acid. The resulting solid was collected by filtration, washed with water (100 ml) and dried to give 44.4 g of ethyl p-hydroxybenzoate.
[2] The yield is based on unrecovered starting material.

Analysis: Calculated for $C_{11}H_{13}ClO_3$: C,57.78;H,5.73. Found: C,57.87;H,5.82

PREPARATION 18

1-[4-(2-Chloroethoxy)-3-methoxyphenyl]ethanone

To a solution of 12.7 g (0.55 mole) of sodium metal in 750 ml of absolute ethanol was added 83.1 g (0.5 mole) of acetovanillone to give a slurry. This slurry was then added over a 3-hr period to a solution of 107.6 g (0.75 mole) of 1-bromo-2-chloroethane in 500 ml of absolute ethanol at reflux. An additional 250 ml of ethanol was used to wash the slurry into the reaction mixture. The mixture was heated at reflux overnight and then concentrated under reduced pressure to give a solid as residue. The solid was partitioned between 1 liter of benzene and 1 liter of water. The aqueous layer was extracted with 500 ml of benzene and the combined organic layers were washed successively with three 200 ml portions of a 5% sodium hydroxide solution, once with water and once with brine. The benzene solution was dried over anhydrous sodium sulfate and concentrated under reduced pressure to give an oil which gradually crystallized. The solid was triturated with petroleum ether, collected by filtration and recrystallized from 2-propanol to yield 48.5 g (42%) of off-white solid. An analytical sample was prepared from isopropyl ether, m.p. 69°–71° C.

Analysis: Calculated for $C_{11}H_{13}ClO_3$: C,57.78;H,5.73. Found: C,57.55;H,5.74.

PREPARATION 19

1-[4-(4-Bromobutoxy)-3-methoxyphenyl]ethanone to a warm solution of 12.7 g (0.55 mole) of sodium metal in 500 ml of absolute ethanol was added a slurry of 83.1 g (0.5 mole) of acetovanillone in 250 ml of absolute ethanol. All solids dissolved and then a solid precipitated. The mixture was stirred at ambient temperature for 1 hr and then added over a 3-hr period to a solution at reflux of 177 g (0.82 mole) of 1,4-dibromobutane in 500 ml of absolute ethanol. After addition was complete, the mixture was heated at reflux overnight. The mixture was concentrated under reduced pressure and the residue was partitioned between 1.5 liter of benzene and 1 liter of water. The mixture was filtered to remove undesirable insoluble material. The filtrate layers were separated and the organic layer was washed with four 300 ml portions of a 5% sodium hydroxide solution once with water and once with brine, dried over anhydrous sodium sulfate and concentrated under reduced pressure to give 138 g of gummy solid as residue. This solid was purified by column chromatography on 1 kg of silica gel, eluting with 2% ethylacetate in benzene to yield 69.6 g (46%) of title compound as an off-white solid. The solid was recrystallized from isopropyl ether, m.p. 52°–54° C.

Analysis: Calculated for $C_{13}H_{17}BrO_3$: C,51.84;H,5.69. Found: C,52.03;H,5.76.

PREPARATION 20

4-Diphenylmethyl)pyridine

A mixture of 99 (0.379 mole) of diphenyl-4-pyridylmethanol, 50 ml of conc. hydrochloric acid, 200 ml of 57% hydroiodic acid and 200 ml of glacial acetic acid was heated at reflux for 4.5 hr and then was stirred at room temperature for 12 hr. The reaction mixture was poured over ice and was made basic with 50% hydroxide. An aqueous solution of sodium thiosulfate was added, and the mixture was extracted with methylene chloride. The methylene chloride solution was dried over magnesium sulfate and the solvent was removed in vacuo. The residue was recrystallized from a mixture of methylene chloride-ether-hexane to give two crops of crystalline solids: Crop I,40.87 g (44.0%),m.p. 124°–126° C.; Crop II, 25.38 g (27.3%), m.p. 123°–125° C. Analysis of the mixture of the Crops I and II was as follows:

Analysis: Calculated for $C_{18}H_{15}N$: C,88.13;H,6.16;N,5.71. Found: C,87.67;H,6.01;N,5.56.

1-(3-Chloropropoxy)-4-methoxybenzene

A solution of sodium hydroxide 20.0 (0.5 mole) in 300 ml of water and p-methoxyphenol, 62.1 g (0.5 mole) in 300 ml of dioxane was stirred for 1 hour at room temperature. 1-Chloro-3-bromopropane (472.35 g, 3.0 mole) in 100 ml of dioxane was added, and the reaction mixture was stirred overnight at 80° C. The lower layer was separated and the aqueous layer extracted with hexane. The lower layer and hexane layer were combined, dried, and solvent was removed in vacuo. The residue was dissolved in chloroform and extracted with 5% sodium hydroxide; removal of chloroform by evaporation gave a yellow oil. A 10-g sample of the oil was subjected to column chromatography on silica gel with an elution series composed of hexane-methylene chloride-methanol. This furnished 9.64 g (79.3% based on the aliquot taken) of pure clear oil.

Analysis: Calculated for $C_{10}H_{13}ClO_2$: C,59.86;H,6.53. Found: C,59.39;H,6.56.

PREPARATION 22

1-[4-(3-Chloropropoxy)phenyl]ethanone

The sodium salt of p-hydroxyacetophenone was prepared in 200 ml of dioxane-400 ml of water from p-hydroxyacetophenone 68.08 g (0.5 mole) and sodium hydroxide 20.0 g, (0.5 mole). The reaction mixture was stirred ¾ hr at room temperature. Next, chlorobromopropane, 472.35 g (3.0 mole) was added along with 200 ml of dioxane and the mixture was heated at 80°–90° C. overnight with stirring. The mixture was diluted to 4 liters with water; the aqueous phase was extracted with hexane and chloroform. These were combined and back extracted with 5% sodium hydroxide. The solvent was removed in vacuo with heating. A 10-g sample of the oil was subject to column chromatography on silica gel using hexane-methylene chloride-methanol. Fractions with similar TLCs were combined and solvent removed. The oil from the column did not analyze, therefore a short-path bulb-bulb distillation was carried out. This produced 4.38 g (37.9%) of clear oil.

Analysis: Calculated for $C_{11}H_{13}ClO_2$: C,62.12;H,6.16. Found: C,61.70;H,6.17.

| $^1$H NMR(CDCL$_3$) Analysis: | | | |
|---|---|---|---|
| δ8.1 | doublet | aromatic portons | 2H |
| δ6.8–7.0 | doublet | aromatic portons | 2H |
| δ4.1–4.3 | triplet | CH$_2$ | 2H |
| δ3.6–3.8 | triplet | —CH$_2$— | 2H |
| δ2.5 | singlet | —C(=O)—CH$_3$ or COCH$_3$ | 2H |
| δ2–2.4 | triplet | —CH$_2$— | 2H |

PREPARATION 23

4-(Diphenylmethyl)piperidine hydrochloride [1:1]

A mixture of 62.69 g (0.256 mole) of diphenyl-4-pyridylmethane and 6.4 g of 10% palladium on carbon (0.0060 mole) in 300 ml of glacial acetic acid and under an atmosphere of hydrogen (44 psi) was shaken on a Parr apparatus at 865° for 4 days. The reaction mixture was filtered, and the solvent was removed in vacuo from the filtrate. The residue was partitioned between methylene chloride and dilute sodium hydroxide. The methylene chloride solution was dried over magnesium sulfate, and the solvent was removed in vacuo to give a solid. This was dissolved in a mixture of methanol-acetonitrile, and excess ethereal hydrogen chloride was added. A precipitate was collected to give 59.13 g (80.3%) of slightly impure title compound as a white, crystalline solid, m.p. 273°–274° C. Part of this was recrystallized from methanol-ether to give an analytically pure sample, m.p. 275.5°–277° C.

Analysis: Calculated for $C_{18}H_{22}ClN$: C, 75.11; H, 7.70; N, 4.87. Found: C, 75.03; H, 7.73; N, 4.93.

PREPARATION 24

α-(4-Fluorophenyl)-α-phenyl-4-pyridinemethanol

To a suspension of 18.5 g (0.761 mole) of magnesium turnings and several crystals of iodine in 800 ml of anhydrous ether, cooled in an ice bath and under an atmosphere of argon was slowly added a solution of p-bromofluorobenzene in 200 ml of ether. The solution was stirred for 2 hr at 25° C. and 97.02 g (0.530 mole) of 4-benzoylpyridine was added as a solid. An additional 1 liter of anhydrous ether was added, and the solution was stirred at 25° C. for 3 hr. The reaction mixture was poured into an icy, aqueous solution of ammonium chloride. The mixture stood in the hood overnight and a white solid was collected. The solid was dissolved in a mixture of methanol-methylene chloride. The solution was filtered and the solvent was removed in vacuo. The residue was crystallized from chloroform-hexane to give 66.68 g (45%) of title compound as a white, crystalline solid, m.p. 189°–192° C. Part of this was recrystallized from methylene chloride-acetonitrile-hexane, m.p. 190°–192° C.

Analysis: Calculated for $C_{18}H_{14}FNO$: C, 77.40; H, 5.05; N, 5.02. Found: C, 77.24; H, 5.03; N, 4.90.

PREPARATION 25

α,α-Bis(4-chlorophenyl)-1-(phenylsulfonyl)-4-piperidinemethanol

Following the procedure of Preparation 7, but substituting p-bromochlorobenzene for p-bromofluorobenzene, the title compound was prepared.

PREPARATION 26

4-[Bis(4-chlorophenyl)methylene]piperidine hydrobromide hydrate [1:1:1]

A mixture of 69.33 g (0.146 mole) of α,α-bis(4-chlorophenyl)-1-(phenylsulfonyl)-4-piperidinemethanol and 26 g (0.277 mole) of phenol in 400 ml of 48% hydrobromic acid was heated at reflux for 6 hr and then was stirred at room temperature for 10 hr. The reaction solution was decanted from a gum which had formed in the bottom of the reaction flask. The gum was washed with several portions of water and then was crystallized from ether to give a solid. The solid was recrystallized from a mixture of methanol-diethyl ether to give 26.52 g (43.6%) of white, crystalline solid, m.p. 106°–109° C.

Analysis: Calculated for $C_{18}H_{20}BrCl_2N$: C, 51.83; H, 4.83; N, 3.36. Found: C, 52.13; H, 4.62; N, 3.38.

PREPARATION 27

1-Chloro-4-(3-chloropropoxy)benzene

A mixture of 77.2 g (0.60 mole) of p-chlorophenol, 189 g (1.2 mole) of 1-bromo-3-chloropropane, 249 g (1.8 mole) of anhydrous potassium carbonate, and 600 ml of acetone was stirred vigorously and heated to reflux for 16 hr under a nitrogen atmosphere. The potassium carbonate was removed by suction filtration, and the acetone and excess bromochloropropane were removed by heating under reduced pressure. The residue was dissolved in petroleum ether, and the resulting solution was cooled in an ice-isopropyl alcohol bath to produce a white solid. The solid was collected by filtration and washed with cold petroleum ether. The filtrate was concentrated and cooled to yield two more crops of white crystals. The combined solids were dried under vacuum at ambient temperature to yield 107 g (87%) of white, flaky solid, m.p. 35°–36° C.

Analysis: Calculated for $C_9H_{10}Cl_2O$: C, 52.71; H, 4.92. Found: C, 52.99; H, 4.87.

PREPARATION 28

4-(3-Chloropropoxy)benzoic acid ethyl ester

Ethyl, 4-hydroxybenzoate 83.1 g (0.50 mole), 107 ml (1.0 mole) of 1-bromo-3-chloropropane, and potassium carbonate (1.5 mole, 207.3 g) were mechanically stirred in 600 ml of refluxing acetone under nitrogen overnight. The potassium carbonate was removed by filtration, and the filtrate was evaporated under reduced pressure to give 122 g of a liquid. This liquid was dissolved in 250 ml of petroleum ether and with stirring and cooling in an ice/2-propanol bath. A white precipitate formed and was collected by filtration and washed with cold petroleum ether to yield 108 g of a solid. An additional 6 g of the product was obtained from the mother liquor. A small sample of the solid was dissolved in petroleum ether at room temperature. The solution was stirred and cooled in an ice bath. White crystals were collected by filtration, washed with cold petroleum ether and dried under vacuum at room temperature, m.p. 24°–25° C.

Analysis: Calculated for $C_{12}H_{15}ClO_3$: C, 59.39; H, 6.23. Found: C, 59.69; H, 6.30.

PREPARATION 29

1-(3-Chloropropoxy)-4-nitrobenzene

A mixture of 7.0 g (0.05 mole) of 4-nitrophenol, 15.7 g (0.1 mole) of 1-bromo-3-chloropropane and 20.7 g (0.15 mole) of anhydrous potassium carbonate in 350 ml of acetone was heated at reflux for 17 hr. The mixture was cooled, filtered, and the filtrate was concentrated to give an oil which crystallized. The solid was collected by filtration, washed with petroleum ether, and dried to yield 10.1 g (94%) of the title compound. An analytical sample was prepared from ethyl ether-petroleum ether, m.p. 37°–39° C.

Analysis: Calculated for $C_9H_{10}ClNO_3$: C, 50.13; H, 4.67; N, 6.50. Found: C, 49.95; H, 4.71; N, 6.51.

PREPARATION 30

4-[Bis(4-fluorophenyl)methyl]1-1piperidinepropanol oxalate hydrate [1:1:1]

A mixture of 10.67 g (0.0372 mole) of 4-[bis(4-fluorophenyl)methyl]-piperidine, 5.42 g (0.039 mole) of 3-bromo-1-propanol and 8 g (0.095 mole) of sodium bicarbonate in 400 ml of 1-butanol was heated at reflux for 21 hr. The solvent was removed in vacuo, and the residue was partitioned between methylene chloride and dilute sodium hydroxide. The methylene chloride solution was dried over magnesium sulfate and the solvent was removed in vaco to give 8.88 g (67.3%) of oil, the free base of the title compound. A small sample of this oil was converted to the oxalate salt, and the salt was recrystallized from methanol-ether to give a white solid, m.p. 89°–94° C. Overall yield was calculated to be 75.1%.

Analysis: Calculated for $C_{23}H_{29}F_2NO_6$: C, 60.92; H, 6.45; N, 3.09. Found: C, 61.49; H, 6.15; N, 3.03.

PREPARATION 31

4-(3-Chloropropoxy)-3-methoxybenzoic acid methyl ester

A mixture of 100 g (0.549 mole) of methylvanillate, 172.8 g (1.1 mole) of 1-bromo-3-chloropropane and 228 g (1.65 mole) of anhydrous potassium carbonate in 1 liter of acetone was heated at reflux for 20 hr. The mixture was cooled, filtered, and the filtrate concentrated to give a white solid as residue. The solid was triturated with petroleum ether, collected by filtration, and dried to yield 137.8 g (97%) of white powder which was recrystallized from isopropyl alcohol, m.p. 104°–105° C.

Analysis: Calculated for $C_{12}H_{15}ClO_4$: C, 55.71; H, 5.84. Found: C, 55.87; H, 5.94.

PREPARATION 32

4-[Bis(4-methoxyphenyl)methyl]pyridine

Anisole, 108.13 g (1.0 mole) was cooled in an ice bath. Concentrated sulfuric acid, 115.3 ml (2.0 mole) was added while stirring the mixture in an ice bath. The temperature rose to 55° C. The reaction was then cooled in the ice bath. To this solution was added 4-pyridine carboxaldehyde, 53.5 g (0.5 mole). The temperature rose to 95° C. and further cooling and stirring brought the temperature down to 20° C. The reaction mixture was heated at 70° C. for 3½ hr. The red gel was made alkaline with 50% sodium hydroxide-ice mix. The alkaline phase was extracted with toluene and the toluene extracted with a saturated sodium chloride solution. The product crystallized from the toluene solution while standing at room temperature. The white solid can be recrystallized from hot hexane-isopropyl alcohol.

A small 2.2 g sample of the product was recrystallized from methylene chloride-hexanes (1:9 v/v) and dried overnight at 80° C. in vacuo. This furnished 1.08 g (48.6% yield based on the aliquot taken) of white crystalline product; m.p. 111.5°–113.5° C.

Analysis: Calculated for $C_{20}H_{19}NO_2$: C, 78.66; N, 6.27; N, 4.59. Found: C, 78.14; H, 6.24; N, 4.54.

PREPARATION 33

4-[Bis(4-methoxyphenyl)methyl]piperidine hydrochloride hydrate [1:1:1]

The precursor pyridine derivative 4-[bis-4-methoxyphenyl)methyl]pyridine was prepared from the reaction of anisole and 4-pyridine carboxaldehyde in the presence of sulfuric acid.

To prepare the title compound, a solution of 4-[bis-(4-methoxyphenyl)methyl]pyridine (70.8 g, 0.232 mole) in 350 ml of acetic acid was hydrogenated with 5% palladium on carbon (7.08 g) for five hours with heat. The hydrogenation was continued overnight at room temperature. The reaction mixture was filtered and rinsed with methanol. The filtrate was stripped of solvent via a rotary evaporator and the residue was partitioned between 5% sodium hydroxide and toluene. The aqueous layer was back extracted with toluene. The organic layer was dried over anhydrous sodium sulfate and filtered. Removal of solvent by means of a rotary evaporator gave 64 g (88.6%) of white solid, the free base. The free base was then converted to the hydrochloride salt by dissolving it in methanol and treating with etheral hydrogen chloride. The white solid was collected by filtration and dried overnight at 80° C. in vacuo in the amount of 2.08 g (69.3%) m.p. 132°–135° C.

Analysis: Calculated for $C_{20}H_{28}ClNO_3$: C, 65.65; H, 7.71; N, 3.383. Found: C, 65.63; H, 7.53; N, 3.90.

PREPARATION 34

4-[Bis(4-methylphenyl)methyl]piperidine hydrochloride [1:1]

The free base of the title compound was prepared by hydrogenation of 4-[(bis-4-methylphenyl)methyl]pyridine in acetic acid using palladium on carbon as catalyst and converted to the hyrochloride salt in methanol-diethyl ether. The sale was recrystallized from methanol-ethyl ether and isopropanol-ethyl ether and dried overnight in vacuo at 80° C. White solid amounting to 46% yield, m.p. 232° C. was obtained.

Analysis: Calculated for $C_{20}H_{26}ClN$: C, 76.05; H, 8.30; N, 4.43. Found: ;C, 75.51; H, 8.33; N, 4.33.

PREPARATION 35

N-[4-(3-Chloropropoxy)phenyl]acetamide

A mixture of 4-acetamidophenol, 182.2 g (1.2 mole), bromochloropropane, 157.4 g (1.0 mole), and potassium carbonate, 145.0 g (1.05 mole) was heated at reflux overnight in 700 ml of acetone. The acetone solution was refrigerated overnight and white crystals formed. This white solid was filtered and washed with acetone. The filtrate was stripped to dryness and the residue was dissolved in chloroform and extracted with 5% sodium hydroxide. Removal of chloroform gave an oil. The white solid was also dissolved in chloroform and extracted with 5% sodium hydroxide. Removal of chloroform gave a white solid. The white solid and oil were combined and placed in acetone in the refrigerator; white crystals were obtained. The white crystals were recrystallized twice from acetone. A 5 g-sample of the white crystals was recrystallized from acetone. This furnished 1.76 g (after drying in vacuo overnight at 80° C. (23%) of white, crystalline product; m.p. 125°–127° C.

Analysis: Calculated for $C_{11}H_{14}ClNO_2$: C, 58.03; H, 6.20; N, 6.15. Found: C, 58.21; H, 6.28; N, 6.15.

PREPARATION 36

1-(3-Chloropropoxy)-3,5-dimethoxybenzene

A mixture of 3,5-dimethoxyphenol 100.0 g (0.6486 mole), chlorobromopropane 148.0 g (0.96 mole) and potassium carbonate 89.6 g (0.96 mole) was heated overnight at gentle reflux in 600 ml of acetone. The reaction mixture was cooled at room temperature, filtered, and stripped to dryness via a rotary evaporator. The resulting oil was dissolved in chloroform and the solution extracted with 5% aqueous sodium hydroxide; removal of chloroform gave a dark brown oil. A 5-g sample of the oil was pumped in vacuo overnight at 80° C. This produced 3.23 g (53.2% yield based on the aliquot taken) of dark brown oil. $H^1(CDCl_3)$: δ 2–2.14 (quintuplet, center methylene protons, 2H), 3.6–4.2 (m, aliphatic protons, 4H), 3.8 (s, OCH$_3$, 6H), 6.1 (s,aromatic protons, 3H).

Analysis: Calculated for $C_{11}H_{15}ClO_3$: C, 57.27; H, 6.56. Found: C, 54.96; H, 6.49.

PREPARATION 37

4-(3-Chloropropoxy)benzonitrile

A mixture of 4-cyanophenol, 125.0 g (1.05 mole), bromochloropropane, 189.0 g (1.2 mole) and potassium carbonate, 145.0 g (1.05 mole) was heated overnight at reflux in 750 ml of acetone. The reaction mixture was filtered and stripped to dryness. The resulting residue was dissolved in chloroform and extracted with 5% sodium hydroxide. Removal of chloroform gave an oil which crystallized to a white solid. A 5-g sample was recrystallized from isopropyl ether. This furnished 1.22 g (24.4%) of white solid, m.p. 40°–44° C. which contained a dimer impurity.

Analysis: Calculated for $C_{10}H_{20}ClNO$: C, 61.39; H, 5.15; N, 7.16. Found: C, 61.57; H, 5.14; N, 7.20.

PREPARATION 38

1-[4-(3-Chloropropoxy)-3-methylphenyl]ethanone

A mixture of 25 g (0.166 mole) of 4- hydroxy-3-methylacetophenone, 45.8 g (0.33 mole) of 1-bromo-3-chloropropane and 69.1 g (0.5 mole) of anhydrous potassium carbonate in 500 ml of acetone was heated at reflux for 20 hr. The mixture was cooled, filtered, and the filtrate concentrated under reduced pressure to give an oil as residue. The oil was crystallized in petroleum ether. The solid was collected by filtration, washed with petroleum ether and dried to yield 35.8 g (95%) of an off-white powder. An analytical sample, m.p. 41.5°–42.5° C. was prepared from petroluem ether.

Analysis: Calculated for $C_{12}H_{15}ClO_2$: C, 63.58; H, 6.67. Found: C, 63.40; H, 6.64.

PREPARATION 39

4-(3-Chloropropoxy)benzamide

A mixture of 50 g (0.365 mole) of 4-hydroxybenzamide, 114.8 g (0.729 mole) of 1-bromo-3-chloropropane and 151.3 g (1.1 mole) of anhydrous potassium carbonate in 1 liter of acetone was heated at reflux for 20 hr. The mixture was concentrated under reduced pressure and the residue was stirred with 1.2 liter of water to remove inorganic solids. The mixture was filtered and the filter cake was washed with water and petroleum ether and dried to yield 75.5 g (97%) of white solid. The solid was recrystallized from ethyl acetate, m.p. 142°–145° C.

Analysis: Calculated for $C_{10}H_{12}ClNO_2$: C, 56.22; H, 5.66; N, 6.56. Found: C, 55.92; H, 5.61; N, 5.56.

PREPARATION 40

1-[4-(5-Chloropentoxy)-3-methoxyphenyl]ethanone

A mixture of 59.7 g (0.36 mole) of acetovanillone, 100 g (0.539 mole) of 1-bromo-5-chloropentane and 138 g (1 mole) of anhydrous potassium carbonate in 1 liter of acetone was heated at reflux for 20 hr. The mixture was filtered and the filtrate was concentrated under reduced pressure to give an oil which crystallized in petroleum ether (30°–60° C.). The solid was collected by filtration, washed with petroleum ether and dried to yield 81.4 g (84%) of fluffy, white solid. The solid was recrystallized from isopropyl ether, m.p. 57°–58° C.

Analysis: Calculated for $C_{14}H_{19}ClO_3$: C, 62.11; H, 7.07. Found: C, 62.14; H, 7.10.

PREPARATION 41

4-(3-Chloropropoxy)-3-methoxybenzeneacetic acid ethyl ester

A mixture of 50 g (0.238 mole) of ethyl homovanillate, 75 g (0.476 mole) of 1-bromo-3-chloropropane and 98.7 g (0.71 mole) of anhydrous potassium carbonate in 1 liter of acetone was heated at reflux for 24 hr. The mixture was filtered and the filtrate was concentrated under reduced pressure to give an oil which gradually crystallized to a semi-solid. The solid was recrystallized from ethyl ether-petroleum ether (30°–60° C.) to yield 44.4 g (65%) of white solid, m.p. 36°–38° C.

Analysis: Calculated for $C_{14}H_{19}ClO_4$: C, 58.64; H, 6.68. Found: C, 58.74; H, 6.74.

PREPARATION 42

1-(3-Chloropropoxy)-4-(methylsulfonyl)benzene

To a solution of 21.7 g (0.1 mole) of 1-(3-chloropropxy)-4-(methylthio)benzene in 100 ml of chloroform was cautiously added a slurry of 51.8 g (0.3 mole) of m-chloroperbenzoic acid in 450 ml of chloroform. The mixture was stirred at ambient temperature for 2 days and then filtered. The filtrate was washed with four portions of a solution comprised of 110 ml of saturated sodium bicarbonate, 110 ml of water, and 30 ml of 20% sodium hydroxide, once with brine, dried (sodium sulfate) and concentrated under reduced pressure to give a solid as residue. The solid was triturated with petroleum ether, collected by filtration and air dried to yield 24.3 g (98%) of white solid. An analytical sample, m.p. 84°–86° C. was recrystallized from 2-propanol.

Analysis: Calculated for $C_{10}H_{13}ClO_3S$: C, 48.29; H, 5.27. Found: C, 48.38; H, 5.30.

PREPARATION 43

5-Oxo-1-(phenylmethyl)-3-pyrrolidinecarboxylic acid, methyl ester

A solution of 158.2 g (1.0 mole) of dimethylitaconate and 107.2 g (1.0 mole) of benzylamine in 750 ml of methanol was let stand at ambient temperature over the weekend. The solution was filtered and the filtrate was concentrated under reduced pressure to give an oil as residue. The oil crystallized when it was triturated with petroleum ether (30°–60° C.). The solid was collected by filtration and dried to yield 225.5 g (97%) of white powder. An analytical sample, m.p. 63°–65° C. was prepared from isopropyl ether.

Analysis: Calculated for $C_{13}H_{15}NO_3$: C, 66.94; H, 6.48; N, 6.01. Found: C, 66.82; H, 6.48; N, 6.01.

PREPARATION 44

1-Benzyl-3-(hydroxymethyl)pyrrolidine oxalate [1:1]

A solution of (60.0 g, 0.2553 mole)5-oxo-1-(phenylmethyl)-3-pyrrolidinecarboxylic acid methyl ester in dry dimethoxyethane was added to a mixture of dimethoxyethane and 47.0 g (1.23 mole) of lithium aluminum hydride. The reaction mixture was stirred 2 hrs at room temperature and then heated at reflux 2 hrs. The mixture was then stirred overnight at room temperature, then quenched by the slow addition of ethyl acetate. More ethyl acetate was added and the use of Celite ® allowed the solid material to be separated from filtrate by filtration. The filtrate was stripped to dryness and dissolved in chloroform. The chloroform layer was extracted with 10% sodium hydroxide. The chloroform layer was dried, filtered, and solvent removed to give an oil. A portion of the oil was converted to the oxalate salt. The salt was recrystallized from methanol-ethyl ether and dried at 80° C. in vacuo overnight to give 2.27 g, 39.4% yield of white, crystalline solid, m.p. 98°–102° C.

Analysis: Calculated for $C_{14}H_{19}NO_5$: C, 59.78; H, 6.81; N, 4.98. Found: C, 59.43; H, 6.79; N, 4.95.

PREPARATION 45

1-[4-(6-Chlorohexyloxy)-3-methoxyphenyl]ethanone

A mixture of 41.6 g (0.25 mole) of acetylvanillone, 76 g (0.375 mole) of 1-bromo-6-chlorohexane and 103.7 g (0.75 mole) of anhydrous potassium carbonate in 750 ml of acetone was heated at reflux 20 hr. The mixture was cooled, filtered, and the filter cake washed with acetone. The combined filtrates were concentrated under vacuum pump pressure at 90° C. to give an oil which gradually crystallized. The residue was triturated with petroleum ether (30°–60° C.), collected by filtration, and dried to yield 59.6 g (84%) of off-white solid. An analytical sample, m.p. 35°–38° C. was prepared from isopropyl ether.

Analysis: Calculated for $C_{15}H_{21}ClO_3$: C, 63.26; H, 7.43. Found: C, 63.50; H, 7.60.

PREPARATION 46

4-(3-Chloropropoxy)benzenesulfonamide

A mixture of 25 g (0.144 mole) of p-hydroxybenzenesulfonamide, 45.5 g (0.289 mole) of 1-bromo-3-chloropropane and 59.7 g (0.432 mole) of anhydrous potassium carbonate in 500 ml of acetone was heated at reflux for 24 hr. The mixture was cooled, filtered and the filtrate concentrated under vacuum pump pressure at 90° C. to give 32.2 g of tan gum as residue. The gum was purified by column chromatography on 600 g of silica gel. Fractions containing the title compound eluted with 8% acetone in benzene were combined and concentrated under reduced pressure to yield 12.2 g (34%) of white solid, m.p. 106°–107.5° C. on recrystallization from 2-propanol.

Analysis: Calculated for $C_9H_{12}NO_3S$: C, 43,29; H, 4.84; N, 5.61. Found: C, 43.48; H, 4.92; N, 5.62.

PREPARATION 47

7-(3-Chloropropoxy)-2H-1-benzopyran-2-one

A mixture of 16.8 g (0.104 mole) of 7-hydroxycoumarin, 31.6 g (0.2 mole) of 1-bromo-3-chloropropane and 41.5 g (0.3 mole) of anhydrous potassium carbonate in 500 ml of acetone was heated at reflux for 24 hr. The mixture was filtered with difficulty to give a milky filtrate. The filtrate was treated with charcoal and filtered through Celite ® to give a clear filtrate. The filtrate was concentrated under reduced pressure to give a solid residue. The solid was triturated with petroleum ether (30°–60° C.), collected by filtration; and dried to yield 19.1 g (77%) of fluffy, white solid. An analytical sample, m.p. 100°–102° C., was obtained on recrystallization from 2-propanol.

Analysis: Calculated for $C_{12}H_{11}ClO_3$: C, 60.39; H, 4.65 Found: C, 60.35; H, 4.68.

PREPARATION 48

7-(3-Chloropropoxy)4-oxo-4H-1-benzopyran-2-carboxylic acid ethyl ester

A mixture of 23.4 g (0.1 mole) of 7-hydroxy-4-oxo-4H-1-benzopyran-2-carboxylic acid ethyl ester, 31.6 g (0.2 mole) of 1-bromo-3-chloropropane and 41.5 g (0.3 mole) of anhydrous potassium carbonate in 500 ml of acetone was heated at reflux for 20 hr. The mixture was cooled and filtered through Celite ®. The filtrate was concentrated under reduced pressure to give a solid residue. The solid was triturated with petroleum ether (30°–60° C.), collected by filtration, and recrystallized from 2-propanol to yield 22.5 g (73%) of white solid, m.p. 107°–108° C.

Analysis: Calculated for $C_{15}H_{15}ClO_5$: C, 57,98; H, 4.87. Found: C, 58.21; H, 4.88.

PREPARATION 49

1-[4-(3-Chloropropoxy)-2-methoxyphenyl]ethanone

A mixture of 10.6 g (0.637 mole) of 1-(4-hydroxy-2-methoxyphenyl)ethanone, 20 g (0.127 mole) of 1-bromo-3-chloropropane and 26.4 g (0.19 mole) of anhydrous potassium carbonate in 250 ml of acetone was heated at reflux for 20 hr. The mixture was cooled, filtered and the filtrate concentrated under vacuum pump pressure at 90° C. to give an oil which gradually crystallized. The solid was triturated with petroleum ether (30°–60° C.), collected by filtration and dried to yield 14.6 g (94%) of white solid, m.p. 47°–49° C. on recrystallizing from isopropyl ether.

Analysis: Calculated for $C_{12}H_{15}ClO_3$: C, 59.39; H, 6.23. Found: C, 59.32; H, 6.26.

PREPARATION 50

1-(3-Chloropropoxy)-4-methylsulfinylbenzene

The title compound is prepared by treating 1-3-(chloropropoxy)-4-methylthiobenzene with sodium perborate in glacial acetic acid.

PREPARATION 51

2-(3-Chloropropoxy)benzonitrile

A mixture of 2-cyanophenol (50.0 g, 0.42 mole), 1-bromo-3-chloropropane (67.7 g, 0.43 mole), and potassium carbonate (58.0 g, 0.42 mole) was heated overnight at gentle reflux in 500 ml of acetone. The reaction mixture was stripped to dryness and the residue was dissolved in chloroform. The chloroform layer was extracted several times with 5% sodium hydroxide. The chloroform layer was dried (anhydrous sodium sulfate), filtered, and the solvent was removed, to give a brown oil (80.09 g). A ten gram portion of this oil was subjected to flash chromatography on silica gel with 10% ethyl acetate-hexanes and 20% ethyl acetate-hexanes used for elution. Fractions were combined and solvent removed in vacuo. The clear oil obtained was dried 18 hrs in vacuo at room temperature and 8 hrs at 80° C. in vacuo. This furnished 5.24 g (50.0% yield—based on aliquot taken) of clear oil. $^1$H HMR (CDCl$_3$); δ 2.1–2.5 (q, 2, —CH$_2$), 3.8 (t, 2, —ClCH$_2$), 4.2 (t, 2, —OCH$_2$), 6.9 (m, 2, aromatic protons ortho and para to ether), 7.5 (m, 2, aromatic protons ortho and para to CN group).

Analysis: Calculated for $C_{10}H_{10}ClNO$: C, 61.39; H, 5.15; N, 7.16. Found: C, 61.27; H, 5.15; N, 7.14.

PREPARATION 52

1-Phenylmethyl-3-pyrrolidinemethanol methanesulfonate (ester) exalate [1:1]

A solution of 113.80 g (0.596 mole) of 1-benzyl-3-(hydroxymethyl)pyrrolidine and triethylamine, 66.0 g (0.66 mole) in 600 ml of acetonitrile was prepared. This solution was cooled in an ice bath. A solution of tosyl chloride, 125.9 g (0.66 mole) in 300 ml of acetonitrile was added dropwise with stirring. The solution was allowed to stir overnight at room temperature. A solid precipitated and the solution was filtered. The solvent was removed by rotary evaporator and the residue was dissolved in chloroform. The chloroform layer was dried (anhydrous sodium sulfate), filtered, and solvent removed to given 232.9 g of a dark brown oil. This oil was converted to the oxalate salt and recrystallized from methanol-ethyl ether. After drying at 80° C. in vacuo overnight, 181.63 g of white, crystalline solid was obtained. A five gram sample was recrystallized again from methanol-ethyl ether and dried at 80° C. in vacuo overnight. A yield of 1.41 g (19.7% overall adjusted for the aliquot taken) of white, crystalline solid, m.p. 147°–149° C. was obtained.

Analysis: Calculated for $C_{21}H_{25}NO_7S$: C, 57.92; H, 5.79; N, 3.22. Found: C, 57.62; H, 5.82; N, 3.22

PREPARATION 53

N-[3-(3-Chloropropoxy)phenyl]urea

A mixture of 45.6 g (0.3 mole of 1-(3-hydroxyphenyl)urea, 94.5 g (0.6 mole) of 1-bromo-3-chloropropane, 124.4 g (0.9 mole) of anhydrous potassium carbonate and 1 liter of acetone was heated at reflux with mechanical stirring for 20 hr. The mixture was concentrated and the residue was slurried with 1.5 liters of water. The mixture was filtered and the filter cake was recrystallized from 2-propanol to yield 57.0 g (83%) of off-white solid, m.p. 141°–143° C.

Analysis: Calculated for $C_{10}H_{13}ClN_2O_2$: C, 52.52; H, 5.73; N, 12.25. Found: C, 52.37; H, 5.79; N, 12.17.

PREPARATION 54

N-[4-(3-Chloropropoxy)phenyl]carbamic acid ethyl ester

A mixture of 6.6 g (0.036 mole) of (4-hydroxyphenyl)carbamic acid ethyl ester, 11.5 g (0.072 mole) of 1-bromo-3-chloropropane, 13.8 g (0.10 mole) of anhydrous potassium carbonate and 150 ml of acetone was heated at reflux for 21 hr. The mixture was cooled and filtered. The filtrate was concentrated under reduced pressure to give a solid residue. The solid was triturated with petroleum ether (30°–60° C.) collected by filtration and recrystallized from isopropanol to yield 7.7 g (83%) of white solid, m.p. 91°–93° C.

Analysis: Calculated for $C_{12}H_{16}ClNO_3$: C, 55.93; H, 6.26; N, 5.43. Found: C, 55.93; H, 6.28; N, 5.46.

PREPARATION 55

α(4-Fluorophenyl)-2-pyridineacetonitrile

A sample of sodium hydride (60%, 1.60 g, 0.04 mole) was washed with dry hexanes. After removal of hexanes a 100 ml portion of dimethyl sulfoxide was added. To this mixture was added a solution of 4-fluorophenylacetonitrile (5.41 g, 0.04 mole). The mixture was stirred 3 hrs at room temperature under nitrogen. 2-Bromopyridine (6.32 g, 0.04 mole) was added to the mixture, the reaction mixture was then stirred overnight at 65° C. The reaction mixture was poured into 1200 ml of water and the aqueous phase was extracted several times with chloroform (the chloroform layer was filtered using Celite ®). The combined chloroform layer was extracted with water and 5% sodium hydroxide. The chloroform layer was dried over sodium sulfate, filtered, and solvent removed to give a red oil. The oil was subjected to flash chromatography on silica gel using 10% ethyl acetate-90% hexanes and 20% ethyl acetate-80% hexanes for elution. Fractions of similar purity was combined and solvent removed in vacuo. The oil obtained was dried in vacuo overnight at 80° C. to give 2.43 g (28.6%) of clear oil.

$^1$H (CDCl$_3$): δ 8.5 (m, 1, proton adjacent to N in pyridine nucleus), 6.8-7.8 (m, 7, aromatics), 5.3 (s, 1, methine).

Analysis: Calculated for C$_{13}$H$_9$FN$_2$: C, 73.57; H, 4.27; N, 13.20. Found: C, 73.23; H, 4.23; N, 13.12

PREPARATION 56

α-(4-Fluorophenyl)-α-[1-[(4-methylphenyl)sulfonyl]-4-piperidinyl]-2-pyridineacetonitrile hydrate [1:0.5]

The sodium salt of the free base of α-(4-fluorophenyl)-2-pyridineacetronitrile was formed in dimethylsulfoxide from sodium hydride (60%, 5.16 g, 0.129 mole) and the free base of α-4-fluorophenyl)-2-pyridineacetonitrile (27.36 g, 0.129 mole). The salt was stirred in dimethylsulfoxide for 4½ hr at room temperature. Next, 4-methylphenylsulfonic acid ester with 1-[(4-methylbenzene) sulfonyl]-4-piperidinol (52.8 g, 0.129 mole) was added and the reaction mixture was stirred 2 hr at room temperature. The reaction mixture was stirred overnight at 80° C. The solvent was removed in vacuo and the residue obtained was dissolved in chloroform. The chloroform was extracted with water and 5% sodium hydroxide. The chloroform layer was dried over sodium sulfate and filtered. Solvent was removed to give a dark brown residue. This material was triturated with acetone to give 36.2 g of white solid. A one gram portion was triturated with acetone and then recrystallized from methylene chloride-acetone. The solids were dried in vacuo overnight at 80° C. to give 0.74 g (62.4% based on aliquot taken) of white crystals, m.p. 228°-229° C.

Analysis: Calc'd for C$_{25}$H$_{24}$FN$_3$O$_2$S.0.5H$_2$O: C, 65.90; H, 5.49; N, 9.16. Found: C, 65.86; H, 5.27; N, 9.16.

PREPARATION 57

α-(4-Fluorophenyl)-α-(4-piperidinyl)-2-pyridineacetonitrile oxalate [2:3]

A solution of α-(4-fluorophenyl)-α-[1-[(4-methylphenyl)sulfonyl]-4-piperidinyl]-2-pyridineacetonitrile (30.86 g, 0.0687 mole) and phenol (75 g, 0.8 mole) in 200 mol of 48% hydrobromic acid was heated at reflux for 3 hrs. The resultant was cooled in ice and made alkaline with ice-50% sodium hydroxide. The aqueous layer was extracted with chloroform and the chloroform layer was extracted with 5% sodium hydroxide. The chloroform layer was dried over sodium sulfate, filtered, and solvent removed to give a dark brown oil. The entire oil was converted to the oxalate salt in methanol-ethyl ether. A one gram portion was taken and recrystallized from methanol-ethyl ether and dried in vacuo at 80° C. overnight. This furnished 0.90 g (80.2% based on aliquot taken) of white, crystalline product, m.p. 98° C. (soften, 70° C.).

Analysis: Calculated for C$_{21}$H$_{21}$FN$_3$O$_6$: C, 58.60; H, 4.92; N, 9.76. Found: C, 58.77; H, 5.01; N, 10.04.

PREPARATION 58

4-Fluoro-α-(4-fluorophenyl)benzeneacetonitrile

4-Fluorophenylacetonitrile (70.0 g, 62.2 ml, d=1.126, 0.518 mole) was heated to 120° C., Bromine (83.0 g, 26.6 ml, d=3.119, 0.525 mole) was added dropwise over 1 hr while maintaining a temperature of 120° C. The solution was stirred for ½ at 120° C. and then flushed vigorously with nitrogen for ¾ hr (solution A).

In a separate 2-liter flask was placed aluminum chloride (85.0 g, 0.644 mole). Fluorobenzene (200 g, 2.08 mole, d=1.024, 195.3 ml) was added dropwise with stirring over ½ hr while flushing with nitrogen (Mixture B).

Solution A was added dropwise to mixture B starting at room temperature. The temperature rose to 50° C. The reaction mixture was stirred at this temperature for ½ hr. The temperature was raised to 70° C. and maintained there for ½ hr. At this point the reaction became uncontrollable and part of the mixture was lost. The remainder was added to ice/75 ml of concentrated hydrochloric acid. The aqueous phase extracted several times with chloroform. The solvent layer was dried, filtered, and solvent removed to give a green solid. The solid was recrystallized from isopropanol; the solid was washed with cold isopropanol twice and dried in vacuo at 55° C. overnight. This produced 29.72 g (25.1%) if light-yellow solid, m.p. 62°-63.5° C.

Analysis: Calculated for C$_{14}$H$_9$F$_2$HL C, 73.36; H, 3.96; N, 6.11. Found: C, 73.55; H, 3.88; N, 6.10.

PREPARATION 59

1-[(4-Methylphenyl)sulfonyl]-α-α-diphenyl-3-piperidineporpanenitrile

The sodium salt of diphenylacetonitrile was formed in 400 ml of dimethylsuloxide from sodium hydride (605, 39.0 g, 0.975 mole) and diphenylacetonitrile (188.90 g, 0.975 mole). The resulting solution was stirred under nitrogen for 1 hr at room temperature. A 90-10 mixture of 3-(chloromethyl)-1-[(4-methylphenyl)sulfonyl]piperidine and 4-methylbenzenesulfonic acid 1-[(4-methylphenyl)sulfonyl]piperidine-3-yl methyl ester (221.42 g, 0.975 mole) dissolved in 400 ml of dimethylsulfoxide was added. The reaction mixture was heated to 85° C. and stirred overnight at 73° C. The dimethylsulfoxide was removed in vacuo, and the residue obtained was dissolved in chloroform. The chloroform layer was extracted with 1N sulfuric acid. The chloroform layer was dried, filtered, and the chloroform was removed by rotary evaporator. A brown residue was obtained which was triturated with isopropyl ether to give a brown solid. A 5-g sample was recrystallized from ethyl acetate-isopropyl ether. This gave 4 g (56.8% based on aliquot taken) of white solid, m.p. 136.5°-137° C.

Analysis: Calculated for C$_{27}$H$_{28}$N$_2$O$_2$S: C, 72.94; H, 6.35; N, 6.30. Found: C, 72.82; H, 6.36; N, 6.29.

PREPARATION 60

α,α-Diphenyl-3-piperidinepropanenitrile fumarate [1:1]

A mixture of 1-[(4-methylphenyl)sulfonyl]-α,α-diphenyl-3-piperidinepropanenitrile (302.41 g, 0.68 mole), hydrogen bromide (48%, 750 ml), and phenol (260 g, 2.76 mole) was stirred vigorously while heating at reflux for 3½ hr. The reaction mixture was cooled to room temperature and made alkaline with 50% hydroxide-ice. The aqueous phase was extracted several times with chloroform, and the chloroform layer was back extracted with 5% sodium hydroxide. The chloroform layer was dried, filtered, and solvent removed. NMR showed about 80% product was obtained. The same sequence was repeated. The chloroform layer gave a brown oil which was converted to the oxalate salt. A portion of this oxalate salt was converted to the free bas by partitioning in chloroform and dilute aqueous sodium hydroxide and separating and evaporating the chloroform layer and converted to the fumarate salt. This salt was recrystallized from methanolethyl ether and dried in vacuo at 80° C. overnight to give 6.53 g of white crystals, m.p. 181°-182° C.

Analysis: Calculated for $C_{24}H_{26}N_2O_4$: C, 70.92; H, 6.45; N, 6.89. Found: C, 70.46; H, 6.41; N, 6.86.

PREPARATION 61

3-(8-Quinolinyloxy)-1-propanol

A solution of 8-hydroxyquinoline (36.0 g, 0.25 mole) and potassium tertbutoxide (28.0 g, 0.25 mole) in 80 ml of dimethyl sulfoxide was stirred for 1 hr at room temperature. 3-Chloro-1-propanol (242.0 g, 0.25 mole) was added and the solution was heated overnight at 70° C. The solution was poured into 500 ml of water. A brown solid/mass was obtained. The solid was washed with several portions of water and then triturated with acetone. The solid was filtered and dried in vacuo at 80° C. overnight to give 35.67 g (70.3%) of light brown solid, m.p. 126°-127° C.

Analysis: Calculated for $C_{12}H_{13}NO_2$: C, 70.92; H, 6.45; N, 6.89. Found: C, 70.94; H, 6.49; N, 6.87.

PREPARATION 62

8-(3-Chloropropoxy)quinoline

A solution of 3-(8-quinolinyloxy)-1-propanol (32.0 g, 0.158 mole) and thinoyl chloride (24.0 g, 0.203 mole) was heated at reflux for 5 hours in 300 ml of dry benzene (dried over 4A molecular sieves). The reaction mixture was cooled to room temperature and then stripped to dryness. The residue was treated with potassium carbonate solution (30 g in 500 ml of water). The gummy residue was dissolved in chlorofrom and extracted with the potassium carbonate solution. The chloroform layer was dried over anhydrous sodium sulfate, filtered, and solvent removed to give a dark mass which crystallized. The mass was treated with 500 ml of boiling hexane. The hexane layer was decanted off from insoluble oil. A white solid crystallized on cooling, and was collected by filtration. The solid was dried in vacuo at room temperature overnight to give 26.69 g (76.2%) of white, crystalline solid, m.p. 69°-71° C.

Analysis: Calculated for $C_{12}H_{12}ClNO$: C, 65.02; H, 5.45; N, 6.32. Found: C, 65.19; H, 5.51; N, 6.27.

PREPARATION 63

4-Methylphenylsulfonic acid ester with 1-[(4-methylbenzene)sulfonyl]-4-piperidinol A solution of 1.63 g (0.0161 mole) of 4-hydrpxypiperidine and 13.91 g (0.0732 mole) of tosyl chloride i n 80 ml of pyridine was stirred at 25° C. overnight. The mixture was quenched in 200 ml of water and the aqueous mixture was extracted with several portions of methylene chloride. The methylene chloride solution was extracted with several portions of 1M sulfuric acid and 1M sodium hydroxide and then was dried over magnesium sulfate. The solvent was removed in vacuo to give a solid. This water recrystallized from methylene chloride-ethyl ether to give 4.82 g (73.3%) of the product, m.p. 140.5°-141° C.

Analysis: Calculated for $C_{19}H_{23}NO_5S_2$: C, 55.73; H, 5.66; N, 3.42. Found: C, 55.60; H, 5.64; N, 3.39.

PREPARATION 64

7-Hydroxy-4-oxo-4H-1benzopyran-2-carboxylic acid ethyl ester

To a warm, stirred solution of 18.4 g (0.8 mole) of sodium metal in 250 ml of absolute ethanol was added dropwise a solution of 30.4 g (0.2 mole) of 2,4-dihydroxyacetophenone and 58.5 g (0.4 mole) of diethyloxalate in 50 ml of absolute ethanol and 50 ml of absolute ethyl ether over a 30-min period. The mixture was heated at reflux for 4 hr and then poured into a solution of 200 ml of concentrated hydrochloric acid and 1.8 liter of water. The mixture was extracted with two 500-ml portions of ethyl ether and the combined extracts were concentrated under reduced pressure to give a solid residue.

The solid was dissolved in a mixture of 250 ml of ethanol and 3 ml of concentrated hydrochloric acid and heated at reflux for 2 hr. The mixture was concentrated under reduced pressure and the solid residue was triturated with ethyl ether, collected by filtration, and recrystallized from 95% ethanol to yield 28.1 g (60%) of tan powder, m.p. 217°-221° C.

Analysis: Calculated for $C_{12}H_{10}O_5$: C, 61;54; H, 4.30. Found: C, 61.68: H, 4.34.

PREPARATION 65

α(4-Fluorophenyl)-α-[1-(phenylsulfonyl)-4-piperidinyl]-2-pyridinemethanol

A solution of 2-bromopyridine (9.26 g, 0.059 mole) in 250 ml of tetrahydrofuran was prepared and cooled to −65° C. in an acetone/dry ice bath. To this solution was added n-butyl lithium (10.5M in hexane, 5.60 ml, 0.05 mole) while maintaining a temperature of −45° C. to −65° C. The solution was stirred for 2 hr at −65° C. A tetrahydrofuran solution of (4-fluorophenyl)[1-(phenylsulfonyl)-4-piperidinyl]methanone (18.2 g, 0.0525 mole) was added dropwise while maintaining a temperature of −65° C. The solution was stirred 72 hr while reaching room temperature. The solution was stripped to dryness. The residue was dissolved in chloroform and extracted with several portions of water. The chloroform layer was dried over sodium sulfate and solvent was removed in vacuo to give a brown oil. This oil was subjected to flash chromatography on silica gel using 30% ethyl acetate/hexanes and 40% ethyl acetate/hexanes for elution. Fractions of similar purity were combined and solvent removed to give a white crystalline solid. This solid was triturated with ethyl ether and chilled in the freezer for 12 hr. The solid was isolated and dried at 80° C. in vacuo overnight. This process provided 12.12 g (54.1% yield) of white, crystalline solid m.p. 160°-163° C.

Analysis: Calculated fpr $C_{23}H_{23}FN_2O_3S$: C, 64.78; H, 5.44; N, 6.57. Found: C, 64.74; H, 5.43; N, 6.49.

PREPARATION 66

2[(4-Fluorophenyl)(4-piperidinyl)methyl]pyridine hydrochloride hydrate [1:2:0.5]

A mixture of α-(4-fluorophenyl)-α-[1-phenylsulfonyl)-4-piperidinyl]-2-pyridinemethanol (62.0 g, 2.0 mole) and 500 ml of 57% hydriodic acid was heated at reflux for 6 hours. The reaction mixture was concentrated and then filtered with Celite ®. The filtrate obtained was stripped to dryness. Ice/water was added and the mixture was made alkaline with 50% sodium hydroxide. The aqueous phase was extracted several times with chloroform. The chloroform layer was dried over sodium sulfate, filtered, and solvent removed to obtain an oil which crystallized on standing at room temperature. The oil was converted to the hydrochloride salt and recrystallized from methanol-ethyl ether. A white solid was obtained which was dried at 80° C. in vacuo overnight. This furnished 15.45 g (71.9% yield) of yellow solid, mp 182°–185° C.

Analysis: Calculated for $C_{17}H_{21}FCl_2N_2.0.5H_2O$: C, 57.96; H, 6.30; N, 7.95. Found: C, 57.46; H, 6.26; N, 7.88.

PREPARATION 67

α,α-Diphenyl-1-(phenylmethyl)-4-piperidinemethanol

A Grignard solution was prepared by the addition of 94.2 g (0.6 mole) of bromobenzene in 250 ml of dry (freshly distilled from lithium aluminum hydride) tetrahydrofuran to a mixture of 12.5 g (0.5 mole) of magnesium chips in 500 ml of dry tetrahydrofuran. After the addition was complete, the mixture was heated at reflux for 15 min to complete formation. To this Grignard reagent at ambient temperature, was added a solution of 44.2 g (0.179 mole) of the base of 1-(phenylmethyl)-4-piperidinecarboxylic acid ethyl ester in 250 ml of tetrahydrofuran in a stream. The solution was stirred overnight at ambient temperature and then poured into 2.5 liters of a saturated ammonium chloride solution. The layers were separated and the aqueous layer was extracted once with 500 ml of methylene chloride and twice with 250 ml of methylene chloride. The combined organic layers were washed successively with 500 ml of water, 750 ml of a 3% sodium hydroxide solution, 250 ml of water and 250 ml of brine. The organic layer was dried over sodium sulfate and concentrated to give a gum as residue. The gum was dissolved in 500 ml of ethyl ether treated with activated charcoal, filtered through Celite ®, and then concentrated to give a gum as residue. The gum crystallized when triturated with petroleum ether (30°–60° C.). The solid was collected by filtration and dried to yield 49.0 g (77%) of title compound as a white solid. An analytical sample, mp 89.5°–90.5° C., was prepared by recrystallization from 2-propanol.

Analysis: Calculated for $C_{25}H_{27}NO$: C, 83.99; H, 7.61; N, 3.92. Found: C, 84,09; H, 7.63; N, 3.97.

PREPARATION 68

α,α-Diphenyl-4-piperidinemethanol

A mixture of 35.8 g (0.1 mole) of α,α-diphenyl-1-(phenylmethyl)-4-piperidinemethanol and 5% palladium on carbon catalyst in 500 ml of absolute ethanol was hydrogenated at 60° C. in a Parr apparatus for 3 days. The mixture was filtered through Celite ® and the filtrate was concentrated to give a solid residue. The solid was triturated with petroleum ether (30°–60° C.), collected by filtration and dried to give 26.7 g of title compound as a white solid. An analytical sample was obtained by recrystallization from 2-propanol-isopropyl ether, mp 160°–161° C.

Analysis: Calculated for $C_{18}H_{21}NO$: C, 80.86; H, 7.92; N, 5.24. Found: C, 80.98; H, 7.96; N, 5.30.

PREPARATION 69

α-(4-Fluorophenyl)-α-methyl-4-piperidinemethanol

To a solution of 49.9 g (0.2 mole) of 1-acetyl-4-(p-fluorobenzoyl)piperidine in 500 ml of tetrahydrofuran was added dropwise 110 ml (0.35 mole) of a 3.2 molar solution of methylmagnesium bromide in ether ether* at ambient temperature. After addition was complete, the mixture was heated at reflux for 1 hr and then at ambient temperature overnight. The mixture was poured into 1.5 liters of a saturated ammonium chloride solution with vigorous stirring. The layers were separated and the aqueous layer was extracted twice with 300 ml portions of methylene chloride. The combined organic layers were washed successively with 250 ml of water, 250 ml of a 40% sodium hydroxide solution, 250 ml of water and 250 ml of brine. The organic layer was dried over sodium sulfate and concentrated under reduced pressure to give 37.3 g (70% yield) of crude alcohol as a gum.

*Available commercially, e.g., Aldrich Chemical Co., Inc., 940 West Saint Paul Avenue, Milwaukee, Wis. 53233 USA.

The gum was dissolved in 400 ml of 95% ethanol, heated with a solution of 22.4 g (0.4 mole) potassium hydroxide in 100 ml of water, and heated at reflux overnight. The solution was concentrated under reduced pressure and the residue was triturated with water. The resulting solid was collected by filtration and recrystallized from 2-propanol to yield 19.8 g (44%) of title compound as an off-white powder, mp 184°–186° C.

Analysis: Calculated for $C_{13}H_{18}FNO$: C, 69.93; H, 8.13; N, 6.27. Found: C, 70.00; H, 8.21; N, 6.27.

PREPARATION 70

α,α-Bis(4-methylphenyl)-1-(phenylmethyl)-4-piperidinemethanol

A Grignard solution was prepared by the addition of 102.6 g (0.6 mole) of 4-bromotoluene in 500 ml of dry tetrahydrofuran to a mixture of 12.5 g (0.5 mole) of magnesium chips in 250 ml of tetrahydrofuran. After the addition was complete, the mixture was heated at reflux for 1 hr to complete formation. To this Grignard reagent at ambient temperature was added in a stream 42.9 g (0.173 mole) of 1-(phenylmethyl)-4-piperidinecarboxylic acid ethyl ester in 250 ml of dry tetrahydrofuran. The solution was stirred at ambient temperature and then poured into 2.5 liters of a saturated ammonium chloride solution. The layers were separated and the aqueous layer was extracted twice with 375 ml portions of methylene chloride. The combined organic layers were washed successively with 500 ml of water, 750 ml of a 3% sodium hydroxide solution, 250 ml of water and 250 ml of brine. The organic layer was dried over sodium sulfate and concentrated under pressure to give a gum as residue. The gum gradually cyrstallized. The solid was triturated with petroleum ether (30°–60° C.), collected by filtration and dried to yield 63.6 g (95%) of title compound as a white solid. An analytical sample was recrystallized from 2-propanol, mp 115°–117° C.

Analysis: Calculated for $C_{27}H_{31}NO$: C, 84.11; H, 8.10; N, 3.63. Found: C, 84.23; H, 8.13; N, 3.66.

PREPARATION 71

α,α-Bis(4-methylphenyl)-4-piperidinemethanol

A solution of 38.5 g (0.1 mole) of α,α-bis(4-methylphenyl)-4-piperidinemethanol in 500 ml of absolute ethanol was hydrogenated at 50 psi and 60° C. over one 5% palladium on carbon catalyst in Parr apparatus for 3 days. The cooled mixture was filtered through Celite ® and the filtrate was concentrated under reduced pressure to give a glass as residue. The glass was crystallized from 2-propanol to yield 17.7 g (60%) of title compound as a white solid, mp 150°-153° C.

Analysis: Calculated for $C_{20}H_{25}NO$: C, 81.31; H, 8.53; N, 4.74. Found: C, 81.18; H, 8.62; N, 4.72.

PREPARATION 72

α,α-Bis(4-methoxyphenyl)-1-(phenylmethyl)-4-piperidinemethanol oxalate hydrate [1:1:0.5] compound with ethanol [1:0.5]

A Grignard reagent was prepared by the addition of a solution of 112.2 g (0.6 mole) of 4-bromoanisole in 500 mo of dry tetrahydrofuran to a mixture of 12.5 g (0.5 mole) of magnesium chips in 250 ml of tetrahydrofuran. After the addition was complete, the mixture was heated at reflux for 0.5 hr to complete formation. To this Grignard reagent at ambient temperature was added a solution of 42.8 g (0.173 mole) of the base of 1-(phenylmethyl)-4-(piperidinecarboxylic acid ethyl ester in 250 ml of tetrahydrofuran in a stream. The mixture was stirred at ambient temperature overnight and then poured into 2.5 liters of a saturated ammonium chloride solution. The layers were separated and the aqueous layer was extracted twice with 375 ml portions of methylene chloride. The combined organic layers were washed successively with 500 ml of water, 750 ml of a 3% sodium hydroxide solution, 250 ml of water and 250 ml of brine. The organic layer was dried over sodium sulfate and concentrated under reduced pressure to give a gum as residue. The gum was dissolved in 2-propanol and converted to the oxalic acid salt. The solid was collected by filtration, washed with 2-propanol and ethyl ether and dried to yield 84.8 g (97%) of title compound as a white powder. An analytical sample was recrystallized from absolute ethanol, mp 128°-131° C. (with decomposition) (slow heating; rapid heating gives mp ~110° C.).

Analysis: Calc'd for $C_{29}H_{33}NO_7.0.5H_2O.C_2H_5OH$: C, 66.74; H, 6.91; N, 2.60. Found: C, 67.08; H, 6.77; N, 2.67.

PREPARATION 73

4-(3-Chloropropoxy)benzoic acid methyl ester

A mixture of 30.4 g (0.2 mole) of methyl-4-hydroxybenzoate*, 63 g (0.4 mole) of 1-bromo-3-chloropropane and 82.9 g (0.6 mole) of anhydrous potassium carbonate in 1 liter of acetone was heated at reflux for 20 hr. The mixture was cooled, filtered and the filtrate concentrated to give an oil as residue. The oil crystallized when triturated with cold petroleum ether (30°-60° C.). The solid was collected by filtration and recrystallized from petroleum ether (60°-110° C.) to yield 42.9 g (94%) of title compound as a white solid, mp 56.5°-59° C.

*Available commercially, e.g., Aldrich Chemical Co., Inc., 940 West Saint Paul Avenue, Milwaukee, Wis. 53233 USA.

Analysis: Calculated for $C_{11}H_{13}ClO_3$: C, 57.78; H, 5.73. Found: C, 57.91; H, 5.80.

PREPARATION 74

α,α-Bis(4-methoxyphenyl)-4-piperidinemethanol

A solution of 36.7 g (0.088 mole) of α,α-bis(4-methoxyphenyl-1-(phenylmethyl)-4-piperidinemethanol in 500 ml of absolute ethanol was hydrogenated over 5% palladium on carbon catalyst at 60° C. in a Parr apparatus for 3 days. The mixture was cooled, filtered through Celite ®, fresh catalyst added to the filtrate and the mixture hydrogenated. This process was repeated until no starting material was present by mass spectral analysis. The filtrate was concentrated and the residue was partitioned between methylene chloride and a 5% sodium hydroxide solution. The organic layer was dried over sodium sulfate and concentrated to give a solid residue. The solid was recrystallized from 2-propanol to yield 8.6 g (30%) of title compound as a white solid, mp 153°-155° C.

Analysis: Calculated for $C_{20}H_{25}NO_3$: C, 73.37; H, 7.70; N, 4.28. Found: C, 73.42; H, 7.72; N, 4.30.

PREPARATION 75

4-(3-Chloropropoxy)-1,1'-biphenyl

A mixture of 34 g (0.2 mole) of 4-phenylphenol, 63 g (0.4 mole) of 1-bromo-3-chloropropane and 82.9 g (0.6 mole) of anhydrous potassium carbonate in 1 liter of acetone was heated at reflux for 17 hr. The mixture was cooled, filtered, and the filtrate concentrated under reduced pressure. The residue was triturated with petroleum ether (30°-60° C.) and a solid crystallized. The solid was collected by filtration and was subjected to flash chromatography on 400 g of silica gel on a 10-cm diameter column to remove starting phenol. The column was eluted with a 1:2 mixture of benzene and cyclohexane, and fractions containing title compound were combined and concentrated to give a solid residue. The solid was triturated with petroleum ether (30°-60° C.), collected by filtration, and dried to yield 35.1 g (71%) of title compound as a white solid. An analytical sample was recrystallized from petroleum ether (60°-110° C.), mp 65°-66° C.

Analysis: Calculated for $C_{15}H_{15}ClO$: C, 73.02; H, 6.13. Found: C, 73.08; H, 6.12.

PREPARATION 76

1-[4-(3-Chloropropoxy)phenyl]-1-propanone

A mixture of 37.6 g (0.25 mole) of 4'-hydroxypropiophenone (97%)*, 78.7 g (0.5 mole) of 1-bromo-3-chloropropane and 103.5 g (0.75 mole) of anhydrous potassium carbonate in 1 liter of acetone was heated at reflux for 18 hr. The mixture was cooled, filtered, and the filtrate concentrated under reduced pressure. The oily residue was dissolved in 500 ml of benzene and the solution stirred with potassium hydroxide pellets for 1.5 hr to remove unreacted phenol. The mixture was filtered and the filtrate was concentrated to give 56.1 g (99% yield) of title compound as an oil. The oil gradually crystallized and a portion of the solid was recrystallized from petroleum ether (60°-110° C.) to yield title compound as a fluffy, white solid, mp 41°-43° C.

*Available commercially, e.g., Aldrich Chemical Co., Inc., 940 West Saint Paul Avenue, Milwaukee, Wis. 53233 USA.

Analysis: Calculated for $C_{12}H_{15}ClO_2$: C, 63.58; H, 6.67. Found: C, 63.46; H, 6.82.

PREPARATION 77

4-[Bis(4-chlorophenyl)hydroxymethyl]-N,N-diethyl-1-piperidinecarboxamide

A Grignard solution was prepared by the treatment of a slurry of 8.5 g (0.35 mole) of magnesium chips in 200 ml of dry tetrahydrofuran with a solution of 72.8 g (0.38 mole) of 1-bromo-4-chlorobenzene in 400 ml of tetrahydrofuran. After the addition was complete, the mixture was heated at reflux for 15 min to complete formation. To the Grignard solution at ambient temperature was added a solution of 38.4 g (0.15 mole) of 1-[(diethylaminocarbonyl]-4-piperidine carboxylic acid ethyl ester in 200 mo of tetrahydrofuran in a stream. The solution was stirred at ambient temperature overnight and poured into 2.5 liters of a saturated ammonium chloride solution. The layers were separated and the aqueous layer was extracted once with 500 ml of methylene chloride and once with 250 ml of methylene chloride. The combined organic layers were filtered through Celite ® and the filtrate was washed successively with 500 ml of water, 750 ml of a 4% sodium hydroxide solution, 250 ml of water and 250 ml of brine. The solution was dried over sodium sulfate and concentrated under reduced pressure to give a gum which gradually crystallized. The solid was triturated with petroleum ether (30°-60° C.), collected by filtration, and dried to yield 56.7 g (87%) of title compound as a white solid. An analytical sample was recrystallized from isopropanol, mp 172°-175° C.

Analysis: Calculated for $C_{23}H_{28}Cl_2N_2O$: C, 63.54; H, 6.48; N, 6.43. Found: C, 63.60; H, 6.64; N, 6.25.

PREPARATION 78

3-Methoxy-4-(phenylmethyloxy)benzaldehyde

A mixture of 4-hydroxy-3-methoxybenzaldehyde (100.0 g, 0.657 mole), benzyl bromide (112.4 g, 0.657 mole), and potassium carbonate (90.8 g, 0.657 mole) was heated overnight at reflux in 600 ml of dry acetonitrile (dried over 4A molecular sieves). The reaction mixture was stripped to dryness on a rotary evaporator. A white solid was obtained which was recrystallized form ethanol and dried in vacuo overnight at 80° C., to give 147.45 g (92.6% yield) of white crystalline product, mp 58°-63° C.

Analysis: Calculated for $C_{15}H_{14}O_3$: C, 74.36; H, 5.83. Found: C, 74.36; H, 5.78.

PREPARATION 79

5-Methoxy-2-nitro-4-(phenylmethoxy)benzaldehyde

Reference: *J. Med. Chem.* 1977, Vol. 20, No. 1, p. 147.
3-Methoxy-4-(phenylmethyloxy)benzaldehyde (48.0 g, 0.198 mole) was added in small portions over 0.5 hour to 200 ml of concentrated nitric acid cooled to 0° C. in an acetone-dry ice bath. The temperature was maintained at 0°-1° C. for ten minutes. The temperature was allowed next to reach 15° C. and suddenly but briefly allowed to rise to 45° C. The temperature was cooled to 20° C. and then the reaction mixture was poured in ice/water. A yellow solid was obtained and filtered and washed with ethyl ether. A two gram sample was recrystallized from isopropanol. The light yellow solid isolated was dried in vacuo overnight at 80° C. to give 0.92 g (32.5% yield) of light yellow solid, mp 122°-124° C.

Analysis: Calculated for $C_{15}H_{13}NO_5$: C, 62.72; H, 4.56; N, 4.88. Found: C, 62.42; H, 4.57; N, 5.17.

PREPARATION 80

5-Methoxy-2-nitro-4-(phenylmethyloxy)benzoic acid

A solution of 5-methoxy-2-nitro-4-(phenylmethyloxy) benzaldehyde (45.11 g, 0.157 mole) in 600 ml of acetone was prepared. To this solution was added 400 ml of 10% potassium permanganate solution over 1 hr. The resultant mixture was stirred for 1 hr at room temperature. The reaction mixture was cooled to room temperature and filtered with Celite ®, acetone was removed. The resulting material was made acidic with concentrated hydrochloric acid. A yellow solid formed and was separated from aqueous solution, and air dried. The yellow solid was dissolved in ethyl acetate, and filtered through sodium sulfate to remove traces of manganese dioxide, after which 25.84 g of yellow solid was obtained. A 2 g sample was recrystallized from isopropyl alcohol. The yellow solid isolated was dried in vacuo overnight at 80° C., to give 1.85 g (50% yield) of yellow solid, mp 188° C. (with decomposition).

Analysis: Calculated for $C_{15}H_{13}NO_6$: C, 59.41; H, 4.32; N, 4.62. Found: C, 59.27; H, 4.40; N, 4.46.

PREPARATION 81

4-(4-Chlorobutyoxy)benzoic acid methyl ester

A mixture of 30.4 g (0.2 mole) of methyl-4-hydroxybenzoate, 68.6 g (0.4 mole) of 1-bromo-4-chlorobutane and 82.9 g (0.6 mole) of anhydrous potassium carbonate in 1 liter of acetone was heated at reflux for 17 hr. The mixture was cooled, filtered, and the filtrate concentrated under reduced pressure to give an oil which crystallized. The solid was triturated with cold petroleum ether (30°-60° C.), collected by filtration, and dried to yield 44.3 g (92%) of title compound as a white solid. An analytical sample, mp 28.5°-29° C., was prepared from petroleum ether (30°-60° C.).

Analysis: Calculated for $C_{12}H_{15}ClO_3$: C, 59.39; H, 6.23. Found: C, 59.30; H, 6.34.

PREPARATION 82

1-[4-(4-Chlorobutoxy)-3-methoxyphenyl]ethanone

A mixture of 16.6 g (0.1 mole) of acetovanillone, 34.3 g (0.2 mole) of 1-bromo-4-chlorobutane and 41.4 g (0.3 mole) of anhydrous potassium carbonate in 500 ml of acetone was heated at reflux for 18 hr. The mixture was cooled, filtered, and the filtrate concentrated under reduced pressure to give an oil which readily crystallized. The solid was triturated with petroleum ether (30°-60° C.), collected by filtration, and dried to yield 24.4 g (95%) of title compound as an off-white solid. An analytical sample, mp 68.5°-70.5° C., was prepared from isopropyl ether.

Analysis: Calculated for $C_{13}H_{17}ClO_3$: C, 60.82; H, 6.67. Found: C, 60.83; H, 6.91.

PREPARATION 83

1-Acetyl-α-(4-fluorophenyl)-α-phenyl-4-piperidinemethanol

A solution (667 ml, 2 mole) phenylmagnesium bromide* (3 molar in ethyl ether) was diluted with 2 liters of anhydrous ethyl ether, cooled to 0°-10° C., and treated with a solution of 148 g (0.6 mole) of 1-acetyl-4-(p-fluorobenzoyl)piperidine in 1.5 liters of anhydrous tetrahydrofuran dropwise over a 1.5 hr period. The mixture was stirred at ambient temperature overnight and then poured into a solution of 107 g (2 mole) of ammonium chloride in 2 liters of cold water. The mixture was extracted thrice with 1 liter portions of benzene. The combined extracts were washed with water, dried over magnesium sulfate, and concentrated to give a semi-solid as residue. The semi-solid was triturated with isopropyl ether and the mass crystallized. The solid was collected by filtration and dried to yield 87.8 g (45%) of title compound as a white solid. An analytical sample was recrystallized from 2-propanol, mp 173°–175° C.

*Available commercially, e.g., Morton Thiokol, Inc., Alpha Products, 152 Andover Street, Danvers, Mass. 01923 USA.

Analysis: Calculated for $C_{20}H_{22}FNO_2$: C, 73.37; H, 6.77; N, 4.28. Found: C, 73.20; H, 6.93; N, 4.22.

PREPARATION 84

α,α-Bis(4-chlorophenyl)-4-piperidinemethanol

To a slurry of 8.5 g (0.225 mole) of lithium aluminum hydride in 400 ml of anhydrous tetrahydrofuran was added a solution of 39.2 g (0.09 mole) of 4-[bis(4-chlorophenyl)hydroxymethyl]-N,N-diethyl-1-piperidinecarboxamide in 400 ml of tetrahydrofuran in a stream over a 15 min period. The mixture was heated at reflux for 24 hr, cooled, and treated successively with 8.5 ml of water, 25 ml of a 3N sodium hydroxide solution and 8.5 ml of water. The mixture was stirred for 0.5 hr and then filtered. The filtrate was concentrated under reduced pressure to give a gum which crystallized. The solid was triturated with petroleum ether (30°–60° C.), collected by filtration and recrystallized from benzene to yield 10.5 g (35%) of title compound as a white solid. An analytical sample was recrystallized from 2-propanol, mp 184°–188° C.

Analysis: Calculated for $C_{18}H_{19}Cl_2NO$: C, 64.30; H, 5.70; N, 4.17. Found: C, 64.59; H, 5.79; N, 4.16.

PREPARATION 85

α,α-Bis(4-fluorophenyl)-4-pyridineethanol

A solution of 27.8 g (0.30 mole) of 4-picoline in 400 ml of tetrahydrofuran and under an atmosphere of nitrogen was cooled to −30° C. in a dry-ice acetone bath. A solution of 2.5 moles n-butyllithium in hexane (119 ml, 0.30 mole) was added over 1 hr and the mixture was stirred for an additional 30 min at −30° C. The reaction mixture was allowed to warm to room temperature over 1.5 hr, and 66.7 g (0.30 mole) of 4,4′-difluorobenzophenone in 100 ml of tetrahydrofuran was added. The mixture was stirred for 2 hr and then was poured into an icy solution of ammonium chloride. A white solid was collected. The aqueous mixture was extracted with several portions of methylene chloride and the methylene chloride then removed in vacuo to give additional solid. The solid fractions were combined and recrystalized from a mixture of ether-hexane to give 63.14 g (67.9% yield) of title compound as a white, crystalline solid: mp 158°–159.5° C.

Analysis: Calculated for $C_{19}H_{15}F_2NO$: C, 73.30; H, 4.86; N, 4.50 Found: C, 73.27; H, 4.79; N, 4.51

PREPARATION 86

α,α-Bis(4-fluorophenyl)-4-piperidineethanol

A mixture of 12.25 g (0.0394 mole) of α,α-bis(4-fluorophenyl)-4-piperidineethanol and 1.3 g of 5% platinum on carbon catalyst in 250 ml of acetic acid was shaken under an atmosphere of hydrogen (53 psi) for 9 hr. The solution was filtered through Celite ®, and the solvent was removed in vacuo. The residue was partitioned between methylene chloride and dilute sodium hydroxide. The solvent was removed in vacuo to give a solid, and recrystallization from acetonitrile gave 10.62 g (85.0% yield of title compound as a white, crystalline solid: mp 169°–171° C.

Analysis: Calculated for $C_{19}H_{21}F_2NO$: C, 71.90; H, 6.67; N, 4.41 Found: C, 71.98; H, 6.75; N, 4.54

PREPARATION 87

α-(4-Fluorophenyl)-α-phenyl-4-piperidinemethanol

A mixture of 16.3 g (0.05 mole) of 1-acetyl-α-(4-fluorophenyl)-α-phenyl-4-piperidinemethanol and 5.6 g (0.1 mole) of potassium hydroxide in 150 ml of 95% ethanol and 20 ml of water was heated at reflux for 18 hr. The mixture was poured into 1.5 liters of ice-water and a solid precipitated. The gummy solid was collected by filtration and dried. The solid was dissolved in ethyl ether, filtered, and the filtrate slowly evaporated to 50 ml. The resulting solid was collected by filtration and recrystallized from 2-propanol:isopropyl ether to yield 3.5 g (25%) of title compound as a white solid, m.p. 144.5°–146° C.

Analysis: Calculated for $C_{18}H_{20}FNO$: C, 75.76; H, 7.06; N, 4.91. Found: C, 75.91; H, 7.20; N, 4.93.

PREPARATION 88

4-[2,2,Bis(4-fluorophenyl)ethyl]pyridine hydrochloride [1:1]

A mixture of 15.05 g (0.0484 mole) of α,α-bis(4-fluorophenyl) ethyl]-4-pyridineethanol, 3.2 g (0.10 mole) of phosphorus and 50 ml of 56.9% hydrogen iodide in 150 ml of glacial acetic acid was heated at reflux for 11 hr. The solvent was removed in vacuo, and the residue was partitioned between methylene chloride and dilute sodium hydroxide. The methylene chloride solution was dried over magnesium sulfate, and the solvent was removed in vacuo to give an oil. This was dissolved in a mixture of methanol and ether, and an excess of ethereal hydrogen chloride was added. The solvent was removed in vacuo, and the residue was recrystallized from a mixture of acetonitrile and ether to give 13.89 g (86.7% yield) of title compound as a white, crystalline solid, m.p. 197°–199° C.

Analysis: Calculated for $C_{19}H_{16}ClF_2N$: C, 68.78; H, 4.86; N, 4.22. Found: C, 68.58; H, 5.17; N, 4.23.

PREPARATION 89

4-[2,2-Bis(4-fluorophenyl)ethyl]piperidine hydrochloride hydrate [1:1:0.5]

A mixture of 10.0 g (0.30 mole) α,α-bis(4-fluoropheny)-4-pyridineethanol of 1.2 g of 5% platinum on carbon catalyst in 200 ml of acetic and was shaken under an atomsphere of hydrogen (49 psi)for 16 hr. The solution was filtered through Celite ®, and the solvent was removed in vacuo. The residue was partitioned between methylene chloride and dilute sodium hydroxide. The solvent was removed in vacuo to give an oil. This was dissolved in methanol, an excess of ethereal hydrogen chloride was added and ether was added. A precipitate was collected to give 7.58 g (72.4%)as a white, crystalline solid, m.p. 171°–173° C.

Analysis: Calculated for $C_{19}H_{22}ClF_2N \cdot 0.5H_2O$: C, 65.80; H, 6.68; N, 4.04. Found: C, 65.79; H, 6.80; N, 4.05.

PREPARATION 90

4-[2,2-Bis(4-fluorophenyl)ethylene]piperidine oxalate[1:1]

A mixture of 8.44 g (0.0266 mole) of α,α-fluorophenyl) -4-piperidineethanol, and 25 ml of concentrated sulfuric acid in 200 ml of glacial acetic acid was heated at reflux for 4 hr. The solvent was removed in vacuo, and the residue was made basic with 50% sodium hydroxide. The basic mixture was extracted with methylene chloride, and the methylene chloride solution was dried over magnesium sulfate. The solvent was removed in vacuo to give an oil. The oil was dissolved in a mixture of methanol/ether, and a slight excess of oxalic acid was added. Ether was added, and a precipitate was collected to give 9.79 g (85.0% yield) of title compound as a white, crystalline solid, m.p. 225°–225.5° C. with decomposition.

Analysis: Calculated for $C_{21}H_{21}F_2NO_4$: C, 64.78; H, 5.44; N, 3.60. Found: C, 64.95; H, 5.56; N, 3.61.

PREPARATION 91

4-[Bis(4-chlorophenyl)methyl]piperidine oxalate hydrate [1:1:0.5]

A mixture of 4-[bis(4-chlorophenyl)methylene]piperidine (13.05 g, 0.041 mole), phosphorus(45.0 g, 1.45 mole), glacial acetic acid (300 ml)and 57% hydriodic acid(230 ml) was heated at reflux for 72 hr. The mixture was cooled to room temperature, stirred 5 min with Celite ®, and filtered. The filtrate was made basic with ice/50% sodium hydroxide. The alkaline layer was extracted with chloroform. The chloroform layer was dried over sodium sulfate, filtered, and solvent removed to give a brown oil. A 0.65 g portion of the oil was converted to the oxalate salt and recrystallized from ethanol-ethyl ether. A white solid was isolated and dried in vacuo overnight at 80° C. This provided 0.46 g (59.1% yield) of white, crystalline solid, m.p. 219°–220° C.

Analysis: Calculated for $C_{20}H_{21}Cl_2NO_4 \cdot 0.5H_2O$: C, 57.29; H, 5.29; N, 3.34. Found: C, 57.26; H, 4.99; N, 3.36.

PREPARATION 92

Cyclohexyl[1-(phenylsulfonyl)-4-piperidinyl]methanone

To a solution of 25.1 g (0.085 mole) of 1-(phenylsulfonyl) -4-piperidine-carboxylic acid, ethyl ester in 500 ml of dry tetrahydrofuran cooled to 0° C. and under an atmosphere of nitrogen, was added 95 ml of a 2 molar solution(0.19 mole) of cyclohexylmagnesium bromide in ether. The mixture was stirred for 2 hr at ambient temperature and then was quenched on an icy solution of ammonium chloride. The mixture was extracted with methylene chloride. The methylene chloride solution was dried over magnesium sulfate, and the solvent was removed in vacuo to give a semisolid material. This was recrystallized from ethanol to give 8.50 g (29.8% yield) of title compound as a white, crystalline solid, m.p. 141°–143° C.

Analysis: Calculated for $C_{18}H_{25}NO_3S$: C, 64.45; H, 7.51; N, 4.18. Found: C, 64.39; H, 7.82; N, 4.20.

PREPARATION 93

4-[2,2-Bis(4-fluorophenyl)ethylene]pyridine

A mixture of 1.57 g (0.0050 mole) of α,α-bis(4-fluorophenyl) -4-pyridineethanol, 10 ml of concentrated sulfuric acid and 80 ml of glacial acetic acid was heated at reflux for 2 hr. The solvent was removed in vacuo, and the residue was made basic with an icy solution of dilute sodium hydroxide. The aqueous mixture was extracted with methylene chloride, and the methylene chloride extract was dried over magnesium sulfate. The solvent was removed in vacuo to give a colorless oil. This was crystallized from ether-hexane to give 0.74 g (50% yield) of title compound as a white, crystalline solid, m.p. 111°–112° C.

Analysis: Calculated for $C_{19}H_{13}F_2N$: C, 77.80; H, 4.47; N, 4.78. Found: C, 77.78; H, 4.42; N, 4.74.

PREPARATION 94

α-Cyclohexyl-α-(4-fluorophenyl)-1(phenylsulfonyl) -4-piperidinemethanol

A solution of (4-fluorophenyl)[1-(phenylsulfonyl) -4-piperidinyl]methanone(20.8 g, 0.06 mole)in 250 ml of tetrahydrofuran (dried over 4A sieves) was prepared. This solution was stirred 0.5 hr under nitrogen atmosphere in an ice bath. Next, cyclohexylmagnesium chloride (35 ml of 2 molar in ethyl ether, 0.070 mole)was added dropwise with a syringe(under nitrogen atmosphere). The resulting solution was stirred for 48 hr allowing the reaction solution to cool to room temperature. The reaction mixture was concentrated to dryness and treated with aqueous ammonium chloride. The aqueous solution was extracted with chloroform, and the chloroform layer was washed with water. The chloroform layer was dried over sodium sulfate and filtered, and solvent removed to give a fluffy, white residue. This material was subjected to flash chromatography on silica gel using 20% ethyl acetate-80% hexanes, and 30% ethyl acetate-70% hexanes for elution. Fractions containing a single spot were combined, and solvent was removed in vacuo. A fluffy, white residue was obtained and dried in vacuo overnight at 80° C. in the presence of phosphorus pentoxide. This procedure produced 16.72 g (74.7% yield) of the title compound as a white, crystalline solid, m.p. 106°–109° C.

Analysis: Calculated for $C_{24}H_{30}FNO_3S$: C, 66.79; H, 7.01; N, 3.24. Found: C, 66.78; H, 7.09; N, 3.21.

PREPARATION 95

α,α-Bis(3-fluorophenyl)-1-piperidinemethanol

To a suspension of 7.78 g (0.33 mole) of magnesium turnings and a crystal of iodine in 800 ml of anhydrous ether under an atmosphere of nitrogen atmosphere was slowly added a solution of 3-bromofluorobenzene in 200 ml of ether. The mixture was stirred for 1.5 hr and 30.6 g (0.103 mole) of ethyl 1-benzenesulfonylisonipecotate was added as a solid. Tetrahydrofuran (300 ml)was added, and the mixture was stirred at room temperature for 12 hr. The mixture was poured into an icy solution of ammonium chloride. The aqueous mixture was extracted with methylene chloride, and the resulting residue was recrystallized from ether to give 24.14 g (52.9%) of the title compound as a white, crystalline solid, m.p. 183°–185° C.

Analysis: Calculated for $C_{24}H_{23}F_2NO_3S$: C, 65.00; H, 5.23; N, 3.16. Found: C, 64.95; H, 5.38; N, 3.15.

PREPARATION 96

4-[Bis(3-fluorophenyl)methyl]piperidine hydrochloride [1:1]

A mixture of 15.25 g (0.0344 mole) of α,α-bis(3-fluorophenyl) -1-phenylsulfonyl-4-piperidinemethanol, 50 mol of 57% hydrogen iodide and 3.4 g (0.11 mole) of phosphorous in 300 ml of glacial acetic acid was heated at reflux for 40 hr. The reaction mixture was filtered, and the solvent was removed from the filtrate in vacuo. The residue was partitioned between methylene chloride and dilute sodium hydroxide. The methylene chloride solution was dried over magnesium sulfate, and the solvent was removed in vacuo. The residue was dissolved in methanol, excess ethereal hydrogen chloride was added and anhydrous ether was added. A white precipitate was collected to give 7.04 g (63.2% yield) of title compound as a white, crystalline solid, m.p. 260°–262° C.

Analysis: Calculated for $C_{18}H_{20}ClF_2N$: C, 66.77; H, 6.23; N, 4.33. Found: C, 66.45; H, 6.26; N, 4.28.

PREPARATION 97

5-Methoxy-2-nitro-4-(phenylmethoxy)benzamide

A solution of 5-methoxy-2-nitro-4-(phenylmethoxy)-benzoic acid(25.84 g, 0.085 mole)and thionyl chloride(200 ml)was heated overnight at gentle reflux in 100 ml of methylene chloride. The reaction mixture was concentrated to dryness and dried in vacuo. To this residue was added 200 ml of dioxane(dried over molecular sieves). Ammonia was slowly added to the solution with constant agitation. A brown solid was formed and the mixture was filtered. The brown solid was washed with dioxane, water, and 2-propanol. The gray solid thus obtained was dried in vacuo at room temperature(23.2 g). A 2 g portion was triturated in refluxing ethanol and then cooled to room temperature. A white solid was collected by filtration and dried in vacuo at 80° C. overnight. This furnished 1.72 g (77.5% yield) of white, crystalline solid, m.p. 222°–223.5° C. with decomposition.

Analysis: Calculated for $C_{15}H_{14}N_2O_5$: C, 59.60; H, 4.67; N, 9.27. Found: C, 59.48; H, 4.68; N, 9.19.

PREPARATION 98

α-Cyclohexyl-α-(4-fluorophenyl)-4-pyridinemethanol

A solution of (4-fluorophenyl)(4-pyridinyl)methanone(23.44 g, 0.12 mole) was prepared in 400 ml of tetrahydrofuran. The solution was chilled in an ice bath and stirred under nitrogen atmosphere for 0.5 hr. A solution of cyclohexylmagnesium chloride (70 ml of a 2 molar solution) was added via syringe and a dark brown solution resulted immediately. This solution was stirred 0.5 hr at room temperature and then heated at reflux for 4 hr. The solution was cooled to room temperature and solvents were removed. The residue was treated with aqueous ammonium chloride and extracted with chloroform. The chloroform layer was dried over sodium sulfate, filtered, and solvent removed to give a dark brown residue. This residue was triturated with ethyl ether and then chilled at about 0° C. and solvent removed to give an oil. This oil was dried in vacuo overnight at 80° C. The oil crystallized to give 2.95 g)33.8% yield) of white crystalline solid, m.p. 78°–81° C.

Analysis: Calculated for $C_{18}H_{20}FN$: C, 80.26; H, 7.48; N, 5.20. Found: C, 79.96; H, 7.45; N, 5.23.

PREPARATION 99

4-[(Cyclohexyl)(4-fluorophenyl)methyl]pyridine

A mixture of the free base of α-cyclohexyl-α-(4-fluorophenyl) -4-pyridinemethanol (16.54 g, 0.058 mole), 57% hydrogen iodide (250 ml), glacial acetic acid (250 ml), and phosphorus (50.0 g) was heated overnight at reflux. The reaction mixture was cooled and filtered with Celite ®. The volume of the filtrate was concentrated to 100 ml. Ice/50% sodium hydroxide was added and the aqueous phase was extracted with chloroform. The chloroform layer was dried over sodium sulfate, filtered, and solvent removed to give a green oil. A 4 g portion of this oil was subjected to flask chromatography on silica gel using 20% ethyl acetate-hexanes for elution. Fractions of similar purity were combined and solvent removed to give an oil. This oil was dried in vacuo overnight at 80° C. The oil crystallized to give 2.95 g (33.9% yield) of white, crystalline solid, m.p. 78°–81° C.

Analysis: Calculated for $C_{18}H_{20}FN$: C, 80.26; H, 7.48; N, 5.20. Found: C, 79.96; H, 7.45; N, 5.23.

PREPARATION 100

4-[(Cyclohexyl)(4-fluorophenyl)methyl]piperidine

A mixture of 4-[(cyclohexyl)(4-fluorophenyl)methyl]pyridine (10.42 g, 0.039 mole), platinum oxide (1.5 g), and 10 drops of concentrated hydrochloric acid in 200 ml of glacial acetic was subjected to hydrogenation at 80° C. and 300 p.s.i. overnight, after which NMR analysis showed 50% desired product and 50% starting material. The reaction was repeated using 5% platinum on carbon at 85° C. and 1400 p.s.i. overnight. The reaction mixture was then cooled to room temperature and filtered. Solvent was removed by rotary evaporator. The oil obtained was dissolved in chloroform and extracted with 5% sodium hydroxide and water. The chloroform layer was dried over sodium sulfate, filtered, and solvent removed to give 9.94 g of brown oil. NMR analysis showed a 75%–25% mixture of product and starting material. The 9.94 g of oil obtained was dissolved in methanol and subjected to flash chromatography on silica gel using methanol and ammonium hydroxidemethanol for elution. Fractions of similar purity were combined and solvent removed. The clear oil obtained was dried in vacuo overnight at 80° C., to give 5.86 g (59.6% yield) of title compound as a clear oil.

$H^1$NMR (CDCl$_3$): δ 6.9–7.2 (d, 7, aromatic), δ 0.8–3.3 (m, 22, aliphatics).

Analysis: Calculated for $C_{18}H_{26}FN$: C, 78.50; H, 9.52; N, 5.09. Found: C, 78.26; H, 9.41; N, 5.06.

PREPARATION 101

1-Acetyl-4-(p-fluorophenyl)piperidine

A mixture of 93 g of (0.7 mole) of aluminum chloride in 150 ml of fluorobenzene was stirred while 70 g (0.37 mole) of 1-acetylisonipecotic acid chloride was added in small portions. After the addition was complete, the mixture was refluxed for 1 hr. The mixture was poured onto ice and the 2 resulting layers were separated. The aqueous layer was extracted twice with chloroform and the chloroform extracts were added to the fluorobenzene which was separated previously. The organic solution was dried over anhydrous sodium sulfate and filtered. The filtrate was concentrated and 73.7 g (80% yield) of 1-acetyl-4-(p-fluorobenzoyl)piperidine was obtained as a crystalline residue. Recrystallization from ligroin-isopropyl ether gave a white, crystalline product melting at 75°–78° C.

Analysis: Calculated for $C_{14}H_{16}FNO_2$: C, 67.45; H, 6.47; N, 5.62. Found: C, 67.26; H, 6.50; N, 5.54.

PREPARATION 102

(4-Fluorophenyl)[1-(phenylsulfonyl)-4-piperidinyl]methanone

A mixture of 4-(4-fluorobenzoyl)piperidine hydrochloride (53.30, 0.219 mole) and benzenesulfonyl chloride (44 g, 0.25 mole) in 500 ml of pyridine was stirred at room temperature overnight. The solvent was removed in vacuo, and the residue was partitioned between methylene chloride and dilute sodium hydroxide. The methylene chloride solution was extracted with dilute sulfuric acid and then dried over magnesium sulfate. The volume was reduced to 400 ml, hexane was added and 39.20 g (50.6%) of title compound was collected as a white, crystalline solid, m.p. 156.5°–158°.

Analysis: Calculated for $C_{18}H_{18}FNO_3S$: C, 62.23; H, 5.22; N, 4.03. Found: C, 62.13; H, 5.20; N, 4.13.

PREPARATION 103

4-[Bis(4-fluorophenyl)methyl]-1-(3-chloropropyl)-piperidine

A solution of 4-[bis(4-fluorophenyl)methyl]-1-piperidinepropanol (40.27 g, 0.117 mole) and thionyl chloride (17.90 g, 0.150 mole) in 350 mL of chloroform was stirred at room temperature for 0.5 hr. The solution was heated at reflux for 6 hr, cooled to room temperature, and then concentrated to dryness. The gum obtained was dissolved in chloroform and extracted with saturated sodium bicarbonate. The chloroform layer was dried (anhydrous sodium sulfate), filtered, and solvent removed to give a reddish-brown oil (42.11 g). An 8 gram sample was subjected to flash chromatography on silica gel using 50-50 v/v of ethyl acetate-hexanes for elution. After combining fractions, removing solvent, and drying the oil obtained in vacuo, 6.84 g (84.6% yield) of brown oil was obtained, the title compound.

$H^1NMR$ ($CDCl_3$): δ: 6.7–7.3 (m, 8, aromatics), 3.4–3.7 (m, 3, methine adjacent to aromatics and methylenes adjacent to Cl), 1.0–3.0 (m, 13, remaining alaphatics).

Analysis: Calculated for $C_{12}H_{24}ClF_2N$: C, 69.32; H, 6.65; N, 3.85. Found: C, 69.09; H, 6.60; N, 3.84.

PREPARATION 104

(4-Fluorophenyl)(4-pyridinyl)methanone

A solution of 4-cyanopyridine (20.8 g, 0.2 mole) in 300 ml of tetrahydrofuan was cooled in an ice bath. Next, a 100 ml solution of p-fluorophenyl magnesium bromide (2 moles in ethyl ether) was added with a syringe under nitrogen atmosphere with stirring. The resulting solution was stirred at room temperature for 1 hr and then heated at reflux for 6 hr. The solution was concentrated to dryness and then transferred (via chloroform) to a mixture of ice and concentrated hydrochloric acid (100 ml). The aqueous phase was made alkaline (using 5% sodium hydroxide solution) and the chloroform layer separated with the aid of Celite®. The chloroform layer was dried over sodium sulfate and filtered, and solvent removed to give a dark brown oil (33.1 g). The oil was subjected to flash chromatography on silica gel using 40% ethyl acetate-hexanes and 50% ethyl acetate-hexanes for elution. Fractions of similar purity were combined and solvent removed to give a yellow solid (25.81 g). A 2 g portion was recrystallized from 100 ml of hexanes. A light yellow solid was isolated and dried in vacuo overnight at room temperature, to give 1.88 g (77.3% yield) of light yellow solid, m.p. 85°–88° C.

Analysis: Calculated for $C_{12}H_8FNO$: C, 71.64; H, 4.01; N, 6.96. Found: C, 71.83; H, 3.95; N, 6.99.

PREPARATION 105

5-Oxo-1-(phenylmethyl)-3-pyrrolidinecarboxylic acid methyl ester

A solution of 158.2 g (1.0 mole) of dimethylitaconate and 107.2 g (1.0 mole) of benzylamine in 750 ml of methanol was let stand at ambient temperature over the weekend. The solution was filtered and the filtrate was concentrated under reduced pressure to give an oil as residue. The oil crystallized when it was triturated with petroleum ether (30°–60° C.). The solid was collected by filtration and dried to yield 225.5 g (97%) of the title compound as a white powder. An analytical sample, m.p. 63°–65° C., was prepared from 2-propyl ether.

Analysis: Calculated for $C_{13}H_{15}NO_3$: C, 66.94; H, 6.48; N, 6.01. Found: C, 66.82; H, 6.48; N, 6.01.

PREPARATION 106

4-[Bis(4-fluorophenyl)hydroxymethyl]-1-(phenylmethyl)-2-pyrrolidinone

A Grignard solution was prepared by the addition of 96.3 g (0.55 mole) of 4-bromofluorobenzene in 150 ml of dry tetrahydrofuran to a mixture of 12.2 g (0.5 mole) of magnesium chips in 250 ml of tetrahydrofuran. After the reaction had subsided, the mixture was diluted with 350 ml of tetrahydrofuran and heated at reflux for 15 min to complete formation.

The Grignard solution was added to a solution of 46.7 g (0.2 mole) of 5-oxo-1-(phenylmethyl)-3-pyrrolidinecarboxylic acid methyl ester in 250 ml of tetrahydrofuran and the mixture was stirred at ambient temperature overnight. The solution was poured into 2.5 liters of a cold ammonium chloride solution. The layers were separated and the aqueous layer was extracted once with 500 ml of methylene chloride and once with 250 ml of methylene chloride. The combined organic layers were washed once with 250 ml of water, once with 250 ml of a 4% sodium hydroxide solution, once with 250 ml of water and once with 250 ml of brine, dried over sodium sulfate and concentrated under reduced pressure to give a gum as residue. The gum crystallized when saturated with petroleum ether. The solid was collected by filtration, washed with petroleum ether and recrystallized from 2-propanol to yield 39.4 g (50%) of the title compound as an off-white solid, m.p. 158°–160° C.

Analysis: Calculated for $C_{24}H_{21}F_2NO_2$: C, 73.27; H, 5.38; N, 3.56. Found: C, 73.09; H, 5.38; N, 3.53.

PREPARATION 107

α,α-Bis(4-fluorophenyl)-1-(phenylmethyl)-3-pyrrolidinemethanol

To a stirred slurry of 7.6 g (0.02 mole) of lithium aluminum hydride in 150 ml of freshly distilled tetrahydrofuran was added dropwise, over a 45 min period, a solution of 38.5 g (0.098 mole) of 4-[bis(4-fluorophenyl)-hydroxymethyl-1-(phenylmethyl)-2-pyrrolidinone in 150 ml of tetrahydrofuran. After the addition was complete, the mixture was heated at reflux for 2 hr and then let stir at ambient temperature overnight. The excess lithium aluminum hydride was decomposed by the successive addition of 8 ml of water, 8 ml of a 15% sodium hydroxide solution, and 24 ml of water. The mixture was stirred for 30 min and filtered. The filtrate was concentrated under reduced pressure and the residue crystallized when triturated with petroleum ether (30°–60° C.). The solid was collected by filtration and recrystallized from 2-propanol to yield 30.3 g (81%) of the title compound as a white solid, mp 99°–100° C.

Analysis: Calculated for $C_{24}H_{23}F_2NO$: C, 75.97; H, 6.11; N, 3.69. Found: C, 76.07; H, 6.06; N, 3.70.

PREPARATION 108

α,α-Bis(4-fluorophenyl)-3-pyrrolidinemethanol

A solution of 26.6 g (0.07 mole) of α,α-bis(4-fluorophenyl)-1-(phenylmethyl)-3-pyrrolidinemethanol in 500 ml of ethanol was hydrogenated at 60 psi and 70° C. over 5% palladium on carbon catalyst for 2 days. The mixture was cooled and filtered through Celite ®. The filtrate was concentrated under reduced pressure to give a solid as residue. The solid was triturated with petroleum ether (30°–60° C.), collected by filtration and dried to yield 18.5 g (91%) of the title compound as a white solid, m.p. 152°–153° C. (2-propanol).

Analysis: Calculated for $C_{17}H_{17}F_2NO$: C, 70.57; H, 5.92; N, 4.84. Found: C, 70.90; H, 6.02; N, 4.83.

PREPARATION 109

4-[(3,4-Difluorophenyl)(4-fluorophenyl)methylene]-piperidine oxalate [1:1]

A mixture of 30.19 g (0.065 mole) of α-(3,4-difluorophenyl)-α-(4-fluorophenyl)-1-phenylsulfonyl-4-piperidine methanol, 4.0 g (0.125 mole) of phosphorus and 160 ml of 47% hydriodic acid in 400 ml of glacial acetic acid was heated at reflux for 52.5 hours. The solvent was removed in vacuo, and the residue was partitioned between methylene chloride and dilute sodium hydroxide. The methylene chloride solution was dried over sodium sulfate and was filtered through a sentered glass funnel (fine porosity), and the solvent was removed in vacuo. The residue was flash chromatographed (silica gel, elution with methanol and then with a 99/1 mixture of methanol/ammonium hydroxide) to give two separate products; the non-salt forms of the title compound and 4-[(3,4-difluorophenyl)(4-fluorophenyl)methyl]piperidine. Both of these were converted to the oxalate salts. The title compound was recrystallized from methanol ether to give 0.47 g (0.24%) of product as a white, crystalline solid, mp 195°–198° C.

Analysis: Calculated for $C_{20}H_{18}F_3NO_4$: C, 61.07; H, 4.61; N, 3.56. Found: C, 60.88; H, 4.57; N, 3.57.

PREPARATION 110

4-[(3,4-Difluorophenyl)(4-fluorophenyl)methyl]piperidine oxalate hydrate [1:1:0.5]

A mixture of 30.19 g (0.065 mole) of α-(3,4-difluoropheny)-α-(4-fluorophenyl)-1-phenylsulfonyl-4-piperidinemethanol, 14.0 g (0.125 mole) of phosphorus and 160 ml of 47% hydriodic acid in 400 ml of glacial acetic acid was heated at reflux for 52.5 hours. The solvent was removed in vacuo, and the residue was partitioned between methylene chloride and dilute sodium hydroxide. The methylene chloride solution was dried over sodium sulfate and was filtered through a sentered glass funnel (fine porosity), and the solvent was removed in vacuo. The residue was flash chromatographed (silica gel, elution with methanol and then with a 99/1 mixture of methanol/ammonium hydroxide) to give two separate products; the non-salt forms of 4-[(3,4-difluorophenyl)(4-fluorophenyl)methylene]-piperidine and the title compound. The title compound was recrystallized from acetonitrile to give 5.64 g. (21.5%) of a white solid, m.p. 78°–83° C.

Analysis: Calculated for $C_{20}H_{20}F_3NO_4 \cdot 0.5H_2O$: C, 59.40; H, 5.23; N, 3.46. Found: C, 59.58; H, 5.05; N, 3.48.

PREPARATION 111

α,α-Bis(4-fluorophenyl)-1-[(4-methylphenyl)sulfonyl]-3-pyrrolidineacetonitrile

The sodium salt of 4-fluoro-α-(4-fluorophenyl)benzeneacetonitrile was prepared in dimethylsulfoxide from 4-fluoro-α-(4-fluorophenyl)benzeneacetonitrile (11.60 g, 0.0506 mole) and sodium hydride (60%; 2.02 g, 0.0506 mole). Next, 1-[(4-methylphenyl)sulfonyl]-3-pyrrolidino(4-methylphenyl)sulfonate ester (20.0 g, 0.0506 mole) in 200 ml of dimethyl sulfoxide was added. The solution was stirred overnight at 55° C. The solvent was then removed. A dark brown oil was obtained and dissolved in chloroform. The organic layer was extracted with 1N sulfuric acid and 5% sodium hydroxide. The chloroform layer was dried (over sodium sulfate) and filtered; solvent was removed to give a dark brown oil. The oil was triturated with 2-propanol and placed in the freezer over the weekend. A brown solid was separated by filtration (18.33 g). A one gram sample of the solid was recrystallized from 2-propanol. A light brown solid was separated and dried in vacuo overnight at 80° C. in the presence of phosphorus pentoxide. This process furnished 0.57 g (45.7% based on aliquot taken) of light brown solid, m.p. 181°–183° C.

Analysis: Calculated for $C_{25}H_{22}F_2N_2O_2S$: C, 66.36; H, 4.90; N, 6.19. Found: C, 65.80; H, 4.91; N, 6.03.

PREPARATION 112

α,α-Bis(4-fluorophenyl)-3-pyrrolidineactonitrile oxalate hydrate [1:1:0.5]

A mixture of α,α-bis(4-fluorophenyl)-1-[(4-methylphenyl)sulfonyl]-3-pyrrolidineacetonitrile (16.6 g, 0.0367 mole), phenol (50 g, 0.53 mole) and 300 ml of 48% hydrobromic acid was heated at reflux for two hours. The reaction mixture was cooled to room temperature and made alkaline with ice/50% sodium hydroxide. The aqueous layer was extracted with chloroform. The chloroform layer was back extracted with 5% sodium hydroxide, dried over sodium sulfate, filtered, and solvent removed to produce a dark brown oil. The dark brown oil was dissolved in chloroform and extracted with 1N sulfuric acid. This acidic layer was discarded. The chloroform layer was extracted with base and solvent was removed to give a dark brown oil. This oil was converted to the oxalate salt, and the salt was recrystallized from methanol-ethyl ether. A white solid was isolated and dried in vacuo overnight at 80° C., to give 7.17 g (49.2%) of the title compound as an off-white solid, mp 88.5°–90° C.

Analysis: Calculated for $C_{20}H_{18}F_2N_2O_4 \cdot 0.5H_2O$: C, 60.45; H, 4.82; N, 7.05. Found: C, 60.52, H, 4.56; N, 7.01.

PREPARATION 113

1-[(4-Methylphenyl)sulfonyl]-3-piperidinemethanol(4-methylphenyl)sulfonate ester A solution of 3-piperidinemethanol (50.0 g, 0.434 mole) in 300 ml of acetonitrile (dried over 4A molecular sieves) was prepared. This solution was cooled in an ice bath, and a solution of triethylamine (150 ml in 200 ml of acetonitrile) was added while simultaneously adding a solution of p-toluenesulfonyl chloride (191 g, 1.0 mole) in 300 ml of acetonitrile. After the additions were complete, the resulting solution was stirred 3.5 hours at room temperature. The mixture was filtered and solvents were removed by a rotary evaporator to give a dark brown oil. The oil was dissolved in chloroform and extracted with 5% sodium hydroxide and also 1N sulfuric acid. The chloroform layer was dried over sodium sulfate and filtered, and solvent was removed to give a dark brown oil. This oil was triturated with isopropyl ether to give a brownish-white solid. This light brown solid was separated and then triturated with hot 2-propanol. The mixture was chilled in the freezer and filtered. A light brown solid was isolated and dried in vacuo overnight at 65° C. (142.29 g). A 5 gram sample of this material was recrystallized from isopropyl alcohol, and the brown solid isolated was dried overnight in vacuo at 80° C. This provided 3.55 g (55% yield based on aliquot taken) of light brown solid, m.p. 108°–109° C.

Analysis: Calculated for $C_{20}H_{25}NO_5S_2$: C, 56.72; H, 5.95; N, 3.31. Found: C, 56.43; H, 6.00; N, 3.32.

PREPARATION 114

α,α-Bis(4-fluorophenyl)-1-[(4-methylphenyl)sulfonyl]-3-piperidinepropanenitrile

The sodium salt of 4-fluoro-60-(4-fluorophenyl)benzeneacetonitrile was prepared in 350 ml of dimethyl sulfoxide (dried over 4A molecular sieves) from sodium hydride (60% 4.37 g, 0.109 mole) and 4-fluoro-α-(4-fluorophenyl)benzeneacetonitrile (25.0 g, 0.109 mole). The resulting dark brown solution was stirred at room temperature for 1 hour. 1-[(4-Methylphenyl)sulfonyl]-piperidinemethanol (4-methylphenyl)sulfonate ester (46.18 g, 0.109 mole) was added and the resulting solution was stirred for 2 hours at room temperature. The solution was then stirred overnight at 60° C. The dimethyl sulfoxide was removed by rotary evaporator. A dark brown residue was obtained which was dissolved in chloroform. The chloroform layer was extracted several times with water. The chloroform layer was dried over sodium sulfate, filtered, and solvent removed to give a thick brown oil. The oil was triturated with isopropyl ether to give a white solid (46.54 g). A 5 g portion of this solid was recrystalizzed from 2-propanol to give a white solid and was isolated and dried in vacuo overnight at 80° C. This furnished 3.96 g (70.4% yield) of the title compound as a white, crytalline product, m.p. 142°–143° C.

Analysis: Calculated for $C_{27}H_{26}F_2N_2O_2S$: C, 67.48; H, 5.45; N, 5.83. Found: C, 67.17; H, 5.46; N, 5.75.

PREPARATION 115

α,α-Bis(3,4-difluorophenyl)-1-(phenylsulfonyl)-4-piperidinemethanol

To a mechanically stirred mixture of 2.70 g (0.11 mole) of magnesium turnings and a crystal of iodine in 100 ml of dry tetrahydrofuran was slowly added a solution of 19.6 g (0.102 mole) of 1,2-difluoro-4-bromobenzene in 50 ml of tetrahydrofuran. The three-necked reaction flask was fitted with a reflux condenser, and the reaction mixture was stirred under an atmosphere of nitrogen. The mixture was stirred for 1 hour, and 11.88 g (0.040 mole) of ethyl N-benzenesulfonyl isonipecotate was added as a solid. The solution was stirred at 23° C. for 12 hours and was poured into an icy solution of ammonium chloride. The aqueous mixture was extracted with methylene chloride, and the methylene chloride solution was dried over magnesium sulfate. The solvent was removed in vacuo, and the residue was recrystallized from methylene chloride-hexane to give 17.43 g (90%) of the title compound as a white solid, m.p. 152°–154° C.

Analysis: Calculated for $C_{24}H_{21}F_4NO_3S$: C, 60.12; H, 4.41; N, 2.92. Found: C, 60.18; H, 4.40; N, 2.95.

PREPARATION 116

α,α-Bis(4-fluorophenyl)-3-piperidinepropanenitrile

A mixture of α,α-bis(4-fluorophenyl)-1-[(4-methylphenyl)sulfonyl]-3-piperidinepropanenitrile (41.21 g, 0.0858 mole) and phenol (100 g, 1.06 mole) was heated at reflux for 2 hours. the reaction mixture was cooled to room temperature and made alkaline with ice and 50% sodium hydroxide. The aqueous layer was extracted with chloroform. The chloroform layer was back extracted with 5% sodium hydroxide. The organic layer was then dried over sodium sulfate and filtered and solvent was removed to give a dark brown oil. This oil was subjected to flash chromatography on silica gel using methanol for elution. Fractions of similar purity were combined and solvent removed. The oil obtained was dried in vacuo overnight at 80° C., to give 18.83 g (67.2% yield) of brown oil.

$H^1$NMR ($CDCl_3$): δ 6.9–7.6 (m, 8, aromatics) 1.1–3.1 (m, 12, aliphatics).

Analysis: Calculated for $C_{20}H_{20}F_2N_2$: C, 73.60; H, 6.18; N, 8.58. Found: C, 73.19; H, 6.11; N, 8.56.

PREPARATION 117

4-[Bis(3,4-difluorophenyl)methylene]piperidine oxalate [1:1]

A mixture of 15.0 g (0.0313 mole) of 60, α-bis(3,4-difluorophenyl)-1-(phenylsulfonyl)-4-piperidinemethanol, 21 g (0.22 mole) of phenol, and 200 ml of 48% hydrobromic acid was heated at reflux for 5 hours and stirred at ambient temperature for 6 hours. The reaction mixture was poured over ice, and the mixture as made basic with 50% sodium hydroxide solution. The basic mixture was extracted with methylene chloride, and the methylene chloride solution was dried over magnesium sulfate. The solvent was removed in vacuo. The residue was dissolved in 300 ml of methanol, 2.90 g (0.032 mole) of oxalic acid was added, and the volume of the solution was reduced to 200 ml. Ether was added until the solution became cloudy, and the solution was placed in the freezer. A white solid was collected to give 8.91 g (69.3%) of the title compound as a crystalline solid, m.p. 202°–203° C.

Analysis: Calculated for $C_{20}H_{17}F_4NO_4$: C, 58.40; H, 4.17; N, 3.41. Found: C, 58.28; H, 4.11; N, 3.38.

PREPARATION 118

4-[α,α-Bis(3-fluorophenyl)hydroxymethyl]-1-phenylmethylpiperidine fumarate [1:1]

A Grignard solution was prepared from 100 g (0.57 mole) of 1-bromo-3-fluorobenzene and 12.2 g (0.5 mole) of magnesium chips in 750 ml of dry tetrahydrofuran. This solution was treated with a solution of 45.8 g (0.185 mole) of ethyl-N-benzylisonipecotate in 250 ml of dry tetrahydrofuran and the mixture was stirred at ambient temperature overnight. The solution was poured into 2.5 liters of a saturated ammonium chloride solution and the layers were separated. The aqueous layer was extracted once with 500 ml of methylene chloride and twice with 250 ml of water, 250 ml of a 4% sodium hydroxide solution, 250 ml of water and 250 ml of brine, dried over sodium sulfate and concentrated to give a glass as residue. The glass was dissolved in 2-propanol and converted to the fumaric acid salt. The solid was collected by filtration and dried to yield 85 g (90%) of the title compound as a white solid. An analytical sample was recrystallized from acetonitrile-water, m.p. 212°–214° C. with decomposition.

Analysis: Calculated for $C_{29}H_{29}F_2NO_5$: C, 68.36; H, 5.74; N, 2.75. Found: C, 68.46; H, 5.74; N, 2.83.

PREPARATION 119

4-[α,α-Bis(3-fluorophenyl)hydroxymethyl]piperidine

A solution of 39.3 g (0.1 mole) of the free base of 4-[α,α-bis(3-fluorophenyl)hydroxymethyl]-1-phenylmethylpiperidine (free base obtained in Preparation 118) in 750 ml of absolute ethanol was hydrogenated over 5% palladium on carbon in a Parr apparatus at 50 psi and 60° C. for 3.5 days. The mixture was cooled and filtered through Celite ®. The filtrate was concentrated and the residue was dissolved in ethyl ether and filtered through cotton to remove some insoluble material. The filtrate was concentrated to give a gum which crystallized when triturated with petroleum ether (30°–60° C.). The solid was collected by filtration and dried to yield 27.9 g (92%) of the title compound as a white solid. An analytical sample, m.p. 117°–118° C., was recrystallized from 2-propyl ether 2-propanol.

Analysis: Calculated for $C_{18}H_{19}F_2NO$: C, 71.27; H, 6.31; N, 4.62. Found: C, 71.24; H, 6.27; N, 4.66.

PREPARATION 120

1-Phenylsulfonyl-4-piperidinecarboxylic acid

In the preparation of α,α-bis(3,4-difluorophenyl)-1-(phenylsulfonyl)-4-piperidinemethanol, the title compound was obtained as a side product. To a mixture of 6.56 g (0.27 mole) of magnesium trimmings and a few crystals of iodine in 500 ml of anhydrous ether under an atmosphere of nitrogen was slowly added a solution of 49.0 g (0.25 mole) of 4-bromo-1,2-difluorobenzene in 100 ml of diethyl ether. The mixture was then stirred for 45 min. Ethyl N-benzenesulfonylisonipecotate (32.77 g, 0.11 mole) was added as a solid, and a gum formed in the bottom of the reaction flask after 20 min. Dry tetrahydrofuran (200 ml) was added, and the reaction mixture was stirred for an additional hour. The reaction mixture was poured into an icy aqueous solution of ammonium chloride. The organic and aqueous phases were separated and the aqueous phase was extracted with several portions of ether. The organic phases were combined and drived over magnesium sulfate, and the solvent was removed in vacuo to give an oil. A NMR of this oil shows it to be a mixture of 4-(phenylthio)butanamide and ethyl N-benzenesulfonylisonipecotate. A solution of the reaction mixture oil in 800 ml of 95% ethanol and 200 ml of 10% was heated at reflux for 16 hr. The solvent was removed in vacuo, and the residue was partitioned between methylene chloride and dilute sodium hydroxide solution. The methylene chloride solution was concentrated to give 32.89 g (62.4%) of α,α-bis(3,4-difluorophenyl)-1-(phenylsulfonyl)-4-piperidinemethanol. The aqueous solution was made acidic with dilute sulfuric acid solution, and the acidic solution was extracted with methylene chloride. The methylene chloride solution was dried over magnesium sulfate. The solvent was removed in vacuo, and the residue was recrystallized from methylene chloride-hexane to give 5.36 g (18.1%) of the title compound as a crystalline solid, m.p. 156°–157.5° C.

Analysis: Calculated for $C_{12}H_{15}NO_4S$: C, 53.52; H, 5.61; N, 5.20. Found: C, 53.19; H, 5.54; N, 5.16.

PREPARATION 121

4-[α,α-Bis(3,4-difluorophenyl)methyl]pyridine

A mechanically stirred mixture of 49.0 g (0.43 mole) 1,2-difluorobenzene, 20.6 g (0.19 mole) of 4-carboxaldehyde and 80 ml of concentrated sulfuric acid was heated at 70° C. for 21 hr. The reaction mixture was poured over ice, and the icy mixture was made basic with 50% sodium hydroxide solution. The resulting mixture was extracted with methylene chloride and the methylene chloride solution was dried over sodium sulfate. The solvent was removed in vacuo to give 54.95 g (89.8%) of a solid. This was recrystallized from a mixture of methylene chloride and hexane to give 44.82 g (74.3%) of the title compound as a crystalline solid, m.p. 79°–82° C. Proton NMR showed that this sample contained ~5% of the 2,3-difluoro isomer.

Analysis: Calculated for $C_{18}H_{11}F_4N$: C, 68.14; H, 3.50; N, 4.14. Found: C, 68.14; H, 3.36; N, 4.46.

PREPARATION 122

4-(3,4-Difluorobenzoyl)pyridine hydrochloride [1:1]

To a mechanically stirred mixture of 3.36 g (0.14 mole) of magnesium turnings and a few crystals of iodine in 300 ml of tetrahydrofuran under a nitrogen atmosphere was added dropwise a solution 25.48 g (0.13 mole) of 1,2-difluoro-4-bromobenzene in 50 ml of tetrahydrofuran. The mixture was stirred at ambient temperature for 1 hr, and 14.0 g (0.14 mole) of 4-cyanopyridine was added as a solid. The mixture was stirred for 7 hr at room temperature and then was poured over ice. The icy mixture was made acidic with dilute sulfuric acid solution, and the aqueous acidic solution was allowed to stand for 40 hr. The aqueous solution was made basic with ammonium hydroxide, and was extracted with methylene chloride. The methylene chloride layer was dried over magnesium sulfate, and the solvent was removed in vacuo. The residue was subjected to flash column chromatography (silica gel, gradient elution with methylene chloride/methanol) to give 1.80 g of the nonsalt form of the title compound which was converted to the hydrochloride salt, and recrystallized from methanol-ether to give 1.40 g (4.2%) of the title compound as a white, crystalline solid, m.p. 146°–148° C. with decomposition.

Analysis: Calculated for $C_{12}H_8ClF_2NO$: C, 56.38; H, 3.15; N, 5.48. Found: C, 56.41; H, 3.07; N, b 5.49.

PREPARATION 123

4-[Bis(3,4-difluorophenyl)methyl]piperidine hydrochloride [1:1]

A mixture of 4-α,α-bis(3,4-difluorophenyl)methyl]pyridine (20.05 g, 0.063 mole) in glacial acetic acid (200 ml), concentrated hydrochloric acid (8 ml) and 5% platinum on carbon catalyst (3.0 g) was subjected to hydrogenation for 3 days at 60° C. The reduction mixture was filtered through Celite ®, and the solvent removed in vacuo. The residue obtained was partitioned between methylene chloride and dilute sodium hydroxide. The solvent was dried over magnesium sulfate, filtered, and solvent removed to give an oil. The oil was pumped in vacuo to a weight of 19.18 g (clear oil).

The oil was first dissolved in methanol and a white solid crystallized. Methanol was removed by a rotary evaporation and the white solid was dissolved in a small amount of methylene chloride and placed on a flash chromatography column. The column was eluted with methanol and 1/99 ammonium hydroxide/methanol. Fractions of similar purity were combined and solvent removed to give a clear oil (15.30 g, 67.5% yield). A 2-g portion of the oil was dissolved in isopropyl alcohol and treated with ethereal hydrogen chloride. A white solid was isolated and dried in vacuo overnight at 80° C. to give 1.35 g (41% yield) of white, crystalline solid, m.p. 263°–268° C.

Analysis: Calculated for $C_{18}H_{18}ClF_4N$: C, 60.09; H, 5.04; N, 3.89. Found: C, 59.71; H, 5.01; N, 3.87.

PREPARATION 124

4-[α,α-Bis(2,4-difluorophenyl)methyl]pyridine hydrochloride [1:1]

Sulfuric acid (40 ml) was cooled in an acetone-dry ice bath. 1,3-Difluorobenzene (45.6 g, 0.4 mole) was added with stirring while maintaining a temperature of 0° C. The resulting solution was allowed to stir until room temperature was obtained. Next, 4-pyridinecarboxaldehyde (21.4 g, 0.2 mole) was added dropwise to the reaction mixture while maintaining a temperature of 0° C. The reaction mixture was stirred until room temperature was obtained and the reaction mixture was then stirred overnight at 70° C. The reaction mixture was cooled to room temperature and made alkaline with ice/50% sodium hydroxide solution. The aqueous layer was extracted several times with chloroform and the organic layer was back extracted with 5% sodium hydroxide solution. The chloroform layer was dried over sodium sulfate and filtered. The organic solvent was removed to give a clear oil (28.30 g, 49.6% yield). A one gram portion of the clear oil was dissolved in 2-propanol and treated with ethereal hydrogen chloride. A white crystalline solid formed and was separated. The solid was dried in vacuo overnight at 80° C. This furnished 0.97 g (39%) of the title compound as a white crystalline solid, m.p. 218°–222° C.

Analysis: Calculated for $C_8H_{12}ClF_4N$: C, 61.12; H, 3.42; N, 3.96. Found: C, 61.00; H, 3.32; N, 3.94.

PREPARATION 125

4-Ethyl-2-methoxyphenol

A mixture of zinc powder, 150 ml of water and 49.9 g (0.3 mole) of acetovanillone was stirred and treated dropwise with 150 ml of concentrated hydrochloric acid. The solution was heated at reflux for 3.5 hr, during which time, after each hour, 10 ml of additional concentrated hydrochloric acid was added. After 3.5 hr the solution was diluted with ethyl alcohol and treated with aqueous ferric chloride solution. The mixture was cooled and filtered and the filter cake washed with water and the combined filtrates saturated with sodium chloride and extracted with ethyl ether (3×150 ml). The combined extracts were dried over sodium sulfate and concentrated to yield 1.4 g of a pink oil. The filter cake was washed with 250 ml of ethyl ether. The mixture was filtered and the filtrate dried over sodium sulfate and concentrated to a gum residue. The above obtained pink oil and gum residue were combined and chromatographed on a 750 g column of silica gel using 1:1 benzene:ligroin as the eluting solvent. Appropriate fractions were combined and concentrated to give 13.2 g (29% yield) of the title compound as an oil.

PREPARATION 126

4-α,α-[Bis(4-fluorophenyl)methyl]-1-piperidine-[(3-chloropropyl)propane]

A solution of 4-[α,α-bis(4-fluorophenyl)methyl]-piperidine, 3-bromopropanol and potassium carbonate in acetonitrile is refluxed for 12 hr to give 4-[α,α-bis(4-fluorophenyl)methyl]-1-piperidinepropanol, which is then reacted neat for approximately 2 hr with thionyl chloride to give the hydrochloride salt of the title compound; which is reacted with sodium bicarbonate in chloroform to give the title compound.

PREPARATION 127

3-(3-Chloropropoxy)benzoic acid ethyl ester

A mixture of 25 g (0.149 mole) of ethyl-3-hydroxybenzoate, 46.9 g (0.3 1 mole) of 1-bromo-3-chloropropane and 62 g (0.45 mole) of anhydrous potassium carbonate in one liter of acetone was heated at reflux for ~23 hr. The mixture was cooled, filtered, and the filtrate concentrated to give an oil as residue. The oil was dissolved in 200 ml of benzene, treated with potassium hydroxide pellets and stirred for 1 hr. The mixture was filtered through Celite ® and the filtrate was concentrated to give 36.5 g of oil as residue. NMR analysis showed it was the desired product.

PREPARATION 128

1-[(Diethylamino)carbonly]-4-piperidine carboxylic acid ethyl ester

To a solution of 72.4 g (0.46 mole) of ethylisonipecotate and 46.5 g (0.46 mole) of triethylamine in 400 ml of methylene chloride was added dropwise with stirring a solution of 62.4 g (0.46 mole) of diethylcarbamyl chloride in 100 ml of methylene chloride. The reaction was exothermic and the reaction mixture began to reflux during addition of the diethylcarbamoyl chloride solution. The mixture was allowed to stir at ambient temperature for 24 hr and then treated with 50 ml of water. The layers were separated, and the organic layer washed with 25 ml of a 2N hydrochloric acid (twice), 50 ml of a saturated sodium bicarbonate solution, 100 ml of a saturated sodium chloride solution and dried over sodium sulfate and finally concentrated to give a tan oil. The oil was subjected to vacuum distillation and appropriate fractions (0.2–0.5 mm Hg, bp 112°–118° C.) collected to give 100.6 g (85% yield) of the desired product.

PREPARATION 129

3-(4-Ethyl-2-methoxyphenoxy)propyl chloride

A mixture of 13.2 g (0.87 mole of 4ethyl-2-methoxyphenol, 27.3 g (0.173 mole) of 1-bromo-3-chloropropane, 35.9 g (0.26 mole) of anhydrous potassium carbonate and 500 ml of acetone was heated at reflux for 20 hr. The reaction mixture was cooled, filtered and the filtrate concentrated to give 18.7 g (94% yield) of oil as a residue. The oil was chromatographed on a 400 g silica gel column using 2:1 benzene:ligroin as the eluting solvent and appropriate fractions collectred. NMR indicated approximately 10–15% of the starting phenol compound remained. The oil was dissolved in 250 ml of benzene and stirred with potassium hydroxide pellets for approximately 4 hr. The mixture was filtered

PREPARATION 130

1-Chloro-3-(4-isopropylphenoxy)propane

A mixture of 27.4 g (0.2 mole) of p-isopropylphenol, 63 g (0.4 mole) of 1-bromo-3-chloropropane and 82.9 g (0.6 mole) of anhydrous potassium carbonate in 1 liter of acetone was heated at reflux for 24 hr. The reaction mixture was cooled, filtered and filtrate concentrated. The residue was dissolved in 200 ml of benzene and treated with potassium hydroxide pellets to remove excess starting phenol. The mixture was stirred in ambient temperature for 0.5 hr, filtered through Celite ® and the filtrate concentrated to give 36.4 g (87% yield) of the title compound as an oil.

PREPARATION 131

1-Chloro-3-(4-methylphenoxy)propane

A mixture of 27 g (0.25 mole) of p-cresol, 78.7 g (0.5 mole) of 1-bromo-3-chloropropane and 103.7 g (0.75 mole) of anhydrous potassium carbonate in 1 liter of acetone was heated at reflux for 24 hr. The reaction mixture was cooled, filtered and concentrated in vacuo at 90° C. to give 47.1 g of an oil residue. The oil was subjected to vacuum distillation to give 39.3 g (85%) of clear oil, bp 85°–90° C. at 0.1 mm Hg.

PREPARATION 132

3-(2-Benzyloxyphenoxy)propyl chloride

A mixture of 50 g (0.25 mole) of 2-benzyloxyphenol, 78.7 g (0.5 mole) of 1-bromo-3-chloropropane and 103.7 g of anhydrous potassium carbonate in 1 liter of actone was heated at reflux for 24 hr. The reaction mixture was cooled, filtered and concentrated in vacuo to give 67.2 g of a tan oil as residue. The oil was dissolved in 300 ml of ethyl ether and washed with 100 ml of a 5% sodium hydroxide solution. A solid precipitated, about 200 ml of water was added and the precipitated sold redissolved. Solvent layers were separated and the ethyl ether layer washed twice with a 5% sodium hydroxide solution. The organic layer was next washed with water, brine, and dried over sodium sulfate and concentrated to give 58.4 g (84%) of oil as product.

PREPARATION 133

1-[4-(3-Chloropropoxy)-2-methoxyphenyl]ethanone

A solution of 4-hydroxy-2-methoxyacetophenone, 1-bromo-3-chloropropane and potassium carbonate in acetone is heated at reflux for about 12 hr to give the title compound.

PREPARATION 134

1-[4-(3-Chloropropxy)-3-methoxyphenyl]ethanone

A solution of acetovanillone, 1-bromo-3-chloropropane and potassium carbonate in acetone is refluxed for about 12 hr to give the title compound.

PREPARATION 135

4-[Bis(2,4-difluorophenyl)methyl]piperidine hydrochloride [1:1]

A mixture of the free base of 4-[α,α-bis(2,4-difluorophenyl)methyl]pyridine hydrochloride [1:1](23.84 g, 0.0752 mole) and 5% platinum on carbon (2.0 g) was subjected to hydrogenation for three days at 60° C. in 400 ml of glacial acetic acid containing 3 ml of concentrated hydrochloric acid. Following hydrogenation, the reaction mixture was cooled to room temperature and filtered. Solvent was removed by rotary evaporator. The residue obtained was dissolved in chloroform and extracted with 5% sodium hydroxide. The chloroform layer was dried over sodium sulfate and filtered. The chloroform layer was removed by rotary evaporator to give a dark residue (24.40 g quantitative). A one-gram sample of this material was converted to the hydrochloride salt and recrystallized from methanol-ethyl ether. A white solid was obtained and dried in vacuo overnight at 80° C. This provided 1.06 g (95.2%) of white, crystalline solid, mp 215°–217° C.

Analysis: Calculated for $C_{18}H_{18}ClF_4N$ : C,60.09;H, 5.04;N, 3.89. Found: C, 59.77;H, 5.02; N, 3.87.

PREPARATION 136

1-(Phenylmethyl)-4-piperidinol 4-methylbenzenesulfonate (ester) hydrochloride [1:1]

A solution of 1-benzyl-4-hydroxypiperidine (95.6 g, 0.5 mole) in 500 ml of pyridine was cooled in an ice bath. To this solution was added dropwise a solution of tosyl chloride (133.5 g, 0.7 mole) in 400 ml of acetonitrile (dried over 4A molecular sieves). Upon the addition to the second solution, a color change from yellow to dark-red was observed. The resulting solution was stirred at room temperature for 4.5 hours. The reaction mixture was concentrated to dryness, and a dark-brown mass was obtained. This material was dissolved in chloroform and extracted with 5% sodium hydroxide. The chloroform layer was dried over sodium sulfate and filtered. The chloroform layer was removed in vacuo to give a dark brown mass. This material was converted to the salt, and the salt was recrystallized from emthanolethyl ether. A light brown solid was isolated and dried in vacuo overnight at 80° C. This procedure provided 68.17 g (35.8%) of light brown solid, mp 169°–171.5° C.

Analysis: Calculated for $C_{19}H_{24}ClNO_3S$:C, 59.75;H, 6.33;N, 3.67.Found: C, 59,74;H, 6.38;N, 3.69.

PREPARATION 137

α, α-Bis(3,4-difluorophenyl)-4-pyridinemethanol

To a magnetically stirred solution of ethyl isonicotinate in dry tetrahydrofuran at 0° C. and under an atmosphere of nitrogen is slowly added a solution 2.2 equivalents of 3,4-difluorophenyl magnesium bromide in tetrahydrofuran. The solution is stirred at ambient temperature of 4 hr and is poured into an icy solution of ammonium chloride. The mixture is extracted with methylene chloride, and the organic phase is dried (sodium sulfate). The solvent is removed in vacuo to give a solid. This solid is recrystallized from methylene chloride/hexane to give the title compound as a white, crystalline solid, mp 147°–149° C.

Analysis: Calculated for $C_{18}H_{11}F_4NO$: C, 64.87;H, 3.33;N, 4.20. Found: C,64.54;H, 3.22; N, 4.20.

PREPARATION 138

4-[Bis-(4-fluorophenyl)methyl]-1-(phenylsulfonyl)-piperidine

A solution of 15.18 g (0.0529 mole) of 4-[bis(4-flurophenyl)methylene]piperidine and 10,89 g (0.0617 mole) of benzenesulfonyl chloride in 350 ml of pyridine was stirred at room temperature for 16 hr. The solvent was removed in vacuo, and the residue was partitioned between methylene chloride and dilute sulfuric acid. The methylene chloride solution was extracted with dilute sodium hydroxide, and the methylene chloride solution was dried over sodium sulfate. The solvent was removed in vacuo, and the residue was dissolved in 200 ml of methanol. A precipitate was collected. This was recrystallized from methylene chloride - methanol to give 11.14 g (49.3%) of the title compound as a white solid: mp 180–184° C.

Analysis: Calculated for $C_{24}H_{23}F_2NO_2S$: C,67.43;H,5.42;N,3.28. Found: C,67.17;H,5.42;N,3.27.

PREPARATION 139

α,α-Bis(3,4-difluorophenyl)-4-piperidinemethanol oxalate hydrate [1:0.5:0.5]

A solution of 4.02 g (0.012 mole) of α,α-bis(3,4difluorophenyl)-4-pyridinemethanol in 150 ml of glacial acetic acid was subjected to catalytic hydrogenation with 0.70 g of 5% platinum on carbon (Parr hydrogenation apparatus; 53 psi of hydrogen) at room temperature for 70 hr. The solution was filtered through Celite ®, and the solvent was removed in vacuo.

The residue was partitioned between methylene chloride and dilute sodium hydroxide, and the methylene chloride solution was dried over sodium sulfate. The solvent was removed in vacuo to give a white solid. This was dissolved in methanol, 1.0 g(0.011 mole) of oxalic acid was added, and anhydrous ether was added. After being cooled in the freezer, the solution produced 0.51 g (10.9%) of the title compound as a white crystalline solid. Anhydrous ether was added to the filtrate, and the solution was placed in the freezer. An additional 2.70 g (57.3%) of the title compound was collected as a white solid: mp 278°–279°. C. (dec).

Analysis: Calculated for $C_{19}H_{18}NO_3 0.5H_2O$: C,58.02;H, 4.87;N, 3.56. Found: C,58.42;H, 4.66;N, 3.61.

PREPARATION 140

α-(4-Fluorophenyl)-α-(4-piperidinyl)-2-pyridinemethanol

To a stirred solution of 36.3 g (0.23 mole) of 2-bromopyridine in 500 ml of anhydrous tetrahydrofuran (THF) at −65° C. was added 88 ml (0.22 mole) of a commercial solution of 2.5 molar n-butyllithium in hexane at such a rate that the temperature did not exceed −60° C. The dark solution was stirred at −65° C. for 1 hr and then treated dropwise with a solution of 24.9 g (0.1 mole ) of 1-acetyl-4-(p-fluorobenzoyl)piperidine in 250 ml of THF at such a rate that the temperature did not exceed −60° C. The mixture was stirred for 1 hr at −65° C. and overnight at ambient temperature. The dark mixture was poured into 2 liters of a saturated ammonium chloride solution. The layers were separated and the aqueous layer was extracted once with a 500-ml portion of methylene chloride. The combined organic layers were washed successively with 500 ml of water, 500 ml of a 4% sodium hydroxide solution, 250 ml of water, and 250 ml of brine.

All of the aqueous layers were combined and allowed to stand in a filter flask for several weeks. As the soluble organic solvents in the aqueous solution evaporated, a solid precipitated. The aqueous solution was decanted and the solid was slurried with water, collected by filtration, and dried. The solid was recrystallized from absolute ethanol-pyridine to yield 4.5 g(14%) of the title compound as an off-white solid, mp 228°–230° C. (dec).

Analysis: Calculated for $C_{17}H_{19}FN_2O$: C,71.31;H,6.69;N,9.78. Found: C,71.43;H,6.54;N,9.52.

PREPARATION 141

α,α-Bis(4-fluorophenyl)-1-(phenylmethyl)-3-piperidinemethanol

The title compound was synthesized by the procedure described in Preparation 4, except that 1-phenylmethyl-3-piperidine carboxylic acid ethyl ester was used in place of 1-(phenylmethyl)-4-piperidinecarbhoxylic acid ethyl ester hydrochloride. The melting range of the white solid thus obtained was 104°–111.5° C.

Analysis: Calculated for $C_{25}H_{25}F_2NO$: C,76.31;H,6.40;N,3.55. Found: C,76.75;H,6.46;N,3.55.

PREPARATION 142

[α,α-Bis(4-fluorophenyl)]-3-pyridineethanol

A Grignard solution was prepared from 19.4 g (0.8 mole) of magnesium chips and 148.8 g (0.85 mole) of 1-bromo-3-fluorobenzene in 1.25 liters of dry tetrahydrofuran (THF). To this solution was added in a stream a solution of 41.3 g (0.25 mole) of ethyl-3-pyridylacetate (Aldrich) in 250 ml of THF. The mixture was stirred at ambient temperature overnight and then poured into 2.5 liters of saturated ammonium chloride solution. The layers were separated and the aqueous layer was extracted once with 500 ml of methylene chloride and twice with 250 ml of methylene chloride. The combined organic layers were washed successively with 250 ml water, 250 ml of a 4% sodium hydroxide solution, 250 ml of water and 250 ml of brine. The organic layer was dried (over sodium sulfate) and concentrated to give a gum which crystallized when triturated with a mixture of 100 ml of petroleum ether (30°–60° C.) and 100 ml of 2-propyl ether. The solid was collected by filtration, air dried and slurried with 500 ml of water.

The solid was collected by filtration, washed with petroleum ether and dried to yield 32.5 g of tan solid. Mass spec shows m/e=312. The solid was slurried with 500 ml of water, collected by filtration and dried.

The solid was next heated to reflux in ~300 ml of 2-propanol and filtered to remove insolubles. The filtrate was concentrated to give a solid residue. The solid was recrystallized from cyclohexane-benzene to yield 24.3 g(31%) of off-white solid, mp 137°–141° C.

Analysis: Calculated for $C_{19}H_{15}F_2NO$: C,73.30;H,4.86;N,4.50. Found: C73.42;H,4.77;N,4.51.

PREPARATION 143

[α,α-Bis(4-fluorophenyl)]-3-piperidineethanol hydrochloride[1:1]

A mixture of 23.8 g (0.076 mole) of [α,α-bis(4-fluorophenyl)]-3-pyridineethanol in 500 ml of glacial acetic acid was hydrogenated over 2.4 g of 5% platinum on carbon in a Parr apparatus for 24 hr. The mixture was filtered through Celite ® and the filtrate was concentrated to give a gummy residue. The residue was partitioned between 300 ml of methylene chloride and 300 ml of a 5% sodium hydroxide solution and a solid precipitated. The solid was collected by filtration and partitioned between 200 ml of methylene chloride and 100 ml of a 5% sodium hydroxide solution. The organic layer was washed with brine, dried over sodium sulfate and concentrated to give a gum as residue. The gum was dissolved in ethyl ether and converted to the hydrochloride salt. The solid was collected by filtration and dried to yield 19.2 g (71%) of the title compound as a white solid, mp 248° C. (dec) (absolute ethanol).

Analysis : Calculated for $C_{19}H_{22}ClF_2NO$: C,64.50;H,6.27;N,3.96. Found: C,64.30;H,6.28;N,3.98.

PREPARATION 144

1-(Phenylmethyl)-3-piperidinecarboxylic acid ethyl ester hydrobromide [1:1]

To a stirred mixture of 35.4 g (0.225 mole) of (±) ethylnipecotate and 31.8 g (0.3 mole) of anhydrous sodium carbonate in 300 ml of absolute ethanol was added dropwise 41 g (0.24 mole) of benzylbromide and the mixture was stirred at ambient temperature for 24 hr. The mixture was filtered and the filtrate was concentrated. The residue was partitioned between 250 ml of methylene chloride and 250 ml of a 5% sodium hydroxide solution. The organic layer was washed with brine, dried over sodium sulfate, and concentrated to give a gummy residue. The residue was triturated with ethyl ether, filtered, and the filtrate treated with hydrogen bromide gas. The solid which precipitated was collected by filtration and recrystallized from 2-propanol to yield 35.0 g (47%) of the title compound as a white solid, mp 148°-152° C.

Analysis: Calculated for $C_{15}H_{22}BrNO_2$:C,54.89;H,6.76;N,4.27. Found: C,54.83;H,6.83;N,4.30.

PREPARATION 145

[α,α-Bis(4-fluorophenyl)]-3-piperidinemthanol

A solution of 26.6 g (0.0676 mole) of α,α-bis(4-fluorophenyl)-1-(phenylmethyl)-3-piperidinemthanol in 750 ml of absolute ethanol was hydrogenated at 60° C. and 50 psi over 5% palladium on carbon in a Parr apparatus for 18 hr. The mixture was filtered through Celite® and the filtrate was concentrad to give a gum which crystallized when triturated with petroleum ester (30°-60° C.) The solid was collected by filtration and recrystallized from cyclohexane to yield 14.8 g (72%) of the title compound as a white shole, mp 114.5°-115.5° C.

Analysis: Calculated for $C_{18}H_{19}F_2NO$: C, 71.27;H, 6.31;N, 4.62. Found: C, 71.43;H, 6.33;N, 4.64.

PREPARATION 146

1-Chloro-3-[(2-phenylmethoxy)phenoxy]propane

A mixture of 50g (0.25 mole) of 2-benzyloxyphenol, 78.7 g (0.5 mole) of 1-bromo-3-chloropropane and 103.7 g (0.75 mole) of anhydrous potassium carbonate in one liter of acetone was heated at reflux for ~24 hr. The mixture was worked up to give 67.2 g of tan oil as residue. The oil was dissolved in ~300 ml of ethyl ether and washed with 100 ml of 5% sodium hydroxide solution and a solid precipitated. Approximately 200 ml of water was added and the solid dissolved. The layers were then separated. This process was repeated twice with 100 ml of 5% sodium hydroxide solution. The organic layer was washed with water and brine, dried over sodium carbonate, and concentrated to give 58.4 g (84%) of oil as residue. NMR was consistent for the title compound.

PREPARATION 147

1-Chloro-3-[2,6(dimethoxy)phenoxy]propane

A reaction mixture consisting of the following was heated for about 18 hr at gentle reflux in 750 ml of acetone:
1. 2,6-dimethoxyphenol (154.17 g, 1 mole)
2. 1-bromo-3-chloropropane (314.8 g, 2 mole), and
3. potassium carbonate (290.0 g, 2.1 mole).

The reaction mixture was filtered and stripped to dryness to give a dark brown oil which was dissolved in chloroform and extracted with dilute (5%) sodium hydroxide solution. An emulsion resulted which was broken by the addition of saturated sodium chloride. The aqueous layer was extracted several times with chloroform. The chloroform layer was back extracted with 5% sodium hydroxide. Removal of chloroform gave a dark brown oil (83.55 g, 36.35 yield). NMR analysis was consistent with the desired product.

PREPARATION 148

1-Chloro-3-[(2-methoxy-4-methyl)phenoxy]propane

A mixture of 50 g (0.326 mole) of 2-methoxy-4-methylphenol, 113.9 g (0.72 mole) of 1-bromo-3-chloropropane and 150 g (1.1 mole) of anhydrous potassium carboxate in one liter of acetone was heated at reflux with stirring for ~20 hr. The mixture was cooled, filtered, and the filtrate concentrated to yield 66.3 g of oil as residue. NMR showed 75% product and 25% phenol present.

The oil was dissolved in 500 ml of acetone and treated with 28 g of 1-bromo-3-chloropropane and 35 g of anhydrous potassium carbonate and the mixture was heated at reflux for ~16 hr. The mixture was worked up as above to yield 67 g of an oil. NMR indicated it was mostly product, but that some replaceable proton was still present. The oil was dissolved in 300 ml of benzene and stirred with potassium hydroxide pellets for 21 hr. The mixture was filtered through Celite® and the filtrate was concentrated to yield 54.7 g (70%) of clear oil. NMR was consistent with the title compound.

PREPARATION 149

1-[2-(b 3-Chloropropoxy)phenyl]ethanone

A mixture of 40.8 g (0.3 mole) of 2-hydroxyacetophenone, 94.4 g (0.6 mole) of 1-bromo-3-chloropropane and 124.4 g (0.9 mole) of anhydrous potassium carbonate in one liter of acetone was heated at reflux for ~18 hr. The mixture was cooled to room temperature, filtered and the filtrate concentrated under vacuum pump pressure to give ~45 g of oil as residue. The oil was dissolved in 200 ml of benzene and stirred with potassium hydroxide pellets for ~2 hr. The mixture was filtered through Celite® and the filtrate was concentrated to yield 29.6 g (46% of light yellow oil. NMR was consistent for desired product. Mass Spectra Analysis shows m/e=213.

PREPARATION 150

1-[3-(3-Chloropropoxy)phenyl]ethanone

A mixture of 40.8 g (0.3 mole) of m-hydroxyacetophenon, 94.4 g (0.6 mole) of 1-bromo-3-chloropropane and 124.4 g (0.9 mole) of anhydrous potassium carbonate in one liter of acetone was heated at reflux for ~20 hr. The mixture was worked up to yield 61.4 g (96%) of dark oil as residue. NMR analysis was consistent for the desired product. Mass Spectra Analysis showed m/e=213.

PREPARATION 151

1-Chloro-3-[(3-methoxy)phenoxy]propane

A mixture of 37.2 g (0.3 mole) of m-methoxyphenol, 94.4 g (0.6 mole) of 1-bromo-3-chloropropane and 124.4 g (0.9 mole) of anhydrous potassium carbonate in one liter of acetone was heated at reflux for ∼20 hr (the reaction mixture turned a dark color when the potassium carbonate was added). The mixture was worked up to give 57.7 g (96%) of yellow oil as residue. NMR Analysis was perfect for desired compound. Mass Spectra Analysis showed m/e=201.

PREPARATION 152

1-Chloro-3-(4-ethylphenoxy)propane

A mixture of 36.6 g (0.3 mole) of 4-ethylphenol, 94.4 g (0.6 mole) of 1l-bromo-3-chloropropane and 124.4 g (0.9 mole) of anhydrous potassium carbonate in one liter of acetone was heated at reflux for ∼24 hr. The mixture was worked-up to yield 48 g (81%) of pale yellow oil. NMR was perfect for desired product. Mass Spectra Analysis shows m/e=199.

PREPARATION 153

1-[4-(3-Chloropropoxy)benzeneacetic acid methyl ester

A mixture of 24.3 g (0.146 mole) of methyl-4-hydroxyphenylacetate, 47.2 g (0.3 mole) of 1-bromo-3-chloropropane and 62.1 g (0.45 mole) of anhydrous potassium carbonate in 500 ml of acetone was heated at reflux for ∼24 hr. The mixture was cooled, filtered and the filtrate concentrated to give 34.8 g (98%) of oil as residue. Mass Spectra Analysis showed m/e=243. NMR is consistent for the desired product.

PREPARATION 154

1-Chloro-3-(2-methylphenoxy)propane

A mixture of 32.4 g (0.3 l mole) of o-cresol, 94.4 g (0.6 mole) of (1-bromo-3-chloropropane and 124.4 g (0.9 mole) of anhydrous potassium carbonate in one liter of acetone was heated at reflux for ∼24 hr. The mixture was worked-up to yield 34.5 g (62%) of pale yellow oil. NMR looked perfect for the desired product. Mass Spectra Analysis showed m/e=185.

PREPARATION 155

1-Chloro-3-(2-ethoxyphenoxy)propane

A mixture of 41.5 g (0.3 mole) of o-ethoxyphenol, 94.4 g (0.6 mole) of 1-bromo-3-chloropropane and 124.4 g (0.9 mole) of anhydrous potassium carbonate in one liter of acetone was heated at reflux for ∼20 hr. The mixture was worked-up to give 34.3 g (53%) of clear oil as residue. NMR was perfect for the desired product. Mass Spectra showed m/e=215.

PREPARATION 156

1-Chloro-3-(3-methylphenoxy)propane

A mixture of 32.4 g (0.3 mole) of m-cresol, 94.4 g (0.6 mole) of 1-bromo-3-chloropropane and 124.4 g (0.9 mole) of anhydrous potassium carbonate in one liter of acetone was heated at reflux for ∼20 hr. The mixture was worked-up to yield 45 g (81%) of pale yellow oil as residue. NMR was consistent for desired product. Mass Spectra Analysis showed m/e=185.

PREPARATION 157

1-Chloro-3-[2-(1-methylethoxy)phenoxy]propane

A mixture of 25 g (0.164 mole) of 2-isopropoxyphenol, 51.7 g (0.33 mole) of 1-bromo-3-chloropropane, and 67.9 g (0.49 mole) of anhydrous potassium carbonate in 500 ml acetone was heated at reflux for ∼20 hr. The mixture was cooled and filtered and the filtrate concentrated. The residue was dissolved in 200 ml of benzene, treated with potassium hydroxide pellets and stirred overnight. The mixture was filtered through Celite ® and the filtrate concentrated to yield 232 g (62%) of oil as residue. Mass Spectra Analysis showed m/e=229, NMR was perfect for desired compound.

PREPARATION 158

[4-(3-Chloropropoxy)phenyl]phenylmethanone

A mixture of 49.7 g (0.20 mole) of 4-hydroxybenzophenone, 78.7 g (0.5 mole) of 1-bromo-3-chloropropane and 103.5 g (0.75 mole) of anhydrous potassium carbonate in one liter of acetone was heated reflux for 20 hr. The mixture was cooled to room temperature, filtered and the filtrate concentrated in give a dark oil as residue. Mass Spectra Analysis showed m/e=275. The oil was dissolved in 300 ml of benzene and stirred with potassium hydroxide pellets over the weekend. The mixture was filtered through Celite ® and the filtrate was concentrated to give 67.4 g (98%) of reddish-brown oil as residue. NMR was perfect for the desired compound.

EXAMPLE 1

4-(Diphenylmethylene)-1-(3-phenoxypropyl)piperidine oxalate [1:1]

A mixture of 3.3 g (0.013 mole) of 4-diphenylmethylenepiperidine, 3.3 g (0.015 mole) of (3-bromopropoxy)benzene and 5.3 g (0.05 mole) of anhydrous sodium carbonate in 100 ml of 1-butanol was heated at reflux for 20 hr. The mixture was concentrated under reduced pressure and the residue was partitioned between water and benzene. The benzene layer was washed with water and brine, dried over anhydrous sodium sulfate and concentrated under reduced pressure to give an oil as residue, the free base of the title compound. The free base was converted to the oxalic acid salt and the solid was recrystallized from absolute ethanol to yield 4.3 g (70%) of the title product as a white powder, m.p. 175°–178° C.

Analysis: Calculated for $C_{29}H_{31}NO_5$: C, 73.55; H, 6.60; N, 2.96. Found: C, 73.59; H, 6.64; N, 2.83.

EXAMPLE 2

α,α-Bis-(4-fluorophenyl)-1-(3-phenoxypropyl)-4-piperidinemethanol oxalate hydrate [1:1:0.5]

A mixture of 3.37 g (0.011 mole) of α,α-bis(p-fluorophenyl)-4-piperidinemethanol, 2.52 g (0.011 mole) of (3-bromopropoxy)benzene and sodium bicarbonate (3.7 g, 0.035 mole) in 200 ml of 1-butanol was heated overnight at reflux. The butanol was removed by the rotary evaporator, and the residue partitioned between chloroform and water. Removal of the chloroform in vacuo gave a dark brown oil, the free base of the title compound. The base was converted to the oxalate salt and recrystallized from methanol-ethyl ether to give 1.41 (23.9%) of white solid, m.p. 163° C.

Analysis: Calculated for $C_{29}H_{31}F_2NO_6 \cdot 0.5H_2O$: C, 64.92; H, 6.01; N, 2.61. Found: C, 65.27; H, 5.87; N, 2.61.

EXAMPLE 3

4-[Bis(4-fluorophenyl)methylene]-1-(3-phenoxypropyl)piperidine oxalate [1:1]

A solution of 7.37 g (0.0168 mole) α,α-bis(4-fluorophenyl)-1-(3-phenoxypropyl)-4-piperidinemethanol in 100 ml of methanol containing 100 ml of 6N hydrochloric acid was gently heated at reflux for 4 hr. The reaction mixture was cooled, made alkaline with ice/50% sodium hydroxide, and diluted to 1 liter with water. The aqueous phase was extracted with chloroform, and removal of chloroform gave an oil. The oil was converted to the oxalate salt and recrystallized from methanol-ethyl ether to give 3.45 g (40.3%) of white solid, m.p. 190°–192° C.

Analysis: Calculated for $C_{29}H_{29}F_2NO_5$: C, 68.36; H, 5.74; N, 2.75. Found: C, 68.43; H, 5.75; N, 2.69.

EXAMPLE 4

α,α-Bis(4-fluorophenyl)-1-(3-phenoxypropyl)-4-piperidinemethanol oxalate [1:1]

To a mixture of 5.10 g (0.21 mole) of magnesium turnings and a crystal of iodine in 800 ml of drytetrahydrofuran (distilled from lithium aluminum hydride) was added a solution of 36.75 g (0.21 mole) of p-bromofluorobenzene in 100 ml of tetrahydrofuran. The reaction flask was cooled in an ice bath during this addition, and the reaction mixture was under an atmosphere of nitrogen. The mixture was stirred at ambient temperature for 1 hr. A solution of 20.17 g (0.0693 mole) of ethyl N-(3-phenoxypropyl)isonipecotate in 100 ml of tetrahydrofuran was added and the solution was stirred at room temperature for 16 hr. The mixture was poured into an icy solution of ammonium chloride and the aqueous mixture was extracted with methylene chloride. The methylene chloride solution was extracted with dilute sodium hydroxide and was dried over magnesium sulfate. The solvent was removed in vacuo to give a gummy residue. The residue was treated with a solution of oxalic acid in methanol and the salt was recrystallized from methanol-ether to give 24.17 g (66.2%) of white, crystalline solid, m.p. 153°–155° C.

Analysis: Calculated for $C_{29}H_{31}F_2NO_6$: C, 66.02; H, 5.92; N, 2.66. Found: C, 65.78; H, 5.93; N, 2.63.

EXAMPLE 5

4-(Diphenylmethyl)-1-(4-phenoxybutyl)piperidine fumarate [1:1]

A solution of 6.99 g (0.0278 mole) of 4-diphenylmethylpiperidine, 6.64 g (0.029 mole) of (4-bromobutoxy)benzene and 5 g (0.060 mole) of sodium bicarbonate in 400 ml of 1-butanol was heated at reflux for 11 hr. The solvent was removed in vacuo, an the residue was partitioned between methylene chloride and dilute sodium hydroxide. The methylene chloride solution was dried over magnesium sulfate, and the solvent was removed in vacuo to give an oil, the free base of the title compound. The base was dissolved in 500 ml of ether, and a small amount of solid was filtered from the solution. To the filtrate was added a solution of 3.2 g (0.0276 mole) of fumaric acid in 60 ml of methanol. A white precipitate was collected to give 7.97 g (55.7%) of white, crystalline solid, m.p. 146°–147° C.

Analysis: Calculated for $C_{32}H_{37}NO_5$: C, 74.54; H, 7.23; N, 2.72. Found: C, 74.68; H, 7.24; N, 2.68.

EXAMPLE 6

4-(Diphenylmethyl)-1-(3-phenoxypropyl)piperidine fumarate [1:1]

Following the procedure of Example 5, 4-(diphenylmethyl)piperidine and (3-bromopropoxy)benzene was reacted to give the free base of the title compound which was reacted with fumaric acid in methanol to give the white fumarate salt in 71% yield, m.p. 171°–172° C.

Analysis: Calculated for $C_{31}H_{35}NO_5$: C, 74.23, H, 7.03; N, 2.79. Found: C, 74.62; H, 7.03; N, 2.73.

EXAMPLE 7

4-[Bis(4-fluorophenyl)methyl]-1-(3-phenoxypropyl)-piperidine oxalate [1:1]

Following the procedure of Example 2,4-[bis(4-fluorophenyl)methyl]piperidine and (3-bromopropoxy)benzene were reacted to give the free base of the title compound which was reacted with oxalic acid, and recrystallizing from methanol-ethyl ether to give the white oxalate salt in 60% yield, m.p. 178°–181° C.

Analysis: Calculated for $C_{29}H_{31}F_2NO_5$: C, 68.09; H, 6.11; N, 2.74. Found: C, 68.37; H, 6.13; N, 2.76.

EXAMPLE 8

4-(Diphenylmethyl)-1-(2-phenoxyethyl)piperidine fumarate [1:1]

Following the procedure of Example 5,4-(diphenylmethyl)piperidine and (2-bromoethoxy)benzene were reacted to give the free base of the title compound which was reacted with fumaric acid in ether-methanol mixture to give the white fumarate salt in 85% yield, m.p. 189°–190° C.

Analysis: Calculated for $C_{30}H_{33}NO_5$: C, 73.90;H,6.82;N,2.87. Found: C,74.07;H,6.91;N,2.85.

EXAMPLE 9

4-[Bis(4-fluorophenyl)methyl]-1-(2-phenoxyethyl)-piperidine oxalate [1:1]

A mixture of 5.83 g (0.02 mole) of 4-[bis(4-fluorophenyl)methyl]piperidine, 4.02 g (0.02 mole) of (2-bromoethoxy)benzene and sodium carbonate (3.18 g, 0.03 mole) was heated overnight at gentle reflux in 300 ml of 1-butanol. The reaction was filtered and solvent removed in vacuo. The residue was dissolved in chloroform and extracted with water and 5% sodium hydroxide. Removal of chloroform gave an oil which was converted to the oxalate salt. The salt was recrystallized from ethanol-ethyl ether to give 6.0 g (60.3%) of white, crystalline product, m.p. 180°–182° C.

Analysis: Calculated for $C_{28}H_{29}F_2NO_5$: C,67.60;H,5.88;N,2.82. Found: C,67.68;H,5.87;N,2.81.

EXAMPLE 10

4-[Bis(4-fluorophenyl)methyl]-1-(4-phenoxybutyl)-piperidine oxalate [1:1]

Following the procedure of Example 2,4-[bis(4-fluorophenyl)methyl]-piperidine and (4-bromopropoxy)benzene were reacted to give the free base of the title compound which was reacted with oxalic acid to give the white oxalate salt (recrystallizing from ethanol-ethyl ether), in 48% yield, m.p. 206° C.

Analysis: Calculated for $C_{30}H_{33}F_2NO_5$: C,68.56;H,6.33;N,2.67. Found: C,68.79;H,6.35;N,2.67.

EXAMPLE 11

4-[(4-Fluorophenyl)-phenylmethyl]-1-(3-phenoxypropyl)piperidine fumarate [1:1]

A mixture of 5.4 g (0.02 mole) of 4-[α-(p-fluorophenyl)-α-phenylmethyl]-piperidine, 4.5 g (0.021 mole) of (3-bromopropoxy)benzene and 8.0 g (0.075 mole) of anhydrous sodium carbonate in 150 ml of acetonitrile was refluxed for about 20 hr and concentrated under reduced pressure to give a gummy residue. The residue was purified by column chromatography on 160 g of Florisil ® and the product was eluted with 2% acetone in benzene to give an oil, the free base of the title compound. The free base was reacted with fumaric acid and the salt was recrystallized from isopropyl alcohol to give 4.0 g (38%) of white solid, m.p. 169°–171° C. (with decomposition).

Analysis: Calculated for $C_{31}H_{34}FNO_5$: C,71.66;H,6.60;N,2.70. Found: C,71.37;H,6.55;N,2.66.

EXAMPLE 12

4[Bis(4-fluorophenyl)methyl]-1-[2-(2,6-dichlorophenoxy)ethyl]-piperidine.

A mixture of 6.13 g (0.021 mole) of 4-[bis(4-fluorophenyl)methyl]piperidine, 5.38 g (0.03 mole) of 2-(2-bromoethoxy)-1,3-dichlorobenzene was heated overnight at gentle reflux in 200 ml of 1-butanol. The reaction mixture was filtered and stripped to dryness. The residue was dissolved in chloroform and extracted with water and 5% sodium hydroxide solution. The oil which was obtained was chromotagraphed on 300 g of silica gel using hexane-ethyl acetate (50/50 v/v) as eluant. The fractions containing product were combined and solvent removed to furnish an oil. The oil was dried overnight in vacuo at 80° C. This furnished 5.99 g (59%) of product oil.

Analysis: Calculated for $C_{26}H_{25}Cl_2F_2NO$: C,65.55;H,5.29;N,2.94. Found: C,65.43;H,5.34;N,2.77. The $^1H$ NMR spectrum of the subject compound was obtained in CDCl$_3$, containing tetramethylsilane and is consistent with the structure indicated by the title,

| 2.2–2.3 δ | aliphatic protons (cyclic) | 7H |
|---|---|---|
| 2.8 δ or triplet | CH$_2$ next to N | 2H |
| 2.8–3.1 δ | Hydrogen next to N | 2H |
| 3.5 δ doublet | methine proton | 1H |
| 4.1 δ triplet | CH$_2$ next to oxygen | 2H |
| 6.8–7.4 δ | aromatic protons | 11H |

EXAMPLE 13

1-[3-(4-Chlorophenoxy)propyl]-α,α-bis(4-fluorophenyl)-4-piperidinemethanol

A mixture of 3.0 g (0.01 mole) of [α,α-bis(p-fluorophenyl)]4-piperidinemethanol, 2.0 g (0.01 mole) of 1-chloro-4-(3-chloropropoxy)benzene, 5.3 g (0.05 mole) of anhydrous sodium carbonate and 0.3 g of potassium iodide in 100 ml of 1-butanol was heated at reflux for 20 hr to give, after working up as in Example 1 (recrystallizing the free base from isopropyl alcohol), 1.7 g (36%) of white solid, m.p. 92°–93° C.

Analysis: Calculated for $C_{27}H_{28}ClF_2NO_2$: C,68.71;H,5.98;N,2.97. Found: C,68.66;H,5.99;N,2.92.

EXAMPLE 14

4-[Bis(4-fluorophenyl)methyl]-1-[3-(2-fluorophenoxy)propyl]piperidine oxalate[1:1]

A mixture of 5.85 g (0.02 mole) of 4-[bis(4-fluorophenyl)methyl]-piperidine, 3.76 g (0.02 mole) of2-(3-chloropropoxy)-1-fluorobenzene, and sodium carbonate (4.80 g, 0.045 mole) in 300 ml of 1-butanol containing 0.3 g of potassium iodide was heated overnight at gentle reflux. The reaction mixture was concentrated to dryness and the resulting oil partitioned between chloroform-5% sodium hydroxide and then between chloroform water. Removal of chloroform gave an oil which was converted to the oxalate salt. The salt was recrystallized from ethanol-ethyl ether. The salt was subsequently triturated with 2-propanol, and was dried overnight at 80° C. to give 5.82 g (55%) of product, m.p. 182°–183° C.

Analysis: Calculated for $C_{29}H_{30}F_3NO_5$: C,65.78;H,5.71;N,2.65. Found: C,66.05;H,5.79;N,2.59.

EXAMPLE 15

4-[Bis(4-fluorophenyl)methyl]-1-[3-(3-fluorophenoxy)propyl]piperidine mandelate[1:1]

Following the procedure of Example 14, 4-[bis(4-fluorophenyl)methyl]-piperidine and 3-(3-chloropropoxy)-1-fluorobenzene were reacted to give the free base of the title compound which was reacted with mandelic acid to give the white mandelate salt (recrystallizing from isopropyl alcohol) in 62% yield, m.p. 145–147.5° C.

Analysis: Calculated for $C_{35}H_{36}F_3NO_4$: C,71.05;H,6.13;N,2.37. Found: C,71.10;H,6.20;N.2.36.

EXAMPLE 16

4-[Bis(4-fluorophenyl)methyl]-1-[3-(4-chlorophenoxy)propyl]piperidine fumarate [1:1]

Following the procedure of Example 14, 4-8 bis(4-fluorophenyl)methyl]piperidine and 1-[4-(3-chloropropoxy)]chlorobenzene were reacted to give the free base of the title compound. The free base was chromatographed on silica gel eluting with hexane-ethyl acetate and reacted with fumaric acid (recrystallizing from methanol-ethyl ether) in 9% yield, m.p. 169°–170° C.

Analysis: Calculated for $C_{31}H_{32}ClF_2NO_5$: C,65.10;H,5.64;N,2.45. Found: C,64.85;H,5.63;N,2.46.

EXAMPLE 17

4-[Bis(4-fluorophenyl)methyl]-1-[3-(4-fluorophenoxy)propyl]piperidine

Following the combined procedures of Examples 14 and 16,4-[bis(4-fluorophenyl)methyl]piperidine and 4-(3-chloropropoxy)-1-fluorobenzene were reacted and worked up by chromatography as in Example 16, to give the free base in 53% yield as a yellow oil after drying in vacuo at 80° C. overnight.

Analysis: Calculated for $C_{27}H_{28}F_3NO$: C,73.78;H,6.42;N,3.19. Found: C,73.64;H,6.39;N,3.14.

EXAMPLE 18

4-[Bis(4-fluorophenyl)methyl]-1-[3-(4methoxyphenoxy)propyl]piperidine fumarate [1:1]

Following the procedure of Example 14, 4-[4-fluorophenyl)methyl]-piperidine and 1-(3-chloropropoxy)-4-methoxybenzene were reacted to give the free base of the title compound which was reacted with fumaric acid to give the white fumarate salt (recrystallizing from methanol-ethyl ether) in 64% yield, m.p. 172°–173° C.

Analysis: Calculated for $C_{32}H_{35}F_2NO_6$: C,67.71;H,6.22;N,2.47. Found: C,67.89;H,6.25;N,2.39.

EXAMPLE 19

4-[Bis(4-fluorophenyl)methyl]-1-[2-methoxyphenoxy)propyl]piperidine

A mixture of 5.99 g (0.021 mole) of 4-[bis(4-fluorophenyl)methyl]piperidine, 4.35 g (0.022 mole) of 2-(3-chloroproxy)-1-methoxybenzene ether, and sodium carbonate (3.18 g, 0.03 mole) in 1-butanol was heated overnight at gentle reflux. The reaction mixture was filtered and stripped to dryness. The residue was dissolved in chloroform and extracted with water and 5% sodium hydroxide. Removal of chloroform gave a dark brown oil. The oil was chromatographed on silica gel using acetone-ethyl acetate for elution. After combining fractions and removing solvent, an oil was obtained. The oil was dried in vacuo at 80° C. overnight. This gave 3.18 g (33.5% of title product.

Analysis: Calculated for $C_{28}H_{31}F_2NO_2$: C,74.48;H,6.92;N,3.12. Found: C,74.42;H,6.95;N,3.00.

The $^1H$ NMR spectrum of the subject compound was obtained in $CDCl_3$, containing tetramethylsilane and is consistent with the structure indicated by the title,

| 6.8 δ | singlet; or protons on ring containing methoxy group. | 4H |
| --- | --- | --- |
| 6.8–7.3 δ | aromatic protons on fluorophenyl rings. | 8H |
| 4.0 δ | triplet $CH_2$—O. | 2H |
| 3.8 δ | singlet O—$CH_3$. | 3H |
| 3.4 δ | doublet; methine proton. | 1H |
| 0.8–3.1 δ | multiplet. | 13H |

EXAMPLE 20

α,α-Bis(45-fluorophenyl)-1-[3-(2-methoxyphenoxy)propyl]-4-piperidinemethanol.

Following the procedure of Example 1, α,α-bis(p-fluorophenyl)-4-piperidinemethanol and 1-chloro-3-(2-methoxyphenoxy)propane were reacted using in addition potassium iodide catalyst to give the title compound in 66% yield, (recrystallizing from isopropyl alcohol), m.p. 127°–218° C.

Analysis: Calculated for $C_{28}N_{31}F_2NO_3$: C,71.93;H,6.68;N,3.00. Found: C,71.88;H,6.67;N,2.98.

EXAMPLE 21

4-[Bis(4-fluorophenyl)methylene]-1-[3-(2-methoxyphenoxy)propyl]-piperidine oxalate [1:1]

Following the procedure of Example 14, 4-[bis(4-fluorophenyl)methylene]piperidine and 2-(3-chloropropoxy)-1-methoxybenzene were reacted using in addition potassium iodide catalyst to give the free base of the title compound which was reacted with oxalic acid to give the white oxalate salt (recrystallizing from methanol-ethyl ether) in 73% yield, m.p. 184°–186° C.

Analysis: Calculated for $C_{30}H_{31}F_2NO_6$: C,66.78;H,5.79;N,2.60. Found: C,66.74;H,5.79;N,2.61.

EXAMPLE 22

4-[Bis(4-fluorophenyl)methyl]-1-[3-(3,4-dimethoxyphenoxy)propyl]-piperidine oxalate [1:1]

A mixture of 6.02 g (0.021 mole) of 4-[bis(4-fluorophenyl)-methyl]piperidine, 4.83 g (0.021 mole) of 4-(3-chloropropoxy)-1,2-dimethoxybenzene, and potassium carbonate (5.52 g, 0.04 mole) was heated at reflux overnight in 300 ml of 1-butanol containing potassium iodide (0.3 g). The reaction mixture was concentrated to dryness and partitioned between chloroform and water several times. The chloroform layer was dried over anhydrous sodium sulfate and then filtered. The chloroform was removed by rotary evaporator. The oil obtained was converted to the oxalate salt and then recrystallized from ethanol-ethyl ether and methanol isopropyl ether. This furnished 7.77 g (64.7%) of white solid, m.p. 188° C.

Analysis: Calculated for $C_{31}H_{35}F_2NO_7$: C65.14;H,6.17;N,2.43. Found: C,64.78;H,6.14;N,2.44.

EXAMPLE 23

4-[Bis(4-methylphenyl)-methyl]-1-[3-(2,6-dimethoxyphenoxy)propyl]-piperidine fumarate [1:1]

Following the procedure of Example 22, 4-[bis(4-methylphenyl)methyl]-piperidine and 2-(3-chloropropoxy)-1,3-dimethoxybenzene were reacted to give the free base of the title compound which was reacted with fumaric acid to give the white fumarate salt (recrystallizing from methanol-ethyl ether) in 66% yield, m.p. 206–207° C.

Analysis: Calculated for $C_{35}H_{43}NO_7$: C,71.29;H,7.35;N,2.38. Found: C,71.24;H,7.38;N,2.36.

EXAMPLE 24

4-[Bis(4-fluorophenyl)methylene]-1-[3-(3,4-dimethoxyphenoxy)propyl]piperidine oxalate [1:1]

Following the procedure of Example 22, 4-[bis(4-fluorophenylmethylene]piperidine and 4-(3-chloropropoxy)-1,2-dimethoxybenzene were reacted to give the free base of the title compound which was reacted with oxalic acid to give the cream colored oxalate salt (recrystallizing from methanol-ethyl ether) in 51% yield, m.p. 173°–176° C.

Analysis: Calculated for $C_{31}H_{33}F_2NO_7$: C,65.37;H,5.84;N,2.46. Found: C,65.02;H,5.83;N,2.50.

EXAMPLE 25

4-[Bis(4-fluorophenyl)methyl]-1-[3-(2,6-dimethoxyphenoxy)propyl]-piperidine oxalate hydrate [1:1:1]

Following the procedure of Example 22, but substituting dimethoxy ethane for butanol, 4-[bis(4-fluorophenyl)methyl]piperidine and 2-(3-chloropropoxy)-1,3-dimethoxybenzene were reacted to give the free base of the title compound which was reacted with oxalic acid to give the white oxalate salt (recrystallizing from methanol-ethyl ether) in 9% yield, m.p. 132°–134° C.

Analysis: Calculated for $C_{31}H_{35}NO_7 \cdot H_2O$: C,63.15;H,6.32;N,2.38. Found: C,62.89;H,5.98;N,2.41.

EXAMPLE 26

4-[Bis(4-fluorophenyl)methyl]-1-[3-(3,5-dimethoxyphenoxy)propyl]-piperidine

A mixture of 5.51 g (0.019 mole) of 4-[bis(4-fluorophenyl)methyl]piperidine, 4.42 g (0.019 mole) of 1-(3-chloropropoxy)-3,5-dimethoxybenzene and potassium carbonate (5.53 g, 0.04 mole) was heated overnight at reflux in 350 ml of 1-butanol containing potassium iodide (0.3 g). The reaction mixture was concentrated to dryness and the residue partitioned between chloroform-5% sodium hydroxide and chloroform-water. Removal of chloroform gave a brown oil. The oil was subjected to chromatography on a silica gel column using a gradient elution series of hexane-ethyl acetate and ethyl acetatedimethoxyethane. After combining proper fractions eluted from the column and removing solvent, the residue oil was dried in vacuo overnight at 80° C. This produced 2.61 g (28.5%) of brown oil.

Analysis: Calculated for $C_{29}H_{33}F_2NO_3$: C,72.33;H,6.91;N,2.91. Found: C,71.62;H,6.80;N,2.98. The $^1$H NMR spectrum of the subject compound was obtained in CDCl$_3$ containing tetramethylsilane and is consistent with the structure indicated by the title: 7.0 δ (multiplet, aromatic protons on fluorophenyl ring), 6.0 (singlet, aromatic protons on methoxyphenyl ring, 3H), 2.8 (triplet, methylene next to ether oxygen, 2H), 3.75 (singlet, OCH$_3$, 6H), 3.4 (doublet, methine attached to two aromatic rings, (1H), 0.75–2.6 (multiplet, remaining aliphatics, 13H).

EXAMPLE 27

4-[Bis(4-methoxyphenyl)methyl]-1-[3,4-dimethoxyphenoxy)propyl]-piperidine

A mixture of 5.58 g (0.02 mole) of 4-[bis(4-methoxyphenyl)methyl]-piperidine, 4.83 g (0.021 mole) of 4-(3-chloroproxy)-1,2-dimethoxybenzene, and potassium carbonate, 5.52 g (0.04 mole) was heated overnight at reflux in 350 ml of 1-butanol containing potassium iodide (0.3 g). The reaction mixture was concentrated to dryness, and the residue partitioned between chloroform-5% sodium hydroxide and chloroform-water. Removal of chloroform gave a dark brown oil. The oil was subjected to column chromatography on a silica gel column with elution via ethyl acetate-dimethoxyethane. This produced 4.72 g (46.7%) of dark brown oil.

Analysis: Calculated for $C_{31}H_{39}NO_5$: C,73.64;H,7.77;N,2.77. Found: C,72.38;H,7.70;pN,2.72. The $^1$H NMR spectrum of the subject compound was obtained in CDCl$_3$ containing tetramethylsilane and is consistent with the structure indicated by the title: δ7.1 multiplet, aromatic protons ortho to methine of

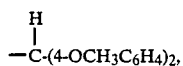

4H), 6.75 (multiplet, aromatic protons adjacent to methoxy groups, 5H), 6.4(multiplet, aromatic protons adjacent to ether linkage, 2H), 3.9 (triplet, methylene protons next to ether linkage, 2H), 3.7 (OCH$_3$, 6H), 3.6 (OCH$_3$, 6H), 3.3 (doublet, methine attached to aromatic rings, 1H), 0.75–3.0 (multiplet, aliphatic protons, 13H).

EXAMPLE 28

4-[Bis(4-methoxyphenyl)methyl]-1-[3-(4-methoxyphenoxy)propyl]-piperidine fumarate hydrate [1:2:0.5]

Following the procedure of Example 22, 4-[bis(4-methoxyphenyl)methyl]piperidine and 4-(3-chloropropoxy)-1-methoxybenzene were reacted to give the free base of the title compound which was separated by extracting with sodium hydroxide-chloroform and reacted with fumaric acid to give the title salt (recrystallizing from methanol-ethyl ether several times as well as isopropyl alcohol) in 15% yield, m.p. 163°–165° C.

Analysis: Calculated for $C_{34}H_{41}NO_8 \cdot 0.5H_2O$: C,67.98;H,7.05;N,2.33. Found: C,68.16;H,6.97;N,2.34.

EXAMPLE 29

1-[4-[3-[4-Bis(4-fluorophenyl)methylene]-1-piperidinyl]propoxy]-phenyl]ethanone oxalate ]1:1]

Following the procedure of Example 2,4-[bis(4-fluorophenyl)methylene]piperidine and 1-[4-(3-chloroproxy)phenyl]ethanone, substituting sodium carbonate for sodium bicarbonate, were reacted to give the free base of the title compound which was reacted with oxalic acid to give the oxalate salt (recrystallizing from ethanol-ethyl ether) in 59% yield, m.p. 196°–198° C.

Analysis: Calculated for $C_{31}H_{31}F_2NO_6$: C,67.50;H,5.66;N,2.54. Found: C,67.18;H,5.68;N,2.43.

EXAMPLE 30

1-4-[3-[4-Bis(4-fluorophenyl)methyl]-1-piperidinyl]-propoxy phenyl]-ethanone oxalate [1:1]

Following the procedure of Example 2,4-[bis(4-fluorophenyl)methyl]-piperidine and 1-[4-(3-chloropropoxy)phenyl]ethanone and substituting sodium carbonate for sodium bicarbonate were reacted to give the free base of the title compound which was reacted with oxalic acid to give the oxalate salt (recrystallizing from methanol-diethyl ether) in 75% yield, m.p. 141°–143° C.

Analysis: Calculated for $C_{31}H_{33}NO_6F_2$: C,67.26;H,6.01;N,2.53. Found: C,66.94;H,6.01;N,2.40.

EXAMPLE 31

1-[4-[3-[4-Bis(4-fluorophenyl)hydroxymethyl]-1-piperidinyl]propoxy]-phenyl]ethanone compound with 2-propanol [1:1]

Following the procedure of Example 1, [α,α-bis(p-fluorophenyl)]-4-piperidinemethanol and 1-[4-(3-chloroproxy)phenyl]ethanone were reacted using potassium iodide catalyst to give the free base of the title compound which when recrystallized from isopropyl alcohol gave the white title compound in 71% yield, m.p. 72°–84° C.

Analysis: Calculated for $C_{29}H_{31}F_2NO_3 \cdot C_3H_8O$: C,71.22;H,7.28;N,2.60. Found: C,71.26;H,7.34;N,2.56.

EXAMPLE 32

1-[4-[3-[4-[Bis(4-fluorophenyl)hydroxymethyl]-1-piperidinyl]propoxy]-3-methylphenyl]ethanone Following the procedure of Example 1,α,α-bis(p-fluorophenyl)-4-piperidinemethanol and 1-[4-(3-chloroproxy)-3-methylphenyl]ethanone were reacted using potassium iodide catalyst to give the white title compound (recrystallizing from isopropyl alcohol) in 76% yield, m.p. 116°–117° C.

Analysis: Calculated for $C_{30}H_{33}F_2NO_3$: C,73.00;H,6.74;N,2.84. Found: C,72.90;H,6.80;N,2.78.

EXAMPLE 33

4-[3-[4-[Bis(4-fluorophenyl)hydroxymethyl]-1-piperidinyl]propoxy]benzonitrile

Following the procedure of Example 1, α,α-bis(p-fluorophenyl)-4-piperidinemethanol and 4-(3-chloropropoxy) benzonitrile were reacted using potassium iodide as catalyst to give the white title compound (recrystallizing from isopropyl alcohol-isopropyl ether) in 30% yield, m.p. 107°-108° C.

Analysis: Calculated for $C_{28}H_{28}F_2N_2O_2$: C,72.71;H,6.10;N,6.06. Found: C,72.82;H,6.11;N,6.05.

EXAMPLE 34

4-[3-[4-[Bis(4-fluorophenyl)methyl]-1-piperidinyl]propoxy]benzonitrile fumarate [1:1]

Following the procedure of Example 22, 4-[bis(4-fluorophenyl)methyl]-piperidine and 4(3-chloropropoxy)cyanobenzene were reacted using potassium iodide catalyst to give the free base of the title compound which was reacted with fumaric acid to give the fumarate salt which was recrystallized from ethanol-ethyl ether in 53% yield, m.p. 167° C.

Analysis: Calculated for $C_{32}H_{32}F_2N_2O_5$: C,68.32;H,5.73;N,4.98. Found: C,68.10;H,5.70;N,4.94.

EXAMPLE 35

4-[3-[4-[Bis(4-fluorophenyl)methyl]-1-piperidinyl]propoxy]benzoic acid ethyl ester hydrochloride [1:1]

A mixture of 6.0 g(0.02 mole) of α,α-bis(p-fluorophenyl)-4-piperidinemethanol, 5.0 g (0.02 mole) of 4-(3-chloropropoxy))benzoic acid methyl ester, 7.4 g (0.07 mole) of anhydrous sodium carbonate, 0.3 g of potassium iodide and 150 ml of dimethylformamide was heated on a steam bath for 20 hr and then poured into 1.5 liter of ice-water. A gum precipitated and the aqueous solution was decanted. The gum was dissolved in benzene and the solution was washed with water and dilute sodium hydroxide solution, dried over anhydrous sodium sulfate and concentrated under reduced pressure to give 9.2 g of gum as residue. The gum was purified by column chromatography on 200 g of Florisil ® and the desired product was eluted with 20% acetone in benzene. The fractions containing the free base of the title compound were combined and concentrated under reduced pressure to give a gum, the free base, as residue. The free base was converted to the hydrochloric acid salt which was recrystallized from 2-propanol to give 5.3 g (49%) of white powder, m.p. 193.5-194.5° C.

Analysis: Calculated for $C_{30}H_{34}ClF_2NO_4$: C,65.66;H,6.28;N,2.57. Found: C,66.16;H,6.32;N,2.56.

EXAMPLE 36

4-[3-[4-[Bis(4-fluorophenyl)hydroxymethyl-1-piperidinyl]propoxy -benzoic acid hydrochloride hydrate [1:1:0.5]

A solution of 2.7 g (0.005 mole) of 4-[3-[4-[bis(4-fluorophenyl)hydroxymethyl]-1-piperidinyl]propoxy]-benzoic acid ethyl ester and 1.2 g(0.022 mole) of potassium hydroxide in 50 ml of ethanol and 20 ml of water was heated on a steam bath for 2 hr. Acetic acid, 10 ml, was added and the solution was poured into 500 ml of ice water and the mixture was allowed to stand at ambient temperature overnight. Sodium chloride was added to the mixture to give a coagulated solid. The solid was collected by filtration and air dried. The solid was dissolved in 20 ml of isopropyl alcohol and the solution was poured into 30 ml of ethereal hydrogen chloride. The salt which gradually crystallized was collected by filtration, washed with ethyl ether and dried to give 0.2 g (8%) of white powder, m.p. 148°-158° C. with decomposition.

Analysis: Calc'd for $C_{19}H_{30}ClF_2NO_4 \cdot 0.5H_2O$: C,63.82;H,5.93;N,2.66. Found: C,53.97;H,6.25;N,2.51.

EXAMPLE 37

4-[3-[4-[Bis(4-fluorophenyl)methylene-1-piperidinyl]propoxy]benzoic acid ethyl ester hydrobromide [1:1]

A mixture of 6.09 g (0.021 mole) of 4-[bis(4-fluorophenyl)methylene]-piperidine, 5.20 g (0.02 mole) of 1-[4-(3-chloropropoxy)-phenyl]carbethoxybenzene and sodium carbonate 4.30 g (0.04 mole) in 230 ml of 1-butanol containing potassium iodide (0.3 g) was heated overnight at gentle reflux. The reaction mixture was concentrated to dryness and partitioned between chloroform water and chloroform -5% sodium hydroxide. Removal of chloroform gave an oil. The oil was converted to the hydrobromide salt using hydrogen bromide in glacial acetic acid. The acetic acid and excess hydrogen bromide were removed in vacuo. The salt was recrystallized from ethanolethyl ether. The salt was washed with water to remove acetamide present as an impurity. The salt was washed with ethyl ether and dried in vacuo overnight at 80° C. A yield of 6.81 g (59.5%) of white solid, m.p. 192°-194° C., was obtained.

Analysis: Calculated for $C_{30}H_{32}BrF_2NO_3$: C,62.94;H,5.63;N,2.45. Found: C,62.83;H,5.58;N,2.45.

EXAMPLE 38

4-[3-[4-[Bis(4-fluorophenylmethyl]-1-piperidinyl]propoxy]benzoic acid ethyl ester hydrobromide [1:1]

Following the procedure of Example 14, 4-[bis (4-fluorophenyl)methyl]-piperidine and 4-(3-chloropropoxy)benzoic acid ethyl ester were reacted using potassium iodide as catalyst to give the free base which was reacted with hydrogen bromide in glacial acetic acid. The oil was stripped to dryness and the solid obtained was recrystallized from isopropyl alcohol-ethyl ether to give the white salt in 20% yield, m.p. 142°-144° C.

Analysis: Calculated for $C_{30}H_{34}BrF_2NO_3$: C,62.72;H,5.97;N,2.44. Found: C,62.66;H,5.95;N,2.45.

EXAMPLE 39

4-[3-[4-[Bis(4-methoxyphenyl)methyl]-1-piperidinyl]propoxy]benzoic acid butyl ester A mixture of 6.22 g (0.02 mole) of 4-[bis(4-methoxyphenyl)methyl]-piperidine, 4.84 g (0.02 mole) of 4-(3-chloropropoxy)benzoic acid ethyl ester, and potassium carbonate, 5.60 g (0.04 mole) in 350 ml of 1-butanol was refluxed overnight with potassium iodide. The reaction mixture was concentrated to dryness and the residue partitioned between chloroform-5% sodium hydroxide then chloroform-water. Removal of chloroform gave an oil. This oil chromatographed on a 200 g silica gel column packed in 50/50 v/v hexane-ethyl acetate. The material was eluted with hexane-ethyl acetate mixtures and finally 1% methanol-ethyl acetate. From the chromatography was obtained 5.09 g (46.6%) of an oil.

Analysis: Calculated for $C_{34}H_{43}NO_5$: C,74.83;H,7.94;N,2.57. Found: C,74.19;H,7.91;N,2.53.

The $^1H$ NMR spectrum was obtained in tetramethylsilane and is consistent with the structure indicated by the title, δ 8.0 (H's ortho to $CO_2$, 2H), 6.8 (m, aromatic, 10H), 4.2(m, $CH_2$ alpha to O, 4H), 3.7 (S, $OCH_3$, 6H), 0.9–3.5 (m, aliphatics, 21H).

EXAMPLE 40

4-[3-[4-[Bis(4-methoxyphenyl)methyl]-1-piperidinyl]-propoxy]benzoic acid ethyl ester fumarate hydrate [1:1:0.5]

Following the procedure of Example 22, but substituting dimethylformamide at 73° C. for butanol, 4-[bis(40methoxyphenyl)methyl]piperidine and 4-(3-chloropropoxy)benzoic acid ethyl ester were reacted to give the free base of the title compound which was reacted with fumaric acid, to give the white fumarate salt (recrystallizing from methanol-ethyl ether) in 27% yield, m.p. 147.5–148.5° C.

Analysis: Calculated for $C_{36}H_{43}NO_9 \cdot 0.5H_2O$: C,67.27;H, 6.90;N,2.18. Found: C,67.26;H,6.78;N,2.19.

EXAMPLE 41

4-[3-[4-[Bis(4-fluorophenyl)hydroxymethyl]-1-piperidinyl]ethoxy]-benzoic acid ethyl ester hydrochloride Following the procedure of Example 35, α,α-bis(p-fluorophenyl)-4-piperidinemethanol and 4-(2-chloroethoxy)benzoic acid ethyl ester are reacted and the hydrochloride salt is prepared.

EXAMPLE 42

4-[3-[4-[Bis(4-fluorophenyl)hydroxymethyl]-1-piperidinyl]propoxy]-3-methoxybenzeneacetic acid ethyl ester hydrochloride Following the procedure of Example 35, α,α-bis(p-fluorophenyl)-4-piperidinemethanol and 4-(3-chloroproxy)-3-methoxybenzeneacetic acid ethyl ester are reacted and the hydrochloride salt is prepared.

EXAMPLE 43

4-[Bis(4-fluorophenyl)methylene]-1-[3-[4-(1,1-dimethylethyl)phenoxy]-propyl]piperidine fumarate [1:1]

Following the procedure of Example 9,4-[bis(4-fluorphenyl) -methylene]piperidine and 4-(3-chloroproxy)-(1,1-dimethylethyl)benzene were reacted using potassium iodide catalyst to give an oil which was dissolved in ethyl acetate and filtered through silica gel to give the free base of the title compound. The free base was reacted with fumaric acid to give the white fumarate salt (recrystallizing from isoproyl alcohol-ethyl ether) in 40% yield, m.p. 208.5°–209.5° C.

Analysis: Calculated for $C_{35}H_{39}F_2NO_5$: C,71.05;H,6.64;N,2.37. Found: C,70.91;H,6.57;N,2.38.

EXAMPLE 44

4-[Bis(4-flurophenyl)methyl]-1-[3-[4-(1,1-dimethylethyl)phenoxy]-propyl]piperidine fumarate hydrate [1:1:0.5]

Following procedure of Example 9,4-[bis(4-fluorophenyl)methyl]-piperidine and 4-(3-chloropropoxy)-(1,1-dimethylethyl)benzene were reacted using potassium iodide catalyst to give the free base title compound which was reacted with fumaric acid to give the white fumarate salt (recrystallizing from methanol-ethyl ether and isopropyl alcohol-ethyl ether) in 55% yield, m.p. 194–196° C. with decomposition.

Analysis: Calculated for $C_{35}H_{41}F_2NO_5 \cdot 0.5H_2O$: C,69.75;H,7.02;N,2.32. Found: C,70.01;H,6.89;N,2.44.

EXAMPLE 45

4-[Bis(4-methoxyphenylmethyl]-1-[3-[4-(1,1dimethylethyl)phenoxy]-propyl]piperidine oxalate [1:1]

Following the procedure of Example 22,4-[bis(4-methoxyphenyl)methyl]piperidine and 4-(3-chloropropoxy)-(1,1-dimethylethyl)benzene were reacted using potassium iodide catalyst to give the free base which was reacted with oxalic acid to give the white oxalate salt (recrystallizing from methanol-ethyl ether) in 35% yield, m.p. 212° C.

Analysis: Calculated for $C_{35}H_{45}NO_7$: C,71.04;H,7.67;N,2.37 Found: C,70.91;H,7.70;N,2.35.

EXAMPLE 46

1-[3-[4-(1,1-Dimethylethyl)phenoxy]propyl]-α,α-bis(4-fluorophenyl)-4-piperidinemethanol Following the procedure of Example 1, α,α-bis (p-fluorophenyl)-4-piperidinemethanol and 4-(3-chloropropoxy)-(1,1-dimethylethyl)benzene were reacted using potassium iodide catalyst to give with white powder (recrystallizing from isopropyl alcohol) in 41% yield, m.p. 126°–127° C.

Analysis: Calculated for $C_{31}H_{37}F_2NO_2$: C,75.43;H,7.56;N,2.84. Found: C,75.21;H,7.58;N,2.82.

EXAMPLE 47

4-[Bis(4-fluorophenyl)methyl]-1-[3-[3-(trifluoromethyl)phenoxy]-propyl]piperidine oxalate [1:1]

Following the procedure of Example 9,4-[bis (4-fluorophenyl)methyl]-piperidine and 1-[3-chloropropoxy]-3-trifluoromethylbenzene were reacted using potassium iodide catalyst to give the free base of the title compound which was reacted with oxalic acid to give the white oxalate salt (recrystallizing from methanol-ethyl ether) in 39% yield, m.p. 185°–186° C.

Analysis: Calculated for $C_{30}H_{30}F_5NO_5$: C,62.17;H,5.22;N,2.42. Found: C,62.54;H,5.27;N,2.52.

EXAMPLE 48

N-[4-[3-[4-[Bis(4-methylphenyl)methyl]-1-piperidinyl]-propoxy]phenyl]acetamide fumarate hydrate [1:1:0.5]

Following the procedure of Example 22 but substituting dimethylformamide at 73° C. for refluxing butanol, 4-[bis-(4-methylphenyl)methyl]-piperidine and N-[4-(3-chloropropoxy)phenyl]acetamide were reacted using potassium iodide catalyst to give the free base of the title compound which was reacted with fumaric acid to give the white fumarate hydrate (recrystallizing from methanol-ethyl ether), m.p. 149°–152° C.

Analysis: Calculated for $C_{35}H_{42}N_2O_6 \cdot 0.5H_2O$: C,70.57;H,7.28;N,4.70. Found: C,70.80;H,7.28;N,4.65.

EXAMPLE 49

N-[4-[3-[4-[Bis(4-fluorophenyl)methyl]-1-piperidinyl]-phenyl]-acetamide hydrobromide [1:1]

A mixture of 25.68 g (0.089 mole) 4-[bis(4-fluorophenyl)methyl]-piperidine, 20.3 g (0.089 mole) of N-[4-(3-chloropropoxy)phenyl]acetamide, and potassium carbonate, (21.4 g, 0.155 mole) was stirred overnight at 70°–80° C. in 350 ml of dimethylformamide. The reaction mixture was concentrated to dryness and the residue was partitioned between chloroform and water; removal of chloroform gave a dark red oil. The oil was dissolved in glacial acetic acid, and the hydrobromide salt was formed with hydrobromic acid in glacial acetic acid. Solvent was removed in vacuo, and the residue was recrystallized from methanol-ethyl ether. A yield of 21.68 g(43.5%) of pale-white solid, m.p. 223°–225° C., was obtained.

Analysis: Calculated for $C_{29}H_{33}BrF_2N_2O_2$: C,62.26;H,5.95;N,5.01. Found: C,61.99;H,5.94;N,5.01.

EXAMPLE 50

4-[3-4-[Bis(4-fluorophenyl)methyl]-1-piperidinyl]-propoxy]benzeneamine fumarate hydrate [1:1:0.5]

A solution of 11.8 g (0.027 mole) of N-[4-[3-[bis(4-fluorophenyl)methyl]-1-piperidinyl]propoxy]acetamide was heated at gentle reflux for four hours in 500 ml of methanol containing 500 ml of 6N hydrochloric acid. The reaction was stopped and allowed to cool overnight. The reaction mixture was evaporated to a small volume on the rotary evaporator, diluted with water and made alkaline with 5% sodium hydroxide. The reaction mixture was then partitioned between the alkaline phase and chloroform. The chloroform layer was dried, filtered, and solvent removed to give an oil. The oil was converted to the fumarate salt and the salt was recrystallized from methanolethyl ether. The white solid obtained was dried overnight in vacuo at 80° C. to give 8.49 g (71%) of white, crystalline product, m.p. 121.5°–124.0° C.

Analysis: Calculated for $C_{31}H_{34}F_2N_2O_5 \cdot 0.5H_2O$: C,66.30;H,6.28;N,4.99. Found: C,66.49;H,6.13;N,4.92.

EXAMPLE 51

N-[4-[3-[4-[Bis(4-fluorophenyl)hydroxymethyl]-1-piperidinyl]propoxy]-phenyl]acetamide hydrochloride hydrate [1:1:1]

A mixture of 3.0 g (0.01 mole) of α,α-bis(p-fluorophenyl)4-piperidinemethanol, 2.3 g (0.01 mole) of N--8 4-(3-chloropropoxy)phenyl]acetamide, 5.3 g (0.05 mole) of anhydrous sodium carbonate and 0.3 g of potassium iodide in 100 ml of 1-butanol gave a gum as residue. The gum was purified by column chromatography on 80 g of Florisil ® and the product was eluted with 20% acetone in benzene. The combined fractions containing product were concentrated under reduced pressure to give a glass as residue. The glass was dissolved in ethyl ether, filtered through cotton, and the filtrate treated with ethereal hydrogen chloride. The resulting solid was collected by filtration, washed with ethy7l ether and dried to yield 2.1 g (38%) of white solid, m.p. 135°–170° C. (with decomposition).

Analysis: Calculated for $C_{29}H_{33}ClF_2N_2O_3 \cdot H_2O$: C,63.44;H,6.43;N,5.10. Found: C,67.05;H,5.83;N,5.74.

EXAMPLE 53

4-[3-[4-[Bis(4-fluorophenyl)hydroxymethyl]-1-piperidinyl]propoxy]-benzamide

Following the procedure of Example 1 and using potassium iodide catalyst, a mixture of 3.0 g (0.01 mole) of α,α-bis(p0fluorophenyl)4-piperidinemethanol, 2.1 g (0.01 mole) or 4-(3-chloropropoxy)benzamide and 6.9 g (0.05 mole) of anhydrous potassium carbonate in 100 ml of 1-butanol were reacted to give 3.0 g (63%) of white powder, m.p., 200°–204° C. The recrystallizing solvent used was absolute ethanol.

Analysis: Calculated for $C_{28}H_{30}F_2N_2O_3$: C69.98;H,6.29;N,5.83. Found:C,69.61;H,6.49;N,5.70.

EXAMPLE 54

4-[Bis(4-fluorophenyl)methyl]-1-[2-(1-naphthalenyloxy)ethyl]piperidine hydrochloride [1:1]

A mixture of 2.84 g (0.0099 mole) of 4-[α,α-bis(p-fluorophenyl)methyl]piperidine, 3.01 g (0.012 mole) of 1-(2-bromoethoxy)naphthalene and 5.0 g (0.060 mole) of sodium bicarbonate in 400 ml of 1-butanol was heated at reflux for 16 hr. The solvent was removed in vacuo and the residue was partitioned between methylene chloride and dilute sodium hydroxide. The methylene chloride solution was dried over magnesium sulfate, and the solvent was removed in vacuo to give an oil. This was dissolved in a mixture of ether and methanol, an excess of ethereal hydrochloride was added, and a white precipitate was collected to give 3.13 g (64%) of white, crystalline solid, m.p. 155°–158° C.

Analysis: Calculated for $C_{30}H_{30}ClF_2NO$: C,72.94;H,6.12;N,2.84.Found: C,73.20;H,6.10;N,2.78.

EXAMPLE 55

4-[Bis(4-fluorophenyl)methyl]-1-[2-(2-naphthalenyloxy)ethyl]piperidine oxalate [1:1]

Following the procedure of Example 54 and substituting 2-(2-bromoethoxy)naphthalene and oxalic acid for hydrogen chloride, the title compound was obtained in 61.9% yield as white, crystalline solid, m.p. 168°–171° C.

Analysis: Calculated for $C_{32}H_{31}F_2NO_5$: C,70.19;H,5.71;N,2.56. Found: C,70.25;H,5.75;N,2.63.

EXAMPLE 56

1-[4-[3-[4-[Bis(4-fluorophenyl)methyl]-1-piperidinyl]-propoxy]-3-methoxyphenyl]ethanone oxalate [1:1]

The title compound was prepared by the method described in U.S. Pat. No. 3,956,296 (see Example 13 of that patent) as follows: A mixture of 4.75 g(0.0165 mole) of 4-[α,α-bis(p-fluorophenyl)methyl]piperidine, 4.0 g (0.0165 mole) of 3-(-acetyl-o-methoxyphenoxy)propyl chloride and 1.4 g (0.0165 mole) of sodium bicarbonate in 60 ml of dimethylformamide was heated at 80° C. for about 2 hours. TLC showed no product at this point. The temperature was raised to 100° C. for 1 hr, at which time TLC showed the reaction to be complete. After cooling, the reaction mixture was filtered and the dimethylformamide was removed under reduced pressure. The crude product was dissolved in chloroform and filtered and filtrate was concentrated under reduced pressure to give 7.7 g(94%) of crude product. The solild was dissolved in benzene and placed on a Florisil ® column. Upon eluting with an acetone-benzene gradient, 5.5 g of product was obtained. The oxalate salt was prepared and upon recrystallization from 2-propanolmethanol, 3.8 g of salt was obtained, m.p. 164.5°–166° C.

Analysis: Calculated for $C_{32}H_{35}F_2NO_7$: C,65.86;H,6.05;N,2.40 Found: C,66.11;H,6.13;N,2.39.

1-[4-[3-4-[Bis(4-fluorophenyl)methyl]-1-piperidinyl]-propoxy]-3-methoxyphenyl]ethanone fumarate [5:6]

A mixture of 58.26 g (0.203 mole) of 4-[bis(4-fluorophenyl)methyl]piperidine, 54.5 g (0.225 mole) of 1-chloro-3-(4-acetyl-2-methoxyphenoxy) propane, 18.7 g (0.223 mole) of sodium bicarbonate and 1.2 g (0.0072 mole) of potassium iodide in 800 ml of 1-butanol was heated at reflux for 16 hr. The hot reaction mixture was filtered, and the solvent was removed in vacuo from the filtrate. The residue was partitioned between methylene chloride and dilute sodium hydroxide. The methylene chloride solution was dried over magnesium sulfate, and the solvent was removed in vacuo to give an oil. The oil was dissolved in 600 ml of anhydrous ether, and 4.91 g of a solid was collected at room temperature. The ether solution was then treated with a solution of 30.2 g (0.26 mole) of fumaric acid in methanol. Anhydrous ether was added and 99.88 g (77.7%), m.p. 160°–163° C., of title compound was isolated. This was recrystallized from 2-propanol-ethyl ether, (2.5 g, 0.0216 mole of additional fumaric acid was added) to give 2 crops of title compound. [Crop I-44.15 g, m.p. 163°–164.5° C.;Crop II-38.75 g, m.p. 161°–163° C.]. An additional 10.00 g (8.786%), m.p. 159°–162° C. of title compound collected from the original ether-methanol filtrate. NMR showed that the salt contained 1.2 equivalent of fumaric acid.

Analysis: Calc'd for $C_{30}H_{33}F_2NO_3.1.2C_4H_4O_4$: C,66.05;H,6.02;N,2.21. Found: C,65.96;H,6.18;N,2.16.

EXAMPLE 58

1-[4-[3-[4-[Bis(4-fluorophenyl)methylene]-1-piperidinyl]propoxy]-3-methoxyphenyl]ethanone oxalate [1:1]

The title compound was prepared by the method described in U.S. Pat. No. 3,922,276 (see Example 12 of that patent) as follows: A mixture of 4.7 g (0.0165 mole) of 4-[α,α-bis(p0fluorophenyl)methylene]piperidine, 4.0 g (0.0165 mole) of 3-(-acetyl-o-methoxyphenoxy)propyl chloride and 1.4 g of sodium bicarbonate in 60 ml of dimethylformamide was heated at 100° C. overnight. After cooling, the reaction mixture was filtered and the dimethyl formamide was removed at reduced pressure. The residual oil was dissolved in benzene and placed on a Florisil ® column. Elution with a gradient of acetone-benzene gave 5.7 g (70%) of a viscous, brown oil. The free base was reacted with oxalic acid to give the oxalate salt, m.p. 169°–170° C., after recrystallization from isopropyl alcohol and drying under vacuum.

Analysis: Calculated for $C_{32}H_{33}F_2NO_7$: C,66.08;H,5.72;N,2.41. Found: C,66.01;H,5.67;N,2.40.

EXAMPLE 59

1-[4-[3-[4-[(4-Fluorophenyl)(phenyl)methylene]-1-piperidinyl]propoxy]3-methoxyphenyl]ethanone oxalate [1:1]

The title compound was prepared by the method described in U.S. Pat. No. 3,922,276 (see Example 12 of that patent) as follows: A mixture of 7.1 g (0.027 mole) of 4-[α-(p-fluorophenyl)-α-phenylmethylene]piperidine, 6.5 g (0.027 mole) of 3-(-acetyl-o-methoxyphenoxy)propyl chloride and 2.3 g (0.027 mole) of sodium bicarbonate in 100 ml of dimethylformamide was stirred and heated at 100° C. for approximately 8 hours. The mixture was filtered and the dimethylformamide was removed under reduced pressure. The residual oil was dissolved in chloroform and the mixture was filtered. The filtrate was concentrated under vacuum to give 11.5 g of crude, free base (92%). The free base was reacted with oxalic acid to give the oxalate salt, m.p. 143°–145° C., after recrystallization from methyl isobutyl ketone.

Analysis: Calculated for $C_{32}H_{34}FNO_7$: C,68.19;H,6.08;N,2.49. Found: C,68.14;H,6.12;N,2.54.

EXAMPLE 60

1-[3-Methoxy-4-[3-[4-[phenyl[3-(trifluoromethyl)-phenyl]methylene]-1-piperidinyl]propoxy]phenyl]ethanone oxalate [1:1]

The title compound was prepared by the method described in U.S. Pat. No. 3,922,276 (see Example 10 of that patent) as follows; A mixture of 5.0 g (0.0157 mole) of 4-[α-phenyl-α-(m-trifluoromethylphenyl)methylene]piperidine, 3.82 g (0.0157 mole) of 3-(p-acetyl-o-methoxyphenoxy)propyl chloride and 2.52 g (0.03 mole) of sodium bicarbonate in 75 ml of 1-butanol was stirred and heated at reflux for 17.5 hrs. The mixture was cooled and filtered, and the filtrate was concentrated under reduced pressure. The glassy residue obtained weighed 4.25 g (52%) and was dissolved in benzene and placed on a Florisil ® column. Using an acetone-benzene gradient elution, product was obtained as a glassy residue. This residue was dissolved in ether and the oxalate salt was obtained. The salt has a glassy appearance, m.p. 120°–125° C.

Analysis: Calculated for $C_{33}H_{34}F_3NO_7$: C,74.59;H,5.58;N,2.28. Found: C,64.34;H,5.72;N,2.04.

EXAMPLE 61

1-[4-[3-[4(Cyclohexylphenylmethylene)-1-piperidinyl]-propoxy]-3-methoxyphenyl]ethanone oxalate [1:1]

The free base of the title compound was obtained as in Example 1 of U.S. Pat. No. 3,922,276 by reacting 4-[(α-cyclohexyl-α-phenyl)methylene]piperidine with 3-(p-acetyl-o-methoxyphenoxy)propyl chloride in a mixture with sodium bicarbonate in dimethylformamide and converted to the oxalate salt, m.p. 184°–185° C.

Analysis: Calculated for $C_{32}H_{41}NO_7$: C,69.67;H,7.49;N,2.54. Found: C,69.83;H,7.58;N,2.56.

EXAMPLE 62

1[4-[3-[4-(Cyclohexylphenylmethyl)-1-piperidinyl]-propoxyl]-3-methoxyphenyl]ethanone oxalate hydrate[1:1:0.5]

A mixture of 5.2 g (0.02 mole) of 4-[(α-cyclohexyl-α-phenyl)]-piperidine, 4.9 g (0.02 mole)of 3-(p-acetyl-o-methoxyphenoxy)propyl chloride and 1.7 g (0.02 mole) of sodium bicarbonate in 100 ml of dimethylformamide was stirred and heated at 100° C. for 4 hrs. The reaction mixture was cooled, filtered, and the dimethylformamide was removed under pressure pressure. The residual material was dissolved in benzene and placed on a Forisil ® column. Elution using an acetone-benzene gradient gave 7.0 g (74.5%) of free base of the title compound. The oxalate salt was prepared and recrystallized from 2-propanol, m.p. 155°–160° C.

Analysis: Calculated for $C_{32}H_{43}NO_7.0.5H_2O$: C, 68.31; H, 7.88; N, 2.49. Found: C, 6860; H, 7.78; N, 2.42.

The free base of the title compound was obtained by reacting 4[(α-acyclohexyl-α-phenyl)methyl]piperidine and 3-(p-acetyl-o-methoxyphenoxy)-propyl chloride in a mixture with sodium bicarbonate, isolated and reacted with oxalic acid. The oxalte salt was recystallized from 2-propanol, m.p. 155°–160° C.

EXAMPLE 63

4-[3-[4-[Bis(4-fluorophenyl)methylene[-1-piperidinyl]-propoxy]-α- methylbenzenemathanol oxalate [1:1].

A solution of 1-[4-[3-[4-bis(4-fluorophenyl)methylene]-1-piperidinyl]-propoxy]phenyl]ethanone, 3.56 g (0.0077 mole) and sodium borohydride, 1.51 g(0.04 mole) was stirred 6 hrs at room temperature. The reaction mixture was concentrated to dryness and partitioned between chloroform-water and chloroform-5% sodium hydroxide. Removal of chloroform gave an oil which was converted to the oxalate salt. Recrystallization from methanol-ethyl ether gave 2.67 g (62.1%) of white, crystalline product, m.p. 142°-145° C.

Analysis: Calculated for $C_{31}H_{33}F_2NO_6$: C, 67.26; H, 6.01; N, 2.3. Found: C, 67.17; H, 5.92; N, 2.47.

EXAMPLE 64

4-[3-[Bis(4-fluorophenyl)methyl)-1-piperidinyl]propoxy]-3-methoxy-α-methylbenzenemethanol.

Sodium borohydride (3.0 g, 0.079 mole) was added to 250 ml of 95% ethanol. To the mixture was added 4.40 g (0.00885 mole) of 1-[3-(p-acetyl-o-methoxyphenoxy)-propyl]-4[α,α-bis(p-fluorphenyl)methyl]piperidine in 100 ml of 95% ethanol over 15 minutes. The resulting solution was stirred 2.5 at room temperature. The reaction mixture was concentrated to dryness and partitioned between chloroform and 5% sodium hydroxide. The organic layer was back extracted with 5% sodium hydroxide and water; removal of chloroform gave an oil. The oil formed a white solid in ethyl ether. The white solid was collected by filtration and recrystallized from methylene chloride-ethyl ether. This furnished 2.16 g (49.2%) of white solid, m.p. 132°-135° C.

Analysis: Calculated for $C_{30}H_{35}F_2NI_3$: C, 72.72; H, 7.12; N, 2.83. Found: C, 72.28; H, 7.21; N, 2.52.

EXAMPLE 65

1-[4-[3[4-(Diphenylmethyl)-1-piperidinyl[propoxy]-3-methoxyphenyl]-ethanone oxalate [1:1].

A mixture of 5.0 g (0.02 mole)of 4-(α-phenylbenzyl)-piperidine, 4.85 g (0.02 mole) of 3-(p-acetyl-o-methoxyphenoxy)propyl chloride, and 3.4 g (0.04 mole) of sodium bicarbonate i 100 ml of dimethylformamide was heated at 100° C. for about 3 hrs. The reaction mixture was cooled, filtered and the filtrate was concentrated under reduced pressure. The residual oil was dissolved in chloroform and the chloroform was filtered to remove insolubles. The filtrate was concentrated under reduced pressure to give 8.6 g of a red oil (94.5%). The oil was dissolved in a mixture of 4:1 ether/2-propanol and treated with 2.3 g of oxalic acid dihydrate. The oxalate salt crystallized upon standing and trituration in ether gave 8.4 g of salt melting at 149°-155° C. Recrystallization from isobutyl methyl ketone gave 7.0 g of the salt, m.p. 153°-155° C. (See Example 11, U.S. Pat. No. 3,956,2961).

Analysis: Calculated for $C_{32}H_{37}NO_7$: C, 70.18; H, 6.81, N, 2.56. Found: C, 70.00; H, 6.76; N, 2.56.

EXAMPLE 66

1-[4-[3-4-[Bis-(4-fluorophenyl)hydroxymethyl]-1-piperidinyl]propoxy]-3-methoxyphenyl]ethanone.

A mixture of 5.0 g (0.0165 mole) of α,α-bis(p-fluorophenyl)-4-piperidine-methanol, 4.0 g (0.0165 mole) of 3-(p-acetyl-o-methoxyphenoxy)propyl chloride and 1.4 g (0.0165 mole) of sodium bicarbonate in 60 ml of dimethylformanide was stirred and heated at 80° C. for two hours. The temperature was raised to 100° C. for one hour. After cooling, the reaction mixture was filtered and the dimethylformamide was removed at reduced pressure. The residual oil which crystallized on standing in ether was dissolved in benzene and placed on a Florisil ® column. Using a gradient elution of acetone-benzene, 1.8 g (21.4%) of product was obtained from the column, m.p. 141.5°-143° C. (See Example 12, U.S. Pat. No. 3,956,296).

Analysis: Calculated for $C_{30}H_{33}F_2NO_4$: C,70.71; H, 6.53, N, 2.75. Found: C, 70.49; H, 6.58; N, 2.59.

EXAMPLE 67

1-[4-[-4-[(4-Fluorophenyl)hydroxyphenylmethyl]-1-piperidinyl]-propoxy]-3-methoxyphenyl]ethanone.

A mixture of 6.5 g (0.023 mole) of α-(p-fluorophenyl)-α-phenyl-4-piperidinemethanol, 5.5 g (0.023 mole) of 3-(p-acetyl-o-methoxyphenoxy)-propyl chloride and 1.92 g (0.023 mole) of sodium bicarbonate in 80 ml of dimethylformamide was heated at 110°-110° C. for 2 hrs. The reaction mixture was cooled and filtered and the dimethylformamide was removed at reduced pressure. The residual oil was dissolved in chloroform and filtered. The chloroform was removed at reduced pressure. The solid residue which remained weighed 8.6 g (77%) and was recrystallized from ethanol to give 3.1 g of material melting at 147°-148° C. A sample was dried over refluxing toluene and submitted for analysis. (See Example 14, U.S. Pat. No. 3,956,296).

Analysis: Calculated for $C_{30}H_{34}FNO_4$: C,73.30; H,6.97; N,2.85. Found: C, 73.15; H,7.05; N, 2.77.

EXAMPLE 68

1[4-[4-(Diphenylhydroxymethyl)-1-piperidinyl]propoxy]-3-methoxyphenyl]ethanone oxalate[1:1]

A mixture of 5.2 g (0.0194 mole)of α,α-diphenyl-4-piperidinemethanol, 4.7 g )0.0194mole) of 3-(p-acetyl-o-methoxyphenoxy)propyl chloride and 1.6 g (0.0194 mole) of sodium bicarbonate in 60 ml of dimethylformamide was stirred at 100° C. for 3 hrs. After cooling, the reaction mixture was filtered and the dimethylformamide was removed under reduced pressure. The residual oil weighed 8.3 g (90%). Some of the product crystallized upon trituration in anhydrous ether and was collected by filtration. The filtrate was evaporated to dryness and the residue was dissolved in hot benzene-isooctane. Upon cooling, the crystalline product was obtained. A total yield of 6.3 g of solid product was obtained. The solid free base was converted to the oxalate salt. Recrystallization from isobutyl methyl ketone gave the off-while solid melting at 74°-176° C. (See Example 15, U.S. Pat. No. 3,956,296).

Analysis: Calculated for $C_{32}H_{37}NO_8$: C,68.19; H,6.62; N,2.49. Found: C,68.34; H,6.75; N,2.42.

EXAMPLE 69

1-[4-8 3-[4-[Hydroxyphenyl]3-(trifluoromethyl)phenyl]methyl]-1-piperidinyl]propoxy]-3-methoxyphenyl]ethanone hydrochloride hydrate [1:1:05]

A mixture of 7.0 g (0.021mole) of α-phenyl-α(m-trifluoromethylphenyl-4-piperidinemethanol, 5.1 g (0.21 mole) of 3-(p-acetyl-o-methoxyphenoxy)-propyl chloride and 3.0 g (0.036 mole) of sodium bicarbonate in 125 ml of dry dimethylformamide was stirred and heated at 90°-95° C. for 5 hours. The mixture was cooled and filtered. An excess of water was added to the reaction mixture. The mixture was extracted several times with benzene and the collected extracts were dried over anhydrous sodium sulfate. The mixture was filtered and the filtrate was concentrated under reduced pressure.

The crude solid which was obtained was dissolved in benzene and placed on a Florisil ® column. Elution using an acetone-benzene gradient gave a gummy solid. The gum was dissolved in either and the hydrochloride salt was prepared. The hydrochloride salt weighed 3.1 g (25%) and became a clear melt at 95° C. (See Example U.S. Pat. No. 3,956,296).

Analysis: Calc'd for $C_{31}H_{35}ClF_3NO_4.0.5H_2O$; C,63.42; H,6.18; N2.39. Found: C,63.68; H,6.03; N,2.33.

EXAMPLE 70

1-[4-[3-[4(Cyclohexlhydroxyphenylmethyl)-1-piperidinyl]propoxy]-3-methoxyphenyl]ethanone hydrochloride [1:1].

A mixture of 3.9 g (0.143 mole) of α-cyclohexyl-α-phenyl-4-piperidinemethanol, 3.5 g (0.143 mole) of 3-(p-acetyl-o-methoxyphenoxy)propyl chloride and 2.35 g (0.28mole) of sodium bicarbonate in 100 ml of dimethylformamide was heated at 100° C. for 4 hours. After cooling, the reaction mixture was diluted with about 600 ml of water and extracted with benzene. The collected benzene extracts were washed with water and dried over anhydrous magnesium sulfate. The mixture was filtered, and the filtrate was concentrated under reduced pressure. A crude solid weighing 5.1 g (74.5%) was obtained. The solid was dissolved in ether, and the ether solution was treated with an excess of ethereal hydrogen chloride. The hydrochloride salt obtained was recrystallized from isobutyl methyl ketone to give 4.0 g of the salt, m.p. 152°–155° C. (See Example 17, U.S. Pat. No. 3,956,296).

Analysis: Calculated for $C_{30}H_{42}ClNO_4$: C,69.82; H,8.20; N,2.71. Found: C,69.50; H,8.31; N,2.62.

EXAMPLE 71

1-[4-[2-[4-[Bis(4-fluorophenyl)hydroxymethyl]-1-piperidinyl]ethoxy]-3-methoxyphenyl]ethanone.

Following the procedure of Example 1 and utilizing potassium iodide catalyst, a mixture of 3.0 g (0.01 mole) of α,α-bis(p-fluorophenyl)-4-piperidinemethanol, 2.3 g (0.01 mole) of 1-[4-(2-chloroethoxy)-3-methoxyphenyl]-ethanone and sodium carbonate in butanol, the title compound was prepared in 22% yield, m.p. 131°–135° C., after recrystallization from isopropyl alcohol.

Analysis: Calculated for $C_{29}H_{31}F_2NO_4$; C,70.29; H,6.31; N,2.83. Found: C,70.00; H,6.39; N,2.60.

EXAMPLE 72

1-[4-[4-[4-Bis(4-fluorophenyl)hydroxymethyl]-1-piperidinyl]butoxy]-3-methoxyphenyl]ethanone.

This compound was prepared according to the procedure used to synthesize the compound of Example 35. A mixture of 3.0 g (0.01 mole) of α,α-bis(p-fluorophenyl)-4-piperidinemethanol, 3.0 g (0.01 mole) of 1-[4-(4-bromobutoxy)-3methoxyphenyl]ethanone, 5.3 g (0.05 mole) of anhydrous sodium carbonate and 0.3 g of potassium iodide in 100 ml of dimethylformamide gave, after purification by column chromatography on Florisil ® (acetone-benzene). 0.8 g (15%) of off-white powder m.p. 104°–105° C., after recrystallization from 2-propanol-isopropyl ether.

Calculated for $C_{31}H_{35}F_2NO$: C,71.11; H,6.74; N,2.68. Found: C,70.84; H,6.71N,2.65.

EXAMPLE 75

1-[4-[5-[4-Bis(4-fluorphenyl)hydroxymethyl]-1piperindyl]pentoxy]-3-methoxyphenyl]ethanone.

Following the procedure of Example 1 and utilizing potassium iodide catalyst, a mixture of 3.0 g (0.01 mole) of α,α-bis(p-fluorophenyl)-4-piperidinemethanol, 2.7 g (0.01 mole) of 1-[4-(5-chloropentoxy)-3-methoxyphenyl]ethanone and 5.3 g (0.05 mole) of anhydrous sodium carbonate in butanol, the title compound was prepared in 65% yield as white solid after recrystallization from isopropyl alcohol, m.p. 117.5°–118.5° C.

Analysis: Calculated fro $C_{32}H_{37}F_2NO_4$; C,71.49; H,6.94; N,2.61. Found: C,71.51; H,7.06; N,2.50.

EXAMPLE 74

1-[2-[2-4[Bis(4-fluorphenyl)methyl9-1-piperidinyl]ethoxy]-3-methoxyphenyl]ethanone.

A mixture of 4-[bis(4-fluorophenyl)methyl]piperidine, 4.88 g (0.017 mole), 1-[4-(2-chloroethoxy)-3methoxyphenyl]ethanone, 3.86 g (0.017 mole), and potassium carbonate, 5.53 g (0.04 mole) was heated overnight at gentle reflux in 350 mol of 1-butanol containing potassium iodide (0.3 g). The reaction mixture was filtered and concentrated to dryness. The dark brown oil obtained was dissolved in chloroform and extracted with 1N sulfuric acid and 5% sodium hydroxide. The chloroform layer was dried, filtered, and solvent removed. This furnished a brown oil which was subjected to flash chromatography on silica gel using hexane-ethyl acetate for elution. A white solid was obtained by evaporating the fractions containing the product. The solid was extracted with ethyl ether and the mixture was placed in the freezer overnight. A white solid was obtained which was dried at 80° C. in vacuo overnight. A yield of 2.2 g (27%) of white, crystalline solid, m.p. 129°–131° C., was obtained.

Analysis: Calculated for $C_{29}H_{31}F_2NO_3$: C,72.63; H,6.52; N,2.92. Found: C,72.52; H,6.45; N,2.87.

EXAMPLE 75

1-[4-[3-[4-[Bis(4-chlorophenyl)methylene]-1-piperindyl]propoxyl]-3-methoxyphenyl]ethanone A mixture of 3.96 g (0.01305 mole) of 4-[bis-(4-chlorophenyl)-methylene]pipridine, 3.16 g (0.013 mole) of 1-[4-(3-chloropropoxy)-3-methoxyphenyl]ethanone, and 3.18 g (0.03 mole) of anhydrous sodium carbonate in 300 ml of 1-butanol containing 0.3 g of potassium iodide was heated overnight at gentle reflux. The reflux mixture was concentrated to dryness and partitioned between chloroform-water and chloroform -5% sodium hydroxide. Removal of chloroform gave an oil which crystallized from isopropyl alcohol. The solid was again crystallized from isopropyl alcohol to give 4.16 g (61%) of light yellow solid, m.p. 143°–144° C.

Analysis: Calculated for $C_{30}H_{31}Cl_2NO_3$: C,68.70; H,5.96; N,2.67. Found: C,69.11; H,6.02; N,2.55.

EXAMPLE 76

1-[4-[3-[4-[(4-Fluorophenyl)phenylmethyl]-1-piperidinyl]propoxy]-3-methoxyphenyl]ethanone oxalate [1:1

A solution of 4.42 g (0.0164 mole)of 4-[-(4-fluorophenyl)phenylmethyl]-pipridine and 4.11 g (0.0170 mole) of 1-8 4-(3-chloropropoxy)-3-methoxyphenyl]ethanone, 0.01 g of potassium iodide and 1-butanol was heated at reflux for 18 hr. The solvent was removed in vacuo, and the residue was partitioned between methylene chloride and dilute sodium hydroxide. The solvent was removed in vacuo to give an oil. A solution of the oil in methanol was treated with an equivalent of oxalic acid, ethyl ether was added, and 6.39 g (68.9%) of white crystalline solid m.p. 161°–163°0 C., was obtained.

Analysis: Calculated for $C_{32}H_{36}FNO_7$: C,67.95; H,6.42; N,2.48 Found: C,67.92; H,6.42; N,2.44.

EXAMPLE 77

1-[4-[3-[4-Bis(4-methoxyphenyl)methyl]-1-piperidinyl]-propoxyl]-3-methoxyphenyl]ethanone oxalate [1:1]

A mixture of 7.78 g (0.025 mole) of 4-bis(4-methoxyphenyl)methyl]-piperidine, 6.05 g (0.025 mole)of 1-[4-(3-chloropropoxy)-3-methoxyphenyl-9 -ethanone, and potassium carbonate (5.53 g, 0.04 mole) in 300 ml of 1-butanol containing potassium iodide (0.3 g) was heated at reflux overnight. The reaction mixture was concentrated to dryness and the residue was partitioned between chloroform and water; removal of chloroform in vacuo gave a dark brown oil. The oil was subjected to column chromatography on silica gel using a gradient elution composed of methanol and ethyl acetate. The corresponding fractions from the column were combined and reacted with oxalic acid. Recrystallization of the salt from methanol-ethyl ether gave 4.16 g (27.4%) of white solid, m.p. 163.5°–165° C.

Analysis: Calculated for $C_{34}H_{41}NO_9$: C,67.20; H,6.80; N,2.31. Found: C,66.76; H,6.84; N,2.26.

EXAMPLE 78

1-[4-[3-[4-Bis(4-methylphenyl)methyl]-1piperidinyl]-propoxy]-3methoxyphenyl]ethanone A mixture of 5.10 g (0.018 mole) 4-[bis(4-methylphenyl)methyl]-piperidine and 4.42 g (0.018 mole) of 1-[4-(3-chloropropoxy)-3-methylphenyl]-ethanone in 350 ml of 1-butanol was heated overnight at gentle reflux with potassium carbonate (5.53 g , 0.04 mole) and potassium iodide (0.3 g). The reaction mixture was stripped to dryness and the resulting residue was partitioned between chloroform-5% sodium hydroxide and chloroform-water. Removal of chloroform gave a dark brown oil. The oil was subjected to column chromatography on a silica gel column with a gradient elution series of hexane-ethyl acetate and ethyl acetate-dimethoxyethane. The proper fractions from the column were combined. This resulted in 2.60 g (29.7%) of oil (after drying in vacuo at 80° C. overnight).

Analysis: Calculated for $C_{32}H_{39}NO_3$; C,79.14; H,8.09; N,2.88. Found: C,78.70; H,8.08; N,2.80.

$^1$HNMR (CDCl$_3$): 7.5 δ(multiplet, protons on ring next to ketone, 2H), 6.7–7.6(multiplet, aromatic proton, 9H), 4.0 (triplet, methylene adjacent to the ether oxygen, 2H), 3.8 singlet, OCH$_3$3H,)3.3 (doublet, methine next to rings, 1H), 2.5 (singlet, methyl of ketone, 3H), 2.2 (singlet, methyl groups attached to aromatic rings, 6H), 1.0–3.0 (multiplet, remaining aliphatic protons, 13H).

EXAMPLE 79

1-[4-[4-[4-Bis(4-fluorophenyl)methyl]-1-piperidinyl]-butoxy]-b 3-methoxyphenyl]ethanone A mixture of 6.15 g (0.02 mole) of 4-4[-bis(4-fluorophenyl)methyl]-piperidine and 6.45 g (0.02 mole) of 1-[4-(4-bromobutoxy)-3-methoxyphenyl]-ethanone in 350 ml of acetonitrile was stirred overnight at room temperature with potassium carbonate, 5.53 g (0.04 mole) and potassium iodide (0.3 g). The mixture was then heated five hours at reflux. The reaction mixture was concentrated to dryness on a rotary evaporator, and the residue was partitioned between chloroform -5% sodium hydroxide and chloroform-water. Removal of chloroform gave a dark brown oil. The oil was subjected to chromatography on a silica gel column and eluted with a hexane-ethyl acetate-dimethoxyethane series. Fractions from the column were combined and solvent removed by pumping in vacuo overnight at 80° C. This provided 3.34 g (31.3%) of brown oil.

Analysis: Calculated for $C_{31}H_{35}F_2NO_3$: C,73.35; H,6.95; N,2.76. Found: C,72.34; H,6.92; N,2.70.

NMR analysis was obtained as follows: $^1$H NMR (CDCl$_3$):

6.8–7.6 δ(multiplet, aromatics, 11H), 4.1 (triplet methylene next to ether linkage, 2H), 3.4–3.6 (doublet, methine attached to two fluorophenyl rings, 1H), 3.8 (singlet, OCH$_3$,3H), 2.5 (singlet, COCH$_3$3H), (1.1–3.0(multiplet, remaining aliphatics, 15H).

EXAMPLE 80

4-[3-[4-Bis(4-fluorophenyl)hydroxymethyl]-1-piperidinyl]propoxy]3-methoxybenzoic acid methyl ester Following the procedure of Example 1 and utilizing potassium iodide catalyst and substituting dimethylfrmamide for butanol, a mixture of 5.4 g (0.021 mole) of 4-(3-chloropropoxy)-3-methoxybenzoic acid methyl ester, 6.0 g (0.02 mole) of [α, α-bis(p-fluorophenyl)]-4-piperidinemethanol, 7.4 g (0.07 mole) of anhydrous sodium carbonate and 0.3 g of potassium iodide in 150 ml of dimethylformamide was reacted to give 5.7 g (53%) of white solid, m.p. 131°–132° C., after recrystallization from isopropyl alcohol.

Analysis: Calculated for $C_{30}H_{33}F_2NO_5$: C,68.56; H6.33; N,2.67. Found: C,68.23; H,6.35; N,2.60.

EXAMPLE 81

α,α-[Bis(4flurophenyl)]-1-[3-[4-(methoxylthio)phenoxy]propyl]-4-piperidinemethanol Following the procedure of Example 1, a mixture of 3.0 g (0.01 mole) of [α,α-bis(p-fluorophenyl)]-4-piperidinemethanol, 2.2 g (0.01 mole) 1-chloro3-(4-methylthiophenoxy)propane, 5.3 g (0.05 mole) of anhydrous sodium carbonate and 0.3 g of potassium iodide in 100 ml of 1-butanol was reacted to give 2.3 g (48%) of white powder, m.p. 113°–115° C., after recrystallization from isopropyl ether.

Analysis: Calculated for $C_{28}H_{31}F_2NO_2S$: C,69.54; H,6.46; N,2.90. Found: C,69.57; H,6.51; N,2.85.

EXAMPLE 82

α,α-[Bis(4-fluorophenyl)]-1-3-[4-(methylsulfonyl)-phenoxy]propyl]-4-piperidinemethanol fumarate [1:1].

Following the procedure of Example 1, a mixture of 3.0 g (0.01 mole) of [α,α-bis(p-fluorophenyl)]-4-piperidinemethanol, 2.5 g (0.01 mole) of -3-chloropropoxy)-4-(methylsulfonyl)benzene, pb 5.3 g (0.05 mole) of anhydrous sodium carbonate and 0.3 g of potassium iodide ion 100 ml of 1-butanol was reacted to give a brown gum as residue. The gummy residue was reacted with fumaric acid and the fumarate salt obtained was recrystallized from acetonitrile to give 3.0 g (48%) of white solid, m.p. 176°–178° C.

Analysis: Calculated for $C_{32}H_{35}F_2NO_8S$: C, 60.85; H, 5.59; N, 2.22. Found: C, 60.72; H, 5.54; N, 2.20.

EXAMPLE 83

4-[3-[4-[Bis(4-fluorophenyl)hydroxymethyl]-1-piperidinyl]propoxy]-3-methoxybenzeneacetic acid ethyl ester hydrochloride Following the procedure of Example 45, α,α-bis(p-fluorophenyl-4-piperidinemethanol and 4-(3-chloropropoxy)-3-methoxybenzeneacetic acid, ethyl ester are reacted and the hydrochloride salt is prepared.

EXAMPLE 84

4-[3-4-[Bis(4-fluorophenyl)hydroxymethyl]-1-piperidinyl]ethoxy]benzoic acid ethyl ester hydrochloride Following the procedure of Example 45, α,α-bis(p-fluorophenyl-4-piperidinemethanol and 4-(2-chloroethoxy)benzoic acid ethyl ester are reacted and the hydrochloride salt is prepared.

EXAMPLE 85

4-[3-[4-[Bis(4-fluorophenyl)hydroxymethyl]-1-piperidinyl]propoxy]-3-methoxybenzeneacetic acid sodium salt hydrate [1:1:0.5]

This compound was prepared according to the procedure of Example 1. A mixture of 3.0 g (0.01 mole) of α,α-bis(p-fluorophenyl)-4-piperidinemethanol, 2.9 g (0.01 mole) of 4-(3-chloropropoxy)-3-methoxybenzeneacetic acid ethyl ester, 5.3 g (0.05 mole) of anhydrous sodium carbonate and 0.3 g of potassium iodide in 150 ml of acetonitrile gave the ester as a gum. The gum was converted to the hydrochloride with ethereal hydrogen chloride to give a white solid. The solid could not be recrystallized so it was partitioned between methylene chloride and a 5% sodium hydroxide solution. An emulsion resulted which was let stand until the layers separated. During this time a solid precipitated. The mixture was filtered. The filter cake was recrystallized from ethyl acetate to yield 0.7 g (13%) of fluffy, white solid, m.p. 102°–112° C.

Analysis: Calc'd for $C_{30}H_{32}F_2NNaO_5.0.5H_2O$: C, 64,74; H, 5.98; N, 2.52. Found: C, 64.50; H, 5.97; N, 2.39.

EXAMPLE 86

7-[3-[4-[Bis(4-fluorophenyl)hydroxymethyl]-1-piperidinyl]propoxy]-2H-1-benzopyran-2-one This compound was prepared according to the procedure of Example 1. A mixture of 3.0 g (0.01 mole) of α,α-bis(p-fluorophenyl)-4-piperidinemethanol, 2.4 g (0.01 mole of 7-(3-chloropropoxy)2H-1-benzopyran-2-one, 5.3 g (0.05 mole) of anhydrous sodium carbonate and 0.3 g of potassium iodide in 100 ml of 1-butanol gave 3.6 g (71%) of pale yellow crystals, m.p. 99°–120° C. with decomposition.

Analysis: Calculated for $C_{30}H_{29}F_2NO_4$: C, 71.27; H, 5.78; N, 2.77 Found: C, 71.02; H, 5.89; N, 2.63.

EXAMPLE 87

2-[3-[4-Bis(4-fluorophenyl)hydroxymethyl]-1-piperidinyl]propoxy]benzoic acid ethyl ester fumarate [4:3]

This compound is prepared according to the procedure of Example 1. A mixture of 3.0 g (0.01 mole) of [α,α-bis(p-fluorophenyl)]-4-piperidinemethanol, 2.4 g (0.01 mole) of 2-(3-chloropropoxy)benzoic acid ethyl ester, 5.3 g (0.05 mole) of anhydrous sodium carbonate and 0.3 g of potassium iodide in 100 ml of dimethylformamide gave 5.7 g of gum as residue. The gum was purified by column chromatography on 100 g of silica gel. Fractions eluted with 35% acetone in benzene were combined and concentrated to give 3.0 g of pale yellow gum as residue. The gum was converted to the fumaric acid salt and the solid was recrystallized twice from 2-propanol to yield 2.0 g (32%) of white solid, m.p. 138°–141° C.

Analysis: Calculated for $C_{33}H_{36}F_2NO_7$: C, 66.43; H, 6.08; N, 2.35. Found: C, 66.25; H, 6.08; N, 2.27.

EXAMPLE 88

2-[3-4-[Bis(4-fluorophenyl)methyl]-1-piperidinyl]-propoxy]benzoic acid ethyl ester A mixture of 32.79 g (0.116 mole) of 4-[bis(4-fluorophenyl)methyl]piperidine, 27.04 g (0.114 mole) of 2-(3-chloropropoxy)benzoic acid ethyl ester, and potassium carbonate, 19.40 g (0.140 mole) was heated overnight at reflux in 500 ml of diethoxyethane containing potassium iodide (0.4 g). The reaction was filtered and concentrated to dryness. The residue obtained was dissolved in chloroform and extracted with 5% sodium hydroxide, sodium sulfite, and water. The chloroform layer was dried (anhydrous sodium sulfate), filtered, and solvent removed to furnish a dark brown oil (56.20 g). The oil was subjected to flash chromatography on an 83.5 g silica gel column (with ethyl acetate). Fractions were combined with similar purity. One sample of 6.49 g (56.5%) was dried in vacuo at 80° C. overnight and analyzed. $^1H$ NMR (CDCl$_3$): 7.8δ (m, 1, aromatic proton ortho to ester), 7.0δ (m, 11, aromatic), 4.3δ (q, 2, C—O—CH$_2$), 4.1δ (t, 2, —OCH$_2$), 3.5δ (d, 1, methine), 1.3δ (t, 3, CH$_3$), 1.7–3.0δ (m, 13, aliphatic).

Analysis: Calculated for $C_{30}H_{33}F_2NO_3$: C, 73.00; H, 6.74; N, 2.84. Found: C, 72.98; H, 6.70; N, 2.93.

EXAMPLE 89

1-[4-[5-[4-[Bis(4-fluorophenyl)methyl]-1-piperidinyl]-pentoxy]-3-methoxyphenyl]ethanone hydrate [1.0.5]

A mixture of 6.03 g (0.021 mole) of 4-[bis(4-fluorophenyl)methyl]piperidine, 5.69 g (0.021 mole) of 1-[4-(5-chloropentoxy)-3-methoxyphenyl]ethanone, and potassium carbonate (5.53 g, 0.04 mole) was heated overnight at gentle reflux in 350 ml of 1-butanol containing potassium iodide (0.2 g). The reaction mixture was cooled at room temperature, filtered, and concentrated to dryness. The residue obtained was dissolved in chloroform and extracted several times with water. The chloroform layer was dried (sodium sulfate), filtered, and solvent removed to give a brown oil. This oil was subjected to flash chromatography on silica gel using ethyl acetate and 2% methanol-ethyl acetate for elution. Fractions of similar purity were combined and solvent removed. The sample was dried in vacuo at 70° C. overnight after being exposed to the atmosphere for 24 hours. A yield of 2.7 g (24.6%) of brown oil was obtained.

$^1$H NMR (CDCl$_3$): 6.8–7.6δ (m, 11, aromatic), 4.1δ (t, 2, —OCH$_2$), 3.9δ (s, 3, OCH$_3$), 3.4–3.6δ (d, 1, methine of difluorophenyl group), 2.5δ (s, 3,

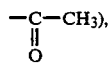

1–3.0δ (m, 18, aliphatics and 0.5 H$_2$O).

Analysis: Calculated for C$_{32}$H$_{37}$NO$_3$.0.5H$_2$O: C, 72.43; H, 7.22; N, 2.64. Found: C, 72.75; H, 7.23; N, 2.57.

EXAMPLE 90

4-[3-[4-[Bis(4-fluorophenyl)methyl]-1-piperidinyl]-propoxy]benzamide fumarate [2:3]

A mixture of 6.10 g (0.021 mole) of 4-[bis(4-fluorophenyl)methyl]piperidine and 4.53 g (0.021 mole of 4-(3-chloropropoxy)benzamide in 350 ml of 1-butanol containing potassium carbonate (5.53 g, 0.021 mole) and potassium iodide (0.2 g) was heated overnight at gentle reflux. The reaction was filtered and stripped to dryness. The residue obtained was dissolved in chloroform and extracted with water. The chloroform layer was dried, filtered, and solvent removed to give an oil. This material was converted to the fumarate salt and recrystallized from methanol-ethyl ether. The white, crystalline solid obtained was dried in vacuo overnight at 65° C. A yield of 5.47 g (40.3%) of white, crystalline product was obtained, m.p. 193°–194° C.

Analysis: Calculated for C$_{34}$H$_{36}$F$_2$N$_2$O$_8$: C, 63.94; H, 5.68; N, 4.39. Found: C, 64.03; H, 5.73; N, 4.37.

EXAMPLE 91

4-[Bis(4-fluorophenyl)methyl]-1-[3-[4-(methylsulfonyl)-phenoxy]propyl]piperidine oxalate [1:1]

A mixture of 6.02 g (0.021 mole) of 4-[bis(4-fluorophenyl(methyl]piperidine and 5.22 g (0.021 mole) of 1-(3-chloropropoxy)-4-(methylsulfonyl)benzene in 350 ml of 1-butanol containing potassium carbonate (5.53 g, 0.04 mole) and potassium chloride (0.2 g) was heated overnight at gentle reflux. The reaction was filtered and concentrated to dryness. The residue obtained was dissolved in chloroform and extracted with water. The chloroform layer was dried, filtered, and solvent removed to give an oil. The dark brown oil was converted to the oxalate salt and recrystallized from methanol-ethyl ether to give a white solid. This material was dried in vacuo overnight at 65° C. A yield of 6.21 g (50.1%) of white, crystalline solid, m.p. 202°–204° C., was obtained.

Analysis: Calculated for C$_{30}$H$_{33}$F$_2$NO$_7$S: C, 61.11; H, 5.64; N, 2.38. Found: C, 60.99; H, 5.64; N, 2.36.

EXAMPLE 92

1-[4-[6-[4-[Bis(4-fluorophenyl)hydroxymethyl]-1-piperidinyl]hexyloxy]-3-methoxyphenyl]ethanone Following the procedure of Example 1 and utilizing potassium iodide catalyst, a mixture of [α,α-bis(p-fluorophenyl)]-4-piperidinemethanol and 1-[4-(6-chlorohexoxy)-3-methoxyphenyl]ethanone and sodium carbonate in butanol, the title compound is prepared.

EXAMPLE 93

1-[4-[3-[4-[Bis(4-fluorophenyl)hydroxymethyl]-1-piperidine]propoxy]-2-methoxyphenyl]ethanone Following the procedure of Examples 1 and 66, [α,α-bis(p-fluorophenyl)]-4-piperidinemethanol and 3-(p-acetyl-m-methoxyphenoxy)propyl chloride are reacted to give the title compound.

EXAMPLE 94

α,α-Bis(4-fluorophenyl)-1-[3-(2-hydroxyphenoxy)-propyl]-4-piperidinemethanol

Following the procedure of Example 2 and using potassium iodide catalyst, α,α-bis(p-fluorophenyl)-4-piperidinemethanol and 2-(3-chloropropoxy)-1-benzyloxybenzene are reacted to give 1-[3-(2-benzyloxyphenoxy)propyl]-α,α-bis(4-fluoropyhenyl)-4-piperidinemethanol which is reacted with hydrogen over palladium on carbon catalyst to give the title compound.

EXAMPLE 95

α,α-[Bis(4-fluorophenyl)-1-[3-[4-(methylsulfinyl)-phenoxy]propyl]-4-piperidine methanol fumarate Following the procedure of Examples 1 and 82, [α,α-bis-fluorophenyl)]-4-piperidinemethanol and 1-(3-chloropropoxy)-4-(methylsulfinyl)benzene are reacted to give the free base of the title compound which is then reacted with fumaric acid to give the title compound.

EXAMPLE 96

4-[3-[4-(Bis(4-fluorophenyl)hydroxymethyl]-1-piperidinyl]propoxy]benzenesulfonamide hydrochloride [1:1]

This compound was prepared according to the procedure of Example 1. A mixture of 3.0 g (0.01 mole) of [α,α-bis(p-fluorophenyl)]-4-piperidinemethanol, 2.5 g (0.01 mole) of 4-(3-chloropropoxy)benzenesulfonamide, 5.3 g (0.05 mole) of anhydrous sodium carbonate and 0.3 g of potassium iodide in 100 ml of 1-butanol gave a gum as residue. The gum was converted to the hydrochloride with ethereal hydrogen chloride and the solid was recrystallized from absolute ethanol to yield 3.5 g (64%) of white solid, m.p. 152°–175° C.

Analysis: Calculated for C$_{27}$H$_{31}$ClF$_2$N$_2$O$_4$S: C, 58.64; H, 5.65; N, 5.06. Found: C, 58,43; H, 5.68; N, 5.06.

EXAMPLE 97

N-[4-[3-[4-[Bis(4-fluorophenyl)hydroxymethyl]-1-piperidinyl]propoxy]phenyl]methanesulfonamide Following the procedure of Example 1, α,α-bis(p-fluorophenyl)-4-piperidinemethanol and N-[4-(3-bromopropoxy)phenyl methanesulfonamide are reacted to give the title compound.

EXAMPLE 98

N-[4-[3-[4-[Bis(4-fluorophenyl)hydroxymethyl]-1-piperidinyl]propoxy]phenyl]-N'-methylurea Following the procedure of Example 1, [α,α-bis(p-fluorophenyl)]-4-piperidinemethanol and N-[4-(3-bromopropoxy)phenyl]-N'-methylurea are reacted to give the title compound.

EXAMPLE 99

[4-[3-[4-[Bis(4-fluorophenyl)hydroxymethyl]-1-piperidinyl]propoxy]phenyl]carbamic acid ethyl ester Following the procedure of Example 1, [α,α-bis(p-fluorophenyl)]-4-piperidinemethanol and [4-(3-bromopropoxy)phenyl]carbamic acid ethyl ester are reacted to give the title compound.

EXAMPLE 100

N-[3-[3-[4-[Bis(4-fluorophenyl)hydroxymethyl]-1-piperidinyl]propoxy]phenyl]urea

Following the procedure of Example 1, [α,α-bis(-fluorophenyl)]-4-piperidinemethanol and N-[3-(3-bromopropoxy)phenyl]urea are reacted to give the title compound.

EXAMPLE 101

4-[3-[4-[Bis(4-fluorophenyl)hydroxymethyl]-1-piperidinyl]propoxy]-3-methoxybenzoic acid sodium salt Following the procedures of Examples 1 and 85 but substituting 4-(3-chloropropoxy)-2-methoxybenzoic acid for the corresponding 3-methoxy compound, the title compound is prepared.

EXAMPLE 102

1-[4-[3-[4-Bis(4-fluorophenyl)hydroxymethyl]-piperidinyl]propoxy]-2-hydroxyphenyl]ethanone Following the procedure of Example 1, α,α-bis(p-fluorophenyl)-4-piperidinemethanol and 1-[4-(3-bromopropoxy)-2-hydroxyphenyl]ethanone are reacted to give the title compound.

EXAMPLE 103

7-[3-[4-[Bis(4-fluorophenyl)hydroxymethyl]-1-piperidinyl]propoxy]-4-oxo-4H-1-benzopyran-2-carboxylic acid ethyl ester hydrochloride [1:1]

A ixture of 3.0 g (0.01 mole) of [α,α-bis(p-fluorophenyl)]-4-piperidinemethanol, 3.1 g (0.01 mole) of 7-(3-chloropropoxy)-4-oxo-4H-1-benzopyran-2-carboxylic acid ethyl ester, 5.3 g (0.05 mole) of anhydrous sodium carbonate and 0.3 g of potassium iodide in 150 ml of acetonitrile heated at reflux for 48 hr gave a gum as residue. The gum was purified by column chromatography on 120 g of Florisil ®. The desired fractions eluted with 10% acetone in benzene were combined and concentrated under reduced pressure to give a glass as residue. The glass was dissolved in ether/2-propanol and treated with ethereal hydrogen chloride. The solid which precipitated was collected by filtration and recrystallized from absolute ethanol to give 1.9 g (31%) of white solid, m.p. 191° C. with decomposition.

Analysis: Calculated for $C_{33}H_{34}ClF_2NO_6$: C, 64.55; H, 5.58; N, 2.28. Found: C, 64.41; H, 5.51; N, 2.26.

EXAMPLE 104

7-[3-[4-[Bis(4-fluorophenyl)hydroxymethyl]-1-piperidinyl]propoxy]-2,3-dihydro-4H-1-benzopyran-4-one hydrochloride Following the procedure of Example 103, [α,α-bis(p-fluorophenyl]-4-piperidinemethanol and 7-(3-bromopropoxy)-2,3-dihydro-4H-1-benzopyran-4-one are reacted to give the title compound.

EXAMPLE 105

1-[4-[3-[4-(Diphenylmethylene)-1-piperidinyl]propoxy]-3-methoxyphenyl]ethanone oxalate hydrate [1:1:0.5]

A mixture of 7.5 g (0.030 mole) of 4-diphenylmethylenepiperidine, 6.3 g (0.032 mole) of 3-(p-acetyl-o-methoxyphenoxy)propyl bromide, 25 g (0.18 mole) of potassium carbonate and 150 ml of toluene was heated at reflux for 16 hr, cooled, filtered and the solvent evaporated at reduced pressure. The residual oil was dissolved in benzene, washed with water, dried over magnesium sulfate and then the solvent was evaporated. The free base was dissolved in 2-propanol and treated with 3.8 g (0.03 mole) of oxalic acid dihydrate in dry ether. The white salt which separated was recrystallized from a 2-propanol-methanol mixture. The produce weighed 8.5 g (54%), m.p. 186°–188° C.

Analysis: Calculated for $C_{32}H_{35}NO_7.0.5H_2O$: C, 69.29; H, 6.54; N, 2.53. Found: C, 69.20; H, 6.49; N, 2.71.

EXAMPLE 106

1-[4-[3-[4-(Cyclohexylphenylmethyl)-1,2,3,6-tetrahydropyridin-1-yl]propoxy]-3-methoxyphenyl]ethanone oxalate hydrate [1:1:0.5]

The free base of the title compound was obtained by reacting 4-(α-cyclohexylphenylmethyl)-1,2,3,6-tetrahydropyridine with 3-(p-acetyl-o-methoxyphenoxy)propyl chloride in a mixture with sodium bicarbonate in dimethylformamide and isolated on a Florisil ® column eluting with benzene. The title salt was prepared, m.p. 110° C.

Analysis: Calculated for $C_{32}H_{41}NO_7.0.5H_2O$: C, 68.55; H, 7.55; N, 2.50. Found: C, 68.79; H, 7.64; N, 2.47.

EXAMPLE 107

1-[4-[3-[4-[Bis(4-fluorophenyl)hydroxymethyl]-1-piperidinyl]propoxy]-2-methoxyphenyl]ethanone hydrochloride [1:1]

This compound was prepared according to the procedure used to synthesize the compound of Example 1. A mixture of 3.0 g (0.01 mole) of [α,α-bis(p-fluorophenyl)]-4-piperidinemethanol, 2.4 g (0.01 mole) of 1-[4-(3-chloropropoxy)-2-methoxyphenyl]ethanone, 5.3 g (0.05 mole) of anhydrous sodium carbonate and 0.3 g of potassium iodide in 100 ml of 1-butanol gave a gum as residue. The gum was purified by column chromatography on 80 g of Florisil ® and the fractions eluted with 20% acetone in benzene were combined and concentrated under reduced pressure to give a solid as residue. The solid was converted to the hydrochloride and this solid was recrystallized from 2-propanol-isopropyl ether to yield 2.2 g (40%) of white power, m.p. 196°–197° C.

Analysis: Calculated for $C_{30}H_{34}ClF_2NO_4$: C, 65.99; H, 6.28; N, 2.57. Found: C, 65.87; H, 6.31; N, 2.54.

EXAMPLE 108

4-[Bis(4-fluorophenyl)methyl]-1-[3-(2,6-dichlorophenoxy)propyl]piperidine

A mixture of 4-[bis(4-fluorophenyl)methyl]piperidine (free base 6.90 g, 0.024 mole), 1,3-dichloro-2-(3-chloropropoxy)benzene (5.72 g, 0.024 mole), and potassium carbonate (5.54 g, 0.04 mole) was heated overnight at gentle reflux in 350 m l of 1-butanol containing potassium iodide (0.2 g). The reaction was concentrated to dryness. The residue was partitioned several times between chloroform and water. The chloroform layer was dried, filtered, and solvent removed to give an oil. The oil was placed in the refrigerator overnight in 50 ml of methanol. A white solid was obtained and dried in vacuo overnight at 80° C. A yield of 3.26 g (27.7%) of white, crystalline solid, m.p. 101.5°–103° C., was obtained.

Analysis: Calculated for $C_{27}H_{27}Cl_2F_2NO$: C, 66.13; H, 5.55; N, 2.85. Found: C, 66.12; H, 5.56; N, 2.88.

EXAMPLE 109

4-[Bis(4-fluorophenyl)methyl]-1-[3-(2,6-dichlorophenoxy)propyl]piperidine oxalate [1:1]

Free base of the compound of Example 108 was converted to the oxalate salt and recrystallized from methanol-ethyl and dried in vacuo at 80° C. overnight, m.p. 158°–161° C.

Analysis: Calculated for $C_{29}H_{29}Cl_2F_2NO_5$: C, 60.01; H, 5.04; N, 2.44. Found: C, 60.02; H, 5.07; N, 2.46.

EXAMPLE 110

2-[3-[4-[Bis(4-fluorophenyl)methyl]-1-piperidinyl]propoxy]benzonitrile

A mixture of 7.41 g (0.025 mole) of [4-[bis(4-fluorophenyl)methyl]piperidine, 4.90 g (0.025 mole) of 2-(3-chloropropoxy)benzonitrile, and potassium carbonate, 5.54 g (0.04 mole) was heated overnight at reflux in 350 ml of 1-butanol containing potassium iodide (0.2 g). The mixture was concentrated to dryness and the resulting residue was partitioned several times between water and chloroform. The chloroform layer was dried (anhydrous sodium sulfate), filtered, and solvent removed to give a brown oil. The oil was triturated with ethyl ether and placed in a freezer overnight. White crystals were obtained and dried in vacuo overnight at room temperature. A yield of 5.15 g (46.1%) of analytically pure material, m.p. 88.5°–90° C., was obtained.

Analysis: Calculated for $C_{28}H_{28}F_2N_2O$: C, 75.31; H, 6.32; N, 6.27. Found: C, 75.16; H, 6.34; N, 6.26.

EXAMPLE 111

α-[1-[3-(4-Acetyl-2-methoxyphenoxy)propyl]-4-piperidinyl]-α-(4-fluorophenyl)-2-pyridineacetonitrile fumarate [1:1]

A mixture of α-(4-fluorophenyl)-α-(4-piperidinyl)-2-pyridineacetonitrile (7.18 g, 0.024 mole), 1-[4-(3-chloropropoxy)-3-methoxyphenyl]ethanone (5.89 g, 0.024 mole), and potassium carbonate (5.54 g, 0.04 mole) was heated overnight in 350 ml of 1-butanol containing potassium iodide (0.15 g). The reaction mixture was concentrated to dryness and the residue obtained was partitioned between chloroform and water. The chloroform layer was extracted in 1N sulfuric acid, 5% sodium hydroxide and water. The chloroform layer was dried over sodium sulfate, filtered, and the solvent removed to give an oil. The oil was converted to the fumarate salt and recrystallized from methanol-ethyl ether. A white solid was obtained and dried in vacuo overnight at 80° C. to give 9.43 g (62.7%) of white crystals, m.p. 166°–167° C. NMR indicated 0.25 $H_2O$ was present.

Analysis: Calculated for $C_{34}H_{36}FN_3O_7.0.25H_2O$: C, 65.64; H, 5.91; N, 6.75. Found: C, 65.57; H, 5.89; N, 6.70.

EXAMPLE 112

α-[1-[3-(4-Acetyl-2-methoxyphenoxy)propyl]-4-piperidinyl]-α-(4-fluorophenyl)-2-pyridineacetonitrile fumarate hydrate [1:1:1]

A portion of the compound prepared in Example 111 was exposed to the air for 3 days, m.p. 166°–167° C.

Analysis: Calculated for $C_{34}H_{36}FN_3O_7.H_2O$: C, 64.24; H, 6.02; N, 6.61. Found: C, 64.07; H, 5.82; N, 6.58.

EXAMPLE 113

α,α-Diphenyl-1-[3-(8-quinolinyloxy)propyl]-3-piperidinepropanenitrile hydrate [1:0.5]

A mixture of α,α-diphenyl-3-piperidinepropanenitrile (8.12 g, 0.028 mole), 8-(3-chloropropoxy)quinoline (6.18 g, 0.028 mole), and potassium carbonate (5.53 g, 0.04 mole) was heated at reflux overnight in 350 ml of 1-butanol containing potassium iodide (0.3 g). The reaction mixture was filtered and concentrated to dryness on a rotary evaporator. The residue obtained was dissolved in chloroform and extracted with 5% sodium hydroxide and water. The chloroform layer was dried over anhydrous sodium sulfate, filtered, and solvent removed to give a dark red mass. This material was subjected to flash chromatography on a silica gel column using 10% methanol-ethyl acetate, 20% methanol-ethyl acetate, and 50% methanol-ethyl acetate for elution. Fractions of similar purity were combined and solvent was removed by rotary evaporator. The red blad residue obtained was dried in vacuo at 80° C. overnight. This furnished 5.29 g (39%) of a dark black residue.

$^1$H NMR (CDCl$_3$): σ8.9 (m, 1, proton ortho to N in ring), 7.9–8.1 (m, 1, proton para to N in ring), 6.9–7.6 (m, 14, aromatics), 4.2 (t, 2, methylenes adjacent to oxygen atom), 1.1–2.7 (m, 16, aliphatic portions and 1 H from 0.5 $H_2O$).

Analysis: Calculated for $C_{32}H_{32}N_3O.0.5\ H_2O$: C, 79.31; H, 7.07; N, 8.67. Found: C, 79.47; H, 7.19; N, 8.69.

EXAMPLE 114

8-[3-[4-[Bis(4-fluorophenyl)methyl]-1-piperidinyl]propoxy]quinoline hemihydrate

A mixture of 4-[α-(p-fluorophenyl)-p-fluorobenzyl]-piperidine (8.03 g, 0.28 mole), 8-(3-chloropropoxy) quinoline (6.18 g, 0.28 mole), and potassium carbonate (5.53 g, 0.04 mole) was heated overnight at gentle reflux in 350 ml of 1-butanol containing potassium iodide (0.3 g). The reaction mixture was filtered through activated charcoal and solvent was removed by rotary evaporator. The dark red residue was dissolved in chloroform and then extracted with 5% sodium hydroxide and water. The chloroform layer was dried over anhydrous sodium filtered, and solvent removed to provide a dark red mass. This material was subjected to flash chromatography on silica gel using 10, 20 and 50% methanol in ethyl acetate for elution. Fractions with similar purity were combined and solvent removed to give dark black mass which was dried at 80° C. in vacuo overnight. This furnished 3.74 g (28) of a dark red mass.

$^1$H NMR (CDCl$_3$: δ8.9 (m, 1, proton ortho to N in ring), 7.9–8.1 (m, 1, proton para to N in ring), 6.8–7.4 (m, 12, aromatics), 4.2 (t, 2, $CH_2$ attached to —O), 3.5 (d, 1, methine attached to aromatic rings), 1.0–3.2 (m, 14, aliphatic protons and 1H for 0.5 $H_2O$).

Analysis: Calculated for $C_{30}H_{312}N_2O.0.5H_2O$: C, 75.53; H, 6.44; N, 5.87. Found: C, 75.66; H, 6.56; N, 5.86.

EXAMPLE 115

2-[3-[4-[Bis(4-fluorophenyl)methyl]-1-piperidinyl]-propoxy]quinoline hydrate [1:0.5]

The sodium salt of 4-[bis(4-fluorophenyl)methyl-1-piperidinepropanol was formed in 300 ml of dimethyl sulfoxide from its free base (6.90 g, 0.02 mole) and sodium hydride (60%, 0.8 g, 0.02 mole). 2-Chloroquinoline (3.26 g, 0.02 mole) was added and the reaction mixture was heated at 60° C. for approximately 72 hr. The reaction mixture was concentrated to dryness and the residue obtained was dissolved in chloroform. This chloroform layer was extracted with water and 5% sodium hydroxide. The chloroform layer was dried over sodium sulfate, filtered, and solvent removed to give an oil. The oil was subjected to flash chromatography on silica gel using ethyl acetate for elution. Fractions of similar purity were combined and solvent removed. The residue was dried in vacuo overnight at 80° C. to give 5.16 g (53.6%) of clear brown oil.

$^1$H NMR (CDCl$_3$): $\delta$6.8–7.9 (m, 14, aromatics), 4.5 (t, 2, —OCH$_2$), 3.4 and 3.6 (d, 1, methine attached to two aromatic rings), 1.2–3.1 (m, 13, aliphatics remaining).

Analysis: Calculated for $C_{30}H_{30}F_2O_7.0.5H_2O$: C, 74.82; H, 6.49; N, 5.82. Found: C, 74.56; H, 6.36; N, 5.69.

EXAMPLE 116

4-[Bis(4-fluorophenyl)methyl]-1-[3-(2-naphthalenyloxy)propyl]-piperidine hydrate [1:0.5]

The sodium salt of 2-naphthol was prepared in 300 ml of dimethyl sulfoxide from 2-naphthol (3.00 g, 0.0208 mole) and sodium hydride (60% 0.83 g, 0.0208 mole). The solution was stirred 1 hr at room temperature and had a clear brown color. Then, 4-[bis(4-fluorophenyl)methyl]-1-(3-chloropropyl)piperidine (free base 7.55 g, 0.0208 mole) in 100 ml of dimethylsulfoxide was added. The resulting solution was stirred overnight at 60° C. The solvent was removed in vacuo, and the residue obtained was partitioned between chloroform-water and chloroform-5% sodium hydroxide. The chloroform layer was dried over sodium sulfate, filtered, and solvent removed to give a brown oil. An oxalate salt could not be obtained in pure form so the oil (free base) was subjected to flash chromatography on silica gel using 50–50 ethylacetate-hexanes and 75–25 ethylacetate-hexanes for elution. Fractions of similar purity were combined and solvent removed to give an oil. The oil was dried in vacuo at 80° C. overnight to give 2.97 g (32.3% yield) of a dark brown glass after being dried overnight at room temperature.

$^1$H NMR (CDCl$_3$): $\delta$6.8–7.8 (m, 15, aromatics), 4–4.3 (t, 2, —OCH$_2$), 3.4–3.6 (d, 1, methine attached to two fluorophenyl groups), 1.1–3.0 (m, 13, aliphatics).

Analysis: Calculated for $C_{30}H_{30}F_2NO.0.5H_2O$: C, 77.48; H, 6.71; N, 2.91. Found: C, 77.86; H, 6.65; N, 2.04.

EXAMPLE 117

3-[3-[4-[Bis(4-fluorophenyl)methyl]-1-piperidinyl]-propoxy]benzonitrile hydrate [1:0.5]

A mixture of 4-[bis(4-fluorophenyl)methyl]piperidine, the free base of Preparation 10 (7.85 g, 0.027 mole), 3-(3-chloropropoxy)-1-benzonitrile (5.33 g, 0.027 mole), and potassium carbonate (5.84 g, 0.027 mole) was heated overnight at reflux in 350 ml of 1-butanol containing potassium iodide (0.2 g). The reaction mixture was filtered and concentrated to dryness. The residue obtained was dissolved in chloroform and extracted with water and 5% sodium hydroxide. The chloroform layer was dried over sodium sulfate, filtered, and solvent removed to give a brown oil. The oil was subjected to flash chromatography on silica gel using ethyl acetate-hexanes for elution. Fractions of similar purity were combined and solvent removed. The dark brown oil obtained was dried in vacuo overnight at 80° C. to give 5.65 g (45.9% yield) of dark brown oil.

H$^1$ NMR (CDCl$_3$): $\delta$6.7–7.3 (m, 12, aromatics), 3.8–4.1 (t, 2, methylenes adjacent to oxygen atom), 3.4–3.6 (d, 1, methine attached to two phenyl rings), 1.1–3.0 (m, 13, remaining aliphatic protons).

Analysis: Calculated for $C_{28}H_{28}F_2N_2O.0.5H_2O$: C, 73.83; H, 6.42; N, 6.15. Found: C, 74.05; H, 6.27; N, 6.09.

EXAMPLE 118

$\alpha,\alpha$-Bis(4-fluorophenyl)-1-[3-(4-methoxyphenoxy)-propyl]-4-piperidine-methanol This compound was prepared according to the procedure used to synthesize the compound of Example 1. A mixture of 3.0 g (0.01 mole) of $\alpha,\alpha$-bis (p-fluorophenyl)-4-piperidinemethanol, 2.0 g (0.01 mole) of 1-chloro-3-(4-methoxyphenoxy) propane, 5.3 g (0.035 mole) of anhydrous sodium carbonate and 0.3 g of potassium iodide in 100 ml of 1-butanol gave 2.3 g (49% yield) of title compound as a white solid, mp 107°–108° C.

Analysis: Calculated for $C_{28}H_{31}F_2NO_3$: C,71.93;H,6.68;N,3.00. Found: C,71.90;H,6.70;N,2.99.

EXAMPLE 119

$\alpha,\alpha$-Bis(4-fluorophenyl)-1-[3-(4-methylphenoxy)-propyl]-4-piperidinemethanol fumarate [1:1]

This compound was prepared according to the procedure used to synthesize the compound of Example 1. A mixture of 3.0 g (0.01 mole) of $\alpha,\alpha$-bis (p-fluorophenyl)-4-piperidinemethanol, 1.8 g (0.01 mole) of 1-chloro-3-(4-methylphenoxy) propane, 5.3 g (0.035 mole) of anhydrous sodium carbonate and 0.3 g of potassium iodide in 100 ml of 1-butanol gave a gum as residue. The gum was purified by column chromatography on 100 g of Florisil ®. Fractions eluted with 10% acetone in benzene were combined and concentrated to give a gum. This gum was converted to the fumaric acid salt and the solid was recrystallized from absolute ethanol to yield 3.2 g (56%) of title compound as a white solid, mp 193°–194° C. with decomposition. pe f 49495948.hsc Analysis: Calculated for $C_{32}H_{35}F_2NO_6$: C,67.71;H,6.22;N,2.47. Found: C,67.93;H,6.25;N,2.53.

EXAMPLE 120

1-[3-(4-Fluorophenoxy)propyl]-$\alpha,\alpha$-bis(4-fluorophenyl)-4-piperidinemethanol fumarate hydrate [1:1:1]

This compound was prepared according to the procedure used to synthesize the compound of Example 1. A mixture of 3.0 g (0.01 mole) of $\alpha,\alpha$-bis (p-fluorophenyl)-4-piperidinemethanol, 1.9 g (0.01 mole) of 1-chloro-3-(4-fluorophenoxy) propane, 5.3 g (0.035 mole) of anhydrous sodium carbonate and 0.3 g of potassium iodide in 100 ml of 1-butanol gave a solid as residue. The solid was further purified by column chromatography on 60 g of Florisil ®. Fractions eluted with 2–10% acetone in benzene were combined and concentrated to give a solid residue. The solid was converted to the furmaric acid salt and this solid was recrystallized from isopropanol to yield 2.2 g (39%) of title compound as a white solid, mp 155°-157° C.

Analysis: Calculated for $C_{31}H_{32}F_3NO_6 \cdot H_2O$: C, 63.14; H, 5.81; N, 2.38. Found: C, 62.99; H, 5.64; N, 2.28.

EXAMPLE 121

1-[4-[3-4-[(4-Fluorophenyl)(2-pyridinyl)methyl]-1-piperidinyl]-propoxy]-3-methoxyphenyl]ethanone A mixture of 2-[(4-fluorophenyl)(4-piperidinyl)methyl]pyridine (6.28 g, 0.0232 mole), 1-[4-(3-chloropropoxy)-3-methoxyphenyl]ethanone (5.62 g, 0.0232 mole), and potassium carbonate (5.53 g, 0.04 mole) was heating overnight at reflux in 350 ml of 1-butanol containing potassium iodide (0.2 g). The reaction mixture was concentrated to dryness and the residue obtained was dissolved in chloroform. The chloroform layer was extracted with 5% sodium hydroxide and water. The chloroform layer was dried over sodium sulfate, filtered, and solvent removed to give a brown oil. This oil was subjected to flash chromatography on silica gel using 10% methanol-ethyl acetate, 20% methanol-ethyl acetate, and 30% methanol-ethyl acetate for elution. Fractions of similar purity were combined and solvent removed to give a brown oil. This material was dried in vacuo overnight at 80° C. to give 6.89 g (62.3% yield) of dark brown oil.

$H^1$ NMR (CDCl$_3$): δ 6.8-7.8 (m, 15, aromatics), 4-4.3 (t, 2, —OCH$_2$), 3.9 (s, 3, —OCH$_3$), 3.6-3.8 (d, 1, C—H attached to pyridine ring), 2.6 (s, 3, C—CH$_3$), 1.2-3.6 (m, 9, remaining aliphatics).

Analysis: Calculated for $C_{29}H_{33}FN_2O_3$: C, 73.09; H, 6.98; N, 5.88. Found: C, 72.51; H, 7.10; N, 5.81.

EXAMPLE 122

[4-[3-[4-[Bis(4-fluorophenyl)hydroxymethyl]-1-piperidinyl]propoxy]phenyl]carbamic acid ethyl ester oxalate hydrate [1:1:1.5]

This compound was prepared according to the procedure used to synthesize the compound of Example 1. A mixture of 3.0 g (0.01 mole) of α,α-bis(4-fluorophenyl)-4-piperidinemethanol, 2.6 (0.01 mole) of N-[4-(3-chloropropoxy) phenyl]carbamic acid ethyl ester, 5.3 g (0.05 mole) of anhydrous sodium carbonate and 0.3 g of potassium iodide in 100 ml of dimethylformamide heated in a steambath for 24 hr gave a gum as residue. The gum was converted to the oxalic acid salt in ethyl acetate and the solid was recrystallized from 2-propanol to yield 32 g (50%) of title compound as a white solid, mp 70°-90° C.

Analysis: Calculated for $C_{32}H_{38}F_2NO_8 \cdot 1.5H_2O$: C, 59.90; H, 6.13; N, 4.37. Found: C, 59.69; H, 5.80; N, 4.21.

EXAMPLE 123

1-[3-(4-Acetyl-2-methoxyphenoxy)propyl]-α,α-bis(4-fluorophenyl-3-pyrrolidinepropanenitrile A mixture of α,α-bis (4-fluorophenyl)-3-pyrrolidinepropanenitrile (5.00 g, 0.016 mole), 1-[4-(3-chjloropropoxy)-3-methoxyphenyl]ethanone (3.88 g, 0.016 mole), and potassium carbonate (5.53 g, 0.04 mole) was heated overnight at reflux in 350 ml of 1-butanol containing potassium iodide (0.2 g). The reaction mixture was cooled to room temperature and filtered. The butanol was removed by rotary evaporator to produce a dark brown oil. This oil was dissolved in chloroform and the organic phase was extracted several times with water. The chloroform layer was dried over sodium sulfate, filtered, and solvent removed to provide a dark brown oil. The entire oil was subjected to flash chromatography on silica gel using ethyl acetate, 5% methanol-ethyl acetate, and 10% methanol-ethyl acetate for elution. Fractions of similar purity were combined and solvent removed in vacuo. A dark brown oil was obtained and dried in vacuo overnight at 80° C. to give 4.33 g (52.2% yield) of a glassy brown residue.

$H^1$ NMR(CDCl$_3$): δ 6.8-7.7 (m, 11, aromatics), 4.0-4.25 (t, 2, —CH$_2$—O), 3.9 (s, 3, —OCH$_3$), 1.5-2.7 (m, 16, aliphatics).

Analysis: Calculated for $C_{31}H_{32}F_2N_2O_3$: C, 71.80; H, 6.22; N, 5.40. Found: C, 71.66; H, 6.29; N, 5.53.

EXAMPLE 124

2-[3-[4-[Bis(4-fluorophenyl)methylene]-1-piperidinyl]-propoxy]phenol

A mixture of 6.0 g (0.02 mole) of α, α-bis(p-fluorophenyl)-4-piperidinemethanol, 5.5 g(0.02 mole) of 3-(2-benzyloxyphenoxy)propyl chloride, 7.4 g (0.07 mole) of anhydrous sodium carbonate and 0.3 g of potassium iodide in 100 ml of 1-butanol was heated at reflux for 24 hr. The mixture was concentrated and the residue was partitioned between benzene and water. The organic layer was washed with water and brine, dried over sodium sulfate and concentrated to give a gum as residue. The gum was converted to a crystalline hydrochloride. The salt changed to an oil upon standing overnight. The oil was partitioned between methylene chloride and a saturated sodium bicarbonate solution. The organic layer was dried over sodium sulfate and concentrated to give a gum as residue.

The gum was dissolved in 500 ml of absolute ethanol and hydrogenated in a Parr apparatus over 5% palladium on carbon catalyst at 70° C. overnight. The mixture was filtered through Celite ® and the filtrate was concentrated to give a gummy solid as residue. The solid was triturated with ethyl ether and the mixture was filtered. The filtrate was slowly evaporated and a solid precipitated. The solid was collected by filtration and recrystallized from isopropyl ether to yield 1.6 g (18% yield) of title compound as a white solid, mp 125°-127° C.

Analysis: Calculated for $C_{27}H_{27}F_2NO_2$: C, 74.46; H, 6.25; N, 3.22. Found: C, 74.47; H, 6.29; N, 3.12.

EXAMPLE 125

1-[3-(4-Ethyl-2-methoxyphenoxy)propyl]-α,α-bis (4-fluorophenyl)-4-piperidinemethanol This compound was prepared according to the procedure used to synthesize the compound of Example 1. A mixture of 3.0 g (0.01 mole) of α,α-bis(p-fluorophenyl)-4-piperidinemethanol, 2.3 g (0.01 mole) of 3-(4-ethyl-2-methoxyphenoxy)propyl chloride, 5.3 g (0.05 mole) of anhydrous sodium carbonate and 0.3 g of potassium iodide in 100 ml of 1-butanol gave 3.7 g (74%) of title compound as a white solid, mp 118°-120° C.

Analysis: Calculated for $C_{30}H_{35}F_2NO_3$: C, 72.70; H, 7.12; N, 2.83. Found: C, 72.72; H, 7.43; N, 2.81.

EXAMPLE 126

1-(3-Phenoxypropyl)-α,α-diphenyl-4-piperidinemethanol

This compound was prepared according to the procedure used to synthesize the compound of Example 1. A mixture of 4.0 g (0.015 mole) of α, α-diphenyl-4-piperidinemethanol, 3.2 g (0.015 mole) of 1-bromo-3- phenoxypropane, 5.3 g (0.05 mole) of anhydrous sodium carbonate and 0.4 g of potassium iodide in 100 ml of 1-butanol gave 3.2 g (53%) of title compound as a white solid, mp 87°-88° C.

Analysis: Calculated for $C_{27}H_{31}NO_2$: C, 80.76; H, 7.78; N, 3.49. Found: C, 80.82; H, 7.79; N, 3.52.

EXAMPLE 127

α,α-Bis(4-fluorophenyl)-1-[3-[4-(methylsulfinyl)-phenoxy]propyl]-4-piperidinemethanol oxalate hydrate [1:1:1.5]compound with 2-propanol [1:0.5].

This compound was prepared according to the procedure used to synthesize the compound of Example 1. A mixture of 3.0 g (0.01 mole) of α,α-bis(p-fluorophenyl)-4-piperidinemethanol, 2.3 g (0.01 mole) of 1-(3-chloropropyl)-4-methylsulfinyl)benzene, 5.3 g (0.05 mole) of anhydrous sodium carbonate and 0.3 g of potassium iodide in 100 ml of 1-butanol gave a gum as residue. The gum was purified by column chromatography on 120 g of Florisil ®. Fractions eluted with 15-25% acetone in benzene were combined and concentrated to give the purified base as an oil. The oil was converted to the oxalic acid salt and the solid was recrystallized from 2-propanol to yield 2.6 g (40% yield) of title compound as a white solid, mp 75°-105° C.

Analysis: Calc'd for $C_{30}H_{33}F_2NO_7S \cdot 1.5\ H_2O \cdot 0.5$ $0.5aC_3H_8O$: C, 58.50; H, 6.23; N, 2.17. Found: C, 58.32; H, 5.99; N, 2.05.

EXAMPLE 128

α,α-Bis(4-fluorophenyl)-1-[3-[4-(1-methylethyl)phenoxy]propyl]-1-piperidinemethanol oxalate [1:1]

This compound was prepared according to the procedure used to synthesize the compound of Example 1. A mixture of 4.6 g (0.015 mole) of α, α-bis(p-fluorophenyl)-4-piperidinemethanol, 3.2 (0.015 mole) of 1-chloro-3-(4-isopropylphenoxy)propane, 5.3 g (0.05 mole) of anhydrous sodium carbonate and 0.4 g of potassium iodide in 100 ml of 1-butanol gave a solid as residue. The solid was converted to the oxalic acid salt and this solid was recrystallized from ethyl acetate to yield 4.6 g (54% yield) of title compound as a white solid, mp 105°-109° C. with decomposition.

Analysis: Calculated for $C_{32}H_{37}F_2NO_6$: C, 67.47; H, 6.55; N, 2.46. Found: C, 66.92; H, 6.61; N. 2.52.

EXAMPLE 129

3-[3-[4-[Bis(4-fluorophenyl)hydroxymethyl]-1-piperidinyl]propoxy]-benzoic acid ethyl ester fumarate [1:1]

This compound was prepared according to the procedure used to synthesize the compound of Example 1. A mixture of 3.0 g (0.01 mole) of α, α-bis(p-fluorophenyl)-4-piperidinemethanol, 2.4 g (0.01 mole) of 3-(3-chloropropoxy)benzoic acid ethyl ester, 3.7 g (0.035 mole) of anhydrous sodium carbonate and 0.4 g of potassium iodide in 100 ml of dimethylformamide gave a gum as residue. The gum was converted to the fumaric acid salt and the solid was recrystallized from acetonitrile to yield 4.2 g (67%) of title compound as a fluffy,, white solid, mp 123°-131° C.

Analysis: Calculated for $C_{34}H_{37}F_2NO_8$: C, 65.27; H, 5.96; N, 2.24. Found: C, 65.09;H, 5.95; N, 2.25.

EXAMPLE 130

1-[4-[3-[4-[Bis(4-methylphenyl)methylene[-1-piperidinyl]propoxy]-3-methoxyphenyl]ethanone This compound was prepared according to the procedure used to synthesize the compound of Example 1. A mixture of 4.6 g (0.015 mole) of α, α-bis(4-methylphenyl)-4-piperidinemethanol, 3.6 g (0.015 mole) of 1-[4-(3-chloropropoxy)-3-methoxyphenyl]ethanone, 5.3 g (0.05 mole) of anhydrous sodium carbonate and 0.4 g of potassium iodide in 100 ml of 1-butanol gave a brown gum as residue. The gum was dissolved in ethyl ether and filtered to remove insolubles. The filtrate was treated with ethereal hydrogen chloride and a solid gradually crystallized. Attempted recrystallization of the solid from 2-propanol failed. The solid was partitioned between methylene chloride and a sodium bicarbonate solution. The organic layer was dried over sodium sulfate and concentrated under reduced pressure to give a brown gum. The gum was converted to the fumaric acid salt. The solid was recrystallized twice from 2-propanol but a satisfactory combustion analysis could not be obtained. This salt was partitioned between methylene chloride and a sodium bicarabonate solution as above to give a gum as residue. The gum crystallized after standing for several days. The solid was triturated with petroleum ether, collected by filtration, and recrystallized from 2-propanol to yield 2.2 g (46%) of title compound as an off-white solid, mp 92°-95° C. with decomposition.

Analysis: Calculated for $C_{32}H_{37}NO_3$: C, 79.47; H, 7.71; N, 2.90. Found: C, 79.18; H, 7.88; N, 2.88.

EXAMPLE 131

1-[4-[3-[4[Bis(4-methylphenyl)hydroxymethyl]-1-piperidinyl]propoxy]-3-methoxyphenyl]ethanone oxalate hydrate [1:1:1]

This compound was prepared according to the procedure used to synthesize the compound of Example 1. A mixture of 4.6 g (0.015 mole) of α, α-bis(4-methylphenyl)-4-piperidinemethanol, 3.6 g (0.015 mole) of 1-[4-(3-chloropropoxy)-3-methoxyphenyl]ethanone, 5.3 g (0.05 mole) of anhydrous sodium carbonate and 0.4 g of potassium iodide in 100 ml of 1-butanol gave a brown gum as residue. The gum was converted to the oxalic acid salt and the solid was recrystallized from absolute ethanol to yield 5.3 g (58%) of title compound as an off-white solid, mp 92°-95° C. with decomposition.

Analysis: Calculated for $C_{34}H_{41}NO_8 \cdot H_2O$: C, 66.97; H, 7.11; N, 2.30. Found: C, 66.61; H, 6.79; N, 2.29.

EXAMPLE 132

4-[3-[4-[Bis(4-fluorophenyl)hydroxymethyl]-1-piperidinyl]propoxyl]-benzoic acid methyl ester fumarate [1:1]

A mixture of 9.1 g (0.03 mole) of α, α-bis(p-fluorophenyl)-4-piperidinemethanol, 6.7 g (0.03 mole) of 4-(3-chloropropoxy)benzoic acid methyl ester, 10.6 g (0.1 mole) of anhydrous sodium carbonate and 0.6 g of potassium iodide in 125 ml of dimethylformamide was heated in a steambath for 25 hr. The reaction mixture was poured into 1.5 liters of ice-water. The resulting solid was collected by filtration, washed with water and dried. The solid was converted to the fumaric acid salt to yield 12.5 g (68%) of title compound as a white solid, mp 140°-174° C. with decomposition.

Analysis: Calculated for $C_{33}H_{35}F_2NO_8$: C, 64.80; H, 5.77; N, 2.29. Found: C, 64.67; H, 5.80; N, 2.34.

EXAMPLE 133

1-[3-(4-Aminophenoxy)propyl]-α,α-bis(4-fluorophenyl)-4-piperidinemethanol oxalate [1:2]

A solution of 2.6 g (0.0054 mole) of α,α-bis(4-fluorophenyl)-1-[3,(4-nitrophenoxy)propyl]-4-piperidinemethanol in 50 ml of tetraydrofuran was hydrogenated at ambient temperature over 5% palladium on carbon catalyst at 40 psi. The mixture was filtered and the filtrate was concentrated to give a gum as residue. The gum was converted to the dioxalate salt and the solid was recrystallized from 95% ethanol to yield 2.1 g (62%) of title compound as an off-white solid, mp 136°–139° C. with decomposition.

Analysis: Calculated for $C_{31}H_{34}F_2N_2O_{10}$: C, 58.86; H, 5.42; N,, 4.43. Found: C, 58.73; H, 5.48; N, 4.43.

EXAMPLE 134

1-[4-[3-[4-[Bis(4-fluorophenyl)methyl]-1-piperidinyl]-propoxy]-2-methoxyphenyl]ethanone oxalate [1:1]

A mixture of 4-[bis(4-fluorophenyl)maethyl]piperidine (5.74 g, 0.02 mole), 1-[4-(3-chloropropoxy)-2-methoxyphenyl]ethanone (4.85 g, 0.02 mole), and potassium carbonate (5.54 g, 0.04 mole) was heated at reflux overnight in 350 of 1-butanol containing potassium iodide (0.2 g). The reaction mixture was concentrated to dryness and the residue obtained was partitioned between chloroform and water. The chloroform layer was extracted with water, dried over sodium sulfate, filtered, and solvent removed to give a brown oil. The oil was converted to the oxalate salt. The oxalate salt was recrystallized from methanol-ethyl ether. A white solid was obtained and dried in vacuo overnight at 80° C. to give 7.04 g (60.3% yield) of white, crystalline product, mp 190.5°–191° C.

Analysis: Calculated for $C_{32}H_{35}F_2NO_7$: C, 65.86; H, 6.05; N, 2.40. Found: C, 65.73; H, 6.05; N, 2.45.

EXAMPLE 135

4-[Bis(4-fluorophenyl)methyl]-1-[3-(4-ethyl-2-methoxyphenoxy)-propyl]piperidine oxalate [1:1]

A mixture of 4-[bis(4-fluorophenyl)methyl]piperidine (5.74 g, 0.024 mole), 1-[4-(3-chloropropoxy)-2-methoxyphenyl]ethanone (5.57 g, 0.024 mole), and potassium carbonate (5.54 g, 0.04 mole) was heated overnight at gentle reflux in 350 ml of 1-butanol containing potassium iodide (0.2 g). The reaction mixture was concentrated to dryness. The residue was partitioned several times between chloroform and water. The chloroform layer was back extracted with water and 5% sodium hydroxide. The chloroform layer was dried over sodium sulfate, filtered, and solvent removed to give an oil. The oil was converted to the oxalate salt and recrystallized from methanol-ethyl ether. A white solid was obtained and dried overnight in vacuo at 80° C. to give 10.04 g (73.4% yield) of white, crystalline product, mp 185°–186° C.

Analysis: Calculated for $C_{32}H_{37}F_2NO_6$: C, 67,47; H, 6.55; N, 2.46. Found: C, 67.41; H, 6.53; N, 2.50.

EXAMPLE 136

1-[3-([1,1'-Biphenyl]-4-yloxy)propyl]-α,α-bis(4-fluorophenyl)-4-piperidinemethanol This compound was prepared according to the procedure used to synthesize the compound of Example 1. A mixture of 3.0 g (0.01 mole) of α, α-bis(p-fluorophenyl)-4-piperidinemethanol, 2.5 g (0.01 mole) of 4-(3-chloropropoxy)-1,1'-biphenyl, 3.7 g (0.035 mole) of anhydrous sodium carbonate and 0.4 g of potassium iodide in 100 ml of 1-butanol gave 3.5 g (69%) of title compound as a white solid, mp 108°–109° C.

Analysis: Calculated for $C_{33}H_{33}F_2NO_2$: C, 77.17; H, 6.48; N, 2.73. Found: C, 76.80; H, 6.83; N, 2.72.

EXAMPLE 137

N-[4-[3-[4-[Bis(4-fluorophenyl)hydroxymethyl]-1-piperidinyl]propoxy]-phenyl]-N'-methylurea To a solution of 4.5 g (0.01 mole) of 1-[3-(4-aminophenoxy)propyl]-α,α-bis(4-fluorophenyl)-4-piperidinemethanol in 50 ml of benzene was added dropwise a solution of 0.6 g (0.01 mole) of methylisocyanate in 10 ml of benzene. The mixture was stirred for 1 hr during which time a solid precipitated. The mixture was diluted with 25 ml of cyclohexane, the solid was collected by filtration and recrystallized from 2-propanol to yield 1.6 g (31%) of title compound as a white solid, mp 177°–178° C.

Analysis: Calculated for $C_{29}H_{33}F_2N_3O_3$: C, 68.35; H, 6.53; N, 8.25. Found: C, 68.69; H, 6.65; N, 8.29.

EXAMPLE 138

N-[4-[3-[4-[Bis(4-fluorophenyl)hydroxymethyl]-1-piperidinyl]propoxy]phenyl]methanesulfonamide fumarate[1:0.5]compound with 2-methoxyethanol [1:1]

To a solution of 4.5 g (0.01 mole) of the base of 1-[3-(4-aminophenoxy)propyl]-α,α-bis(4-fluorophenyl)-4-piperidinemethanol and 1.5 g (0.015 mole) of triethylamine in 50 ml of benzene and 100 mol of ethyl acetate was added dropwise a solution of 1.2 g (0.01 mole) of methanesulfonyl chloride in 10 ml of benzene. A gum immediately precipitated. The mixture was stirred at ambient temperature for 2 hr and then treated with a saturated sodium bicarbonate solution. The mixture was stirred for 0.5 hr during which time all solids dissolved. The layers were separated and the organic layer was washed with brine, dried over sodium sulfate and concentrated under reduced pressure to give a gum as residue. The gum was converted to the fumaric acid salt and the solid was recrystallized from,2-methoxyethanol to yield 4.0 g (61%) of title compound as a tan solid, mp 153°–156° C. with decomposition.

Analysis: Calc'd for $C_{30}H_{34}F_2N_2O_6S \cdot C_3H_8O_2$: C, 59.62; H, 6.37; N, 4.21. Found: C, 59.84; H, 6.59; N, 4.17.

EXAMPLE 139

1-[4-[3-[4-[Bis(4-fluorophenyl)hydroxymethyl]-1-piperidinyl]propoxy]phenyl]-1-propanone compound with 2-propanol [1:1]

This compound was prepared according to the procedure used to synthesize the compound of Example 1. A mixture of 3.0 g (0.01 mole) of α,α-bis(p-fluorophenyl)-4-piperidinemethanol, 2.3 g (0.01 mole) of 1-[4-(3-chloropropoxy)phenyl]-1-propanone, 3.7 g (0.035 mole) of anhydrous sodium carbonate and 0.4 g of potassium iodide in 100 mol of 1-butanol gave 3.7 g (76%) of title compound as a white solid, mp 57°–62° C.

Analysis: Calculated for $C_{30}H_{33}F_2NO_3 \cdot C_3H_8O$: C, 71.59; H, 7.46; N, 2.53. Found: C, 71,42; H, 7.29; N, 2.63.

EXAMPLE 140

1-[4-[3-[4-[Bis(4-methoxyphenyl)hydroxymethyl]-1-piperidinyl]propoxy]-3-methoxyphenyl]ethanone oxalate [1:1]

This compound was prepared according to the procedure used to synthesize the compound of Example 1. A mixture of 3.2 g (0.01 mole) of α,α-bis(4-methoxyphenyl)-4-piperidinemethanol, 2.4 g (0.01 mole) of 1-[4-(3-chloropropoxy)-3-methoxyphenyl]ethanone, 3.7 g (0.035 mole) of anhydrous sodium carbonate and 0.4 g of potassium iodide in 100 ml of 1-butanol gave a gum as residue. The gum was purified by columm chromatography on 100 g of Florisil ®. Fractions eluted with 5–40% acetone in benzene were combined and concentrated under reduced pressure to give a brown glass as residue. The glass was converted to the oxalic acid salt. The solid was recrystallized from absolute ethanol yield 3.3 g (53%) of the title compound as a white solid, mp 139°–142° C. with decomposition.

Analysis: Calculated for $C_{34}H_{41}NO_{10}$: C, 65.48; H, 6.63; N, 2.25. Found: C, 65.38; H, 6.70; N, 2.38.

EXAMPLE 141

1-[4-[6-[4-[Bis(4-fluorophenyl)hydroxymethyl]-1-piperidinyl]hexyloxy]-3-methoxyphenyl]ethanone hydrochloride [1:1]

This compound was prepared according to the procedure used to synthesize the compound of Example 1. A mixture of 3.0 g (0.01 mole) of α,α-bis(p-fluorophenyl)-4-piperidinemethanol, 2.8 g (0.01 mole) of 1-[4-(4-chlorohexyloxy)-3-methoxyphenyl]ethanone, 5.3 g (0.05 mole) of anhydrous sodium carbonate and 0.3 g of potassium iodide in 100 ml of 1-butanol gave a gum as resiude. The gum was purified by column chromatography on 80 g of Florisil ®. Fractions eluted with 2–5% acetone in benzene were combined and concentrated to give a glass as residue. The glass was dissolved in anhydrous ethyl ether, filtered and the filtrate treated with ethereal hydrogen chloride. A gummy solid precipitated. This solid was triturated with fresh ethyl ether until a fine, white solid resulted. The solid was collected by filtration and dried to yield 1.0 g (17%) of title compound as a white solid, mp 182°–186° C. with decomposition.

Analysis: Calculated for $C_{33}H_{40}ClF_2NO_4$: C, 67.37; H, 6.86; N, 2.38. Found: C, 67.17; H, 6.94; N, 2.37.

EXAMPLE 142

α,α-Bis(4-fluorophenyl)-1-[3-[4-(1-hydroxyethyl)-2-methoxyphenoxy]-4-piperidinemethanol oxalate hydrate [1:1:1.5]

To a stirred slurry of 0.6 g (0.015 mole) of lithium aluminum hydride in 50 ml of dry tetrahydrofuran was added a solution of 5.6 g (0.015 mole) of 1-[4-[3-[4-[bis(4-fluorophenyl)hydroxymethyl]-1-piperidinyl]-propoxy]-3-methoxyphenyl]ethanone in 100 ml of dry tetrahydrofuran. The mixture was stirred at ambient temperature for 2 hr and then cautiously treated successively with 1 ml of water, 1 ml of water, 1 ml of a 20% sodium hydroxide solution and 3 ml of water. The mixture was stirred for 0.5 hr, filtered and the filtrate concentrated to give a gummy solid as residue. The gum was converted to the oxalic acid salt. The gum was recrystallized from 2-propanol and then from absolute ethanol-ethyl ester to yield 3.5 g (39%) of title compound as a white solid, mp 81°–87° C. with decomposition.

Analysis: Calculated for $C_{32}H_{37}F_2NO_8 \cdot 1.5H_2O$: C, 61.14; H, 6.41; N, 2.23. Found: C, 61.13; H, 5.97; N, 2.17.

EXAMPLE 143

4-[4-[4-[Bis(4-fluorophenyl)hydroxymethyl]-1-piperidinyl]butoxy]benzoic acid methyl ester fumarate [1:1]

This compound was prepared according to the procedure used to synthesize the compound of Example 1. A mixture of 9.1 g (0.03 mole) of α,α-bis(p-fluorophenyl)-4-piperidinemethanol, 7.3 g (0.03 mole) of 4-(4-chlorobutoxy)benzoic acid methyl ester, 10.6 g (0.1 mole) of anhydrous sodium carbonate and 0.5 g of potassium iodide in 125 ml of dimethylformamide gave a gum as residue. The gum was converted to the fumaric acid salt and the solid was recrystallized from acetonitrile-dimethylformamide to yield 12.2 g (65%) of title compound as a white solid, mp 186°–188° C.

Analysis: Calculated for $C_{34}H_{37}F_2NO_8$: C, 65.27; H, 5.96; N, 2.24. Found: C, 65.23; H, 6.00; N, 2.32.

EXAMPLE 144

1-[4-[3-[4-[2,2-Bis(4-fluorophenyl)-2-hydroxyethyl]-1-piperidinyl]propoxy]-3-methoxyphenyl]ethanone fumarate hydrate [1:1:1]

A mixture of 4.52 g (0.0143 mole) of α,α-bis(4-fluorophenyl)-4-piperidineethanol, 3.75 g (0.0155 mole) of 3-(4-acetyl-2-methoxyphenoxy)-1-chloropropane, 4.1 g (0.049 mole) of sodium bicarbonate, and 0.20 g (0.0012 mole) of potassium iodide in 300 ml of 1-butanol was heated at reflux for 8 hr. The solvent was removed in vacuo, and the residue was partitioned between methylene chloride and dilute sodium hydroxide. The methylene chloride solution was treated with a small portion of activated charcoal and was dried over magnesium sulfate. The solvent was removed in vacuo to give the non-salt form of the title compound. This was converted to the fumarate salt and the salt was crystallized from methanol/ether to give 5.94 g (64.9%) of the title compound as a white, crystalline solid, mp 135°–136° C.

Analysis: Calculated for $C_{35}H_{41}F_2NO_9$: C, 63.92; H, 6.28; N, 2.13. Found: C, 64.03; H, 6.07; N, 2.16.

EXAMPLE 145

1-[4-[3-[4-[[2,2-Bis(4-fluorophenyl)ethyl]-1-piperidinyl]-propoxy]-3-methoxyphenyl]ethanone fumarate [1:1]

A mixture of 5.15 g (0.0148 mole) of 4-[2,2-bis(4-fluorophenyl)ethyl]piperidine hydrochloride hydrate [1:1:1], 3.71 (0.0153 mole) of 3-(4-acetyl-2-methoxyphenoxy)-1-chloropropane, 1.59 g (0.015 mole) of sodium carbonate, 2.30 g (0.0274 mole) of sodium bicarbonate and a 0.2 g (0.0012 mole) of potassium iodide in 400 ml of 1-butanol was heated at reflux for 12 hr. The solvent was removed in vacuo, and the residue was partitioned between methylene chloride and dilute sodium hydroxide. The methylene chloride solution was dried over magnesium sulfate, and the solvent was removed in vacuo to give the free base of the title compound as an oil. This was converted to the fumarate salt, and the salt was recrystallized from methanol-ether to give 5.87 g (63.6 g) of title compound as a white, crystalline solid, mp 156°–157° C.

Analysis: Calculated for $C_{35}H_{39}F_2NO_7$: C, 67.40; H, 6.30; N, 2.25. Found: C, 67.51; H, 6.34; N, 2.29.

EXAMPLE 146

1-[4-[3-[4-[2,2-Bis(4-fluorophenyl)ethylene]-1-piperidinyl]propoxy]-3-methoxyphenyl]ethanone fumarate [1:1]

A solution of 3.89 g (0.013 mole) of 4-[2,2-bis(4-fluorophenyl)ethylene]piperidine, 3.20 g (0.013 mole) of 3-(4-acetyl-2-methoxyphenoxy)-1-chloropropane and 2.02 g (0.024 mole) of sodium bicarbonate in 400 ml of 1-butanol was heated at reflux for 14 hr. The solvent was removed in vacuo, and the residue was partitioned between methylene chloride and dilute sodium hydroxide. The methylene chloride solution was dried over magnesium sulfate, and the solvent was removed in vacuo to give an oil. This was subjected to flash column chromatography (silica gel; eluted with 99/1 mixture of methylene chloride and methanol) to give the free base of the title compound. This was converted to the fumarate salt, and the salt was recrystallized from methanol/ether to give 5.19 g (64.2%) of title compound as a white, crystalline solid, mp 179°–179.5° C.

Analysis: Calculated for $C_{35}H_{37}F_2NO_7$: C, 67.62; H, 6.00; N, 2.25. Found: C, 67.59; H, 6.00; N, 2.23.

EXAMPLE 147

α-(4-Fluorophenyl)-α-[1-(3-phenoxypropyl)-4-piperidinyl]-2-pyridineacetonitrile oxalate [1:1.5]

A mixture of α-(4-fluorophenyl)-α-(4-piperidinyl)2-pyridineacetonitrile (11.30 g, 0.0383 mole), 3-phenoxypropyl bromide (8.20 g, 0.0383 mole), and potassium bicarbonate (4.0 g, 0.04 mole) was heated overnight at reflux in 350 ml of acetonitrile (dried over 4A molecular sieves). The reaction mixture was cooled to room temperature and filtered, and solvent removed by rotary evaporation. A dark brown oil was obtained and dissolved in chloroform. The chloroform layer was extracted with 5% sodium hydroxide and water, dried over sodium sulfate and filtered, and the solvent was removed to give a brown oil. A 0.55 g sample of the oil was converted to the oxalate salt in methanol-ethyl ether. A white, crystalline solid was isolated and dried in vacuo overnight at 80° C., to give 0.35 g (48.4% yield) of product, mp 121°–125° C.

Analysis; Calculated for $C_{30}H_{31}FN_3O_7$: C, 63.82; H, 5.53; N, 7.44. Found: C, 63.78; H, 5.56; N, 7.67.

EXAMPLE 148

1-[4-[3-[4-[Bis(4-chlorophenyl)methyl]-1-piperidinyl]propoxy]-3-methoxyphenyl]ethanone oxalate hydrate [1:1:0.5]

A mixture of 4-[bis(4-chlorophenyl)methyl]piperidine (11.39 g, 0.0357 mole), 1-[4-(3-chloropropoxy)-3-methoxyphenyl]ethanone (8.64 g, 0.0357 mole), and potassium carbonate (5.54 g, 0.04 mole) was heated overnight at reflux in 300 ml of 1-butanol containing potassium iodide (0.2 g). The reaction mixture was concentrated to dryness, and the residue obtained was partitioned several times between chloroform and water. The chloroform layer was dried over sodium sulfate ad filtered, and the solvent was removed to give a dark brown oil. This oil was converted to the oxalate salt and the salt was recrystallized from methanol-ethyl ether. A yellow solid was isolated and dried in vacuo overnight at 80° C. The yellow solid was next exposed to the atmosphere for 24 hours and submitted for analysis. This procedure produced 6.65 g (30% yield) of light yellow solid, mp 160°–171° C.

Analysis: Calculated for $C_{32}H_{35}Cl_2NO_7.0.5H_2O$: C, 61.44; H, 5.80; N, 2.24. Found: C, 61.40; H, 5.71; N, 2.24.

EXAMPLE 149

1-[4-[3-[4-[Bis(4-chlorophenyl)hydroxymethyl]-1-piperidinyl]propoxy]-3-methoxyphenyl]ethanone oxalate [1:1.5]

This compound was prepared according to the procedure used to synthesize the compound of Example 1. A mixture of 2.5 g (0.0075 mole) of α,α-bis(4-chlorophenyl)-4-piperidinemethanol, 1.8 g (0.0075 mole) of 1-[4-(3-chloropropoxy)-3-methoxyphenyl]ethanone, 3.7 g (0.035 mole) of anhydrous sodium carbonate and 0.4 g of potassium iodide in 100 ml of 1-butanol gave a gummy solid as residue. This solid was converted to the oxalic acid salt and the solid was recrystallized from absolute ethanol to yield 1.4 g (30%) of title compound as a pale-yellow solid, mp 89°–113° C. with decomposition.

Analysis: Calculated for $C_{33}H_{36}Cl_2NO_{10}$: C, 58.50; H, 5.36; N, 2.07. Found: C, 58.22; H, 5.32; N, 2.07.

EXAMPLE 150

4-[3-[4-[Bis(4-fluorophenyl)methyl]-1-piperidinyl]propoxy]-3-methoxybenzoic acid methyl ester The sodium salt of methyl vanillate was formed from methyl vanillate (11.26 g, 0.062 mole) and sodium hydride (2.47 g, 60%, 0.062 mole) in 300 ml of dimethyl sulfoxide (dried over 4A molecular sieves). During the formation of this sodium salt, the dimethyl sulfoxide solution turned light green. The salt was stirred 0.5 hr at room temperature under nitrogen atmosphere. Next, 4-[bis(4-fluorophenyl)methyl]-3-chloropropyl)piperidine (21.32 g, 0.062 mole) in 100 ml of dimethyl sulfoxide was added dropwise. The resulting solution was stirred overnight at 60° C. The warm reaction mixture was concentrated to dryness on a rotary evaporator. The residue was dissolved in chloroform and extracted several time with water. The chloroform layer was dried over sodium sulfate, filtered, and solvent removed to give a dark brown oil (31.35 g). The oil was dissolved in ethyl acetate and placed on an 800 g silica gel column. This column was eluted with ethyl acetate. Fractions of similar purity were combined and dried in vacuo at 80° C. overnight to give 22.70 g (71.9% yield) of brown oil.

H$^1$NMR(CDCl$_3$): δ 6.7–7.7 (m, 11, aromatics), 4.0–4.3 (t, 2, —OCH$_2$), 3.9 (s, 6, OCH$_3$ of ether and ester), 3.5 (d, 2, methine group attached to two fluorophenyl groups), 1.3–3.0 (m, 12, remaining aliphatics).

Analysis: Calculated for $C_{30}H_{33}F_2NO_4$: C, 70.71; H, 6.53; N, 2.75. Found: C, 70.48; H, 6.60; N, 2.71.

EXAMPLE 151

1-[4-[3-[4-[Bis(3-fluorophenyl)methyl]-1-piperidinyl]propoxy]-3-methoxyphenyl]ethanone fumarate [1:1]

A mixture of 5.32 g (0.019 mole) of 4-[bis(3-fluorophenyl)methyl]piperidine, 4.80 g (0.020 mole) of 3-(4-acetyl-2-methoxyphenoxy)-1-chloropropane, 2.4 g (0.029 mole) of sodium bicarbonate and 0.20 g (0.0012) mole of potassium iodide in 400 ml of 1-butanol was heated at reflux for 23 hr. The solvent was removed in vacuo and the residue was partitioned between methylene chloride and dilute sodium hydroxide. The methylene chloride solution was dried over magnesium sulfate and the solvent was removed in vacuo to give an oil. This was dissolved in methanol and the solution was treated with an excess of fumaric acid. Ether was added and a gum formed. The gum was triturated with acetonitrile to give 1.75 g (15.1%) of the title compound as a white crystalline solid, mp 180°–181° C.

Analysis: Calculated for $C_{34}H_{37}F_2NO_7$: C, 66.98; H, 6.12; N, 2.30. Found: C, 66.70; H, b 6.11; N, 2.32. The solvent was removed in vacuo from the filtate and the residue was recrystallized from a mixture of methanol-ether-acetonitrile to give 2.83 g (24.4) of title compound, mp 181°–182° C.

Analysis: Calculated for $C_{34}H_{37}F_2NO_7$: C, 66.98; H, 6.12, 2.30. Found: C, 66.95; H, 6.09; N, 2.28.

EXAMPLE 152

4-[3-[4-[Hydroxy(diphenyl)methyl]-1-piperdinyl]-propoxy]benzoic acid methyl ester This compound was prepared according to the procedure used to synthesize the compound of Example 1. A mixture of 5.3 g (0.02 mole) of α,α-diphenyl-4-piperidinemethanol, 4.6 g (0.02 mole) of 4-(3-chloropropoxy)benzoic acid methyl ester, 7.4 g (0.07 mole) of anhydrous sodium carbonate and 0.5 g of potassium iodide in 100 ml of dimethylformamide give 6.8 g (74%) of title compound as a fluffy, white solid, mp 146°–147° C.

Analysis: Calculated for $C_{29}H_{33}NO_4$: C, 75.59; H, 7.24; N, 3.05. Found: C, 75.68; N, 7.22; N, 3.11.

EXAMPLE 153

1-[4-[6-[4-[Bis(4-fluorophenyl)methyl]-1-piperdinyl]-hexyloxy]-3-methoxyphenyl]ethanone A mixture of 4-[bis(4-fluorophenyl)methyl]piperidine (7.90 g, 0.0275 mole), 1-[4-(6-chlorohexyloxy)-3-methoxyphenyl]ethanone (7.82 g, 0.025 mole), and potassium carbonate (5.54 g, 0.04 mole) was heated overnight at reflux in 400 ml of 1-butanol containing potassium iodide (0.2 g). The mixture was cooled to room temperature and filtered. Butanol was removed by rotary evaporation. The brown oil obtained was dissolved in chloroform and extracted several times with water. The chloroform layer was dried over sodium sulfate, filtered, and solvent removed to give a brown oil. This oil was dissolved in ethyl acetate and subjected to flash chromatography on silica gel using ethyl acetate and 5% methanol-ethyl acetate for elution. Fractions of similar purity were combined and solvent removed to give an oil. The oil was dried at 80° C. overnight in vacuo to give 7.28 g (54.4% yield) of title compound as a light brown oil.

$H^1NMR(CDCl_3)$: 67 6.7–7.5 (m, 11, aromatics), 4–4.2 (m, 2, —OCH$_2$), 3.9 (s, 3, —OCH$_3$), 3.4–3.6 (d, 1, methine on carbon attached to two fluorophenyl groups), 2.6 (s, 3;

1.5–3.0 (m ,13, remaining aliphatics).

Analysis: Calculated for $C_{33}H_{39}F_2NO_3$: C, 73.99; H, 7.34; N, 2.61. Found: C, 73.92; H, 7.54; N, 2.62.

EXAMPLE 154

4-[3-[4-[Bis(4-fluorophenyl)methyl]-1-piperidinyl]-propoxy]-3-methoxybenzoic acid hydrate [1:0.5]

A solution of 4-[3-[4-[bis(4-fluorophenyl)methyl]-1-piperidinyl]-propoxy-3-methoxybenzoic acid methyl ester (18.58 g, 0.0365 mole) in 400 ml of ethanol was heated for 6 hr at reflux with potassium hydroxide (16.8 g) in 50 ml of water. The ethanol was removed by rotary evaporation. Next, 1N sulfuric acid (~200 ml) was added. The aqueous phase was made neutral to litmus paper by the addition of 5% sodium hydroxide. The neutral aqueous layer was extracted several times with chloroform. The chloroform layer was dried over sodium sulfate, filtered, and solvent removed to give a white solid. The white solid was triturated with ethyl ether and cooled to about 0° C. The white solid was then collected by filtration and dried in vacuo overnight at 80° C. to give 11.38 g (61.8% yield) of white, crystalline product, the title compound, mp 123°–126° C.

Analysis: Calculated for $C_{29}H_{31}F_2NO_4.0.5H_2O$: C, 69.03; H, 6.39; N, 2.78. Found: C, 69.18; H, 6.32; N, 2.78.

EXAMPLE 155

4-[Bis(4-fluorophenyl)methyl]-1-[3-(3-methoxyphenoxy)propyl]piperidine hydrate [1:0.5]

The sodium salt of m-methoxyphenol was prepared in dimethyl sulfoxide from sodium hydride (60%, 1.10 g, 0.027 mole) and m-methoxyphenol (3.36 g, 0.027 mole). The salt was stirred for 0.75 hr at room temperature and a clear brown solution was obtained. Next, 4-[bis(4-fluorophenyl)methyl]-1-(3-chloropropyl)piperidine (9.34 g, 0.027 mole) in 100 ml of dimethyl sulfoxide was added. The resulting solution was stirred overnight at 55° C. The solvent was removed in vacuo and the oil obtained was subjected to flash chromatography on silica gel using 50% hexanes-ethyl acetate for elution. Fractions of similar purity were combined and solvent removed. A brown oil was obtained and dried at 80° C. overnight in vacuo in give 3.96 g (31.8%) of brown oil.

$^1H$ NMR(CDCl$_3$): δ 6.3–7.3 (m, 12, aromatics), 3.8–4.1 (m, 2, —OCH$_2$), 3.7 (S, 3, —OCH$_3$), 3.4–3.6 (d, 1, methine attached to two fluorophenyl rings), 1.2–3.0 (m, 13), remaining aliphatic protons).

Analysis: Calculated for $C_{28}H_{31}F_2NO_2.0.5H_2O$: C, 73.02; H, 7.00; N, 3.04. Found: C, 72.66; H, 6.89; N, 3.06.

EXAMPLE 156

1-[4-[3-[4-[Cyclohexyl(4-fluorophenyl)methyl]-1-piperdinyl]propoxy]-3-methoxyphenyl]ethanone A mixture of 4-[cyclohexyl(4-fluorophenyl)methyl]-piperidine (5.71 g, 0.0207 mole), 1-[4-(3-chloropropoxy)-3-methoxyphenyl]ethanone (5.03 g, 0.207 mole), and potassium carbonate (5.53 g, 0.04 mole) was heated overnight at reflux in 350 ml of 1-butanol containing potassium iodide (0.2 g). The reaction mixture was cooled to room temperature and filtered. The 1-butanol was removed by rotary evaporation to give a brown oil. This oil was dissolved in chloroform and the chloroform layer was extracted with 5% sodium hydroxide and water. The chloroform layer was dried over sodium sulfate, filtered, and solvent removed to give a brown oil. This oil was subjected to flash chromatography on silica gel. Elution was performed using ethyl acetate, 5% methanol-ethyl acetate, and 10% methanol-ethyl acetate. Separate fractions of similar purity were combined and solvent was removed to give a yellow oil. This oil was dried in vacuo overnight at 80° C. to give 7.36 g (73.8%) of title compound.

¹H NMR(CDCl₃): δ 6.7–7.4 (m, 7, aromatics), 4.0 (m, 2, —O—CH₂), 3.9 (s, 3, —O—CH₃), 2.5 (s, 3,

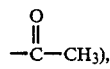

1.0–3.0 (m, 25, remaining aliphatics).

Analysis: Calculated for C₃₀H₄₀FNO₃: C, 74.81; H, 8.37; N, 2.91. Found: C, 74.39; H, 8.36; N, 2.81.

EXAMPLE 157

2-[4-Fluorophenyl)[1-(3-phenoxypropyl)-4-piperidinyl]methyl]pyridine hydrate [1:0.5]

A solution of α-(4-fluorophenyl)-α-[1-(3-phenoxypropyl)-4-piperidinyl]-2-pyridineacetonitrile oxalate [1:1.5] (2.34 g, 0.00545 mole) in 75 ml of glacial acetic acid containing 10 drops of concentrated hydrochloric acid was prepared. To this solution was added 2 grams of platinum on carbon catalyst (1%). After reacting with hydrogen for 5 days at 80° C. and 1000 psi, the reaction mixture was allowed to cool to room temperature. The mixture was filtered through Celite ® and the filtrate washed with glacial acetic acid. The acetic acid was removed by rotary evaporation. The residue obtained was dissolved in chloroform, and the solution was extracted with 5% sodium hydroxide. The chloroform was dried over sodium sulfate and filtered, and the solvent removed to give a brown oil. This oil was subjected to flash chromatography on silica gel using 5% methanol-ethyl acetate for elution. Fractions of similar purity were combined and solvent removed to give a brown oil. The oil was dried in vacuo overnight at 80° C. to give 0.35 (15.5% yield) of brown oil.

¹H NMR(CDCl₃): δ8.5 (m, 1, proton adjacent to nitrogen atom in pyridine ring), 6.8–7.5 (m, 12, aromatics), 4.0 (t, 2, —OCH₂—), 3.6 (d, 1, methine proton attached to carbon bonded to fluorophenyl ring and also pyridine ring), 1.0–3.0 (m, 13, remaining aliphatic protons).

Analysis: Calculated for C₂₉H₂₉FN₂O.0.5H₂O: C, 75.52; H, 7.31; N, 6.77. Calculated for C₂₉H₂₉FN₂O.0.25H₂O: C, 76.35; H, 7.27; N, 6.85. Found: C, 76.28; H, 7.14; N, 6.85.

EXAMPLE 158

1-[4-[3-[4-[(3,4-Difluorophenyl)(4-fluorophenyl)methyl]-1-piperidinyl]propoxy]-3-methoxyphenyl]ethanone oxalate [1:1]

A mixture of 2.68 g (0.036 mole) of 4-[3,4-difluorophenyl)methyl]piperidine, 2.50 g (0.110 mole) of 1-chloro-3-(4-acetyl-2-methoxyphenoxy)propane, 3.0 g (0.036 mole) of sodium bicarbonate, and 0.20 g (0.0012 mole) of potassium iodide in 300 ml of 1-butanol was heated at reflux for 30 hours. The solvent was removed in vacuo, and the residue was partitioned between methylene chloride and dilute sodium hydroxide. Methylene chloride solution was dried over sodium sulfate, and the solvent was removed in vacuo to give an oil. The oil was flash chromatographed (silica gel, elution with 95/5 methylene chloride-methanol) to give the nonsalt form of the title compound. This was converted to the oxalate salt, and the salt was recrystallized from methanol-ether to give 3.85 g (72.7%) of the title compound as a white, crystalline solid, m.p. 170°–171° C.

Analysis: Calculated for C₃₂H₃₄F₃NO₄: C, 63.89; H, 5.70; N, 2.33. Found: C, 63.87; H, 5.71; N, 2.34.

EXAMPLE 159

1-[4-[3-[3-[Bis(4-fluorophenyl)hydroxymethyl]-1-pyrrolidinyl]propoxy]-3-methoxyphenyl]ethanone A mixture of 2.9 g (0.01 mole) of α,α-bis(4-fluorophenyl)-3-pyrrolidinemethanol, 2.4 g (0.01 mole) of 1-[4-(3-chloropropoxy)-3-methoxyphenyl]ethanone, b 5.3 g (0.05 mole) of anhydrous sodium carbonate and 0.3 g (0.002 mole) of potassium iodide in 100 ml of 1-butanol was heated at reflux for 24 hr. The mixture was concentrated under reduced pressure and the residue partitioned between 100 ml of benzene and 100 ml of water. The benzene layer was washed with water and brine, dried over sodium sulfate and concentrated under reduced pressure to give a brown gum. The gum was purified by columne chromatography on 80 g of Florisil ® using a gradient elution system of 0–10% acetone in benzene. The fractions containing the desired product were combined and concentrated under reduced pressure to give 3.2 g of a brown gum. This gum was further purified by high-pressure liquid chromatography (Waters Associates Prep LC/System 500A; Prep-Pak 500 silica; 1% methanol in methylene chloride; flow rate 150 ml/min). The fractions containing the desired product were combined and concentrated under reduced pressure to yield 1.7 g (34% yield) of the title compound as a light-yellow, glassy solid, m.p. 44°–46° C.

Analysis: Calculated for C₂₉H₃₁F₂NO₄: C, 70.29; H, 6.31; N, 2.83. Found: C, 69.60; H, 6.26; N, 2.86.

EXAMPLE 160

1-[3-(4-Acetyl-2-methoxyphenoxy)propyl]-α,α-bis(4-fluorophenyl)-3-pyrrolidineacetonitrile A mixture of α,α-bis(4-fluorophenyl)-3-pyrrolidineacetonitrile (5.13 g, 0.0172 mole), 1-[4-(3-chloropropoxy)-3-methoxyphenyl]ethanone (4.17 g, 0.0172 mole), and potassium carbonate (5.53 g, 0.04 mole) was heated overnight at reflux in 350 ml of 1-butanol containing potassium iodide (0.2 g). The butanol was removed by rotary evaporation. The residue obtained was dissolved in chloroform and extracted several times with water. The chloroform layer was dried over sodium sulfate, filtered, and solvent removed in vacuo to give a dark brown oil. The oil was subjected to flash chromatography on silica gel using ethyl acetate and 25% methanol-75% ethyl acetate for elution. Fractions of similar purity were combined and solvents removed. A dark brown oil was obtained and dried in vacuo 2 days at 80° C. to give 5.85 g (57.5% yield) of the title compound as a dark brown gum.

¹H NMR (CDCl₃): δ6.8–7.6 (m, 11, aromatics), 4.3 (t, 2, —OCH₂—), 3.9 (s, 3—OCH₃), 2.6 (s, 3, —COCH₃—), 1.3–3.8 (m, 11, aliphatics).

Analysis: Calculated for C₃₀H₃₀F₂N₂O₃: C, 7.41; H, 5.99; N, 5.55. Found: C, 70.94; H, 5.99; N, 5.51.

EXAMPLE 161

1-[(3-(4-Acetyl-2-methoxyphenoxy)propyl]-α,α-bis(3-fluorophenyl)-4-piperidinemethanol This compound was prepared according to the procedure used to synthesize the compound of Example 1. A mixture of 3.0 g (0.01 mole) of 4-[α,α-bis(4-fluorophenyl)hydroxymethyl]piperdine, 2.4 g (0.01 mole) of 1-[4-(3-chloropropoxy)-3-methoxyphenyl]ethanone, 3.7 g (0.035 mole) of anhydrous sodium carbonate and 0.4 g of potassium iodide in 100 ml of 1-butanol gave 3.6 g (71%) of the title compound as an off-white solid, m.p. 149°–151° C. (absolute ethanol).

Analysis: Calculated for $C_{30}H_{35}F_2NO_4$: C, 70.71; H, 6.53; N, 2.75. Found: C, 70.66; H, 6.53; N, 2.79.

EXAMPLE 162

1-[3-(4-Acetyl-2-methoxyphenoxy)propyl]-α,α-bis(4-fluorophenyl)-3-piperidinepropanetrile hydrate [1:0.5]

A mixture of 1-[4-(3-chloropropoxy)-3-methoxyphenyl]ethanone (4.95 g, 0.0184 mole), α,α-bis(4-fluorophenyl)-3-piperidinepropanenitrile (6.00 g, 0.0184 mole), and potassium carbonate (5.54 g, 0.04 mole) was heated overnight at reflux. The mixture was cooled to room temperature and concentrated to dryness on a rotary evaporator. The residue was partitioned between chloroform and water. The chloroform layer was back-extracted with water and 5% sodium hydroxide solution. The chloroform layer was dried over sodium sulfate, filtered, and solvent removed to give a dark brown oil. The oil was subjected to flash chromatography on silica gel using 75% ethyl acetate-25% hexanes and 100% ethyl acetate for elution. Fractions of similar purity were combined and solvent removed. A dark brown oil was obtained and dried in vacuo at 80° C. to give 5.90 g (59.2% yield) of title compound as a yellowish-brown gum.

$H^1$NMR (CDCl₃): δ6.8–7.8 (m, 11, aromatics) 4.1 (s, 3, —OCH₃), 4.2 (m, 2, —OCH₂), 2.6 (s, 3,

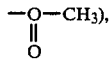

1.1–2.8 (m, 15, aliphatics).

Analysis: Calculated for $C_{32}H_{34}F_2N_2O_3 \cdot 0.5H_2O$: C, 70.96; H, 6.51; N, 5.17. Found: C, 71.58; H, 6.49; N, 5.12.

EXAMPLE 163

1-[4-[3-[4-[Bis(3,4-difluorophenyl)methyl]-1-piperidinyl]propoxy]-3-methoxyphenyl]ethanone A mixture of the free base of 4-[bis(4-fluorophenyl)methyl]piperidine hydrochloride [1:1] (6.46 g, 0.02 mole), 1-[4-(3-chloropropoxy-3-methoxyphenyl]ethanone (4.84 g, 0.02 mole), and potassium carbonate (5.54 g, 0.04 mole) was heated overnight at reflux in 1-butanol (350 ml (containing potassium iodide (0.2 g). The mixture was cooled to room temperature and then concentrated to dryness. The residue obtained was partitioned between chloroform and 5% sodium hydroxide solution. The chloroform layer was dried over sodium sulfate, filtered, and solvent removed in vacuo to give a yellow residue (11.17 g). The oil was subjected to flash chromatography on silica gel using ethyl acetate, 5% methanol-ethyl acetate and 10% methanolethyl acetate for elution. Fractions of similar purity were combined and solvent removed. A thick viscous oil was obtained and dried in vacuo overnight at 80° C. This procedure furnished 6.74 g (63.4%) of the title compound as a viscous oil.

$H^1$ NMR CDCl₃: δ6.8–7.6 (m, 9, aromatics), 4.1–4.3 (t, 2, —O—CH₂), 3.9 (s, 3, —OCH₃), 2.5 (s, 3,

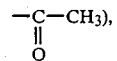

1.2–3.6 (m, 14, remaining aliphatics).

Analysis: Calculated for $C_{30}H_{31}F_4NO_3$: C, 68.05; H, 5.90; N, 2.64. Found: C, 67.49; H, 6.06; N, 2.56.

EXAMPLE 164

[[4-[3-[4-[Bis(4-fluorophenyl)hydroxymethyl]-1-piperidinyl]propoxy]phenyl]amino]-oxoacetic acid ethyl ester To a solution of 4.5 g (0.01 mole) of the base of 1-[3-(4-aminophenoxy)propyl]-α,α-bis(4-fluorophenyl)-4-piperidinemethanol (free base obtained in Preparation 133), and 1.5 g (0.015 mole) of triethylamine in 50 ml of benzene is added dropwise a solution of 1.4 g (0.01 mole) of ethyloxolyl chloride in 10 ml of benzene. The mixture is stirred at ambient temperature for 3 hr and then treated with 50 ml of water. The layers are separated and the organic layer is washed with brine, dried over sodium sulfate, and concentrated to give the title compound.

EXAMPLE 165

[[4-[3-[4-(Bis(4-fluorophenyl)hydroxymethyl]-1-piperidinyl]propoxy]phenyl]amino]-oxoacetic acid A solution of [[4-[3-[4-[Bis(4-fluorophenyl)hydroxymethyl]-1-piperidinyl]propoxy]phenyl]amino]oxoacetic acid ethyl ester in 50 ml of ethanol is treated with 20 ml of a 2N sodium bicarbonate solution and the mixture is heated at reflux overnight. The mixture is cooled and poured into 500 ml of water containing 10 ml of acetic acid. The resulting solution is collected by filtration and dried to give the title compound.

EXAMPLE 166

α,α-Bis(4-fluorophenyl)-1-[3-[4-(dimethylamino)phenoxy]propyl]-4-piperidinemethanol A solution of 4.8 g (0.01 mole) of α,α-bis(4-fluorophenyl)-1-[3-(4-nitrophenoxy)propyl-4-piperidinemethanol (obtained in Example 52) and 2.0 g (0.025 mole) of 37% formalin in 100 ml of absolute ethyl alcohol is hydrogenated at ambient temperature over 5% palladium on carbon catalyst overnight. The mixture is filtered through Celite ® and the filtrate is concentrated to give the title compound.

EXAMPLE 167

1-[4-[3-[4-[Bis(4-fluorophenyl)hydroxymethyl]-1-piperidinyl]propoxy]phenyl]-2,2-dimethyl-1-propanone A mixture of 3.0 g (0.01 mole) of α,α-bis(p-fluorophenyl)-4-piperidinemethanole, 2.5 g (0.01 mole) of [4-(3-chloropropoxy)phenyl][tertiarybutyl]ketone, b 3.7 g )0.035 mole) of anhydrous sodium carbonate and 0.4 g of potassium iodide in 100 ml of 1-butanol is heated at reflux overnight. The mixture is concentrated and the residue is partitioned between benzene and water. The organic layer is dried over sodium sulfate and concentrated to give the desired title compound.

EXAMPLE 168

1-[4-[3-[4-[Bis(2,4-Difluorophenyl)methyl]-1-piperidinyl]propoxy]-3-methoxyphenyl]ethanone oxalate [1:1]

A mixture of the free base of 4-[bis(2,4-difluorophenyl)methyl]piperidine hydrochloride [1:1 (7.30 g, 0.023 mole), 1-[4-(3-chloropropoxy)-3-methoxyphenyl]ethanone (5.57 g, 0.023 mole), and potassium carbonate (5.54 g, 0.04 mole) was heated overnight at reflux in 350 ml of 1-butanol containing potassium iodide (0.2 g). The reaction mixture was filtered and then concentrated to dryness. The residue was dissolved in chloroform, and the solution was extracted with 5% sodium hydroxide. The chloroform layer was dried over sodium sulfate and filtered. The removal of chloroform provided a dark brown oil (quantitative). This material was converted to the oxalate salt in methanol-ethyl ether. A white solid was isolated and dried in vacuo overnight at 80° C. This procedure furnished 8.23 g (57.7%) of white, crystalline product, mp 151°-153° C.

Analysis: Calculated for $C_{32}H_{33}F_4NO_7$: C, 62.03; H, 5.37; N, 2.26. Found: C, 62.10; H, 5.37; N, 2.33.

EXAMPLE 169

[[4-[3-[4-Bis(4-fluorophenyl)hydroxymethyl]-1-piperidinyl]propoxy]phenyl]amino]oxoacetic acid ethyl ester fumarate [1:0.5]

To a solution of 2.4 g (0.0054 mole) of the free base of 1-[3-(4-aminophenoxy)propyl]-α,α-bis(4-fluorophenyl)-4-piperidinemethanol oxalate [1:2] and 1.5 g (0.015 mole) of triethylamine in 50 ml of benzene was added dropwise a solution of 1.0 g (0.008 mole) of ethyl oxalyl chloride in 10 ml of benzene, and the mixture was stirred at ambient temperature overnight. The mixture was treated with 20 ml of water and vigorously stirred. The layers were separated, and the organic layer was washed with a saturated sodium bicarbonate solution, dried over sodium sulfate and concentrated to give a gum as residue. The gum was dissolved in ethyl ether and filtered to remove insolubles. The filtrate was concentrated, and the gummy residue was converted to the fumaric acid salt. The salt was recrystallized from absolute ethanol-water to yield 1.1 g (33%) of the title compound as a white solid, mp 215°-216° C. (dec.).

Analysis: Calculated for $C_{33}H_{36}F_2N_2O_7$: C, 64.91; H, 5.94; N, 4.59. Found: C, 64.62; H, 5.90; N, 4.59.

EXAMPLE 170

α,α-Bis(4-fluorophenyl)-1-[3-(2-methoxy-4-methylphenoxy)propyl]-4-piperidinemethanol This compound was prepared according to the procedure used to synthesize the compound of Example 1. A mixture of 4.5 g (0.015 mole) of [α,α-bis(4-fluorophenyl)]-4-piperidinemethanol, 3.2 g (0.015 mole) of 1-chloro-3-(2-methoxy-4-methylphenoxy)propane, 5.3 g (0.05 mole) of anhydrous sodium carbonate and 0.4 g of potassium iodide in 100 ml of 1-butanol gave 5.4 g (75%) of the title compound as a white solid, mp 121°-122° C. (2-propanol).

Analysis: Calculated for $C_{29}H_{33}F_2NO_3$: C, 72.33; H, 6.91; N, 2.91. Found: C, 72.34; H, 6.95; N, 2.90.

EXAMPLE 171

1-[2-[3-[4-Bis(4-fluorophenyl)hydroxymethyl]-1-piperidinyl]propoxy]phenyl]ethanone This compound was prepared according to the procedure used to synthesize the compound of Example 1. A mixture of 3.0 g (0.01 mole) of [α,α-bis(4-fluorophenyl)]-4-piperidinemethanol, 2.1 g (0.01 mole) of 2'-(3-chloropropoxy)acetophenone, 3.7 g (0.035 mole) of anhydrous sodium carbonate and 0.4 g of potassium iodide in 100 ml of 1-butanol gave 3.4 g (71%) of the title compound as a white solid, mp 113°-114° C. Analysis: Calculated for $C_{29}H_{31}F_2NO_3$: C, 72.63; H, 6.52; N, 2.92. Found: C, 72.54; H, 6.56; N, 2.92.

EXAMPLE 172

1-[3-[3-[4-[Bis(4-fluorophenyl)hydroxymethyl]-1-piperidinyl]propoxy]phenyl]ethanone oxalate hydrate [1:1:1]

This compound was prepared according to the procedure used to synthesize the compound of Example 1. A mixture of 3.0 g (0.01 mole) of [α,α-bis(4-fluorophenyl)]-4-piperidinemethanol, 2.1 g )0.01 mole) of 3'-(3-chloropropoxy)acetophenone, 13.7 g (0.035 mole) of anhydrous sodium carbonate and 0.4 g of potassium iodide in 100 ml of 1-butanol gave a gum as residue. The gum was converted to the oxalic acid salt and the solid was recrystallized from 2-propanol to yield 4.4 g (75%) of the title compound as a tan solid, mp 95°-100° C.

Analysis: Calculated for $C_{31}H_{33}NO_7 \cdot H_2O$: C, 63.36; H, 6.00; N, 2.38. Found: C, 62.94; H, 6.02; N, 2.20.

EXAMPLE 173

α,α-Bis(4-fluorophenyl)-1-[3-(3-methoxyphenoxy)propyl]-4-piperidinemethanol

This compound was prepared according to the procedure used to synthesize the compound of Example 1. A mixture of 3.0 (0.01 mole) of [α,α-bis(4-fluorophenyl)]-4-piperidinemethanol, 2.0 g (0.01 mole) of 1-chloro-3-(3-methoxyphenyoxy)propane, 3.7 g (0.035 mole) of anhydrous sodium carbonate and 0.4 g of potassuim iodide in 100 ml of 1-butanol gave 3.1 g (66%) of the title compound as a white solid, mp 107°-108° C. (2-propanol).

Analysis: Calculated for $C_{28}H_{31}F_2NO_3$: C, 71.93; H, 6.68; N, 3.00. Found: C, 71.90; H, 6.70; N, 3.01.

EXAMPLE 174

1-[3-(4-Ethylphenoxy)propyl]-α,α-bis(4-fluorophenyl)-4-piperidinemethanol oxalate [1:1]

This compound was prepared according to the procedure used to synthesize the compound of Example 1. A mixture of 3.0 g (0.01 mole) of [α,α-bis(4-fluorophenyl)]-4-piperidinemethanol, 2.0 g (0.01 mole) of 1-chloro-3-(4-ethylphenoxy)propane, 3.7 g (0.035 mole) of anhydrous sodium carbonate and 0.4 g of potassium iodide in 100 ml of 1-butanol gave a solid as residue. This solid was converted to the oxalic acid salt and the salt was recrystallized from 2-propanol to yield 3.0 g (54%) of the title compound as a white solid, mp 132°-135° C.

Analysis: Calculated for $C_{31}H_{35}F_2NO_6$: C, 67.01; H, 6.35; N, 2.52. Found: C, 66.60; H, 6.32; N, 2.51.

EXAMPLE 175

1-[3-(4-Ethoxyphenoxy)propyl]-α,α-bis(4-fluoro-phenyl)-4-piperidinemethanol

This compound was prepared according to the procedure used to synthesize the compound of Example 1. A mixture of 3.0 g (0.01 mole) of [α,α-bis(4-fluorophenyl)]-4-piperidinemethanol, 2.1 g (0.01 mole) of 1-chloro-3-(2-ethoxyphenoxy)propane, 3.7 g (0.035 mole) of anhydrous sodium carbonate and 0.4 g of potassium iodide in 100 ml of 1-butanol gave 3.6 g (75%) of the title compound as an off-white solid, mp 89°–91° C. (petroleum ether, 60°–110° C.). Analysis: Calculated for $C_{29}H_{33}F_2NO_3$: C, 72.33; H, 6.91; N, 2.91. Found: C, 72.39; H, 6.90; N, 2.96.

EXAMPLE 176

α,α-Bis(4-fluorophenyl)-1-[3-(2-methylphenoxy)-propyl]-4-piperidinemethanol

This compound was prepared according to the procedure used to synthesize the compound of Example 1. A mixture of 3.0 g (0.01 mole) of [α,α-bis(4-fluorophenyl)]-4-piperidinemethanol, 1.8 g (0.01 mole) of 1-chloro-3-(2-methylphenoxy)prpane, 3.7 g (0.035 mole) of anhydrous sodium carbonate and 0.4 g of potassium iodide in 100 ml of 1-butanol gave 2.5 g (56%) of the title compound as a white solid, mp 108.5°–109° C. (petroleum ether, 60°–110° C.).

Analysis: Calculated for $C_{28}H_{31}F_2NO_2$: C, 74.48; H, 6.92; N, 3.10. Found: C, 74.57; H, 6.92; N, 3.11.

EXAMPLE 177

α,α-Bis(4-fluorophenyl)-1-[3-(3-methylphenoxy)-propyl]-4-piperidinemethanol

This compound was prepared according to the procedure used to synthesize the compound of Example 1. A mixture of 3.0 g (0.01 mole) of [α,α-bis(4 -fluorophenyl)]-4-piperidinemethanol, 1.8 g (0.01 mole) of 1-chloro-3-(3-methylphenoxy)propane, 3.7 g (0.035 mole) of anhydrous sodium carbonate and 0.4 g of potassium iodide in 100 ml of 1-butanol gave 2.8 g (62%) of the title compound as a white solid, mp 112.5°–114° C. (2-propanol).

Analysis: Calculated for $C_{28}H_{31}F_2NO_2$: C, 74.48; H, 6.92; N, 3.10. Found: C, 74.44; H, 6.95; N, 3.15.

EXAMPLE 178

α,α-Bis(4-fluorophenyl)-1-[3-(2-phenylmethoxy)-phenoxy]propyl]-4-piperidinemethanol fumarate [1:1]

This compound was prepared according to the procedure used to synthesize the compound of Example 1. A mixture of 7.6 g (0.025 mole) of [α,α-bis(4-fluorophenyl)]-4-piperidinemethanol, 6.9 g (0.025 mole) of 1-chloro-3-(2-benzyloxyphenoxy)propane, 8.5 g (0.08 mole) of anhydrous sodium carbonate and 0.4 g of potassium iodide in 150 ml of 1-butanol gave a gum as residue. The gum was converted to the fumaric acid salt and the solid was recrystallized from acetonitrile to yield 10.5 g (64%) of the title compound as an off-white solid, mp 172°–174° C.

Analysis: Calculated for $C_{38}H_{39}F_2NO_7$: C, 69.18; H, 5.96; N, 2.12. Found: C 69.15; H, 5.92; N, 2.19.

EXAMPLE 179

α,α-Bis(4-fluorophenyl)-1-[3-(2-hydroxyphenoxy)-propyl]-4-piperidinemethanole fumarate [1:1] with ethyl acetate [1:1]

A solution of 6.1 g (0.011 mole) of α,α-bis(4-fluorophenyl)-1-[3-[2-(phenylmethoxy)phenoxy]propyl]-4-piperidinemethanol dissolved in 200 ml of absolute ethanol was hydrogenated in a Parr apparatus over 5% palladium on carbon catalyst at 60° C. overnight. The cooled mixture was filtered through Celite ® and the filtrate was concentrated to give a gum as residue. The dark gum was dissolved in ethyl ether and filtered to remove insolubles. The filtrate was concentrated to give 2.8 g of tan gum as residue. The gum was dissolved in ethyl acetate and mixed with an equivalent amount of fumaric acid dissolved in ethyl acetate. The solution was filtered and a solid crystallized from the filtrate. The solid was collected by filtration and dried to yield 2.3 g (32%) of the title compound as a white solid, mp 106°–116° C. (dec). The presence of 1 mole of ethyl acetate was confirmed by $^1H$ NMR. Analysis: Calculated for $C_{31}H_{33}F_2NO_7 \cdot C_4H_8O$: C, 63.92; H, 6.28; N, 2.13. Found: C, 63.62; H, 6.08; N, 2.24.

EXAMPLE 180

α,α-Bis(4-fluorophenyl)-1-[3-[2-(1-methylethoxy)-phenoxy)propyl]-4-piperidinemethanol This compound was prepared according to the procedure used to synthesize the compound of Example 1. A mixture of 3.0 g (0.01 mole) of [α,α-bis(4-fluorophenyl)]-4-piperidinemethanol, 2.3 g (0.01 mole) of 1-chloro-3-[2-(1-methylethoxy)phenoxy]propane, 3.7 g (0.035 mole) of anhydrous sodium carbonate and 0.4 g of potassium iodide in 100 ml of 1-butanol gave 2.9 g (58%) of the title compound as a fluffy, white solid, mp 75°–79° C. (2-propyl ether).

Analysis: Calculated for $C_{30}H_{35}F_2NO_3$: C, 72.70; H, 7.12; N, 2.83. Found: C, 72.65; H, 7.47; N, 2.69,.

EXAMPLE 181

4-[3-[4-[Bis(4-fluorophenyl)hydroxymethyl]-1-piperidinyl]propoxy]benzeneacetic acid ethyl ester oxalate [1:1] with ethyl acetate [1:0.5]

This compound was prepared according to the procedure used to synthesize the compound of Example 1. A mixture of 7.6 g (0.025 mole) of [α,αbis(4-fluorophenyl)]-4-piperidinemethanol, 6.1 g (0.025 mole) of 4-(3-chloropropoxy)benzeneacetic acid methyl ester, 9.5 g (0.09 mole) of anhydrous sodium carbonate and 0.4 g of potassium iodide in 150 ml of dimethylformamide gave a gum as residue. The gum was purified by column chromatography on 250 g of Florsil ®. Fractions eluted with 5–25% acetone in benzene were combined and concentrated to give a gum as residue. The gum was converted to the oxalic acid salt and the solid was recrystallized from ethyl acetate to yield 7.0 g (43%) of the title compound as a white compound as a white solid, mp 93°–98° C. (dec).

Analysis: Calc'd for $C_{32}H_{35}F_2NO_8 \cdot 0.5C_4H_8O$: C, 63.44; H, 6.10; N, 2.18. Found: C, 63.00; H, 5.99; N, 2.23.

EXAMPLE 182

4-[3-[4-Bis(4-fluorophenyl(hydroxymethyl]-1-piperidinyl]propoxy]N,N-dimethylbenzamide fumarate[1:1]

This compound was prepared according to the procedure used to synthesize the compound of Example 1. A mixture of 3.0 g (0.01 mole) of [α,α-bis(4-fluorophenyl)]-4-piperidinemethanol, 2.4 g (0.01 mole) of 4-(3-chloropropoxy)-N,N-dimethylbenzamide, 3.7 g (0.035 mole) of anhydrous sodium carbonate and 0.4 g of potassium iodide in 100 ml of 1-butanol gave a gum as residue. The gum was converted to the fumaric acid salt and the solid was recrystallized from acetonitrile-water to yield 4.0 g (65% of the title compound as a white solid, mp 166°–168° C.

Analysis: Calculated for $C_{34}H_{38}F_2N_2O_7$: C, 65.37; H, 6.13; N, 4.48. Found: C, 65.21; H, 6.12; N, 4.45.

EXAMPLE 183

1-3-(2,6-Dimethoxyphenoxy)propyl]α,α-bis(4-fluorophenyl)-4-piperidinemethanol

This compound was prepared according to the procedure used to synthesize the compound of Example 1. A mixture of 3.0 g (0.01 mole) of [α,α-bis(4-fluorophenyl-4-piperidinemethanol, 2.3 g (0.01 mole) of 1-(3-chloropropoxy)-2,6-dimethoxybenzene, 3.7 g (0.035 mole) of anhydrous sodium carbonate and 0.4 g of potassium iodide in 100 ml of 1-butanol gave 2.0 g (40%) of the title compound as a white solid, mp 136°–137° C. (2-propyl ether/2-propanol).

Analysis: Calculated for $C_{29}H_{33}F_2NO_4$: C, 70.00; H, 6.68; N, 2.81. Found: C, 70.15; H, 6.78; N, 2.85.

EXAMPLE 184

[4-[3-[4-[Bis(4-fluorophenyl)hydroxymethyl]-1-piperidinyl]propoxy]phenyl]phenylmethanone fumarate [1:1].

This compound was prepared according to the procedure used to synthesize the compound of Example 1. A mixture of 3.0 g (0.01 mole) of [αα-bis(4-fluorophenyl)]-4-piperidinemethanol, 3.7 g (0.035 mole) of anhydrous sodium carbonate and 0.4 g of potassium iodide in 100 ml of 1-butanol gave a gum as residue. The gum was converted to the fumaric acid salt and the solid was recrystallized from absolute ethanol to yield 4.3 g (65%) of the title compound as a tan solid, mp 200°–201° C. (dec).

Analysis: Calculated for $C_{38}H_{37}F_2NO_7$: C, 69.39; H, 5.67; N, 2.13. Found: C, 69.36; H, 5.63; N, 2.17.

EXAMPLE 185

1-[4-[3-[4-[Bis(3,4-difluorophenyl)hydroxymethyl]1-piperidinyl]-propoxy]-3-methoxyphenyl]ethanone This compound was prepared according to the procedure used to synthesize the compound of Example 1. A mixture of 1.4 g (0.004 mole) of α,α-bis(3,4-difluorophenyl)-4-piperidinemethanol, 1.0 g (0.004 mole) of 1-[4-(3-chloropropoxy)-3-methoxyphenyl]ethanone, 1.6 g (0.015 mole) of anhydrous sodium carbonate and 0.4 g of potassium iodide in 100 ml of 1-butanol gave 1.1 g (48%) of the title compound as an off-white solid, mp 143°–146° C. (2-propanol).

Analysis: Calculated for $C_{30}H_{31}F_4NO_4$: C, 66.05; H, 5.73; N, 2.57. Found: C, 66.03; H, 5.89; N, 2.50.

EXAMPLE 186

4-[3-[4-[Bis(4-fluorophenyl)hydroxymethyl]-1-piperidinyl]propoxy]benzeneacetic acid hydrate [1:0.5]

A mixture of 3.7 g (0.0073 mole) of the free base of 4-[3-[4-[bis(4-fluorophenyl)hydroxymethyl]-1-piperidinyl]propoxy]benzeneacetic acid ethyl ester oxalate [1:1], 0.8 g (0.0145 mole) of potassium hydroxide, 10 ml of water and 50 ml of 95% ethanol was heated at reflux under a nitrogen atmosphere for 1.5 hr. The solution was poured into a mixture of 1.3 g (0.022 mole) of glacial acetic acid in 500 ml of ice water and let stand at ambient temperature overnight. The solid which had precipitated was collected by filtration, washed with water, air dried, and recrystallized from 2-propanol to yield 2.9 g (78%) of the title compound as a white solid, mp 113°–121° C. (dec).

Analysis: Calculated for $C_{29}H_{31}F_2NO_4.0.5H_2O$: C, 69.03; H, 6.39; N, 2.78. Found: C, 69.35; H, 6.43; N, 2.74.

EXAMPLE 187

1-[4-[3-[3-[Bis(4-fluorophenyl)hydroxymethyl]-1-piperidinyl]propoxy]-3-methoxyphenyl]ethanone This compound was prepared according to the procedure used to synthesize the compound of Example 1. A mixture of 3.0 g (0.01 mole) of [α,α-bis(4-fluorophenyl)]-3-piperidinemethanol, 2.4 g (0.01 mole) of 1-[4-(3-chloropropoxy)-3-methoxyphenyl]ethanone, 3.7 g (0.035 mole) of anhydrous sodium carbonate and 0.4 g of potassium iodide in 100 ml of 1-butanol gave 4.0 g (78%) of the title compound as an off-white solid, mp 100°–105° C. (2-propanol).

Analysis: Calculated for $C_{30}H_{33}F_2NO_4$: C, 70.71; H, 6.53; N, 2.75. Found: C, 70.62; H, 6.61; N, 2.77.

EXAMPLE 188

1-[4-[3-[3-[2,2-Bis(4-fluorophenyl)-2-hydroxyethyl]-1-piperidinyl]propoxy]-3-methoxyphenyl ethanone fumarate [1:1]

This compound was prepared according to the procedure used to synthesize the compound of Example 1. A mixture of 3.7 g (0.012 mole) of the base of [α,α-bis(4-fluoropheny]-3-piperidineethanol hydrochloride [1:1], 2.8 g free (0.012 mole) of 1-[4-(3-chloropropoxy)-3-methoxyphenyl]ethanone, 4.3 g (0.04 mole) of anhydrous sodium carbonate and 0.5 g of potassium iodide in 100 ml of 1-butanol gave a gum as residue. The gum was purified by column chromatography on 120 g of Florisil ®. Fractions eluted with 20–60% acetone in benzene were combined and concentrated to give a gum. This gum was converted to the fumaric acid salt and the solid was recrystallized from ethyl acetate-acetonitrile to yield 2.6 g (35%) of the title compound as a white solid, mp 133°–136° C.

Analysis: Calculated for $C_{35}H_{39}F_2NO_8$: C, 65.72; H, 6.15; N, 2.19. Found: C, 65.41; H, 6.15; N, 2.18.

TABLE 1

$$\text{Ar}\underset{R}{\overset{(A)_d}{\diagdown}}C=(Q)_n\text{-ring-}N-(CH_2)_m-O-D$$
$$)_p$$

| Ex. No. | P | Ar | R | (A)d | (Q)n | Ring Position | m | D | Salt |
|---|---|---|---|---|---|---|---|---|---|
| 1 | 1 | C₆H₅— | C₆H₅— | — | — | 4 | 3 | C₆H₅— | oxalate |
| 2 | 1 | 4-F—C₆H₄— | 4-F—C₆H₄— | OH | — | 4 | 3 | C₆H₅— | oxalate 0.5 H₂O |
| 3 | 1 | 4-F—C₆H₄— | 4-F—C₆H₄— | — | — | 4 | 3 | C₆H₅— | oxalate |
| 4 | 1 | 4-F—C₆H₄— | 4-F—C₆H₄— | OH | — | 4 | 3 | C₆H₅— | fumarate |
| 5 | 1 | C₆H₅— | C₆H₅— | H | — | 4 | 4 | C₆H₅— | fumarate |
| 6 | 1 | C₆H₅— | C₆H₅— | H | — | 4 | 4 | C₆H₅— | fumarate |
| 7 | 1 | 4-F—C₆H₄— | 4-F—C₆H₄— | H | — | 4 | 3 | C₆H₅— | oxalate |
| 8 | 1 | C₆H₅— | C₆H₅— | H | — | 4 | 2 | C₆H₅— | fumarate |
| 9 | 1 | 4-F—C₆H₄— | 4-F—C₆H₄— | H | — | 4 | 4 | C₆H₅— | oxalate |
| 10 | 1 | 4-F—C₆H₄— | 4-F—C₆H₄— | H | — | 4 | 2 | C₆H₅— | oxalate |
| 11 | 1 | 4-F—C₆H₄— | C₆H₅— | H | — | 4 | 3 | C₆H₅— | fumarate |
| 12 | 1 | 4-F—C₆H₄— | 4-F—C₆H₄— | H | — | 4 | 2 | 2,6-Cl₂—C₆H₃— | — |
| 13 | 1 | 4-F—C₆H₄— | 4-F—C₆H₄— | H | — | 4 | 3 | 4-Cl—C₆H₄— | oxalate |
| 14 | 1 | 4-F—C₆H₄— | 4-F—C₆H₄— | H | — | 4 | 3 | 2-F—C₆H₄— | mandelate |
| 15 | 1 | 4-F—C₆H₄— | 4-F—C₆H₄— | H | — | 4 | 3 | 3-F—C₆H₄— | fumarate |
| 16 | 1 | 4-F—C₆H₄— | 4-F—C₆H₄— | OH | — | 4 | 3 | 4-Cl—C₆H₄— | — |
| 17 | 1 | 4-F—C₆H₄— | 4-F—C₆H₄— | H | — | 4 | 3 | 4-F—C₆H₄— | — |
| 18 | 1 | 4-F—C₆H₄— | 4-F—C₆H₄— | H | — | 4 | 3 | 4-OCH₃—C₆H₄— | fumarate |
| 19 | 1 | 4-F—C₆H₄— | 4-F—C₆H₄— | OH | — | 4 | 3 | 2-OCH₃—C₆H₄— | — |
| 20 | 1 | 4-F—C₆H₄— | 4-F—C₆H₄— | — | — | 4 | 3 | 2-OCH₃—C₆H₄— | oxalate |
| 21 | 1 | 4-F—C₆H₄— | 4-F—C₆H₄— | H | — | 4 | 3 | 2-OCH₃—C₆H₄— | oxalate |
| 22 | 1 | 4-F—C₆H₄— | 4-F—C₆H₄— | H | — | 4 | 3 | 3,4-(OCH₃)₂—C₆H₃ | fumarate |
| 23 | 1 | 4-CH₃—C₆H₄— | 4-CH₃—C₆H₄— | — | — | 4 | 3 | 2,6-(OCH₃)₂—C₆H₃ | — |
| 24 | 1 | 4-F—C₆H₄— | 4-F—C₆H₄— | — | — | 4 | 3 | 3,4-(OCH₃)₂—C₆H₃ | — |
| 25 | 1 | 4-F—C₆H₄— | 4-F—C₆H₄— | H | — | 4 | 3 | 2,6-(OCH₃)₂—C₆H₃ | oxalate, H₂O |
| 26 | 1 | 4-F—C₆H₄— | 4-F—C₆H₄— | H | — | 4 | 3 | 3,5-(OCH₃)₂—C₆H₃ | — |
| 27 | 1 | 4-OCH₃—C₆H₄— | 4-OCH₃—C₆H₄— | H | — | 4 | 3 | 3,4-(OCH₃)₂—C₆H₃ | — |
| 28 | 1 | 4-OCH₃—C₆H₄— | 4-OCH₃—C₆H₄— | H | — | 4 | 3 | 4-OCH₃—C₆H₄— | fumarate, 0.5 H₂O |
| 29 | 1 | 4-F—C₆H₄— | 4-F—C₆H₄— | — | — | 4 | 3 | 4-C(O)CH₃—C₆H₄— | oxalate |
| 30 | 1 | 4-F—C₆H₄— | 4-F—C₆H₄— | H | — | 4 | 3 | 4-C(O)CH₃—C₆H₄— | oxalate |
| 31 | 1 | 4-F—C₆H₄— | 4-F—C₆H₄— | OH | — | 4 | 2 | 4-C(O)CH₃—C₆H₄— | 2-propanolate |
| 32 | 1 | 4-F—C₆H₄— | 4-F—C₆H₄— | OH | — | 4 | 3 | 2-CH₃—4-C(O)CH₃—C₆H₃— | — |
| 33 | 1 | 4-F—C₆H₄— | 4-F—C₆H₄— | OH | — | 4 | 3 | 4-CN—C₆H₄— | fumarate |
| 34 | 1 | 4-F—C₆H₄— | 4-F—C₆H₄— | H | — | 4 | 3 | 4-C(O)OC₂H₅—C₆H₄— | HCl |
| 35 | 1 | 4-F—C₆H₄— | 4-F—C₆H₄— | OH | — | 4 | 3 | 4-C(O)OH—C₆H₄— | HCl, 0.5 H₂O |
| 36 | 1 | 4-F—C₆H₄— | 4-F—C₆H₄— | OH | — | 4 | 3 | 4-C(O)OC₂H₅—C₆H₄— | HBr |
| 37 | 1 | 4-F—C₆H₄— | 4-F—C₆H₄— | H | — | 4 | 3 | 4-C(O)OC₂H₅—C₆H₄— | HBr |
| 38 | 1 | 4-F—C₆H₄— | 4-F—C₆H₄— | H | — | 4 | 3 | 4-C(O)OC₂H₅—C₆H₄— | — |
| 39 | 1 | 4-OCH₃—C₆H₄— | 4-OCH₃—C₆H₄— | — | — | 4 | 3 | 4-C(O)OC₂H₉—C₆H₄— | fumarate, 0.5 H₂O |
| 40 | 1 | 4-OCH₃—C₆H₄— | 4-OCH₃—C₆H₄— | OH | — | 4 | 3 | 4-C(O)OC₂H₅—C₆H₄— | HCl |
| 41 | 1 | 4-F—C₆H₄— | 4-F—C₆H₄— | OH | — | 4 | 2 | 4-C(O)OC₂H₅—C₆H₄— | HCl |
| 42 | 1 | 4-F—C₆H₄— | 4-F—C₆H₄— | — | — | 4 | 3 | 2-OCH₃—4-CH₂—C(O)OC₂H₅—C₆H₄— | — |
| 43 | 1 | 4-F—C₆H₃— | 4-F—C₆H₄— | H | — | 4 | 3 | 4-t-butyl-C₆H₄— | fumarate |
| 44 | 1 | 4-F—C₆H₄— | 4-F—C₆H₄— | H | — | 4 | 3 | 4-t-butyl-C₆H₄— | fumarate, 0.5 H₂O |
| 45 | 1 | 4-OCH₃—C₆H₄— | 4-OCH₃—C₆H₄— | H | — | 4 | 3 | 4-t-butyl-C₆H₄— | oxalate |

TABLE 1-continued $$\text{Ar}(A)_d\diagdown \diagup \text{C}=(Q)_n-\diagup\diagdown_{)p}N-(CH_2)_m-O-D$$
$$R \diagup$$

| Ex. No. | p | Ar | R | (A)d | (Q)n | Ring Position | m | D | Salt |
|---|---|---|---|---|---|---|---|---|---|
| 46 | 1 | 4-F—C$_6$H$_4$— | 4-F—C$_6$H$_4$— | OH | — | 4 | 3 | 4-t-butyl-C$_6$H$_4$— | — |
| 47 | 1 | 4-F—C$_6$H$_4$— | 4-F—C$_6$H$_4$— | H | — | 4 | 3 | 3-CF$_3$—C$_6$H$_4$— | oxalate |
| 48 | 1 | 4-CH$_3$—C$_6$H$_4$— | 4-CH$_3$—C$_6$H$_4$— | H | — | 4 | 3 | 4-NHC(O)CH$_3$—C$_6$H$_4$— | fumarate, 0.5 H$_2$O |
| 49 | 1 | 4-F—C$_6$H$_4$— | 4-F—C$_6$H$_4$— | H | — | 4 | 3 | 4-NHC(O)CH$_3$—C$_6$H$_4$— | HBr |
| 50 | 1 | 4-F—C$_6$H$_4$— | 4-F—C$_6$H$_4$— | H | — | 4 | 3 | 4-NH$_2$—C$_6$H$_4$— | fumarate, 0.5 H$_2$O |
| 51 | 1 | 4-F—C$_6$H$_4$— | 4-F—C$_6$H$_4$— | OH | — | 4 | 3 | 4-NHC(O)CH$_3$—C$_6$H$_4$— | HCl, H$_2$O |
| 52 | 1 | 4-F—C$_6$H$_4$— | 4-F—C$_6$H$_4$— | OH | — | 4 | 3 | 4-NO$_2$—C$_6$H$_4$— | — |
| 53 | 1 | 4-F—C$_6$H$_4$— | 4-F—C$_6$H$_4$— | OH | — | 4 | 3 | 4-C(O)NH$_2$—C$_6$H$_4$— | HCl |
| 54 | 1 | 4-F—C$_6$H$_4$— | 4-F—C$_6$H$_4$— | H | — | 4 | 2 | 1-C$_{10}$H$_7$— | oxalate |
| 55 | 1 | 4-F—C$_6$H$_4$— | 4-F—C$_6$H$_4$— | H | — | 4 | 2 | 1-C$_{10}$H$_7$— | oxalate |
| 56 | 1 | 4-F—C$_6$H$_4$— | 4-F—C$_6$H$_4$— | H | — | 4 | 3 | 2-OCH$_3$—4—C(O)CH$_3$—C$_6$H$_3$— | 1.2 fumarate |
| 57 | 1 | 4-F—C$_6$H$_4$— | 4-F—C$_6$H$_4$— | H | — | 4 | 3 | 2-OCH$_3$—4-C(O)CH$_3$—C$_6$H$_3$— | oxalate |
| 58 | 1 | 4-F—C$_6$H$_4$— | C$_6$H$_5$— | — | — | 4 | 3 | 2-OCH$_3$—4-C(O)CH$_3$—C$_6$H$_3$— | oxalate |
| 59 | 1 | 3-CF$_3$—C$_6$H$_4$— | C$_6$H$_5$— | — | — | 4 | 3 | 2-OCH$_3$—4-C(O)CH$_3$—C$_6$H$_3$— | oxalate |
| 60 | 1 | C$_6$H$_5$— | C$_6$H$_5$— | — | — | 4 | 3 | 2-OCH$_3$—4-C(O)CH$_3$—C$_6$H$_3$— | oxalate |
| 61 | 1 | C$_6$H$_5$— | C$_6$H$_{11}$— | H | — | 4 | 3 | 2-OCH$_3$—4-C(O)CH$_3$—C$_6$H$_3$— | oxalate, 0.5 H$_2$O |
| 62 | 1 | C$_6$H$_5$— | C$_6$H$_{11}$— | — | — | 4 | 3 | 2-OCH$_3$—4-C(O)CH$_3$—C$_6$H$_3$— | oxalate |
| 63 | 1 | 4-F—C$_6$H$_4$— | 4-F—C$_6$H$_4$— | H | — | 4 | 3 | 4-CHOHCH$_3$—C$_6$H$_4$— | — |
| 64 | 1 | 4-F—C$_6$H$_4$— | 4-F—C$_6$H$_4$— | H | — | 4 | 3 | 2-OCH$_3$—4-CHOHCH$_3$-C$_6$H$_3$— | oxalate |
| 65 | 1 | 4-F—C$_6$H$_4$— | C$_6$H$_5$— | OH | — | 4 | 3 | 2-OCH$_3$—4-C(O)CH$_3$—C$_6$H$_3$— | — |
| 66 | 1 | 4-F—C$_6$H$_4$— | 4-F—C$_6$H$_4$— | OH | — | 4 | 3 | 2-OCH$_3$—4-C(O)CH$_3$—C$_6$H$_3$— | — |
| 67 | 1 | 4-F—C$_6$H$_4$— | C$_6$H$_5$— | OH | — | 4 | 3 | 2-OCH$_3$—4-C(O)CH$_3$—C$_6$H$_3$— | oxalate |
| 68 | 1 | C$_6$H$_5$— | C$_6$H$_5$— | OH | — | 4 | 3 | 2-OCH$_3$—4-C(O)CH$_3$—C$_6$H$_3$— | HCl, 0.5 H$_2$O |
| 69 | 1 | 3-CF$_3$—C$_6$H$_4$— | 4-F—C$_6$H$_4$— | OH | — | 4 | 3 | 2-OCH$_3$—4-C(O)CH$_3$—C$_6$H$_3$— | HCl |
| 70 | 1 | C$_6$H$_5$— | C$_6$H$_{11}$— | OH | — | 4 | 2 | 2-OCH$_3$—4-C(O)CH$_3$—C$_6$H$_3$— | — |
| 71 | 1 | 4-F—C$_6$H$_4$— | 4-F—C$_6$H$_4$— | H | — | 4 | 2 | 2-OCH$_3$—4-C(O)CH$_3$—C$_6$H$_3$— | — |
| 72 | 1 | 4-F—C$_6$H$_4$— | 4-OCH$_3$—C$_6$H$_4$— | H | — | 4 | 4 | 2-OCH$_3$—4-C(O)CH$_3$—C$_6$H$_3$— | — |
| 73 | 1 | 4-F—C$_6$H$_4$— | 4-CH$_3$—C$_6$H$_4$— | H | — | 4 | 5 | 2-OCH$_3$—4-C(O)CH$_3$—C$_6$H$_3$— | — |
| 74 | 1 | 4-F—C$_6$H$_4$— | 4-F—C$_6$H$_4$— | OH | — | 4 | 4 | 2-OCH$_3$—4-C(O)CH$_3$—C$_6$H$_3$— | — |
| 75 | 1 | 4-F—C$_6$H$_4$— | 4-Cl—C$_6$H$_4$— | OH | — | 4 | 3 | 2-OCH$_3$—4-C(O)—OCH$_3$—C$_6$H$_3$— | — |
| 76 | 1 | 4-F—C$_6$H$_4$— | C$_6$H$_5$— | H | — | 4 | 3 | 2-OCH$_3$—4-C(O)CH$_3$—C$_6$H$_3$— | oxalate |
| 77 | 1 | 4-OCH$_3$—C$_6$H$_4$— | 4-OCH$_3$—C$_6$H$_4$— | H | — | 4 | 3 | 2-OCH$_3$—4-C(O)CH$_3$—C$_6$H$_3$— | oxalate |
| 78 | 1 | 4-CH$_3$—C$_6$H$_4$— | 4-CH$_3$—C$_6$H$_4$— | H | — | 4 | 3 | 2-OCH$_3$—4-C(O)CH$_3$—C$_6$H$_3$— | — |
| 79 | 1 | 4-F—C$_6$H$_4$— | 4-F—C$_6$H$_4$— | OH | — | 4 | 3 | 2-OCH$_3$—4-C(O)CH$_3$—C$_6$H$_3$— | — |
| 80 | 1 | 4-F—C$_6$H$_4$— | 4-F—C$_6$H$_4$— | OH | — | 4 | 3 | 4-SCH$_3$—C$_6$H$_4$— | — |
| 81 | 1 | 4-F—C$_6$H$_4$— | 4-F—C$_6$H$_4$— | OH | — | 4 | 3 | 4-S(O)$_2$CH$_3$—C$_6$H$_4$— | — |
| 82 | 1 | 4-F—C$_6$H$_4$— | 4-F—C$_6$H$_4$— | H | — | 4 | 3 | 2-OCH$_3$—4-CH$_2$—C(O)OC$_2$H$_5$—C$_6$H$_3$— | fumarate |
| 83 | 1 | 4-F—C$_6$H$_4$— | 4-F—C$_6$H$_4$— | H | — | 4 | 3 | 4-C(O)OC$_2$H$_5$—C$_6$H$_4$— | HCl |
| 84 | 1 | 4-F—C$_6$H$_4$— | 4-F—C$_6$H$_4$— | OH | — | 4 | 2 | 4-C(O)OC$_2$H$_5$—C$_6$H$_4$— | HCl |
| 85 | 1 | 4-F—C$_6$H$_4$— | 4-F—C$_6$H$_4$— | OH | — | 4 | 3 | 2-OCH$_3$—4-CH$_2$C(O)—ONa—C$_6$H$_3$— | 0.5 H$_2$O |

TABLE 1-continued

Structure: Ar(A)_d-C(R)(=(Q)_n)-N-(CH2)_m-O-D with ring position p

| Ex. No. | P | Ar | R | (A)d | (Q)n | Ring Position | m | D | Salt |
|---|---|---|---|---|---|---|---|---|---|
| 86 | 1 | 4-F—C6H4— | 4-F—C6H4— | OH | — | 4 | 3 | (6-methyl-2H-chromen-2-one structure) | 0.75 fumarate |
| 87 | 1 | 4-F—C6H4— | 4-F—C6H4— | OH | — | 4 | 3 | 2-C(O)OC2H5—C6H4— | — |
| 88 | 1 | 4-F—C6H4— | 4-F—C6H4— | H | — | 4 | 3 | 2-C(O)OC2H5—C6H4— | 0.5 H2O |
| 89 | 1 | 4-F—C6H4— | 4-F—C6H4— | H | — | 4 | 5 | 2-OCH3—4-C(O)CH3—C6H3— | 1.5 fumarate |
| 90 | 1 | 4-F—C6H4— | 4-F—C6H4— | H | — | 4 | 3 | 4-C(O)NH2—C6H4— | oxalate |
| 91 | 1 | 4-F—C6H4— | 4-F—C6H4— | H | — | 4 | 3 | 4-S(O)2CH3—C6H4— | — |
| 92 | 1 | 4-F—C6H4— | 4-F—C6H4— | OH | — | 4 | 6 | 2-OCH3—4-C(O)CH3—C6H3— | — |
| 93 | 1 | 4-F—C6H4— | 4-F—C6H4— | OH | — | 4 | 3 | 3-OCH3—4-C(O)CH3—C6H3— | — |
| 94 | 1 | 4-F—C6H4— | 4-F—C6H4— | OH | — | 4 | 3 | 2-OH—C6H4— | — |
| 95 | 1 | 4-F—C6H4— | 4-F—C6H4— | OH | — | 4 | 3 | 4-S(O)CH3—C6H4— | fumarate |
| 96 | 1 | 4-F—C6H4— | 4-F—C6H4— | OH | — | 4 | 3 | 4-S(O)2NH2—C6H4— | HCl |
| 97 | 1 | 4-F—C6H4— | 4-F—C6H4— | OH | — | 4 | 3 | 4-NHS(O)2CH3— | — |
| 98 | 1 | 4-F—C6H4— | 4-F—C6H4— | OH | — | 4 | 3 | 4-NHC(O)NHCH3—C6H4— | — |
| 99 | 1 | 4-F—C6H4— | 4-F—C6H4— | OH | — | 4 | 3 | 4-NHC(O)OC2H5—C6H4— | — |
| 100 | 1 | 4-F—C6H4— | 4-F—C6H4— | OH | — | 4 | 3 | 3-NHC(O)NH2—C6H4— | — |
| 101 | 1 | 4-F—C6H4— | 4-F—C6H4— | OH | — | 4 | 3 | 2-OCH3—4-C(O)OH—C6H3— | sodium |
| 102 | 1 | 4-F—C6H4— | 4-F—C6H4— | OH | — | 4 | 3 | 3-OH—4-C(O)CH3—C6H4— | — |
| 103 | 1 | 4-F—C6H4— | 4-F—C6H4— | OH | — | 4 | 3 | (6-methyl-4H-chromen-4-one with 2-C(O)OC2H5) | HCl |
| 104 | 1 | 4-F—C6H4— | 4-F—C6H4— | OH | — | 4 | 3 | (6-methyl-chroman-4-one structure) | HCl |
| 105 | 1 | C6H5— | C6H5— | H | — | 4 | 3 | 2-OCH3—4-C(O)CH3—C6H3— | oxalate, 0.5 H2O |
| 106 | 1 | C6H5— | C6H11— | OH | — | 4* | 3 | 2-OCH3—4-C(O)CH3—C6H3— | oxalate, 0.5 H2O |
| 107 | 1 | 4-F—C6H4— | 4-F—C6H4— | H | — | 4 | 3 | 3-OCH3—4-C(O)CH3—C6H3— | HCl |
| 108 | 1 | 4-F—C6H4— | 4-F—C6H4— | H | — | 4 | 3 | 2,6-Cl2—C6H3— | — |
| 109 | 1 | 4-F—C6H4— | 4-F—C6H4— | H | — | 4 | 3 | 2,6-Cl2—C6H3— | oxalate |
| 110 | 1 | 4-F—C6H4— | 4-F—C6H4— | —CN | — | 4 | 3 | 2-CN—C6H4— | — |
| 111 | 1 | 4-F—C6H4— | 2-pyridinyl | — | — | 4 | 3 | 2-OCH3—4-C(O)CH3—C6H3— | fumarate |

TABLE 1-continued $$\text{Ar}\underset{R}{\overset{(A)d}{\underset{|}{C}}}=(Q)_n\underset{}{\overset{}{\underset{}{\bigg\langle}}}N-(CH_2)_m-O-D$$

| Ex. No. | p | Ar | R | (A)d | (Q)n | Ring Position | m | D | Salt |
|---|---|---|---|---|---|---|---|---|---|
| 112 | 1 | 4-F—C<sub>6</sub>H<sub>4</sub>— | 2-pyridinyl | —CN | — | 4 | 3 | 2-OCH<sub>3</sub>—4-C(O)CH<sub>3</sub>—C<sub>6</sub>H<sub>3</sub>— | fumarate, H<sub>2</sub>O |
| 113 | 1 | C<sub>6</sub>H<sub>5</sub>— | C<sub>6</sub>H<sub>5</sub>— | —CN | —CH<sub>2</sub>— | 3 | 3 | quinolin-8-yl | 0.5 H<sub>2</sub>O |
| 114 | 1 | 4-F—C<sub>6</sub>H<sub>4</sub>— | 4-F—C<sub>6</sub>H<sub>4</sub>— | H | — | 4 | 3 | quinolin-8-yl | 0.5 H<sub>2</sub>O |
| 115 | 1 | 4-F—C<sub>6</sub>H<sub>4</sub>— | 4-F—C<sub>6</sub>H<sub>4</sub>— | H | — | 4 | 3 | quinolin-2-yl | 0.5 H<sub>2</sub>O |
| 116 | 1 | 4-F—C<sub>6</sub>H<sub>4</sub>— | 4-F—C<sub>6</sub>H<sub>4</sub>— | H | — | 4 | 3 | napthal-2-yl | 0.5 H<sub>2</sub>O |
| 117 | 1 | 4-F—C<sub>6</sub>H<sub>4</sub>— | 4-F—C<sub>6</sub>H<sub>4</sub>— | H | — | 4 | 3 | 3-CN—C<sub>6</sub>H<sub>4</sub>— | 0.5 H<sub>2</sub>O |
| 118 | 1 | 4-F—C<sub>6</sub>H<sub>4</sub>— | 4-F—C<sub>6</sub>H<sub>4</sub>— | OH | — | 4 | 3 | 4-OCH<sub>3</sub>—C<sub>6</sub>H<sub>4</sub>— | fumarate |
| 119 | 1 | 4-F—C<sub>6</sub>H<sub>4</sub>— | 4-F—C<sub>6</sub>H<sub>4</sub>— | OH | — | 4 | 3 | 4-CH<sub>3</sub>—C<sub>6</sub>H<sub>4</sub>— | fumarate, H<sub>2</sub>O |
| 120 | 1 | 4-F—C<sub>6</sub>H<sub>4</sub>— | 4-F—C<sub>6</sub>H<sub>4</sub>— | OH | — | 4 | 3 | 4-F—C<sub>6</sub>H<sub>4</sub>— | — |
| 121 | 1 | 4-F—C<sub>6</sub>H<sub>4</sub>— | 2-pyridinyl | H | — | 4 | 3 | 2-OCH<sub>3</sub>—4-C(O)CH<sub>3</sub>—C<sub>6</sub>H<sub>3</sub>— | — |
| 122 | 1 | 4-F—C<sub>6</sub>H<sub>4</sub>— | 4-F—C<sub>6</sub>H<sub>4</sub>— | OH | — | 4 | 3 | 4-NHC(O)OC<sub>2</sub>H<sub>5</sub>—C<sub>6</sub>H<sub>3</sub>— | oxalate, 1.5 H<sub>2</sub>O |
| 123 | 0 | 4-F—C<sub>6</sub>H<sub>4</sub>— | 4-F—C<sub>6</sub>H<sub>4</sub>— | CN | CH<sub>2</sub> | 3 | 3 | 2-OCH<sub>3</sub>—4-C(O)CH<sub>3</sub>—C<sub>6</sub>H<sub>3</sub>— | — |
| 124 | 1 | 4-F—C<sub>6</sub>H<sub>4</sub>— | 4-F—C<sub>6</sub>H<sub>4</sub>— | — | — | 4 | 3 | 2-OH—C<sub>6</sub>H<sub>4</sub>— | — |
| 125 | 1 | 4-F—C<sub>6</sub>H<sub>4</sub>— | 4-F—C<sub>6</sub>H<sub>4</sub>— | OH | — | 4 | 3 | 2-OCH<sub>3</sub>—4-C<sub>2</sub>H<sub>5</sub>—C<sub>6</sub>H<sub>3</sub>— | — |
| 126 | 1 | C<sub>6</sub>H<sub>5</sub>— | C<sub>6</sub>H<sub>5</sub>— | OH | — | 4 | 3 | C<sub>6</sub>H<sub>5</sub>— | oxalate, 1.5 H<sub>2</sub>O, 0.5 2-propanolate |
| 127 | 1 | 4-F—C<sub>6</sub>H<sub>4</sub>— | 4-F—C<sub>6</sub>H<sub>4</sub>— | OH | — | 4 | 3 | 4-S(O)CH<sub>3</sub>—C<sub>6</sub>H<sub>4</sub>— | oxalate |
| 128 | 1 | 4-F—C<sub>6</sub>H<sub>4</sub>— | 4-F—C<sub>6</sub>H<sub>4</sub>— | OH | — | 4 | 3 | 4-CH(CH<sub>3</sub>)<sub>2</sub>—C<sub>6</sub>H<sub>4</sub>— | fumarate |
| 129 | 1 | 4-F—C<sub>6</sub>H<sub>4</sub>— | 4-F—C<sub>6</sub>H<sub>4</sub>— | OH | — | 4 | 3 | 3-C(O)OC<sub>2</sub>H<sub>5</sub>—C<sub>6</sub>H<sub>4</sub>— | — |
| 130 | 1 | 4-CH<sub>3</sub>—C<sub>6</sub>H<sub>4</sub>— | 4-CH<sub>3</sub>—C<sub>6</sub>H<sub>4</sub>— | — | — | 4 | 3 | 2-OCH<sub>3</sub>—4-C(O)CH<sub>3</sub>—C<sub>6</sub>H<sub>3</sub>— | oxalate, H<sub>2</sub>O |
| 131 | 1 | 4-CH<sub>3</sub>—C<sub>6</sub>H<sub>4</sub>— | 4-CH<sub>3</sub>—C<sub>6</sub>H<sub>4</sub>— | OH | — | 4 | 3 | 2-OCH<sub>3</sub>—4-C(O)CH<sub>3</sub>—C<sub>6</sub>H<sub>3</sub>— | fumarate |
| 132 | 1 | 4-F—C<sub>6</sub>H<sub>4</sub>— | 4-F—C<sub>6</sub>H<sub>4</sub>— | OH | — | 4 | 3 | 4-C(O)OCH<sub>3</sub>—C<sub>6</sub>H<sub>4</sub>— | 2.0 oxalate |
| 133 | 1 | 4-F—C<sub>6</sub>H<sub>4</sub>— | 4-F—C<sub>6</sub>H<sub>4</sub>— | H | — | 4 | 3 | 4-NH<sub>2</sub>—C<sub>6</sub>—H<sub>4</sub>— | oxalate |
| 134 | 1 | 4-F—C<sub>6</sub>H<sub>4</sub>— | 4-F—C<sub>6</sub>H<sub>4</sub>— | OH | — | 4 | 3 | 3-OCH<sub>3</sub>—4-C(O)CH<sub>3</sub>—C<sub>6</sub>H<sub>3</sub>— | oxalate |
| 135 | 1 | 4-F—C<sub>6</sub>H<sub>4</sub>— | 4-F—C<sub>6</sub>H<sub>4</sub>— | H | — | 4 | 3 | 2-OCH<sub>3</sub>—4-C<sub>2</sub>H<sub>5</sub>—C<sub>6</sub>H<sub>3</sub>— | oxalate |
| 136 | 1 | 4-F—C<sub>6</sub>H<sub>4</sub>— | 4-F—C<sub>6</sub>H<sub>4</sub>— | OH | — | 4 | 3 | 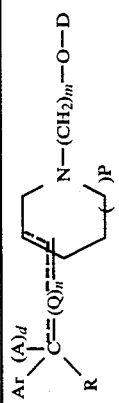 | — |
| 137 | 1 | 4-F—C<sub>6</sub>H<sub>4</sub>— | 4-F—C<sub>6</sub>H<sub>4</sub>— | OH | — | 4 | 3 | 4-NHC(O)NHCH<sub>3</sub>—C<sub>6</sub>H<sub>4</sub>— | — |
| 138 | 1 | 4-F—C<sub>6</sub>H<sub>4</sub>— | 4-F—C<sub>6</sub>H<sub>4</sub>— | OH | — | 4 | 3 | 4-NHS(O)<sub>2</sub>CH<sub>3</sub>—C<sub>6</sub>H<sub>4</sub>— | 0.5 fumarate, 2-methoxy-ethanolate |
| 139 | 1 | 4-F—C<sub>6</sub>H<sub>4</sub>— | 4-F—C<sub>6</sub>H<sub>4</sub>— | OH | — | 4 | 3 | 4-C(O)C<sub>2</sub>H<sub>5</sub>—C<sub>6</sub>H<sub>4</sub>— | 2-propanolate |
| 140 | 1 | 4-OCH<sub>3</sub>—C<sub>6</sub>H<sub>4</sub>— | 4-OCH<sub>3</sub>—C<sub>6</sub>H<sub>4</sub>— | OH | — | 4 | 3 | 2-OCH<sub>3</sub>—4-C(O)CH<sub>3</sub>C<sub>6</sub>H<sub>3</sub>— | oxalate |
| 141 | 1 | 4-F—C<sub>6</sub>H<sub>4</sub>— | 4-F—C<sub>6</sub>H<sub>4</sub>— | OH | — | 4 | 6 | 2-OCH<sub>3</sub>—4-C(O)CH<sub>3</sub>—C<sub>6</sub>H<sub>3</sub>— | HCl |
| 142 | 1 | 4-F—C<sub>6</sub>H<sub>4</sub>— | 4-F—C<sub>6</sub>H<sub>4</sub>— | OH | — | 4 | 3 | 2-OCH<sub>3</sub>—4-CH(OH)—(CH<sub>3</sub>)—C<sub>6</sub>H<sub>3</sub>— | oxalate, 1.5 H<sub>2</sub>O |
| 143 | 1 | 4-F—C<sub>6</sub>H<sub>4</sub>— | 4-F—C<sub>6</sub>H<sub>4</sub>— | OH | — | 4 | 4 | 4-C(O)OCH<sub>3</sub>—C<sub>6</sub>H<sub>4</sub>— | fumarate, H<sub>2</sub>O |
| 144 | 1 | 4-F—C<sub>6</sub>H<sub>4</sub>— | 4-F—C<sub>6</sub>H<sub>4</sub>— | H | CH<sub>2</sub> | 4 | 4 | 2-OCH<sub>3</sub>—4-C(O)CH<sub>3</sub>—C<sub>6</sub>H<sub>3</sub>— | fumarate |
| 145 | 1 | 4-F—C<sub>6</sub>H<sub>4</sub>— | 4-F—C<sub>6</sub>H<sub>4</sub>— | OH | CH<sub>2</sub> | 4 | 3 | 2-OCH<sub>3</sub>—4-C(O)CH<sub>3</sub>—C<sub>6</sub>H<sub>3</sub>— | fumarate |
| 146 | 1 | 4-F—C<sub>6</sub>H<sub>4</sub>— | 4-F—C<sub>6</sub>H<sub>4</sub>— | OH | CH | 4 | 3 | 2-OCH<sub>3</sub>—4-C(O)CH<sub>3</sub>—C<sub>6</sub>H<sub>3</sub>— | 1.5 oxalate |
| 147 | 1 | 4-F—C<sub>6</sub>H<sub>4</sub>— | 2-pyridinyl | CN | — | 4 | 3 | C<sub>6</sub>H<sub>5</sub>— | |
| 148 | 1 | 4-Cl—C<sub>6</sub>H<sub>4</sub>— | 4-Cl—C<sub>6</sub>H<sub>4</sub>— | H | — | 4 | 3 | 2-OCH<sub>3</sub>—4-C(O)CH<sub>3</sub>—C<sub>6</sub>H<sub>3</sub>— | oxalate, 0.5 H<sub>2</sub>O |

TABLE 1-continued

Structure:
$$\text{Ar}(A)_d\text{-C(R)=}(Q)_n\text{-[ring]}_p\text{-N-(CH}_2)_m\text{-O-D}$$

| Ex. No. | P | Ar | R | (A)d | (Q)n | Ring Position | m | D | Salt |
|---|---|---|---|---|---|---|---|---|---|
| 149 | 1 | 4-Cl—C₆H₄— | 4-Cl—C₆H₄— | OH | — | 4 | 3 | 2-OCH₃—4-C(O)CH₃—C₆H₃— | 1.5 oxalate |
| 150 | 1 | 4-F—C₆H₄— | 4-F—C₆H₄— | H | — | 4 | 3 | 2-OCH₃—4-C(O)OCH₃—C₆H₃— | fumarate |
| 151 | 1 | 3-F—C₆H₄— | 3-F—C₆H₄— | H | — | 4 | 3 | 2-OCH₃—4-C(O)OCH₃—C₆H₃— | — |
| 152 | 1 | C₆H₅— | C₆H₅— | OH | — | 4 | 3 | 4-C(O)OCH₃—C₆H₄— | — |
| 153 | 1 | 4-F—C₆H₄— | 4-F—C₆H₄— | H | — | 4 | 6 | 2-OCH₃—4-C(O)CH₃—C₆H₃— | — |
| 154 | 1 | 4-F—C₆H₄— | 4-F—C₆H₄— | H | — | 4 | 3 | 2-OCH₃—4-C(O)OCH₃—C₆H₃— | 0.5 H₂O |
| 155 | 1 | 4-F—C₆H₄— | 4-F—C₆H₄— | H | — | 4 | 3 | 3-OCH₃—C₆H₄— | 0.5 H₂O |
| 156 | 1 | 4-F—C₆H₄— | C₆H₁₁— | H | — | 4 | 3 | 2-OCH₃—4-C(O)CH₃—C₆H₃— | — |
| 157 | 1 | 4-F—C₆H₄— | 2-pyridinyl | H | — | 4 | 3 | C₆H₅— | 0.5 H₂O |
| 158 | 1 | 3,4 F₂—C₆H₃— | 4-F—C₆H₄— | OH | — | 4 | 3 | 2-OCH₃—4-C(O)CH₃—C₆H₃— | oxalate |
| 159 | 0 | 4-F—C₆H₄— | 4-F—C₆H₄— | CN | — | 3 | 3 | 2-OCH₃—4-C(O)CH₃—C₆H₃— | — |
| 160 | 0 | 4-F—C₆H₄— | 3-F—C₆H₄— | OH | — | 3 | 3 | 2-OCH₃—4-C(O)CH₃—C₆H₃— | — |
| 161 | 1 | 3-F—C₆H₄— | 4-F—C₆H₄— | CN | — | 3 | 3 | 2-OCH₃—4-C(O)CH₃—C₆H₃— | 0.5 H₂O |
| 162 | 1 | 4-F—C₆H₄— | 4-F—C₆H₄— | CN | CH₂ | 3 | 3 | 2-OCH₃—4-C(O)CH₃—C₆H₃— | — |
| 163 | 1 | 3,4-F₂—C₆H₃— | 3,4-F₂—C₆H₃— | H | — | 4 | 3 | 2-OCH₃—4-C(O)CH₃—C₆H₃— | — |
| 164 | 1 | 4-F—C₆H₄— | 4-F—C₆H₄— | OH | — | 4 | 3 | 4-[NH[C(O)C(O)—OC₂H₅]]—C₆H₄— | — |
| 165 | 1 | 4-F—C₆H₄— | 4-F—C₆H₄— | OH | — | 4 | 3 | 4-[NH[C(O)C(O)—OH]]—C₆H₄— | — |
| 166 | 1 | 4-F—C₆H₄— | 4-F—C₆H₄— | OH | — | 4 | 3 | 4-N(CH₃)₂—C₆H₄— | — |
| 167 | 1 | 4-F—C₆H₄— | 4-F—C₆H₄— | OH | — | 4 | 3 | 4-[C(O)C(CH₃)₃]—C₆H₄— | — |
| 168 | 1 | 4-F—C₆H₄— | 4-F—C₆H₄— | OH | — | 4 | 3 | 4-CH₃—C(O)C(O)—C₆H₃— | oxalate |
| 169 | 1 | 2,4-F₂—C₆H₃— | 2,4-F₂—C₆H₃— | OH | — | 4 | 3 | 4-NH[—C(O)C(O)—O—C₂H₅]—C₆H₄— | 0.5 fumarate |
| 170 | 1 | 4-F—C₆H₄— | 4-F—C₆H₄— | OH | — | 4 | 3 | 4-CH₃—2-OCH₃—C₆H₃— | — |
| 171 | 1 | 4-F—C₆H₄— | 4-F—C₆H₄— | OH | — | 4 | 3 | 2-C(O)CH₃—C₆H₄— | — |
| 172 | 1 | 4-F—C₆H₄— | 4-F—C₆H₄— | OH | — | 4 | 3 | 3-C(O)CH₃—C₆H₄— | oxalate, H₂O |
| 173 | 1 | 4-F—C₆H₄— | 4-F—C₆H₄— | OH | — | 4 | 3 | 3-CH₃O—C₆H₄— | — |
| 174 | 1 | 4-F—C₆H₄— | 4-F—C₆H₄— | OH | — | 4 | 3 | 4-C₂H₅—C₆H₄— | oxalate |
| 175 | 1 | 4-F—C₆H₄— | 4-F—C₆H₄— | OH | — | 4 | 3 | 2-C₂H₅—O—C₆H₄— | — |
| 176 | 1 | 4-F—C₆H₄— | 4-F—C₆H₄— | OH | — | 4 | 3 | 2-CH₃—C₆H₄— | — |
| 177 | 1 | 4-F—C₆H₄— | 4-F—C₆H₄— | OH | — | 4 | 3 | 3-CH₃—C₆H₄— | — |
| 178 | 1 | 4-F—C₆H₄— | 4-F—C₆H₄— | OH | — | 4 | 3 | 2-(C₆H₅—CH₂—O—)—C₆H₄— | fumarate |
| 179 | 1 | 4-F—C₆H₄— | 4-F—C₆H₄— | OH | — | 4 | 3 | 2-OH—C₆H₄— | fumarate, with ethyl acetate |
| 180 | 1 | 4-F—C₆H₄— | 4-F—C₆H₄— | OH | — | 4 | 3 | 2-[(CH₃)₂CH—O—]—C₆H₄— | — |
| 181 | 1 | 4-F—C₆H₄— | 4-F—C₆H₄— | OH | — | 4 | 3 | 4-[CH₃—O—C(O)—CH₂—]—C₆H₄ | oxalate, with 0.5 ethyl acetate |
| 182 | 1 | 4-F—C₆H₄— | 4-F—C₆H₄— | OH | — | 4 | 3 | 4-[(CH₃)₂N—C(O)—]—C₆H₄ | fumarate |
| 183 | 1 | 4-F—C₆H₄— | 4-F—C₆H₄— | OH | — | 4 | 3 | 2,6-(—O—CH₃)₂—C(O)—C₆H₃— | — |
| 184 | 1 | 4-F—C₆H₄— | 4-F—C₆H₄— | OH | — | 4 | 3 | 4[—C₆H₅—C(O)—]—C₆H₄— | fumarate |
| 185 | 1 | 4-F—C₆H₄— | 4-F—C₆H₄— | OH | — | 4 | 3 | 4[—CH₂—C(O)—CH₃]—C₆H₄ | — |
| 186 | 1 | 4-F—C₆H₄— | 4-F—C₆H₄— | OH | — | 4 | 3 | 4[—CH₂—C(O)—CH₃]—C₆H₄— | — |
| 187 | 1 | 4-F—C₆H₄— | 4-F—C₆H₄— | OH | — | 4 | 3 | 2-OCH₃—4-C(O)CH₃—C₆H₃— | 0.5 H₂O |
| 188 | 1 | 4-F—C₆H₄— | 4-F—C₆H₄— | OH | CH₂ | 4 | 3 | 2-OCH₃—4-C(O)CH₃—C₆H₃— | — |

*1,2,3,6-tetrahydropyridine.

PHARMACOLOGY METHODS

Antiallergy Screening Method—Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp. 205–209 (1977) which measures the effect of oral administration of a compound on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 255). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml)±S.D. A significant decrease ($p<0.05$) in the edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data are analyzed with the Dunnett's t-test that compares several treated groups with a control group. Differences between groups are determined by the studentized Range Test. Regression analysis may be used to determine relative potency.

Guinea Pig Anaphylaxis Method

The method used to test antiallergy effectiveness of the compounds in guinea pigs as compared to other drugs is as follows:

Guinea pigs are first sensitized to egg albumin (EA, Sigma Chemical Co., St. Louis, Mo.), at least 20 days prior to aerosol challenge by receiving 0.5 ml of EA-AlOH$_3$ conjugate (33 µg EA/ml) intramuscularly in each hind leg.

On the test day, fasted, sensitized guinea pigs are divided into a control group (8 animals per group) and test groups of four animals per group by using random number tables generated by an IBM scrambler. The reference; e.g., theophylline or test drug (Formula I compound) dissolved or suspended in 0.5% Tween 80 in distilled water or the control article (0.5% Tween 80 in distilled water) are administered orally in a volume of liquid at 10 ml/kg. Either 1, 5, or 24 hours following the oral administration of the test drug, reference drug, or control article, each animal is placed in an aerosolization chamber. EA (10 mg/ml) aerosolized at a rate of 10 liters of air/min is delivered into the chamber for a maximum of 5 minutes. The anaphylactic response consists of coughing, dyspena, reeling, collapse and death. Upon collapsing, the animals are removed from the chamber. Animals are considered protected if they do not collapse within 5 min of exposure to the aerosolized antigen. The number of animals that collapse in each group is recorded. ED$_{50}$ for collapse is calculated by the method of Litchfield and Wilcoxon (1949), J. PHARMACOL. EXP. THERAP. 95, 99–113 for evaluation of dose-effect experiments.

Comparisons of ED$_{50}$S from different experimental trials and determinations of relative potency are determined by the Litchfield and Wilcoxon method, ibid. The following conditions must be met before an experiment is acceptable:

(1) Control groups shows collapse in 7/8 or 8/8 animals, and (2) Theophylline reference group shows protection in ¾ or 4/4 animals treated 1 hr to 5 hr prior to antigen exposure.

Pharmaceutical Compositions and Administration

Compositions for administration to living animals are comprised of at least one of the compounds of Formula I according to the antiallergy method of the invention in association with a pharmaceutical carrier or excipient. Effective quantities of the compounds may be administered in any one of various ways, for example, orally as in elixirs, capsules, tablets or coated tablets, parenterally in the form of sterile solutions, suspensions, and in some cases intravenously in the form of sterile solutions, intranasally and to the throat or bronchial region in the form of drops, gargles, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or arachis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the pharmacology tests on guinea pigs in comparison to certain other antiallergy drugs suggest an effective dose for an adult will be in the range of 0.5 to 10 mg for the more active compounds with a daily dosage amounting to about 2 to 40 mg/day.

Based on the animal data, unit dosages containing an amount of compound equivalent to about 0.01 to 0.1 mg of active drug per kilogram of body weight are contemplated. Daily dosages of about 0.05 to 0.5 mg/kg of body weight are contemplated for humans and obviously several small dosage forms may be administered at one time. However, the amount of the active compounds administered need not be limited by these contemplations due to uncertainty in transposing animal data to human treatment.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:

1. A method of inhibiting Type 1 allergic responses in a living animal body which comprises administering to said body an effective amount of a compound selected from the group having the formula:

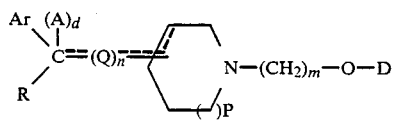

wherein:
P is zero, one or two;
m is one to six inclusive;
A is hydrogen, hydroxy, or cyano;
d is zero or one;
Q is —CH—, —CH$_2$— or

n is zero or one;
and when Q is —CH— and n is 1, a double bond is formed with one of the adjacent carbons, but not both, and when n and d are zero at the same time, a double bond is formed between the α-carbon and a carbon of the central heterocyclic amine ring;
Ar, D and R are selected from the group consisting of:

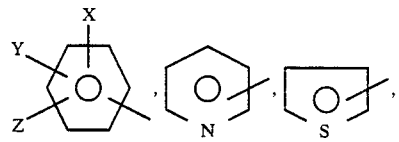

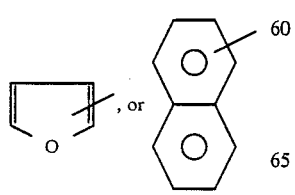

and in addition, R may have the values;

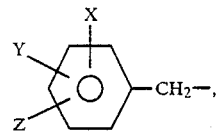

cycloalkyl or loweralkyl; and
D may have additionally the values;

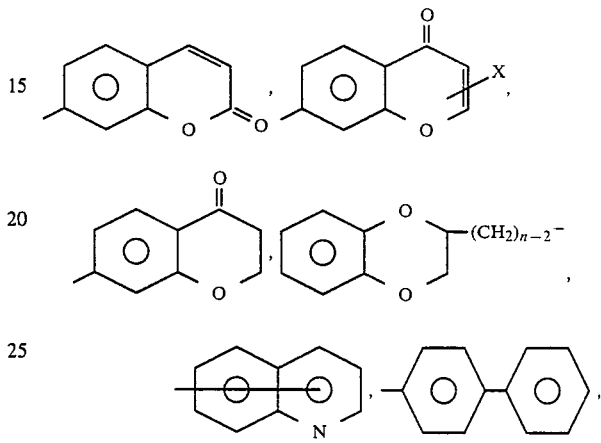

or Ar(CH$_2$)$_{1-4}$; X, Y and Z are selected from the group consisting of hydrogen, loweralkyl, halogen,

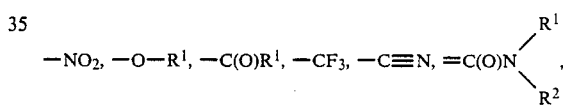

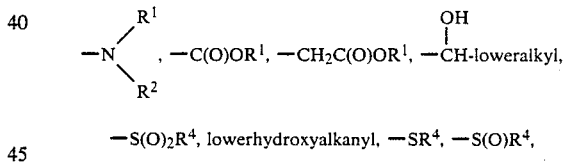

—S(O)$_2$R$^4$, lowerhydroxyalkanyl, —SR$^4$, —S(O)R$^4$,

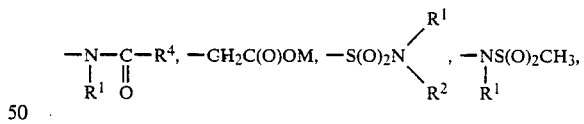

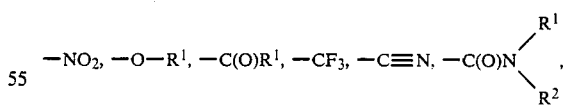

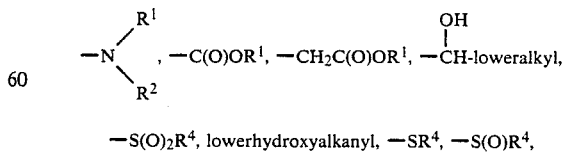

—S(O)$_2$R$^4$, lowerhydroxyalkanyl, —SR$^4$, —S(O)R$^4$,

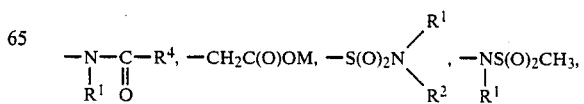

-continued

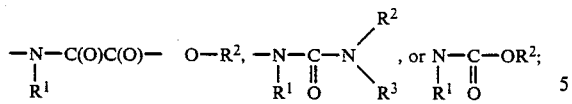

$R^1$, $R^2$ and $R^3$, same or different, are selected from hydrogen, loweralkyl, phenyl and phenyl-loweralkyl;

$R^4$ is selected from loweralkyl, phenyl and phenyl-loweralkyl;

M is a pharmaceutically acceptable metal ion;

and the pharmaceutically acceptable salts thereof, including acid addition salts, quaternary salts and hydrates and alcoholates thereof.

2. The method of claim 1 wherein the compound used is 4-[(4-fluorophenyl)methyl]-phenylmethyl]-1-(3-phenoxypropyl)piperidine or a pharmaceutically acceptable salt thereof.

3. The method of claim 1 wherein the compound used is 1-[4-[3-[4-[bis-(4-fluorophenyl)methyl]hydroxymethyl]-1-piperidinyl]propoxy]phenyl]ethanone or a pharmaceutically acceptable salt thereof.

4. The method of claim 1 wherein the compound used is 1-[4-[3-[4-[bis-(4-fluorophenyl)methyl]1-piperidinyl]-propoxy]-3-methoxyphenyl]ethanone oxalate [1:1].

5. The method of claim 1 wherein the compound used is 1-[4-[3-[4-[(4-fluorophenyl)hydroxyphenylmethyl]-1-piperidinyl]-3-methoxyphenyl]ethanone or a pharmaceutically acceptable salt thereof.

6. The method of claim 1 wherein the compound used is 1-[4-[3-[4-(diphenylhydroxymethyl)-1-piperidinyl]-3-methoxyphenyl]ethanone or a pharmaceutically acceptable salt thereof.

7. A method of inhibiting Type 1 allergic responses in a living animal body which comprises administering to said body an effective amount of a compound selected from the group having the formula:

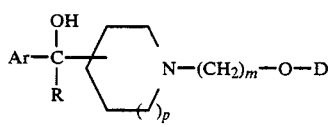

wherein:
p is zero or one;
m is one to six inclusive;
Ar, D and R are selected from the group consisting of:

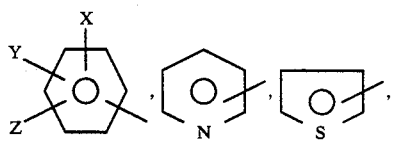

and in addition, R may have the values:

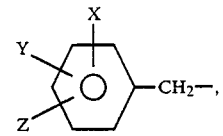

cycloalkyl or loweralkyl; and
D may have additionally the values:

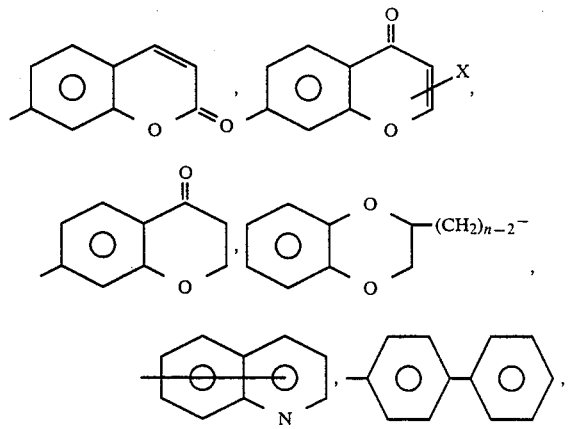

or $Ar(CH_2)_{1-4}$; X, Y, and Z are selected from the group consisting of hydrogen, loweralkyl, halogen,

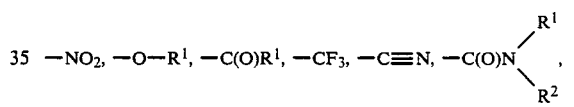

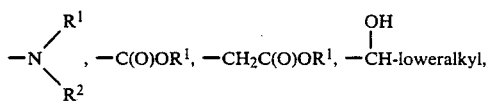

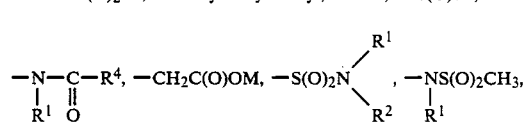

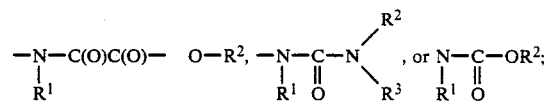

$R^1$, $R^2$ and $R^3$, same or different, are selected from hydrogen, loweralkyl, phenyl and phenyl-loweralkyl;

$R^4$ is selected from loweralkyl, phenyl and phenyl-loweralkyl;

M is a pharmaceutically acceptable metal ion;

and the pharmaceutically acceptable salts thereof, including acid addition salts, quaternary salts and hydrates and alcoholates thereof.

8. The method of claim 1 wherein the compound used is 4-[bis(4-fluorophenyl)methyl]-1-[3-(2-naphthalenyloxy)propyl]piperidine or a phermaceutically acceptable salt thereof.

9. The method of claim 1 wherein the compound used is 3-[3-[4-[bis(4-fluorophenyl)methyl]-1-piperidinyl]-

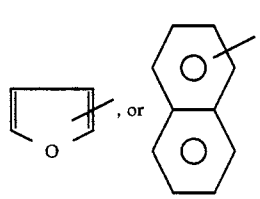

propoxy]benzonitrile or a pharmaceutically acceptable salt thereof.

10. The method of claim 1 wherein the compound used is α,α-bis(4-fluorophenyl)-1-[3-(4-methoxyphenoxy)propyl]-4-piperidinemethanol or a pharmaceutically acceptable salt thereof.

11. The method of claim 1 wherein the compound used is α,α-bis(4-fluorophenyl)-1-[3-(4-methylphenoxy)propyl]-4-piperidinemethanol or a pharmaceutically acceptable salt thereof.

12. The method of claim 1 wherein the compound used is 1-[3-(4-fluorophenoxy)propyl]-α,α-bis(4-fluorophenyl)-4-piperidinemethanol or a pharmaceutically acceptable salt thereof.

13. The method of claim 1 wherein the compound used is 1-[4-[3-[4-[(4-fluorophenyl)(2-pyridinyl)methyl]-1-piperidinyl]propoxy]-3-methoxyphenyl]ethanone or a pharmaceutically acceptable salt thereof.

14. The method of claim wherein the compound used is [4-[3-[4-[Bis(4-fluorophenyl)hydroxymethyl]-1-piperidinyl]propoxy]phenyl]carbamic acid ethyl ester or a pharmaceutically acceptable salt thereof.

15. The method of claim 1 wherein the compound used is 1-[3-(4-acetyl-2-methoxyphenoxy)propyl]α,α-bis(4-fluorophenyl)-3-pyrrolidinepropanenitrile or a pharmaceutically acceptable salt thereof.

16. The method of claim 1 wherein the compound used is 2-[3-[4-[bis(4-fluorophenyl)methylene]-1-piperidinyl]propoxy]phenol or a pharmaceutically acceptable salt thereof.

17. The method of claim 1 wherein the compound used is 1-[3-(4-ethyl-2-methoxyphenoxy)propyl]-α,α-bis(4-fluorophenyl)-4-piperidinemethanol or a pharmaceutically acceptable salt thereof.

18. The method of claim 1 wherein the compound used is 1-(3-phenoxypropyl)-α,α-diphenyl-4-piperidinemethanol or a pharmaceutically acceptable salt thereof.

19. The method of claim wherein the compound used is α,α-Bis(4-fluorophenyl)-1-[3-[4-(methylfulfinyl)phenoxy]propyl]-4-piperidinemethanol or a pharmaceutically acceptable salt thereof.

20. The method of claim 1 wherein the compound used is α,α-Bis(4-fluorophenyl)-1-[3-[4-(1-methylethyl)phenoxy]propyl]-4-piperidinemethanol or a pharmaceutically acceptable salt thereof.

21. The method of claim 1 wherein the compound used is 3-[3-[4-[bis(4-fluorophenyl)hydroxymethyl]-1-piperidinyl]propoxy]benzoic acid ethyl ester or a pharmaceutically acceptable salt thereof.

22. The method of claim 1 wherein the compound used is 1-[4-[3-[4-[bis(4-methylphenyl)methylene]-1-piperidinyl]propoxy]-3-methoxyphenyl]ethanone or a pharmaceutically acceptable salt thereof.

23. The method of claim 1 wherein the compound used is 1-[4-[3-[4-[bis(4-methylphenyl)hydroxymethyl]-1-piperidinyl]propoxy]-3-methoxyphenyl]ethanone or a pharmaceutically acceptable salt thereof.

24. The method of claim 1 wherein the compound used is 4-[3-[4-bis(4-fluorophenyl)hydroxymethyl]-1-piperidinyl]propoxy]benzoic acid methyl ester or a pharmaceutically acceptable salt thereof.

25. The method of claim 1 wherein the compound used is 1-[3-(4-aminophenoxy)propyl]-α,α-bis(4-fluorophenyl)-4-piperidinemethanol or a pharmaceutically acceptable salt thereof.

26. The method of claim 1 wherein the compound used is 1-[4-[3-[4-[bis(4-fluorophenyl)methyl]-1-piperidinyl]propoxy]-2-methoxyphenyl]ethanone or a pharmaceutically acceptable salt thereof.

27. The method of claim 1 wherein the compound used is 4-[bis(4-fluorophenyl)methyl]-1-[3-(4-ethyl-2-methoxyphenoxy)propyl]piperidine or a pharmaceutically acceptable salt thereof.

28. The method of claim 1 wherein the compound used is 1-[3-([1,1'-biphenyl]-4-yloxy)propyl]-α,α-bis(4-fluorophenyl)-4-piperidinemethanol or a pharmaceutically acceptable salt thereof.

29. The method of claim 1 wherein the compound used is N-[4-[3-[4-[bis(4-fluorophenyl)hydroxymethyl]-1-piperidinyl]propoxy]phenyl]-N'-methylurea or a pharmaceutically acceptable salt thereof.

30. The method of claim 1 wherein the compound used is N-[4-[3-[4-[bis(4-fluorophenyl)hydroxymethyl]-1-piperidinyl]propoxy]phenyl]methanesulfonamide or a pharmaceutically acceptable salt thereof.

31. The method of claim 1 wherein the compound used is 1-[4-[3-[4-[bis(4-fluorophenyl)hydroxymethyl]-1-piperidinyl]propoxy]phenyl]-1-propanone or a pharmaceutically acceptable salt thereof.

32. The method of claim 1 wherein the compound used is 1-[4-[3-[4-[bis(4-methoxyphenyl)hydroxymethyl]-1-piperidinyl]propoxy]-3-methoxyphenyl]ethanone or a pharmaceutically acceptable salt thereof.

33. The method of claim 1 wherein the compound used is 1-[4-[6-[4-[bis(4-fluorophenyl)hydroxymethyl]-1-piperidinyl]hexyloxy]-3-methoxyphenyl]ethanone or a pharmaceutically acceptable salt thereof.

34. The method of claim 1 wherein the compound used is α,α-bis(4-fluorophenyl)-1-[3-[4-(1-hydroxyethyl)-2-methoxyphenoxy]-4-piperidinemethanol or a pharmaceutically acceptable salt thereof.

35. The method of claim 1 wherein the compound used is 4-[4-[4-[bis(4-fluorophenyl)hydroxymethyl]-1-piperidinyl]butoxy]benzoic acid methyl ester or a pharmaceutically acceptable salt thereof.

36. The method of claim 1 wherein the compound used is 1-[4-[3-[4-[2,2-bis(4-fluorophenyl)-2-hydroxyethyl]-1-piperidinyl]propoxy]-3-methoxyphenyl]ethanone or a pharmaceutically acceptable salt thereof.

37. The method of claim 1 wherein the compound used is 1-[4-[3-[4-[2,2-bis(4-fluorophenyl)ethyl]-1-piperidinyl]propoxy]-3-methoxyphenyl]ethanone or a pharmaceutically acceptable salt thereof.

38. The method of claim 1 wherein the compound used is 1-[4-[3-[4-[2,2-bis(4-fluorophenyl)ethylene]-1-piperidinyl]propoxy]-3-methoxyphenyl]ethanone or a pharmaceutically acceptable salt thereof.

39. The method of claim 1 wherein the compound used is α-(4-fluorophenyl)-α-[1-(3-phenoxypropyl)-4-piperidinyl]-2-pyridineacetonitrile or a pharmaceutically acceptable salt thereof.

40. The method of claim 1 wherein the compound used is 1-[4-[3-[4-[bis(4-chlorophenyl)methyl]-1-piperidinyl]propoxy]-3-methoxyphenyl]ethanone or a pharmaceutically acceptable salt thereof.

41. The method of claim 1 wherein the compound used is 1-[4-[3-[4-[bis(4-chlorophenyl)hydroxymethyl]-1-piperidinyl]propoxy]-3-methoxyphenyl]ethanone or a pharmaceutically acceptable salt thereof.

42. The method of claim 1 wherein the compound used is 4-[3-[4-[bis(4-fluorophenyl)methyl]-1-piperidinyl]propoxy]-3-methoxybenzoic acid methyl ester or a pharmaceutically acceptable salt thereof.

43. The method of claim 1 wherein the compound used is 1-[4-[3-[4-[bis(3-fluorophenyl)methyl]-1- piperidinyl]propoxy]-3-methoxyphenyl]ethanone or a pharmaceutically acceptable salt thereof.

44. The method of claim 1 wherein the compound used is 4-[3-[4-[hydroxy(diphenyl)methyl]-1-piperidinyl]propxy]benzoic acid methyl ester or a pharmaceutically acceptable salt thereof.

45. The method of claim 1 wherein the compound used is 1-[4-[6-[4-[bis(4-fluorophenyl)methyl]-1-piperidinyl]hexyloxy]-3-methoxyphenyl]ethanone or a pharmaceutically acceptable salt thereof.

46. The method of claim 1 wherein the compound used is 4-[3-[4-[bis(4-fluorophenyl)methyl]-1-piperidinyl]propoxy]-3-methoxybenzoic acid or a pharmaceutically acceptable salt thereof.

47. The method of claim 1 wherein the compound used is 4-[bis(4-fluorophenyl)methyl]-1-[3-(3-methoxyphenoxy)propyl]piperidine or a pharmaceutically acceptable salt thereof.

48. The method of claim 1 wherein the compound used is 1-[4-[3-[4-[cyclohexyl(4-fluorophenyl)methyl]-1-piperidinyl]propoxy]-3-methoxyphenyl]ethanone or a pharmaceutically acceptable salt thereof.

49. The method of claim 1 wherein the compound used is 2-[(4-fluorophenyl)[1-(3-phenoxypropyl)-4-piperidinyl]methyl]pyridine or a pharmaceutically acceptable salt thereof.

50. The method of claim 1 wherein the compound used is 1-[4-[3-[4-[(3,4-difluorophenyl)(4-fluorophenyl)methyl]-1-piperidinyl]propoxy]-3-methoxyphenyl]ethanone or a pharmaceutically acceptable salt thereof.

51. The method of claim 1 wherein the compound used is 1-[4-[3-[3-[bis(4-fluorophenyl)hydroxymethyl]-1-pyrrolidinyl]propoxy]-3-methoxyphenyl]ethanone or a pharmaceutically acceptable salt thereof.

52. The method of claim 1 wherein the compound used is 1-[3-[4-acetyl-2-methoxyphenoxy)propyl]-$\alpha,\alpha$-bis(4-fluorophenyl)-3-pyrrolidineacetonitrile or a pharmaceutically acceptable salt thereof.

53. The method of claim 1 wherein the compound used is 1-[3-(4-acetyl-2-methoxyphenoxy)propyl]-$\alpha,\alpha$-bis(3-fluorophenyl)-4-piperidinemethanol or a pharmaceutically acceptable salt thereof.

54. The method of claim 1 wherein the compound used is 1-[3-(4-acetyl-2-methoxyphenoxy)propyl]-$\alpha,\alpha$-bis(4-fluorophenyl)-3-piperidinepropanenitrile or a pharmaceutically acceptable salt thereof.

55. The method of claim 1 wherein the compound used is 1-[3-(4-acetyl-2-methoxyphenoxy)propyl]-$\alpha,\alpha$-bis(4-fluorophenyl)-4-piperidineacetamide or a pharmaceutically acceptable salt thereof.

56. The method of claim 1 wherein the compound used is 1-[4-[3-[4-[bis(3,4-difluorophenyl)methyl]-1-piperidinyl]propoxy]-3-methoxyphenyl]ethanone or a pharmaceutically acceptable salt thereof.

57. The method of claim 1 wherein the compound used is $\alpha,\alpha$-bis(4-fluorophenyl)-1-[3-(2-methoxy-4-methylphenoxy)propyl]-4-piperidinemethanol or a pharmaceutically acceptable salt thereof.

* * * * *